US010253355B2

(12) United States Patent
Richards et al.

(10) Patent No.: US 10,253,355 B2
(45) Date of Patent: Apr. 9, 2019

(54) INSTRUMENT AND SYSTEM FOR RAPID MICROORGANISM IDENTIFICATION AND ANTIMICROBIAL AGENT SUSCEPTIBILITY TESTING

(71) Applicant: Accelerate Diagnostics, Inc., Tucson, AZ (US)

(72) Inventors: William L. Richards, Tucson, AZ (US); Austin Ashby, Tucson, AZ (US); Matthew Ketterer, Tucson, AZ (US); Kevin Marshall, Tucson, AZ (US); Josh Harrison, Tucson, AZ (US); Matthew Mette, Marana, AZ (US); Paul Richards, Tucson, AZ (US); Wayne Showalter, Tucson, AZ (US); Jasmin Cote, Quebec (CA); Phillip C. Halbert, San Francisco, CA (US); Solene Bourgeois, San Francisco, CA (US); Steven W. Metzger, Tucson, AZ (US); Ken Hance, Tucson, AZ (US); Meghan Mensack, Tucson, AZ (US); Carlos Michel, Tucson, AZ (US); Elke Allers, Tucson, AZ (US); Dulini Gamage, Tucson, AZ (US); Landon Prisbrey, Tucson, AZ (US); Oleg Gusyatin, Tucson, AZ (US); Alena Shamsheyeva, Tucson, AZ (US); Ben Turng, Suzhou (CN); Andrew Ghusson, Tucson, AZ (US); Kurt Reinhardt, Tucson, AZ (US)

(73) Assignee: Accelerate Diagnostics, Inc., Tucson, AZ (US)

( * ) Notice: Subject to any disclaimer, the term of this patent is extended or adjusted under 35 U.S.C. 154(b) by 39 days.

(21) Appl. No.: 15/283,922

(22) Filed: Oct. 3, 2016

(65) Prior Publication Data
US 2017/0023599 A1 Jan. 26, 2017

Related U.S. Application Data

(63) Continuation-in-part of application No. 15/085,953, filed on Mar. 30, 2016, now Pat. No. 10,023,895.

(60) Provisional application No. 62/268,340, filed on Dec. 16, 2015, provisional application No. 62/260,085, filed on Nov. 25, 2015, provisional application No. 62/194,142, filed on Jul. 17, 2015, provisional application No. 62/152,773, filed on Apr. 24, 2015, provisional application No. 62/140,300, filed on Mar. 30, 2015.

(51) Int. Cl.
| | | |
|---|---|---|
| C12Q 1/6841 | (2018.01) | |
| C12Q 1/02 | (2006.01) | |
| G02B 7/28 | (2006.01) | |
| G01N 21/64 | (2006.01) | |
| G01N 35/02 | (2006.01) | |
| H04N 5/232 | (2006.01) | |
| G01N 35/00 | (2006.01) | |
| C12M 1/34 | (2006.01) | |
| G01N 35/10 | (2006.01) | |
| B01L 3/00 | (2006.01) | |

(52) U.S. Cl.
CPC .......... *C12Q 1/6841* (2013.01); *C12Q 1/025* (2013.01); *G01N 21/6458* (2013.01); *G01N 35/00069* (2013.01); *G01N 35/025* (2013.01); *G02B 7/28* (2013.01); *H04N 5/23212* (2013.01); *B01L 3/545* (2013.01); *C12M 41/36* (2013.01); *G01N 35/1002* (2013.01); *G01N 2021/6419* (2013.01); *G01N 2035/00158* (2013.01); *G01N 2035/00346* (2013.01); *G01N 2035/1032* (2013.01)

(58) Field of Classification Search
CPC ..... C12Q 1/025; C12Q 1/6841; G01N 35/025
See application file for complete search history.

(56) References Cited

U.S. PATENT DOCUMENTS

| | | |
|---|---|---|
| 2,666,355 A | 1/1954 | Trurnit |
| 3,493,772 A | 2/1970 | Daughters, II et al. |
| 3,532,790 A | 10/1970 | Greenberg et al. |

(Continued)

FOREIGN PATENT DOCUMENTS

| | | |
|---|---|---|
| AU | 772760 | 5/2004 |
| EP | 0498920 | 8/1992 |

(Continued)

OTHER PUBLICATIONS

Bloem et al., "Fully Automatic Determination of Soil Bacterium Numbers, Cell Volumes, and Frequencies of Dividing Cells by Confocal Laser Scanning Microscopy and Image Analysis," *Appl Environ Microbiol.* 61:926-936, 1995.

(Continued)

*Primary Examiner* — Narayan K Bhat
(74) *Attorney, Agent, or Firm* — Klarquist Sparkman, LLP

(57) ABSTRACT

A system for automated microorganism identification and antibiotic susceptibility testing comprising a reagent cartridge, a reagent stage, a cassette, a cassette, stage, a pipettor assembly, an optical detection system, and a controller is disclosed. The system is designed to dynamically adjust motor idle torque to control heat load and employs a fast focus process for determining the true focus position of an individual microorganism. The system also may quantify the relative abundance of viable microorganisms in a sample using dynamic dilution, and facilitate growth of microorganisms in customized media for rapid, accurate antimicrobial susceptibility testing. Automated quality control test components and methods of their use are also disclosed.

22 Claims, 99 Drawing Sheets

Specification includes a Sequence Listing.

(56) References Cited

U.S. PATENT DOCUMENTS

| | | | |
|---|---|---|---|
| 3,637,313 A | 1/1972 | Upatnieks |
| 3,792,081 A | 2/1974 | Higuchi et al. |
| 3,811,036 A | 5/1974 | Perry |
| 3,832,532 A | 8/1974 | Praglin et al. |
| 3,854,480 A | 12/1974 | Zaffaroni |
| 3,904,293 A | 9/1975 | Gee |
| 3,926,564 A | 12/1975 | Giaever |
| 3,935,073 A | 1/1976 | Waters |
| 3,938,515 A | 2/1976 | Leeper et al. |
| 3,957,362 A | 5/1976 | Mancini et al. |
| 3,961,628 A | 6/1976 | Arnold |
| 4,069,307 A | 1/1978 | Higuchi et al. |
| 4,070,248 A | 1/1978 | Schmidt |
| 4,076,591 A | 2/1978 | Heden |
| 4,136,250 A | 1/1979 | Mueller et al. |
| 4,199,449 A | 4/1980 | Slejko |
| 4,199,499 A | 4/1980 | Smithwick, Jr. et al. |
| 4,200,493 A | 4/1980 | Wilkins et al. |
| 4,220,152 A | 9/1980 | Dresback |
| 4,224,439 A | 9/1980 | Ayers et al. |
| 4,233,847 A | 11/1980 | Walker |
| 4,246,343 A | 1/1981 | Wilkins et al. |
| 4,259,442 A | 3/1981 | Gayral |
| 4,282,287 A | 8/1981 | Giese |
| 4,288,543 A | 9/1981 | Sielaff et al. |
| 4,313,734 A | 2/1982 | Leuvering |
| 4,325,910 A | 4/1982 | Jordan |
| 4,330,440 A | 5/1982 | Ayers et al. |
| 4,332,476 A | 6/1982 | Stenberg et al. |
| 4,351,337 A | 9/1982 | Sidman |
| 4,357,142 A | 11/1982 | Schall, Jr. et al. |
| 4,363,634 A | 12/1982 | Schall, Jr. |
| 4,383,757 A | 5/1983 | Phillips |
| 4,390,343 A | 6/1983 | Walter |
| 4,423,099 A | 12/1983 | Mueller et al. |
| 4,450,150 A | 5/1984 | Sidman |
| RE31,712 E | 10/1984 | Giese |
| 4,478,822 A | 10/1984 | Haslam et al. |
| 4,478,914 A | 10/1984 | Giese |
| 4,481,137 A | 11/1984 | Ohnishi et al. |
| 4,487,839 A | 12/1984 | Kamentsky |
| 4,500,778 A | 2/1985 | Kusaka et al. |
| 4,508,832 A | 4/1985 | Carter et al. |
| 4,509,841 A | 4/1985 | Sakai et al. |
| 4,521,522 A | 6/1985 | Lundstrom et al. |
| 4,537,861 A | 8/1985 | Elings et al. |
| 4,540,881 A | 9/1985 | Hayashi et al. |
| 4,548,990 A | 10/1985 | Mueller et al. |
| 4,558,012 A | 12/1985 | Nygren et al. |
| 4,588,624 A | 5/1986 | Nygren et al. |
| 4,613,567 A | 9/1986 | Yasoshima et al. |
| 4,626,674 A | 12/1986 | Oinoue |
| 4,643,968 A | 2/1987 | Weaver |
| 4,655,595 A | 4/1987 | Bjork et al. |
| 4,657,543 A | 4/1987 | Langer et al. |
| 4,661,913 A | 4/1987 | Wu et al. |
| 4,663,296 A | 5/1987 | Revillet et al. |
| 4,693,884 A | 9/1987 | Kleiner et al. |
| 4,693,972 A | 9/1987 | Mansour et al. |
| 4,713,441 A | 12/1987 | Heller et al. |
| 4,716,123 A | 12/1987 | Wood |
| 4,752,567 A | 6/1988 | De Brabander et al. |
| 4,764,342 A | 8/1988 | Kelln et al. |
| 4,772,484 A | 9/1988 | Kitchell et al. |
| 4,778,758 A | 10/1988 | Ericsson et al. |
| 4,805,623 A | 2/1989 | Jobsis |
| 4,814,144 A | 3/1989 | Edelmann et al. |
| 4,857,313 A | 8/1989 | Song et al. |
| 4,876,208 A | 10/1989 | Gustafson et al. |
| 4,877,659 A | 10/1989 | Vince |
| 4,882,168 A | 11/1989 | Casey et al. |
| 4,885,077 A | 12/1989 | Karakelle et al. |
| 4,933,147 A | 6/1990 | Hollar et al. |
| 4,959,301 A | 9/1990 | Weaver et al. |
| 5,002,792 A | 3/1991 | Vegoe |
| RE33,581 E | 4/1991 | Nicoli et al. |
| 5,017,009 A | 5/1991 | Schutt et al. |
| 5,066,465 A | 11/1991 | Kano et al. |
| 5,079,144 A | 1/1992 | Carr et al. |
| 5,079,172 A | 1/1992 | Hari et al. |
| 5,082,630 A | 1/1992 | Partin et al. |
| 5,089,606 A | 2/1992 | Cole et al. |
| 5,149,543 A | 9/1992 | Cohen et al. |
| 5,173,164 A | 12/1992 | Egen et al. |
| 5,196,527 A | 3/1993 | Ookuma et al. |
| 5,208,037 A | 5/1993 | Wright et al. |
| 5,218,039 A | 6/1993 | Stoy et al. |
| 5,239,170 A | 8/1993 | Hughlett |
| 5,240,618 A | 8/1993 | Caldwell et al. |
| 5,288,611 A | 2/1994 | Kohne |
| 5,314,805 A | 5/1994 | Haugland et al. |
| 5,329,461 A | 7/1994 | Allen et al. |
| 5,350,697 A | 9/1994 | Swope et al. |
| 5,405,783 A | 4/1995 | Pirrung et al. |
| 5,466,416 A | 11/1995 | Ghaed et al. |
| 5,468,606 A | 11/1995 | Bogart et al. |
| 5,488,567 A | 1/1996 | Allen et al. |
| 5,491,097 A | 2/1996 | Ribi et al. |
| 5,494,829 A | 2/1996 | Sandstrom et al. |
| 5,496,701 A | 3/1996 | Pollard-Knight |
| 5,556,764 A | 9/1996 | Sizto et al. |
| 5,578,460 A | 11/1996 | Ebersole et al. |
| 5,599,668 A | 2/1997 | Stimpson et al. |
| 5,604,099 A | 2/1997 | Erlich et al. |
| 5,622,868 A | 4/1997 | Clarke et al. |
| 5,623,707 A | 4/1997 | Kusaka |
| 5,648,652 A | 7/1997 | Sekiya et al. |
| 5,656,432 A | 8/1997 | Claverys et al. |
| 5,789,173 A * | 8/1998 | Peck ................ C12Q 1/689 |
| | | 356/442 |
| 5,792,622 A | 8/1998 | Botsford |
| 5,824,494 A | 10/1998 | Feldberg |
| 5,828,716 A | 10/1998 | Bisconte de Saint Julien |
| 5,843,651 A | 12/1998 | Stimpson et al. |
| 5,849,486 A | 12/1998 | Heller et al. |
| 5,863,754 A | 1/1999 | Bajard |
| 5,866,345 A | 2/1999 | Wilding et al. |
| 5,872,013 A | 2/1999 | Leunissen et al. |
| 5,888,760 A | 3/1999 | Godsey et al. |
| 5,922,593 A | 7/1999 | Livingston |
| 5,939,291 A | 8/1999 | Loewy et al. |
| 5,958,704 A | 9/1999 | Starzl et al. |
| 5,976,821 A | 11/1999 | Huston et al. |
| 5,981,268 A | 11/1999 | Kovacs et al. |
| 5,993,634 A | 11/1999 | Simpson et al. |
| 6,017,696 A | 1/2000 | Heller |
| 6,043,048 A | 3/2000 | Johnston et al. |
| 6,051,380 A | 4/2000 | Sosnowski et al. |
| 6,054,270 A | 4/2000 | Southern |
| 6,086,824 A | 7/2000 | Fanning et al. |
| 6,096,272 A * | 8/2000 | Clark ................ G01N 21/253 |
| | | 422/64 |
| 6,099,803 A | 8/2000 | Ackley et al. |
| 6,101,946 A | 8/2000 | Martinsky |
| 6,103,479 A | 8/2000 | Taylor |
| 6,107,054 A | 8/2000 | Gibbs |
| 6,122,599 A | 9/2000 | Mehta |
| 6,136,171 A | 10/2000 | Frazier et al. |
| 6,143,247 A | 11/2000 | Sheppard, Jr. et al. |
| 6,153,400 A | 11/2000 | Matsumura et al. |
| 6,153,416 A | 11/2000 | Yuan |
| 6,169,394 B1 | 1/2001 | Frazier et al. |
| 6,176,620 B1 | 1/2001 | Obara |
| 6,214,560 B1 | 4/2001 | Yguerabide et al. |
| 6,221,592 B1 | 4/2001 | Schwartz et al. |
| 6,241,894 B1 | 6/2001 | Briggs et al. |
| 6,242,188 B1 | 6/2001 | Dattagupta et al. |
| 6,245,508 B1 | 6/2001 | Heller et al. |
| 6,251,615 B1 | 6/2001 | Oberhardt |
| 6,251,616 B1 | 6/2001 | Barbera-Guillem et al. |
| 6,251,624 B1 | 6/2001 | Matsumura et al. |
| 6,264,825 B1 | 7/2001 | Blackburn et al. |
| 6,270,953 B1 | 8/2001 | Malcus-Vocanson et al. |
| 6,274,384 B1 | 8/2001 | Starzl et al. |

(56) References Cited

U.S. PATENT DOCUMENTS

| | | | |
|---|---|---|---|
| 6,290,839 B1 | 9/2001 | Kayyem et al. |
| 6,372,895 B1 | 4/2002 | Bentsen et al. |
| 6,379,897 B1 | 4/2002 | Weidenhammer et al. |
| 6,391,264 B2 | 5/2002 | Hammer et al. |
| 6,391,546 B1 | 5/2002 | Karube et al. |
| 6,391,577 B1 | 5/2002 | Mikkelsen et al. |
| 6,391,937 B1 | 5/2002 | Beuhler et al. |
| 6,395,506 B1 | 5/2002 | Pitner et al. |
| 6,403,367 B1 | 6/2002 | Cheng et al. |
| 6,416,969 B2 | 7/2002 | Matsumura et al. |
| 6,432,694 B1 | 8/2002 | Malmqvist |
| 6,437,551 B1 | 8/2002 | Krulevitch et al. |
| 6,472,166 B1 | 10/2002 | Wardlaw et al. |
| 6,472,228 B2 | 10/2002 | Wang et al. |
| 6,548,263 B1 | 4/2003 | Kapur et al. |
| 6,551,841 B1 | 4/2003 | Wilding et al. |
| 6,565,727 B1 | 5/2003 | Shenderov |
| 6,573,088 B2 | 6/2003 | Gemmell et al. |
| 6,596,532 B1 | 7/2003 | Hyman et al. |
| 6,605,453 B2 | 8/2003 | Ozkan et al. |
| 6,607,888 B2 | 8/2003 | Schwartz et al. |
| 6,611,765 B2 | 8/2003 | Boeufgras et al. |
| 6,642,682 B1 | 11/2003 | Perkins et al. |
| 6,696,286 B1 | 2/2004 | Halverson et al. |
| 6,703,819 B2 | 3/2004 | Gascoyne |
| 6,716,620 B2 | 4/2004 | Bashir et al. |
| 6,809,862 B2 | 10/2004 | Behnsen et al. |
| 6,841,379 B2 | 1/2005 | Matson |
| 6,844,028 B2 | 1/2005 | Mao et al. |
| 6,872,545 B2 | 3/2005 | Griner et al. |
| 6,900,030 B2 | 5/2005 | Pitner et al. |
| 6,951,714 B2 | 10/2005 | Giovannoni et al. |
| 7,067,194 B2 | 6/2006 | Mao et al. |
| 7,108,775 B2 | 9/2006 | Bahatt et al. |
| 7,115,384 B2 | 10/2006 | Clark et al. |
| 7,123,345 B2 | 10/2006 | Sugihara et al. |
| 7,214,299 B2 | 5/2007 | Armstrong |
| 7,250,775 B1 | 7/2007 | Collins et al. |
| 7,258,837 B2 | 8/2007 | Yager et al. |
| 7,306,924 B2 | 12/2007 | Gomez et al. |
| 7,341,841 B2 | 3/2008 | Metzger et al. |
| 7,348,183 B2 | 3/2008 | Fritsch et al. |
| 7,397,540 B2 | 7/2008 | Lundgren et al. |
| 7,413,891 B2 | 8/2008 | Bashir et al. |
| 7,429,355 B2 | 9/2008 | Bishop et al. |
| 7,435,579 B2 | 10/2008 | Bashir et al. |
| 7,451,646 B2 | 11/2008 | Cleland et al. |
| 7,481,977 B2 | 1/2009 | Percival et al. |
| 7,510,637 B2 | 3/2009 | Barlow et al. |
| 7,561,789 B2 | 7/2009 | Border et al. |
| 7,564,245 B2 | 7/2009 | Lee |
| 7,576,307 B2 | 8/2009 | Yazdanfar et al. |
| 7,601,300 B2 | 10/2009 | Blanton et al. |
| 7,622,078 B2 | 11/2009 | Pagés Pinyol |
| 7,629,029 B2 | 12/2009 | Mao et al. |
| 7,642,068 B2 | 1/2010 | Steiner et al. |
| 7,651,837 B2 | 1/2010 | Ohno et al. |
| 7,670,793 B2 | 3/2010 | Glencross |
| 7,678,256 B2 | 3/2010 | Davalos et al. |
| 7,687,239 B2 | 3/2010 | Goldberg et al. |
| 7,689,022 B2 | 3/2010 | Weiner et al. |
| 7,723,095 B2 | 5/2010 | Cleuziat et al. |
| 7,754,148 B2 | 7/2010 | Yu et al. |
| 7,829,275 B2 | 11/2010 | Franzen et al. |
| 7,842,504 B2 | 11/2010 | Devlin, Sr. |
| 7,873,268 B2 | 1/2011 | Segawa et al. |
| 7,901,624 B2 * | 3/2011 | Hansen ............... G01N 1/38 422/63 |
| 7,910,062 B2 | 3/2011 | Yu et al. |
| 7,955,555 B2 | 6/2011 | Blecka et al. |
| 8,014,583 B2 | 9/2011 | Zahniser |
| 8,029,746 B2 | 10/2011 | Yu et al. |
| 8,058,078 B2 | 11/2011 | Hansen et al. |
| 8,071,319 B2 | 12/2011 | Metzger et al. |
| 8,102,276 B2 | 1/2012 | Sugiura |
| 8,168,443 B2 | 5/2012 | Yu et al. |
| 8,178,602 B2 | 5/2012 | Mao et al. |
| 8,188,438 B2 | 5/2012 | Li |
| 8,304,245 B2 | 11/2012 | Kuypers et al. |
| 8,323,466 B2 | 12/2012 | Kim et al. |
| 8,329,437 B1 | 12/2012 | Ayliffe |
| 8,335,393 B2 | 12/2012 | Kotani |
| 8,354,307 B2 | 1/2013 | Lee |
| 8,361,298 B2 | 1/2013 | Sabin et al. |
| 8,361,299 B2 | 1/2013 | Sabin et al. |
| 8,364,409 B2 | 1/2013 | Rieder et al. |
| 8,368,964 B2 | 2/2013 | Xu et al. |
| 8,372,353 B2 | 2/2013 | Lee et al. |
| 8,372,600 B2 | 2/2013 | Sachs et al. |
| 8,391,582 B2 | 3/2013 | Weiner et al. |
| 8,421,484 B2 | 4/2013 | Prodan et al. |
| 8,460,887 B2 | 6/2013 | Goldberg et al. |
| 8,478,445 B2 | 7/2013 | Hansen et al. |
| 8,481,281 B2 | 7/2013 | Demirev et al. |
| 8,508,652 B2 | 8/2013 | Albu et al. |
| 8,512,636 B2 | 8/2013 | Blanton et al. |
| 8,513,001 B2 | 8/2013 | Weiss et al. |
| 8,563,298 B2 | 10/2013 | Lowery, Jr. et al. |
| 8,603,769 B2 | 12/2013 | Feng et al. |
| 8,614,056 B2 | 12/2013 | Davis et al. |
| 8,635,028 B2 | 1/2014 | Sengupta et al. |
| 8,647,835 B2 | 2/2014 | Walsh et al. |
| 8,652,800 B2 | 2/2014 | Walsh et al. |
| 8,703,061 B2 | 4/2014 | Guzman |
| 8,709,344 B2 | 4/2014 | Bishop et al. |
| 8,765,062 B2 | 7/2014 | Linder et al. |
| 8,779,779 B2 | 7/2014 | Wang et al. |
| 8,780,181 B2 | 7/2014 | Olesen et al. |
| 8,804,105 B2 | 8/2014 | Ayliffe |
| 8,821,814 B2 | 9/2014 | Cho et al. |
| 8,828,680 B2 | 9/2014 | Williams et al. |
| 8,841,118 B2 | 9/2014 | Robinson et al. |
| 8,895,255 B1 | 11/2014 | Goldberg et al. |
| 8,911,987 B2 | 12/2014 | Robinson et al. |
| 8,932,523 B2 | 1/2015 | Linder et al. |
| 8,943,588 B1 | 1/2015 | Speegle et al. |
| 8,969,072 B2 | 3/2015 | Robinson et al. |
| 8,970,826 B2 | 3/2015 | Liu et al. |
| 9,007,233 B2 | 4/2015 | Sugiura |
| 9,048,771 B2 | 6/2015 | Ohba et al. |
| 9,057,714 B2 | 6/2015 | Gomm et al. |
| 9,090,462 B2 | 7/2015 | Straus |
| 9,133,498 B2 | 9/2015 | Kwon et al. |
| 9,150,900 B2 | 10/2015 | Bishop et al. |
| 9,213,043 B2 | 12/2015 | Cook et al. |
| 9,248,422 B2 | 2/2016 | Ching et al. |
| 9,274,132 B2 | 3/2016 | Wilson et al. |
| 9,290,382 B2 | 3/2016 | Straus |
| 9,353,396 B2 | 5/2016 | Demirev et al. |
| 9,405,288 B2 | 8/2016 | Ogata |
| 9,434,937 B2 | 9/2016 | Metzger et al. |
| 9,567,621 B2 | 2/2017 | Robinson et al. |
| 9,657,327 B2 | 5/2017 | Metzger et al. |
| 9,677,109 B2 | 6/2017 | Shamsheyeva et al. |
| 9,714,420 B2 | 7/2017 | Metzger et al. |
| 9,841,422 B2 | 12/2017 | Goldberg et al. |
| 2001/0009774 A1 | 7/2001 | Shin et al. |
| 2001/0053535 A1 | 12/2001 | Bashir et al. |
| 2002/0028489 A1 | 3/2002 | Ammann et al. |
| 2002/0028519 A1 | 3/2002 | Yguerabide et al. |
| 2002/0031795 A1 | 3/2002 | James et al. |
| 2002/0119455 A1 | 8/2002 | Chan |
| 2002/0127144 A1 | 9/2002 | Mehta |
| 2002/0148729 A1 | 10/2002 | Armstrong |
| 2002/0155490 A1 | 10/2002 | Skinner et al. |
| 2002/0155591 A1 | 10/2002 | Farina et al. |
| 2002/0164677 A1 | 11/2002 | Giovannoni et al. |
| 2002/0197709 A1 | 12/2002 | Van der Weide et al. |
| 2003/0023149 A1 | 1/2003 | Montemagno et al. |
| 2003/0032171 A1 * | 2/2003 | Gemmell ............ G01N 35/0092 435/286.2 |
| 2003/0032173 A1 | 2/2003 | Farina et al. |
| 2003/0036054 A1 | 2/2003 | Ladisch et al. |
| 2003/0119028 A1 | 6/2003 | Graves et al. |

(56) References Cited

U.S. PATENT DOCUMENTS

| | | |
|---|---|---|
| 2003/0124623 A1 | 7/2003 | Yager et al. |
| 2003/0134269 A1 | 7/2003 | Hirai et al. |
| 2003/0147132 A1 | 8/2003 | Behnsen et al. |
| 2003/0153023 A1 | 8/2003 | Starzl et al. |
| 2003/0157587 A1 | 8/2003 | Gomez et al. |
| 2003/0170613 A1 | 9/2003 | Straus |
| 2003/0186341 A1 | 10/2003 | Kuhn et al. |
| 2003/0211566 A1 | 11/2003 | Gazenko |
| 2003/0224436 A1 | 12/2003 | Nelson et al. |
| 2004/0052426 A1 | 3/2004 | Landesman |
| 2004/0089546 A1 | 5/2004 | Bahatt et al. |
| 2004/0168916 A1 | 9/2004 | Fuchs et al. |
| 2004/0189311 A1 | 9/2004 | Glezer et al. |
| 2005/0048599 A1 | 3/2005 | Goldberg et al. |
| 2005/0059105 A1 | 3/2005 | Alocilja et al. |
| 2005/0112544 A1 | 5/2005 | Xu et al. |
| 2005/0114041 A1 | 5/2005 | Gawad et al. |
| 2005/0118705 A1 | 6/2005 | Rabbitt et al. |
| 2005/0121596 A1 | 6/2005 | Kam et al. |
| 2005/0202523 A1 | 9/2005 | Shaw et al. |
| 2005/0208592 A1 | 9/2005 | Caron et al. |
| 2005/0213374 A1 | 9/2005 | Xu et al. |
| 2005/0221403 A1 | 10/2005 | Gazenko |
| 2005/0238652 A1 | 10/2005 | Tsuji et al. |
| 2005/0255445 A1 | 11/2005 | Van Damme et al. |
| 2005/0287572 A1 | 12/2005 | Mathies et al. |
| 2006/0120916 A1 | 6/2006 | Kolari et al. |
| 2006/0141618 A1 | 6/2006 | Yasuda et al. |
| 2006/0166184 A1 | 7/2006 | Yasuda et al. |
| 2006/0194307 A1 | 8/2006 | Yasuda et al. |
| 2006/0243594 A1 | 11/2006 | Schnelle et al. |
| 2007/0037225 A1 | 2/2007 | Metzger et al. |
| 2007/0202538 A1 | 8/2007 | Glezer et al. |
| 2007/0238146 A1 | 10/2007 | Tyler et al. |
| 2007/0298513 A1 | 12/2007 | Starzl et al. |
| 2008/0014181 A1 | 1/2008 | Ariff et al. |
| 2008/0046286 A1 | 2/2008 | Halsted |
| 2008/0072664 A1 | 3/2008 | Hansen et al. |
| 2008/0138799 A1 | 6/2008 | Cheng et al. |
| 2008/0193965 A1 | 8/2008 | Zeng et al. |
| 2008/0221805 A1 | 9/2008 | Andrews |
| 2008/0241858 A1 | 10/2008 | Metzger et al. |
| 2009/0012723 A1 | 1/2009 | Treado et al. |
| 2009/0051372 A1 | 2/2009 | Sethu et al. |
| 2009/0104689 A1 | 4/2009 | Kim et al. |
| 2009/0203063 A1 | 8/2009 | Wheeler et al. |
| 2009/0208072 A1 | 8/2009 | Seibel et al. |
| 2010/0048428 A1 | 2/2010 | Coyer et al. |
| 2010/0075340 A1 | 3/2010 | Javanmard |
| 2010/0099139 A1 | 4/2010 | Ben-David et al. |
| 2010/0120016 A1 | 5/2010 | Li et al. |
| 2010/0129858 A1 | 5/2010 | Walsh et al. |
| 2010/0248281 A1 | 9/2010 | Straus |
| 2010/0267165 A1 | 10/2010 | Bruls et al. |
| 2011/0023690 A1 | 2/2011 | Wilson |
| 2011/0042582 A1* | 2/2011 | Ingber ............... G01N 21/0303 250/458.1 |
| 2011/0117577 A1 | 5/2011 | Reboud et al. |
| 2011/0136165 A1 | 6/2011 | Vojnovic et al. |
| 2011/0183856 A1 | 7/2011 | Agan et al. |
| 2011/0237446 A1 | 9/2011 | Treado et al. |
| 2011/0242308 A1 | 10/2011 | Igarashi et al. |
| 2011/0256617 A1 | 10/2011 | Cocchi et al. |
| 2012/0028342 A1 | 2/2012 | Ismagilov et al. |
| 2012/0077206 A1 | 3/2012 | Metzger et al. |
| 2012/0103817 A1 | 5/2012 | Omori et al. |
| 2012/0105837 A1 | 5/2012 | Ingber |
| 2012/0142032 A1 | 6/2012 | Morgan |
| 2012/0149584 A1 | 6/2012 | Olle |
| 2012/0169863 A1 | 7/2012 | Bachelet et al. |
| 2012/0223217 A1 | 9/2012 | Zheng et al. |
| 2012/0244519 A1 | 9/2012 | Olesen et al. |
| 2012/0258874 A1 | 10/2012 | Narain et al. |
| 2013/0017534 A1 | 1/2013 | Nickel et al. |
| 2013/0045878 A1 | 2/2013 | McCue |
| 2013/0089886 A1 | 4/2013 | Feng et al. |
| 2013/0115607 A1 | 5/2013 | Nielsen et al. |
| 2013/0183694 A1 | 7/2013 | Janetzko et al. |
| 2013/0217063 A1 | 8/2013 | Metzger et al. |
| 2013/0271060 A1 | 10/2013 | Messersmith et al. |
| 2013/0295588 A1 | 11/2013 | Watkins et al. |
| 2013/0295597 A1 | 11/2013 | DeWitte et al. |
| 2013/0324437 A1 | 12/2013 | Pogliano et al. |
| 2013/0345525 A1 | 12/2013 | Kline |
| 2014/0038171 A1 | 2/2014 | Metzger et al. |
| 2014/0179726 A1 | 6/2014 | Bajaj et al. |
| 2014/0199719 A1 | 7/2014 | Shih et al. |
| 2014/0234949 A1 | 8/2014 | Wasson et al. |
| 2014/0278136 A1 | 9/2014 | Shamsheyeva et al. |
| 2014/0278143 A1 | 9/2014 | Garstecki et al. |
| 2014/0323340 A1 | 10/2014 | Goldberg et al. |
| 2014/0343868 A1 | 11/2014 | Colwell et al. |
| 2015/0168290 A1 | 6/2015 | Shachaf |
| 2015/0225762 A1 | 8/2015 | Metzger et al. |
| 2015/0293270 A1 | 10/2015 | Jarvius et al. |
| 2015/0301002 A1 | 10/2015 | DeWitte et al. |
| 2015/0337351 A1 | 11/2015 | Metzger |
| 2016/0010138 A1 | 1/2016 | Shamsheyeva et al. |
| 2016/0051985 A1 | 2/2016 | Knight et al. |
| 2016/0238826 A1 | 8/2016 | Shields et al. |
| 2016/0279633 A1 | 9/2016 | Bachelet et al. |
| 2016/0289729 A1 | 10/2016 | Richards et al. |
| 2016/0348091 A1 | 12/2016 | Metzger et al. |
| 2017/0029864 A1 | 2/2017 | Straus |
| 2017/0218426 A1 | 8/2017 | Shamsheyeva et al. |
| 2017/0234781 A1 | 8/2017 | Prisbrey et al. |
| 2018/0080932 A1 | 3/2018 | Goldberg et al. |
| 2018/0135093 A1 | 5/2018 | Ashby et al. |

FOREIGN PATENT DOCUMENTS

| | | |
|---|---|---|
| EP | 1648286 | 4/2006 |
| EP | 2 645 108 A1 | 10/2013 |
| EP | 2 987 851 A1 | 2/2016 |
| EP | 2507663 B1 | 2/2017 |
| GB | 1520733 | 8/1978 |
| JP | 52102491 | 8/1977 |
| JP | 58198759 | 11/1983 |
| JP | H11505405 | 5/1999 |
| JP | 2001509008 | 7/2001 |
| JP | 2002500892 | 1/2002 |
| JP | 2002502597 | 1/2002 |
| JP | 2002330799 | 11/2002 |
| JP | 2003527601 | 9/2003 |
| JP | 200481019 | 3/2004 |
| JP | 2004513628 | 5/2004 |
| WO | WO 1989001162 | 2/1989 |
| WO | WO 8910566 A1 | 11/1989 |
| WO | WO 1990011525 | 10/1990 |
| WO | WO 1991004491 | 4/1991 |
| WO | WO 1993013197 | 7/1993 |
| WO | WO 1994002831 | 2/1994 |
| WO | WO 1994011728 | 5/1994 |
| WO | WO 1995008640 | 3/1995 |
| WO | WO 1995028641 | 10/1995 |
| WO | WO 1996014431 | 5/1996 |
| WO | WO 1998022618 | 5/1998 |
| WO | WO 1998022808 | 5/1998 |
| WO | WO 1998040741 | 9/1998 |
| WO | WO 1999020789 | 4/1999 |
| WO | WO 1999037799 | 7/1999 |
| WO | WO 1999040174 | 8/1999 |
| WO | WO 1999058948 | 11/1999 |
| WO | WO 2000024941 | 5/2000 |
| WO | WO 2001031332 | 5/2001 |
| WO | WO 2001069230 | 9/2001 |
| WO | WO 2001079529 A1 | 10/2001 |
| WO | WO 2002038724 | 5/2002 |
| WO | WO 2002088299 | 11/2002 |
| WO | WO 2003012525 A1 | 2/2003 |
| WO | WO 2003022999 | 3/2003 |
| WO | WO 2003025208 | 3/2003 |
| WO | WO 2003048736 | 6/2003 |
| WO | WO 2003065009 | 8/2003 |

(56) References Cited

FOREIGN PATENT DOCUMENTS

| WO | WO 2003073100 | | 9/2003 |
|---|---|---|---|
| WO | WO 2005027714 | | 3/2005 |
| WO | WO 2006015374 | | 2/2006 |
| WO | WO 2006028601 | A2 | 3/2006 |
| WO | WO 2006066216 | | 6/2006 |
| WO | WO 2006113930 | A2 | 10/2006 |
| WO | WO 2006135904 | | 12/2006 |
| WO | WO 2009124068 | | 10/2009 |
| WO | WO 2010062350 | | 6/2010 |
| WO | WO 2010062352 | | 6/2010 |
| WO | WO 2011/035304 | A2 | 3/2011 |
| WO | WO 2012122314 | | 9/2012 |
| WO | WO 2012162133 | | 11/2012 |
| WO | WO 2013072069 | A1 | 5/2013 |
| WO | WO 2013/130875 | A1 | 9/2013 |
| WO | WO 2013/177277 | A1 | 11/2013 |
| WO | WO 2014040088 | | 3/2014 |
| WO | WO 2014100456 | | 6/2014 |
| WO | WO 2014145899 | | 9/2014 |
| WO | WO 2014153194 | | 9/2014 |
| WO | WO 2014169921 | A1 | 10/2014 |
| WO | WO 2016/037051 | A1 | 3/2016 |
| WO | WO2016207065 | A1 | 12/2016 |

OTHER PUBLICATIONS

EP 16200084.8 Extended European Search Report dated Aug. 1, 2017 (17 pages).
Bello, M., "Electrolytic modification of a buffer during a capillary electrophoresis run," *J Chromatogr*. 744:81-91, 1996.
Jiang et al., "Human Adenoviruses and Coliphages in Urban Runoff-Impacted Coastal Waters of Southern California," *App Environ Micriobiol*. 67:179-184, 2001.
Alban et al., "A novel experimental design for comparative two-dimensional gel analysis: Two-dimensional difference gel electrophoresis incorporating a pooled internal standard," *Proteomics* 3:36-44, 2003.
Inoue et al., "On-chip culture system for observation of isolated individual cells," *Lab on a Chip* 1:50-55, 2001.
Rodrigues and Kroll, "Rapid selective enumeration of bacteria in foods using a microcolony epifluorescence microscopy technique," *J Appl Bacteriol*. 64:65-78, 1988.
Zhu et al., "Filter-based microfluidic device as a platform for immunofluorescent assay of microbial cells," *Lab Chip* 4:337-341, 2004.
EP 16192372.7 Extended European Search Report and Written Opinion dated Feb. 28, 2018 (11 pages).
Unknown, "Bacterial Counts—Quantitative Analysis of Microbes," Biology 251 General Microbiology Lab, July 30, 2013, pp. 1-5, retrieved from internet: URL:http://biolabs.tmc.edu/Micro%20Web/BacterialCounts.pdf [retrieved on Oct. 21, 2016].
EP 14762411.8 Extended European Search Report dated Nov. 7, 2016 (11 pages).
PCT/US2016/025075, International Search Report and Written Opinion dated Nov. 15, 2016 (36 pages).
Pagola et al., "The structure of malaria pigment b-haematin," *Nature* 404:307-310, 2000.
Palarasah er al., "Sodium Polyanethole Sulfonate as an Inhibitor of Activation of Complement Function in Blood Culture Systems," *J Clin Microbiol*. 48:908-914, 2010.
EP 13835702.5 Office Action dated Oct. 16, 2017 (9 pages).
Olsvik et al., "Magnetic Separation Techniques in Diagnostic Microbiology", *Clin Microbiol Rev*. 7:43-54, 1994.
Levin-Reisman et al., "Automated Imagining With ScanLag Reveals Previously Undetectable Bacterial Growth Phenotypes," *Nature Methods* 7:737-739, 2010.
Tokuda et al. "Optical and Electric Multifunctional CMOS Image Sensors for On-Chip Biosensing Applications," *Materials* 4:84-102, 2011.
EP16200084.8 Partial European Search Report dated Mar. 1, 2017.

Accelerate Diagnostics: "Accelerate ID/AST," Vimeo, May 18, 2015, pp. 1-6, XP054976621, Retrieved from the Internet: URL:https://vimeo.com/128112270 [retrieved on Jun. 22, 2016].
Accelerate Diagnostics: "Fast Phenotypic Antibiotic Susceptibility Testing: Connie Price, M.D.," YouTube, Aug. 28, 2015, pp. 1-6, XP054976622, Retrieved from the Internet: URL:https://www.youtube.com/watch?v=ln1GW54atXE&index=3&list=PLsmqpsknnk2_ENp8Xd3BhK0vu9nfU0p6y [retrieved on Jun. 22, 2016].
Alere, Inc., "Adult Isolator Tube Solution Material Safety Data Sheet," (2010).
Aminian et al., "A Conformal Bayesian Network for Classification of Mycobacterium Tuberculosis Complex Lineages," BMC Bioinformatics, 11(Suppl 3): S4 (2010).
Anzaldi et al., "Overcoming the Heme Paradox: Heme Toxicity and Tolerance in Bacterial Pathogens," Infect. Immun. 78(12): 4977-4989 (2010).
Ateya et al., "Volume Cytometry: Microfluidic Sensor for High-Throughput Screening in Real Time," Analytical Chem., 77:1290-1294, (2005).
Atlas and Snyder, Handbook of Media for Clinical Microbiology, 2006. CRC press.
Bae et al., "Immunosensor for Detection of Yersinia Enterocolitica Based on Imaging Ellipsometry," Analytical Chem., 76:1799-1803, (2004).
Baker et al., "The Bactericidal Action of Synthetic Detergents," J Exp Med. 74:611 620, 1941.
Balaban et al., "Bacterial Persistence as a Phenotypic Switch," Science, 305, pp. 1622-1625, (2004).
Barton et al., "Measurement of Bacterial Growth Rates on Polymers," J. Biomed. Mater Res., 32, pp. 271-278, (1996).
Bayoudh et al., "Electrical Detection and Characterization of Bacterial Adhesion Using Electrochemical Impedance Spectroscopy-Based Flow Chamber," Colloids and Surfaces A: Physicochem. Eng. Aspects, 318:291-300, (2008).
Beaglehole, "Performance of a Microscopic Imaging Ellipsometer," Rev. Sci. Instrum., 59:12, pp. 2557-2559. (1988).
Belding et al., "Effect of Sodium Polyanetholesulfonate on Antimicrobial Systems in Blood," Appl. Microbiol. 24(5): 691-698 (1972).
Benecky et al., "Simultaneous Detection of Multiple Analytes Using Copalis Technology: A Reduction to Practice," Clin. Chem., 44:9, pp. 2052-2054, (1998).
Boehm et al., "On-Chip Microfluidic Biosensor for Bacterial Detection and Identification," Sensors and Actuators, 126:508-514, (2007).
Bridson, E.Y., and Gould, G.W., "Quantal Microbiology," Lett. Appl. Microbiology, 30:95-98, (2000).
Burnham C-1358: Poster—"Rapid Detection of Klebsiella pneumoniae Carbapenemase (KPC) Producing Isolates Using the BACcel™ Digital Microscopy System," Presented at ASM 2013 May 18, 2013, Denver, CO.
Burnham et al., "Rapid Ertapenem Susceptibility Testing and Klebsiella pneumoniae Carbapenemase (KPC) Phenotype Detection in Klebsiella pneumoniae Using Automated Microscopy of Immobilized Live Bacterial Cells," J Clin Microbiol, 52:982-986, 2014.
Cabrera et al., "Continuous Concentration of Bacteria in a Microfluidic Flow Cell Using Electrokinetic Techniques," Electrophoresis 22:355-362, 2001.
Chan et al., "Evaluation of Lysis Filtration as an Adjunct to Conventional Blood Culture," J. Clin. Pathol. 39: 89-92 (1986).
Cheung et al., "Microfluidic Impedance-Based Flow Cytometry," Cytometry A, 77A, pp. 648-666, (2010).
Choi et al., "Rapid antibiotic susceptibility testing by tracking single cell growth in a microfluidic agarose channel system," Lab Chip 13:280-287, 2013.
Cooper et al. D-4013: Poster—"Potential Impact of Rapid Phenotype Identification on Antimicrobial Prescribing," Presented at the 48th ICAAC and IDSA Oct. 28, 2008, Washington, DC.
Dai et al., "Electrokinetic Trapping and Concentration Enrichment of DNA in a Microfluidic Channel," J. Am. Chem. Soc., 125" 13026-13027, (2003).
Daims et al., "Quantification of Uncultured Microorganisms by Fluorescence Microscopy and Digital Image Analysis," Appl. Microbiol. Biotechnol., 75"237-248, (2007).

(56) References Cited

OTHER PUBLICATIONS

De Brabander et al., "Detection of Gold Probes With Video-Enhanced Contrast Microscopy: Nanovid Microscopy," Amer. J., Anat. 185:282-295, (1989).

Delehanty, J.B., and Ligler, F.S., "A Microarray Immunoassay for Simultaneous Detection of Proteins and Bacteria," Anal. Chem., 74:5681-5687, (2002).

Desai, M.J., and Armstrong, D.W., "Separation, Identification, and Characterization of Microorganisms by Capillary Electrophoresis," Microbiology and Molecular Biology Reviews, 67, pp. 38-51, (2003).

Dorn et al., "Blood Culture Technique Based on Centrifugation: Developmental Phase," J. Clin. Micro. 3(3): 251-257 (1976).

Douglas et al. Poster—"Rapid Microbiological Identification and Major Drug Resistance Phenotyping with Novel Multiplexed Automated Digital Microscopy (MADM) for Ventilator-Associated Pneumonia (VAP) Surveillance," Presented at ATS 2011 May 16, 2011, Denver, CO.

Douglas et al., Rapid Automated Microscopy for Microbiological Surveillance of Ventilator-associated Pneumonia, Am J Respir Crit Care Med. 191:566-573, 2015.

Dwek et al., "Synchronization of Cell Division in Microorganisms by Percoll Gradients," J. Bacteriol. 144(1):17-21 (1980).

Elfwing et al., "Observing Growth and Division of Large Numbers of Individual Bacteria by Image Analysis," Appl. Environ. Micro., 70, pp. 675-678, (2004).

Elghanian et al., "Selective Colorimetric Detection of Polynucleotides Based on the Distance-Dependent Optical Properties of Gold Nanoparticles," Science, 277, pp. 1078-1081, (1997).

Ertl et al., "Electrochemical Biosensor Array for the Identification of Microorganisms Based on Lectin-Lipopolysaccharide Recognition," Analytical Chem., 73: 4241-4248, (2001).

Ertl et al., "Rapid Identification of Viable *Escherichia coli* Subspecies with Electrochemical Screen-Printed Biosensor Array," Biosensors Bioelectronics, 18, pp. 907-916, (2003).

Eun et al., "Encapsulating Bacteria in Agarose Microparticles Using Microfluidics for High-Throughput Cell Analysis and Isolation," ACS Chem. Biol., 18:260-266, (2011).

Fesenko et al., "Biosensing and Monitoring of Cell Populations Using the Hydrogel Bacterial Microchip," Biosens Bioelectron. 20:1860-1865, 2005.

Forero et al., "Automatic Identification Techniques of Tuberculosis Bacteria," Proc. SPIE 5203, Applications of Digital Image Processing XXVI, (Tescher, A.G., Ed.) SPIE Proceedings, 5203:71-81, (2003).

Friedman et al., "Precise Temporal Modulation in the Response of the SOS DNA Repair Network in Individual Bacteria," PLoS Bio. 3:1261-1268, (2005).

Gadkari, "Optimal Hydrogels for Fast and Safe Delivery of Bioactive Compounds," A Thesis Submitted to the Faculty of Drexel University, (2007).

Gamage et al. 2556: Poster—"Rapid Detection of Clinically Important *Staphylococcus aureus* Resistance Phenotypes Directly from Positive Blood Cultures Using Automated Microscopy," Presented at ASM2014 May 20, 2014, Boston, MA.

Gao et al., "Epipolarization Microscopic lmmunogold Assay: A Combination of Immunogold Silver Staining, ELISA and Epipolarization Microscopy," Biotech. & Histochem., 70:211-216, (1995).

Gast, R.K. et al., "Detection of *Salmonella entertidis* in Incubated Pools of Egg Contents by Fluorescence Polarization and Lateral Flow Immunodiffusion," Poultry Science, 82:687-690, (2003).

Gawad et al., "Micromachined Impedance Spectroscopy Flow Cytometer for Cell Analysis and Particle Sizing," Lab on a Chip, 1, pp. 76-82, (2001).

Geerts et al., "Nanovid Microscopy," Nature, 1991, 351:765-766, (1991).

Geesey, and White,"Determination of Bacterial Growth and Activity at Solid-Liquid Interfaces," Annu. Rev. Microbiol., 44:579-602, (1990).

Gomez et al., "Microfluidic Biochip for Impedance Spectroscopy of Biological Species," Biomedical Microdevices, 3:3. pp. 201-209, (2001).

Greef et al., "Identification and Growth Rate Quantitation of Individual Bacterial Clones Using a Novel Microfluidic Concentration Device," Accelr8 Technology Corporation (1 page), 2006.

Hach Company, "Heterotrophic Bacteria, Pour Plate Method," Edition 7 (10 pages), 2012.

Hance et al. K-392: Poster—"Rapid Identification of Live *Acinetobacter* spp. in Bronchoalveolar Lavage Specimens by Automated Immunofluorescence Microscopy," Presented at the 47th ICAAC Sep 27. 2007.

Hance et al. C-065: Poster—"A Rapid Indirect Enzyme-Linked Immunosorbent Assay for Identification of *Acinetobacter* spp. from Cultured Isolates," Presented at the American Society for Microbiology 108th General Meeting Jun. 2, 2008.

Hance et al. P0539: Poster—"Pathogen Identification from Positive Blood Cultures Using Automated Sample Preparation and Automated Fluorescent in situ Hybridization (FISH)," Presented at ECCMID 2014, May 11, 2014, Barcelona, Spain.

Hance et al. Poster 2032: Poster—"Rapid Bacterial Identification Directly from Positive Blood Cultures Using Automated Sample Preparation and Multiplexed Fluorescence in situ Hybridization (FISH)," ASM2014, Boston, MA May 20, 2014.

Heileman et al., "Dielectric Spectroscopy as a Viable Biosensing Tool for Cell and Tissue Characterization and Analysis," Biosensors and Bioelectronics, 49, pp. 348-359, (2013).

Huang et al., "Electric Manipulation of Bioparticles and Macromolecules on Microfabricated Electrodes," Analytical Chem., 73, pp. 1549-1559, (2001).

Huang et al., "Lysozyme for Capture of Microorganisms on Protein Biochips," Enzyme and Microbial. Technol., 33:958-966, (2003).

Inverness Medical Group, "Wampole Isostat Microbial Tubes, Instructions for Use and Supplementary Application Notes," (2008).

Iregui et al., "Clinical Importance of Delays in the Initiation of Appropriate Antibiotic Treatment for Ventilator-Associated Pneumonia," Chest 122:262-268, 2002.

Isse et al., "Digital Transplantation Pathology: Combining Whole Slide Imaging, Multiplex Staining and Automated Image Anlaysis," Am J Transplant. 12:27-37, 2012.

Jampachaisri et al., "Classification of oligonucleotide fingerprints: application for microbial community and gene expression analyses," Bioinformatics 21: 3122-3130 (2005).

Ji et al., "Real-time Detection of Bacterial Contamination in Dynamic Aqueous Environments Using Optical Sensors," Analytical Chem., 76:1411-1418, (2004).

Jin et al., "A Biosensor Concept Based on Imaging Ellipsometry for Visualization of Biomolecular Interactions," Analytical Biochem., 232:69-72, (1995).

Kastenholz, B. "Comparison of the Electrochemical Behavior of the High Molecular Mass Cadmium Proteins in Arabidopsis Thaliana and in Vegetable Plants on Using Preparative Native Continuous Polyacrylamide Gel Electrophoresis (PNC-PAGE)," Electroanalysis 18:103-106 (2006).

Kim and Soh, "Simultaneous Sorting of Multiple Bacterial Targets Using Integrated Dielectrophoretic-Magnetic Activated Cell Sorter," Lab Chip 9:2313-2318, 2009.

Kim et al., "Programmed Trapping of Individual Bacteria Using Micrometre-Size Sieves," Lab on a Chip, 11, pp. 1089-1095. (2011).

Koh et al., "Integrating Polymerase Chain Reaction, Valving, and Electrophoresis in a Plastic Device for Bacterial Detection," Analytical Chem., 75:4591-4598, (2003).

Kremser, et al., "Capillary Electrophoresis of Biological Particles: Viruses, Bacteria, and Eukaryotic Cells," Electrophoresis 25: 2282-2291 (2004).

Kubitschko et al.,"Sensitivity Enhancement of Optical lmmunosensors with Nanoparticles," Analytical Biochem., 253, pp. 112-122, (1997).

Kuehn et al., "Automated Confocal Laser Scanning Microscopy and Semiautomated Image Processing for Analysis of Biofilms," Appl. Environ. Microbio., 64:4115-4127, (1998).

(56) References Cited

OTHER PUBLICATIONS

Kumar et al., "Duration of Hypotension Before Initiation of Effective Antimicrobial Therapy is the Critical Determinant of Survival in Human Septic Shock," Crit Care Med. 34:1589-1596, 2006.
Lagally et al., "Integrated Portable Genetic Analysis Microsystem for Pathogen/Infectious Disease Detection," Analytical Chem., 76, pp. 3162-3170, (2004).
Lawrence, J.R., et al., "Computer-Enhanced Darkfield Microscopy for the Quantitative Analysis of Bacterial Growth and Behavior on Surfaces," J. Microbial. Methods 10:123-138, (1989).
Lerner, "Bayesian Fluorescence in Situ Hybridisation Signal Classification," Artif. Intell. Med. 30: 301-316 (2004).
Lisby et al. ePoster "Performance of the new Accelerate ID/AST System in Highly Resistant Acinetobacter baumannii Bloodstream Infection Isolates, Compared to Routine Laboratory Testing," ECCMID Apr. 23, 2015, Copenhagen, Denmark.
Liu et al., "CMEIAS: A Computer-Aided System for the Image Analysis of Bacterial Morphotypes in Microbial Communities," Microb. Ecol., 41:173-194, (2001).
Lloyd, D., and Hayes, A.J., "Vigour, Vitality and Viability of Microorganisms," FEMS Microbio. Lett., 133:1-7, (1995).
Lochhead. "Microfluidic Devices that Capture Bacteria for Growth and Kill Analysis," Nov. 14, 2006, XP055207195, retrieved from the Internet: URL:http://acceleratediagnostics.com/docs/AVS_2006_Capture.pdf [retrieved on Aug. 11, 2015].
Luna et al.,"Appropriateness and Delay to Initiate Therapy in Ventilator-Associated Pneumonia," Eur Respir J. 27:158-164, 2006.
Maeyama et al., "Confocal Imaging of Biofilm Formation Process Using Fluoroprobed *Escherichia coli* and Fluorostained Exopolysaccharide," J. Biomed. Mater Res., 70:274-282, (2004).
Magnusdottir, et al. "Collection of Capillary Electrophoresis Fractions on a Moving Membrane," From Methods in Molecular Biology, vol. 162: Capillary Electrophoresis of Nucleic Acids, vol. 1: Introduction to the Capillary Electrophoresis of Nucleic Acids. 22: 323-331 (2001).
Markx, G. H. et al., "Dielectrophoretic Separation of Cells: Continuous Separation," Biotechnol. Bioeng., 45:337-343, (1995).
Markx, G.H. et al., "Dielectrophoretic Characterization and Separation of Micro-Organisms" Microbiology, 140:585-591 (1994).
Meinders et al., "In Situ Enumeration of Bacterial Adhesion in a Parallel Plate Flow Chamber—Elimination or in Focus Flowing Bacteria From the Analysis," J. Microbiol. Methods, 16:119-124, (1992).
Metzger et al. C-163: Poster—"Direct Observation of Inducible Clindamycin Resistance in *Staphylococcus aureus* Using Single Live Cell Imaging," Presented at the American Society for Microbiology General Meeting May 23, 2006.
Metzger C-032: Poster—"Direct Identification of Methicillin Resistant *Staphylococcus aureus* (MRSA) Using Small Numbers of Immobilized Cells and Response to Oxacillin (OCA) by Automated Growth Analysis," Presented at the American Society for Microbiology 107th General Meeting, May 22, 2007.
Metzger et al. D-892: Poster—"Identification of mecA in *Staphylococcus aureus* Using Small Numbers of Immobilized Cells and the Response to Cefoxitin (FOX) by Automated Growth Analysis," Presented at the 47th ICAAC Sep. 28, 2007.
Metzger et al. C-005: Poster—"Direct Identification of MRSA and MLSB Phenotypes in *Staphylococcus aureus* Using Small Numbers of Immobilized Cells," Presented at the American Society for Microbiology 108th General Meeting Jun. 2, 2008.
Metzger et al. C-145: Poster—"Direct Detection and Enumeration of Viable Bacteria in Human Bronchoalveolar Lavage Specimens Using Automated Growth Rate Analysis," Presented at the American Society for Microbiology 108th General Meeting Jun. 2, 2008.
Metzger et al. D-282: Poster—"Direct Identification of the ESBL Phenotype in Enterobacteriaceae Isolates Using Small Numbers of Immobilized Cells," Presented at the 48th ICAAC and IDSA Oct. 25, 2008, Washington, DC.
Metzger et al. C-207: Poster—"Rapid Identification of Resistance Phenotypes in Gram-Negative Bacilli Using Automated Digital Microscopy," Presented at the 109th General Meeting of the ASM, Philadelphia, PA, May 23, 2009.
Metzger et al. C-1140: Poster—"Rapid Quantitation and Identification of Pseudomonas aeruginosa, *Staphylococcus aureus*, and Acinetobacter baumannii in Bronchoalveolar Lavage Fluid," Presented at the 110th General Meeting of the ASM May 24, 2010, San Diego, CA.
Metzger et al. Poster: "Same-Day ID and Resistance Phenotyping Directly from Respiratory Specimens by Automated Microscopy," Presented at ASM 2011, New Orleans, May 22, 2011.
Metzger et al. Poster—"Automated 4-Hour Detection of Heteroresistant Vancomycin-Intermediate *Staphylococcus aureus* (hVISA)," Presented at ASM 2011 May 22, 2011, New Orleans.
Metzger et al. D-791: Poster—"Direct-From-Remnant-Specimen Quantitative Identification Using Automated Microscopy," Presented at the 50th ICAAC, Sep. 13, 2010, Boston, MA.
Metzger and Dunne D-102: Poster—"Same-Shift ID Directly from Respiratory Specimens by Automated Microscopy," Presented at 51st ICAAC Sep. 17, 2011, Chicago, IL.
Metzger et al. C-157: Poster—"3-Hour ESBL Detection from Positive Blood Cultures Using Multiplexed Automated Digital Microscopy (MADM)," Presented at ASM 2012 Jun. 17, 2012, San Francisco, CA.
Metzger et al. C-751: Poster—"Rapid and Automated Specimen Preparation for Clinical Microbiology," Presented at ASM 2012 Jun. 17, 2012, San Francisco, CA.
Metzger D-1410: Poster—"Same-Day Blood Culture with Digital Microscopy," Presented at ICAAC 2012 Sep. 11, 2012, San Francisco, CA.
Metzger et al., "Rapid Simultaneous Identification and Quantitation of *Staphylococcus aureus* and Pseudomonas aeruginosa Directly from Bronchoalveolar Lavage Specimens Using Automated Microscopy," Diagn Microbiol Infect Dis. 79:160-165, 2014.
Miller et al., "SOS Response Induction by Beta-Lactams and Bacterial Defense Against Antibiotic Lethality," Science, 305:1629-1631, 2004.
Mishra et al., "On-Chip Micro-Biosensor for the Detection of Human CD4+ Cells Based on AC Impedance and Optical Analysis," Biosensors and Bioelectronics, 21:696-704, (2005).
Moffitt et al., "The Single-Cell Chemostat: An Agarose-Based, Microfluidic Device for High-Throughput, Single-Cell Studies of Bacteria and Bacterial Communities," Lab Chip 12:1487-1494, 2012.
Mohamad et al., "Bacteria Identification from Microscopic Morphology Using Naïve Bayes," IJCSEIT 4:1-9, 2014.
Molin et al., "Rapid Detection of Bacterial Growth in Blood Cultures by Bioluminescent Assay of Bacterial ATP," J. Clin. Microbiol. 18:521-525 (1983).
Mueller et al., "Issues in Pharmacokinetics and Pharmacodynamics of Anti-Infective Agents: Kill Curves Versus MIC," Antimicrob. Agents Chemother., 48:369-377, (2004).
Oheim, "High-Throughput Microscopy Must Re-Invent the Microscope Rather Than Speed up its Functions," Br. J. Pharmacol., 152:1-4, (2007).
Okano et al., "Using Microparticle Labeling and Counting for Attomole-Level Detection in Heterogeneous Immunoassay," Analytical Biochem., 202:120-125, (1992).
Orjih, "Heme Polymerase Activity and the Stage Specificity of Antimalarial Action of Chloroquine," J. Pharm. Exp. Ther. 282(1): 108-112 (1997).
Ozkan et al., "Electro-Optical Platform for the Manipulation of Live Cells," Langmuir, 19:1532-1538, (2003).
Plowman, "Planar Integrated Optical Methods for Examining Thin Films and Their Surface Adlayers," Biomaterials, 19:341-355, (1998).
Price et al. ePoster "Rapid Identification and Antimicrobial Susceptibility Testing of Bacteria in Bloodstream Infections Using the Accelerate ID/AST Technology," ECCMID Apr. 23, 2015, Copenhagen, Denmark.
Price et al., "Rapid Antibiotic Susceptibility Phenotypic Characterization of *Staphylococcus aureus* Using Automated Microscopy of Small Numbers of Cells," J Microbiol Methods. 98:50-58, 2014.

(56) References Cited

OTHER PUBLICATIONS

Probst et al., "Polydimethylsiloxane Sub-Micron Traps for Single-Cell Analysis of Bacteria," Micromachines, 4:357-369, (2013).
Rabinovitch et al., "Removal and Inactivation of *Staphylococcus epidermidis* Biofilms by Electrolysis," Applied and Environmental Microbiology, 72:6364-6366, (2006).
Rajagopal et al., "Eight Gram-Negative Bacteria are 10,000 Times More Sensitive to Cationic Detergents than to Anionic Detergents," Can J Microbiol. 49:775-779, 2003.
RMM Product Matrix, http://rapidmicromethods.com/files/matrix.php, accessed Jul. 27, 2016. (13 pages).
Rohner et al., "Advantage of Combining Resin with Lytic BACTEC Blood Culture Media," J. Clin. Micro. 35(10): 2634-2638 (1997).
Rohner et al., "Evaluation of the New Improved BHI-Lysis Blood Culture Medium for the BCB Roche System," Eur. J. Clin. Micro. Infect. Dis. 10: 620-624, 1991.
Rösch et al., "Chemotaxonomic Identification of Single Bacteria by Micro-Raman Spectroscopy: Application to Clean-Room-Relevant Biological Contaminations," Applied and Environmental Microbiology, 71: 1626-1637, (2005).
Rose et al., "Using the Membrane Filter in Clinical Microbiology," Med. Lab. 3: 22-23, 29, 43, 1969. Note: The numbered pages omitted from this article are advertisements.
Rowe et al., "Array Biosensor for Simultaneous Identification of Bacterial, Viral, and Protein Analytes," Analytical Chem., 71:3846-3652, (1999).
Salmon et al., "Video-Enhanced Differential Interference Contrast Light Microscopy," BioTechniques, 7:624-633, (1989).
Sapsford et al., "Detection of *Campylobacter* and *Shigella* Species in Food Samples Using an Array Biosensor," Analytical Chem., 76:433-440, (2004).
Schrot et al., "Method for Radiorespirometric Detection of Bacteria in Pure Cultures and in Blood," Appl. Micro. 26(2): 867-873 (1973).
Shamsheyeva et al. 2538: Poster—"Rapid Antimicrobial Susceptibility Testing of Non-Fermenting Gram-Negative Bacilli Directly from Positive Blood Cultures by Automated Microscopy," Presented at ASM2014, May 20, 2014, Boston, MA.
Shamsheyeva et al. 2555: Poster—"Evaluation of an Antimicrobial Susceptibility Testing Algorithm to Determine Minimum Inhibitory Concentration Using Growth of Immobilized Staphylococcal Cells Measured by Automated Microscopy," Presented at ASM2014, May 20, 2014, Boston, MA.
Shamsheyeva et al. D-873: Poster "Evaluation of an Antimicrobial Susceptibility Testing Algorithm for Gram-Positive Bacteria Directly from Positive Blood Culture Using Automated Microscopy Analysis of Susceptibility Patterns," Presented at ICAAC Sep. 7, 2014, Washington, DC.
Shamsheyeva et al. P0332: Poster—"Next Generation Automated Phenotypic Antibiotic Susceptibility Testing Utilizing Automated Microscopy Analysis of Bacterial Cells," Presented at ECCMID 2014 May 10, 2014, Barcelona, Spain.
Shamsheyeva et al. P0335: Poster—"5-Hour Antibiotic Susceptibility Testing of Enterococcus faecium and E. faecalis, and Acinetobacter baumannii Directly from Positive Blood Cultures Using Automated Microscopy," Presented at ECCMID 2014 May 10, 2014, Barcelona, Spain.
Sippy et al., "Rapid Electrochemical Detection and Identification of Catalase Positive Micro-Organisms", Biosensors & Bioelectronics, 18:741-749, (2003).
Stewart et al., "Aging and Death in an Organism that Reproduces by Morphologically Symmetric Division," PLoS Biology, 3:295-300 (2005).
Stimpson et al., "Real-Time Detection of DNA Hybridization and Melting on Oligonucleotide Arrays by Using Optical Wave Guides," Genetics, Proc. Natl. Acad. Sci. USA, 92:6379-6383, (1995).
Stuart, "The Value of Liquid for Blood Culture," J. Clin. Path. 1: 311-314 (1948).
Sun et al., "Single-Cell Microfluidic Impedance Cytometry: A Review," Microfluidics and Nanofluidics, 8: 423-443, (2010).

Suo et al., "Immunoimmobilization of Living *Salmonella* for Fundamental Studies and Biosensor Applications," in *Salmonella*—A Diversified Superbug, Chapter 25, pp. 497-522, (2012).
Taton et al., "Two-Color Labeling of Oligonucleotide Arrays via Size-Selective Scattering of Nanoparticle Probes," J. Am. Chem. Soc., 123:5164-5165, (2001).
Tison, D.L., "Culture Confirmation of *Escherichia coli* Serotype 0157:H7 by Direct Immunofluorescence," J. Clin. Microbio., 28, 612-613, (1990).
Tsang et al., "Characterization of Murine Monoclonal Antibodies Against Serogroup B *Salmonellae* and Application as Serotyping Reagents," J. of Clin. Micro., 29, pp. 1899-1903, (1991).
Van der Borden et al., Electric Current-Induced Detachment of *Staphylococcus epidermidis* Biofilms from Surgical Stainless Steel, Appl. Environ. Microbiol., 70:6871-6874, (2004).
Van Soestbergen and Lee, "Pour Plates or Steak Plates?," Appl Microbiol. 18:1092-1093, 1969.
Varshney et al., "A Label-Free, Microfluidics and Interdigitated Array Microelectrode-Based Impedance Biosensor in Combination with Nanoparticles Immunoseparation for Detection of *Escherichia coli* O157:H7 in Food Samples," Sensors and Actuators, 128:99-107, (2007).
Vega, et al., "Effect of Ionic Strength and Porosity on Ion Diffusion in Agarose Gels," Summer Bioengineering Conference, Sonesta Beach Resort in Key Biscayne, Florida, 1-2 (2003).
Vener et al., "A Novel Approach to Nonradioactive Hybridization Assay of Nucleic Acids Using Stained Latex Particles," Analytical Biochem., 198, pp. 308-311, (1991).
Von Haebler et al., "The Action of Sodium Polyanethol Sulphonate ("Liquoid") on Blood Cultures," J. Pathol. Bacteriol. 46(2): 245-252 (1938).
Wallace et al. D-918: Poster—"Rapid Identification of Gram-negative Bacteria in Positive Blood Culture Broth Using a Multiplex Fluorescence in situ Hybridization (FISH) Assay and Automated Microscopy," Presented at ICAAC Sep. 7, 2014, Washington, DC.
Weeratna et al., "Gene Expression Profiling: From Microarrays to Medicine", J. Clin. Immunol, 24: 213-224, (2004).
Willaert, "Cell Immobilization and its Applications in Biotechnology: Current Trends and Future Prospects," in Fermentation Microbiology and Biotechnology, Chapter 12, p. 313-368, 2006.
Wit, P., and Busscher, H.J., "Application of an Artificial Neural Network in the Enumeration of Yeasts and Bacteria Adhering to Solid Substrata," J. Microbio. Methods, 32, pp. 281-290, (1998).
Wu, et al., "Microfluidic Continuous Particle I Cell Separation via Electroosmotic-Flow-Tuned Hydrodynamic Spreading," J. Micromech. Microeng., 17, pp. 1992-1999, (2007).
Yang, et al., "Electrical/ Electrochemical Impedance for Rapid Detection of Foodborne Pathogenic Bacteria," Biotechnology Advances, 26, pp. 135-150, (2008).
Yeung et al., "Bayesian Model Averaging: Development of an Improved Multi-Class, Gene Selection and Classification Tool for Microarray Data," Bioinformatics 21: 2394-2402 (2005).
Zhou, et al., "Automated Image Analysis for Quantitative Fluorescence in Situ Hybridization with Environmental Samples," App. Environ. Microbio. 73(9):2956-2962 (2007).
Zierdt et al., "Development of a Lysis-Filtration Blood Culture Technique," J. Clin. Micro. 5(1): 46-50 (1977).
Zierdt et al., "Lysis-Filtration Blood Culture Versus Conventional Blood Culture in a Bacteremic Rabbit Model," J Clin Microbiol. 15:74-77, 1982.
Zierdt, "Blood-Lysing Solution Nontoxic to Pathogenic Bacteria," J. Clin. Micro., 15(1): 172-174 (1982).
Zierdt, "Simplified Lysed-Blood Culture Technique," J. Clin. Micro. 23(3): 452-455 (1986).
CIPO; Office Action dated Jan. 27, 2014 in Canadian Application No. 2,532,414.
CIPO; Office Action dated Mar. 26, 2015 in Canadian Application No. 2,532,414.
EP 03716230.2, European Search Report dated Oct. 15, 2007.
EP 04809482.5, European Office Action dated Jul. 10, 2014.
EP 04809482.5, European Office Action dated Jun. 17, 2010.
EP 04809482.5, European Office Action dated Mar. 13, 2008.

(56) References Cited

OTHER PUBLICATIONS

EP 04809482.5, Supplementary European Search Report dated Oct. 19, 2007.
EP 05854636.7, European Office Action dated Mar. 3, 2014.
EP 05854636.7, European Search Report dated Feb. 13, 2013.
EP 12754797.4, Intention to Grant dated May 21, 2015.
EP 12754797.4, Supplementary European Search Report dated Sep. 24, 2014.
EP 13835702.5, European Partial Supplementary Search Report dated Feb. 25, 2016 (8 pages).
EP 13835702.5, European Supplementary Search Report dated Jun. 24, 2016 (12 pages).
EP 13835702.5, Rules 70(2) and 70a(2) EPC Communication dated Jul. 12, 2016 (1 page).
EP 14762411.8 Partial Supplementary European Search Report dated Jul. 29, 2016 (10 pages).
EP 98911454, European Search Report dated Aug. 5, 2004.
PCT/US1998/04086, International Preliminary Examination Report dated Jun. 11, 1999.
PCT/US1998/04086, International Search Report dated Jul. 14, 1998.
PCT/US1999/010917, International Search Report dated Jul. 30, 2001.
PCT/US2003/006086, International Search Report dated Jun. 27, 2003.
PCT/US2004/022025, International Preliminary Report on Patentability dated Sep. 26, 2006.
PCT/US2004/022025, International Search Report dated Aug. 7, 2006.
PCT/US2004/022025, Written Opinion dated Aug. 7, 2006.
PCT/US2005/045961, International Preliminary Report on Patentability dated Oct. 30, 2007.
PCT/US2005/045961, International Search Report dated Oct. 15, 2007.
PCT/US2005/045961, Written Opinion dated Oct. 15, 2007.
PCT/US2009/038988, International Preliminary Report on Patentability dated Oct. 5, 2010.
PCT/US2009/038988, International Search Report and Written Opinion dated Jun. 8, 2009.
PCT/US2012/028139, International Preliminary Report on Patentability dated Sep. 19, 2013.
PCT/US2012/028139, Search Report and Written Opinion dated Sep. 28, 2012.
PCT/US2013/059104, International Preliminary Report on Patentability dated Mar. 10, 2015.
PCT/US2013/059104, International Search Report and Written Opinion dated Jan. 10, 2014.
PCT/US2014/030745, International Search Report and Written Opinion dated Aug. 27, 2014.
PCT/US2015/032290; International Search Report and Written Opinion dated Aug. 24, 2015 (13 pages).
PCT/US2016/025075 Invitation to Pay Additional Fees with Partial International Search dated Jul. 6, 2016.

* cited by examiner

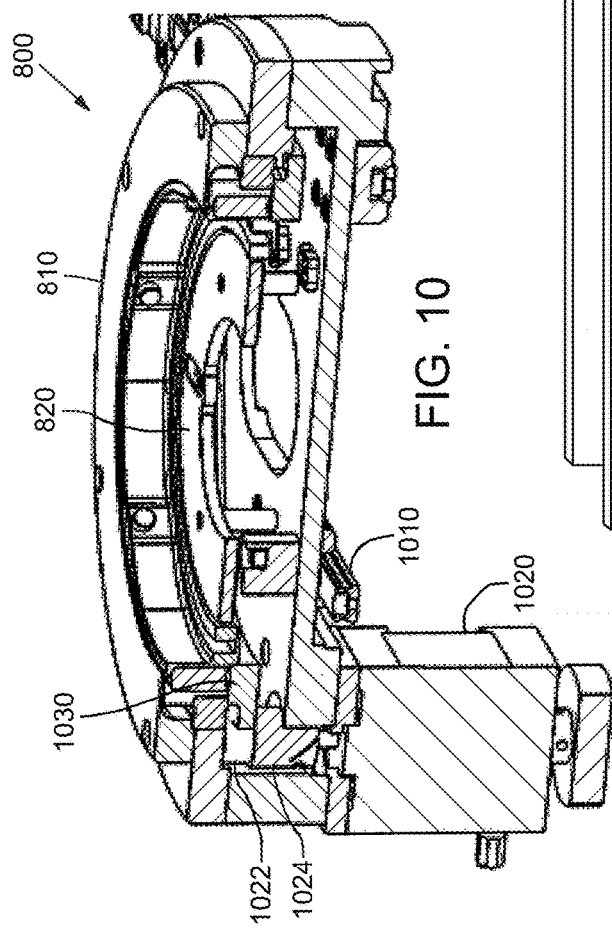
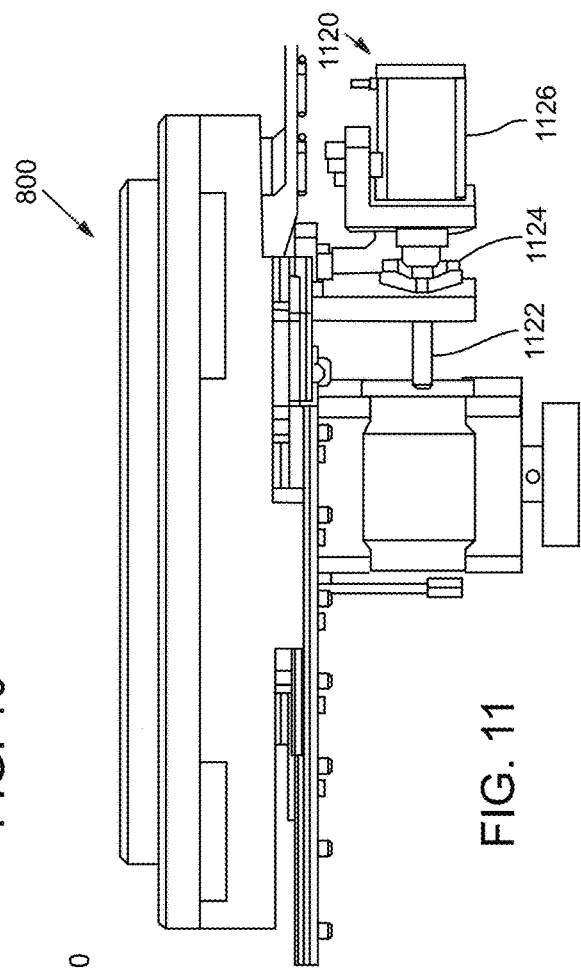
FIG. 10
FIG. 11

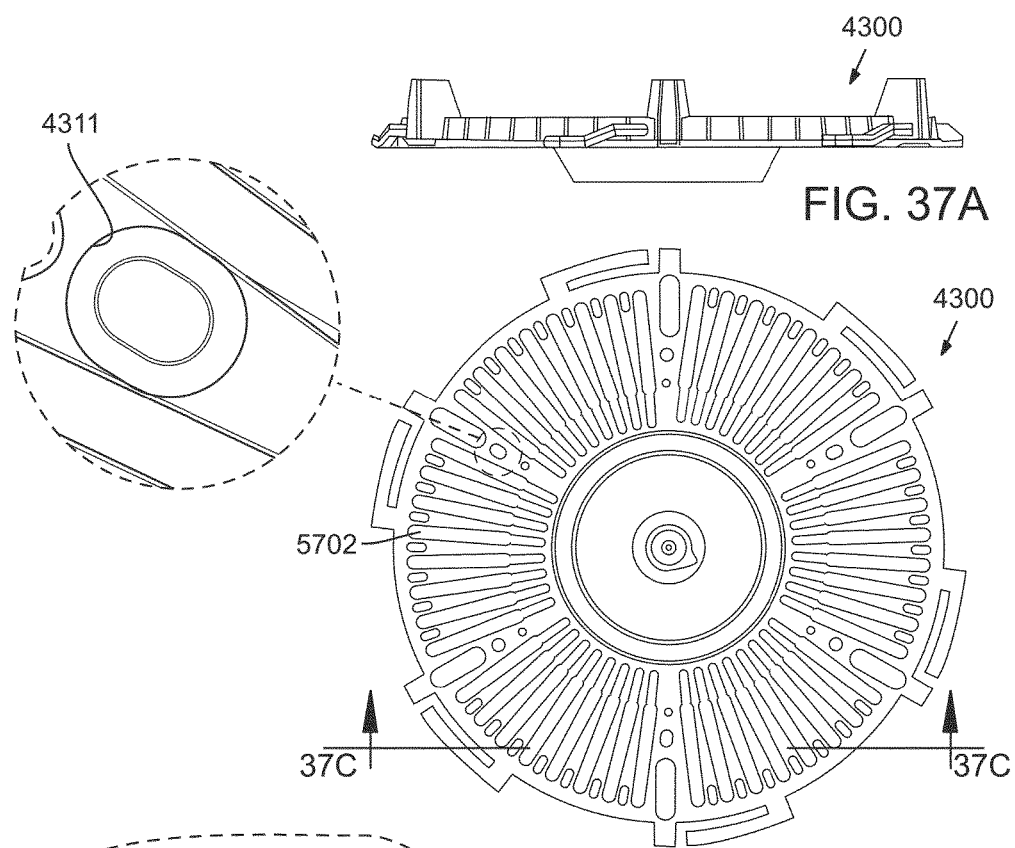
FIG. 37A
FIG. 37B
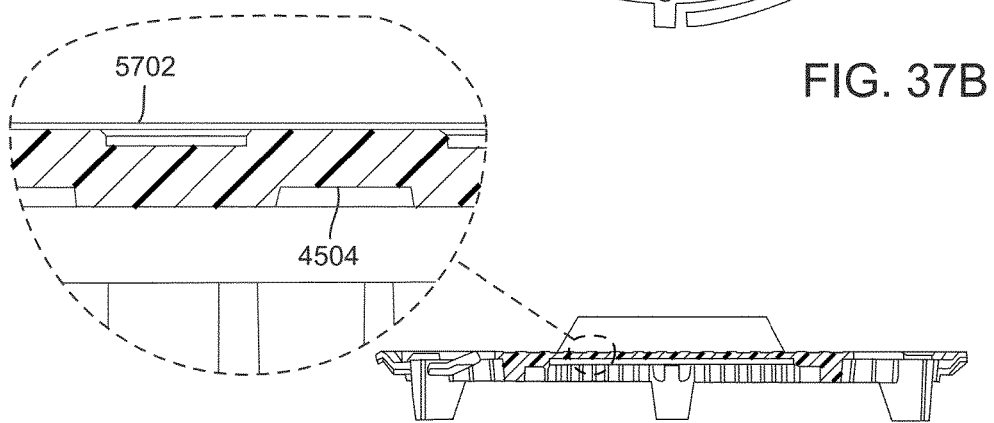
FIG. 37C

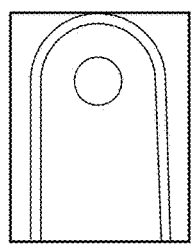
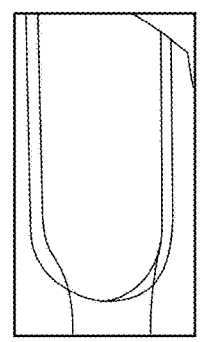
FIG. 56
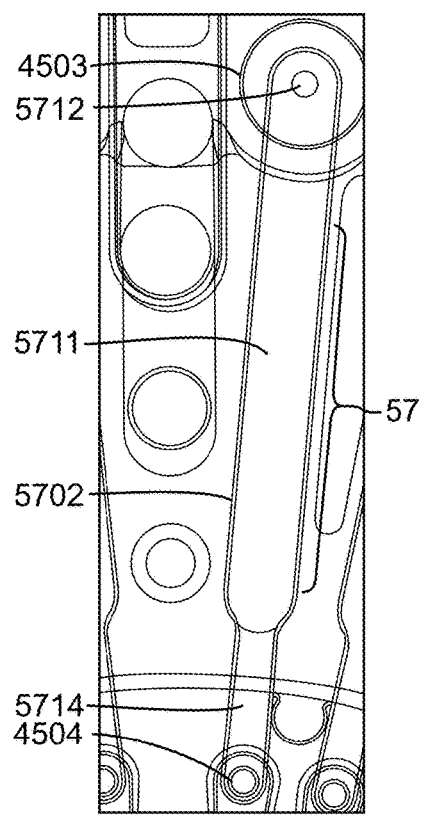
FIG. 57
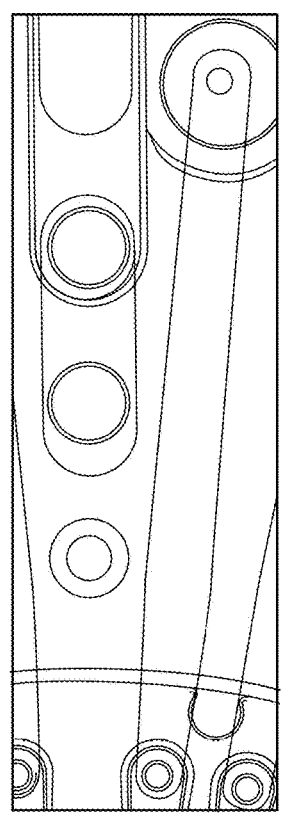
FIG. 58

FIG. 108

| 1 KLE/CNS beads | 2 ABA beads | 3 EFM/CGL beads | 4 STR/ENT beads | 5 |
|---|---|---|---|---|
| 6 SLU beads | 7 | 8 | 9 | 10 |
| 11 EFS beads | 12 PRO beads | 13 | 14 | 15 |
| 16 ECO beads | 17 | 18 SAUR 43300 | 19 | 20 |
| 21 CIT beads | | | 24 PAE beads | 25 CALB 96268 |

FIG. 109

| 1 | 2 | 3 | 4 | 5 ECOL 25922 |
|---|---|---|---|---|
| 6 | 7 | 8 ECOL 35218 | 9 | 10 SAUR 29213 |
| 11 | 12 | 13 | 14 EFAE 29212 | 15 PSAR 27853 |
| 16 | 17 | 18 SAUR 43300 | 19 | 20 SAUR BAA 977 |
| 21 | 22 | 23 | 24 | 25 CALB 96268 |

INSTRUMENT AND SYSTEM FOR RAPID MICROORGANISM IDENTIFICATION AND ANTIMICROBIAL AGENT SUSCEPTIBILITY TESTING

CROSS REFERENCE TO RELATED APPLICATIONS

This is a continuation-in-part of U.S. application Ser. No. 15/085,953, filed Mar. 30, 2016, which claims the benefit of U.S. Provisional Application No. 62/268,340, filed Dec. 16, 2015; U.S. Provisional Application No. 62/260,085, filed Nov. 25, 2015; U.S. Provisional Application No. 62/194,142, filed Jul. 17, 2015; U.S. Provisional Application No. 62/152,773, filed Apr. 24, 2015; and U.S. Provisional Application No. 62/140,300, filed Mar. 30, 2015.

FIELD

The present disclosure relates to an instrument and system for performing microorganism identification and antimicrobial susceptibility testing.

SUMMARY

The disclosed system is an automated microscopy system designed to provide rapid and accurate microorganism identification and antibiotic susceptibility testing results. This automated microscopy system comprises a reagent cartridge comprising a plurality of wells; a reagent stage, wherein the reagent stage comprises an annular shape defining an interior opening, wherein the regent stage is configured to rotate in a first plane, and wherein the reagent stage is configured to receive the reagent cartridge; a cassette comprising a plurality of microfluidic channels, each of the plurality of microfluidic channels comprising an inlet port configured to receive a pipette tip; a cassette stage located within the interior opening of the reagent stage, wherein the cassette stage is configured to rotate and move laterally in the first plane, and wherein the cassette stage is configured to receive the cassette; a pipettor assembly configured to move a plurality of reagents between the plurality of wells of the reagent cartridge and the inlet ports of each of the plurality of microfluidic channels; an optical detection system configured to obtain dark field and fluorescence photomicrographs of a microorganism contained in the plurality of microfluidic channels; and a controller configured to direct operation of the system and process microorganism information derived from photomicrographs obtained by the optical detection system.

The system may further comprise an optical detection system comprising a rapid focus algorithm that calculates the virtual true focus position of an individual microorganism at a given location within about 500 ms, which via repeated imaging over a period of time, permits identification of responses of that microorganism to environmental conditions. The disclosed system can be used for imaging microorganisms tagged with fluorescent labels, such as fluorescently labeled probes that recognize and bind to complementary bacterial sequences. In some embodiments, the system accomplishes this in a process that comprises utilizing custom image analysis software to assign unique spatial XY coordinates to individual microbes bound to labeled probes and to identify characteristics of them. Morphological and other data obtained from captured images are inputted to a probability expectation model of distribution to identify one or more microorganisms in patient samples. The system may further comprise a Proportional-Integral-Derivative ("PID") controller algorithm that dynamically adjusts motor idle torque to control heat load. Moreover, following identification of microorganisms, the system may subject identified microorganisms to antimicrobial susceptibility analysis. For example, the microorganisms can be grown in Mueller-Hinton nutrient-depleted media to differentiate antimicrobial-resistant cells from filamentous, antimicrobial-susceptible cells, often within about 12 hours of growth. Likewise, fastidious microorganisms may be grown in 1% phytone tryptose Mueller Hinton Agar for determination of antimicrobial susceptibility and/or minimum inhibitory concentration of antimicrobial agents. The system may further comprise a system comprising a dynamic dilution algorithm that determines a target dilution factor for a sample to achieve dilution of the sample to a target concentration (such as number of cells per field of view or number of clones or colonies per field of view).

Also disclosed are components and methods for quality control (QC) testing of the systems and methods for microbial identification and antibiotic susceptibility testing described herein. In some embodiments, an automated antibiotic susceptibility testing (AST) QC component is provided. The AST QC test component comprises a frame including a plurality of wells; at least one clip attached to the frame and at least one microbial isolate in at least one of the plurality of wells; and a means of identifying the component as an AST QC test by an automated system. In some examples, the AST QC component includes at least one clip that interacts with a reagent cartridge and at least one clip that interacts with a microbial identification QC component. In other embodiments, an automated microbial identification (ID) QC component is provided. The microbial ID QC component includes a frame including a plurality of wells; at least one clip attached to the frame; at least one target microbial nucleic acid molecule in at least one of the plurality of wells; and a means of identifying the component as an AST QC test by an automated system. The microbial ID QC component is configured to have a complementary shape to an antibiotic susceptibility QC component. In some examples, at least one clip of the ID QC component interacts with an AST QC component. In some examples, the AST QC component is provided in a kit, optionally with an ID QC component.

The AST QC and ID QC components can be used for QC testing of microbial identification and antibiotic susceptibility testing using the systems and methods provided herein. In some embodiments, an AST QC component is attached to a reagent cartridge in the sample vial position and inserted into a system disclosed herein. The one or more microbial isolates in the AST QC component are introduced into the plurality of microfluidic channels of the cassette of the system and the one or more microbial isolates are grown in the presence or absence of one or more antimicrobial agents. The growth of the microbial isolates is monitored over time and susceptibility or resistance of the one or more microbial isolates to the one or more antimicrobial agents is determined. The results can be provided to a user by generating a QC test report.

In some embodiments, the AST QC testing is carried out in conjunction with ID QC testing. Both the AST QC and ID QC components are attached to the reagent cartridge in the sample vial position, wherein the microbial ID QC component is configured to have a complementary shape to the AST QC component and the ID QC component is substantially flush with the AST QC component. The reagent cartridge including the AST QC component and the ID QC component is inserted in the system. In addition to the AST QC testing described above, at least one of the target microbial nucleic acid molecules is introduced to the plurality of microfluidic channels of the cassette and one or more labeled target probes that recognize and bind sequences of the at least one target microbial nucleic acid molecules is introduced into the at least one of the plurality of microfluidic channels containing the target microbial nucleic acid molecule. The labeled probes are incubated with the at least one target microbial nucleic acid molecule for a time sufficient to enable binding of the probes to target microbial nucleic acid molecule and a signal from the one or more labeled target probes is detected. Presence of a signal indicates a positive ID result and absence of a signal indicates a negative ID result. The results of the test are provided by generating an ID QC test report. In some examples, the at least one target microbial nucleic acid molecule is coupled to a microsphere.

Features of the system are described in more detail in U.S. Provisional Patent Applications 62/152,773, 62/194,142, and 62/260,085.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the drawing figures, wherein like numerals denote like elements.

FIG. 9 and FIG. 10 are sectioned perspective views of the reagent stage and the cassette stage.

FIG. 11 is a section view in elevation of the cassette stage.

FIGS. 37A-37C are a collection of section views and detail views of features of the cassette.

FIGS. 56-58 are plan views of portions of the cassette magnified to show details of the flow channels.

FIGS. 85A-85C plot log of bacterial dark phase intensity versus time. FIGS. 85A and 85B show growth in medium having approximately 87% reduction in Mueller Hinton nutrients, compared to growth in standard Mueller-Hinton media (FIG. 85C). FIGS. 85D-85F show quantitative representation of the data shown in FIGS. 85A-85C, respectively, represented as rate of bacterial cell division.

FIG. 87A: Sample is loaded onto gel with pores smaller than bacterial/yeast cells. FIG. 87B: When a voltage is applied, debris migrates into gel leaving bacteria/yeast behind. FIG. 87C: Voltage is briefly reversed to allow negatively-charged bacteria/yeast to move to the center of the well for ease of retrieval.

FIG. 88A: Sample inoculum is introduced into flowcell. FIG. 88B: When an electric field is applied, negatively-charged bacterial/yeast cells migrate to the lower surface where they are captured on the positively-charged poly-L-lysine capture coating on the lower surface of the flowcell. Indium tin oxide (ITO) electrode layers are between the poly-L-lysine coating and the glass bottom surface.

*freundii, Citrobacter koseri*, not differentiated); PAE, *Pseudomonas aeruginosa*; SAU, *Staphylococcus aureus*; AO, acridine orange.

Figure 93A:
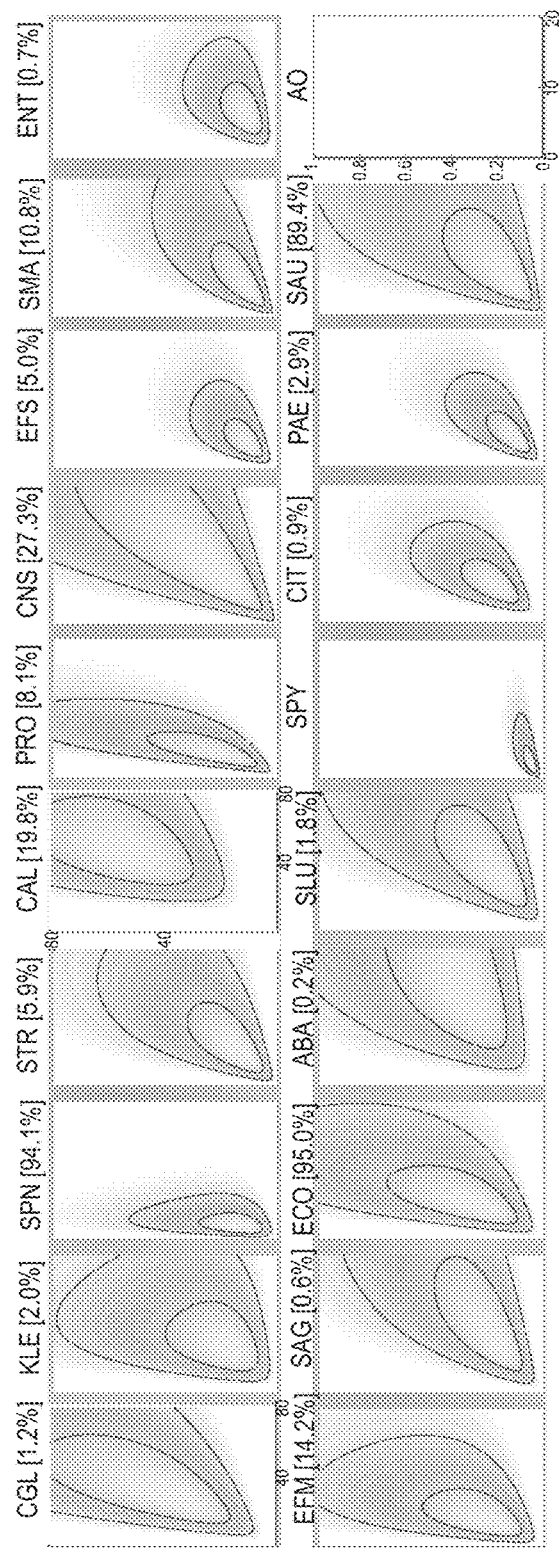
FIG. 93A illustrates the likelihood function for inference of the distribution outcome for 19 microorganisms. CGL, *Candida glabrata*; KLE, *Klebsiella* spp. (*K. pneumoniae, K. oxytoca*, not differentiated); SPN, *Streptococcus pneumoniae*; STR, *Streptococcus* spp. (*S. mitis, S. gallolyticus, S. agalactiae, S. pneumoniae*, not differentiated); CAL, *Candida albicans*; PRO, *Proteus* spp. (*Proteus vulgaris, Proteus mirabilis*, not differentiated); CNS, coagulase negative *Staphylococcus*; EFS, *Enterococcus faecalis*; SMA, *Serratia marcescens*; ENT, *Enterobacter* spp. (*Enterobacter aerogenes, Enterobacter cloacae*, not differentiated); EFM, *Enterococcus faecium* and other *Enterococcus* spp., not differentiated, excluding *Enterococcus faecalis*; SAG, *Streptococcus agalactiae*; ECO, *Escherichia coli*; ABA, *Acinetobacter baumannii*; SLU, *Streptococcus lugdunensis*; SPY, *Streptococcus pyogenes*; CIT, *Citrobacter* spp. (*Citrobacter*
Figure 93B:
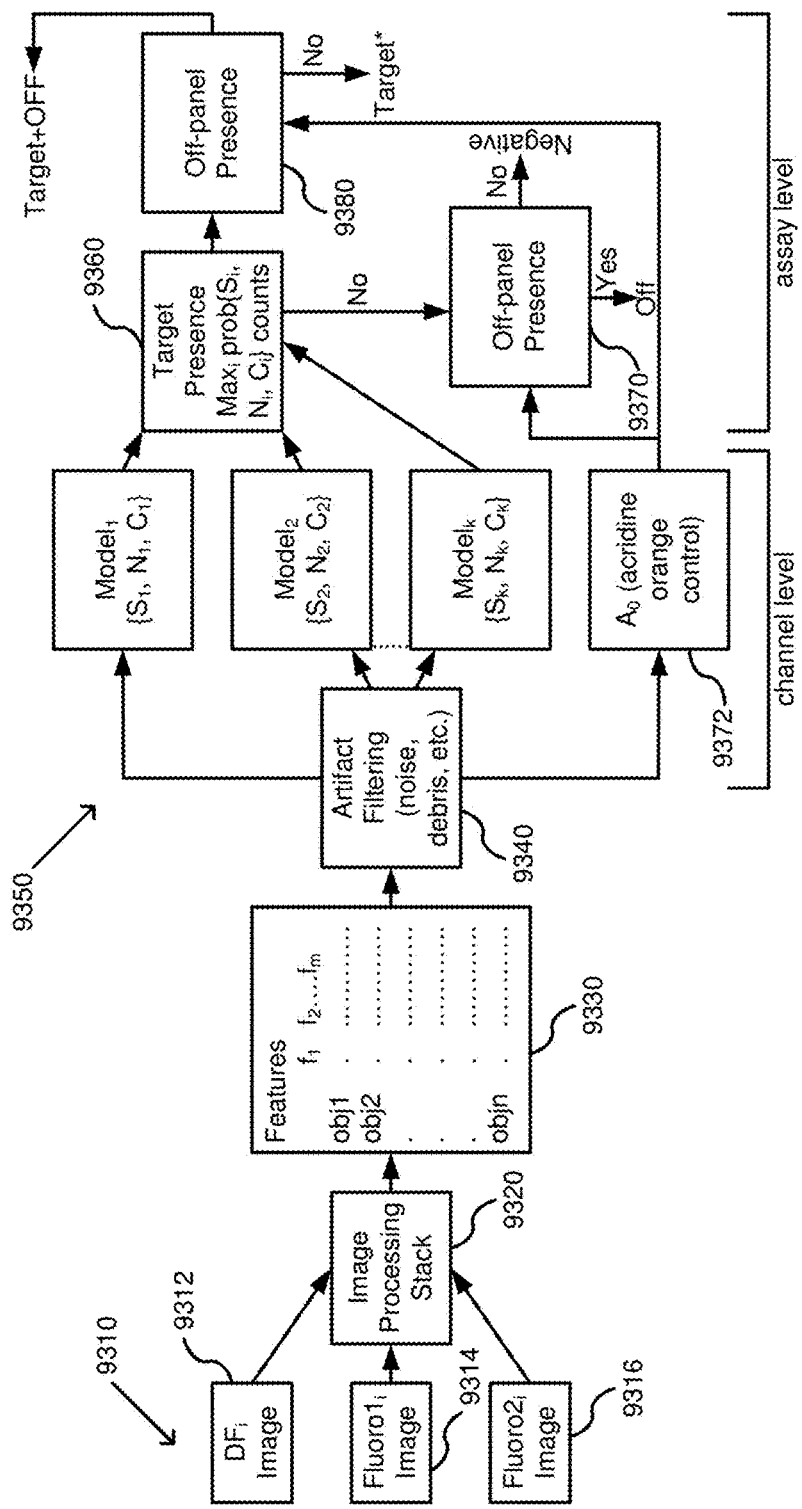

FIG. 93B is a flowchart of a method for identifying microorganisms.

Figure 93C:
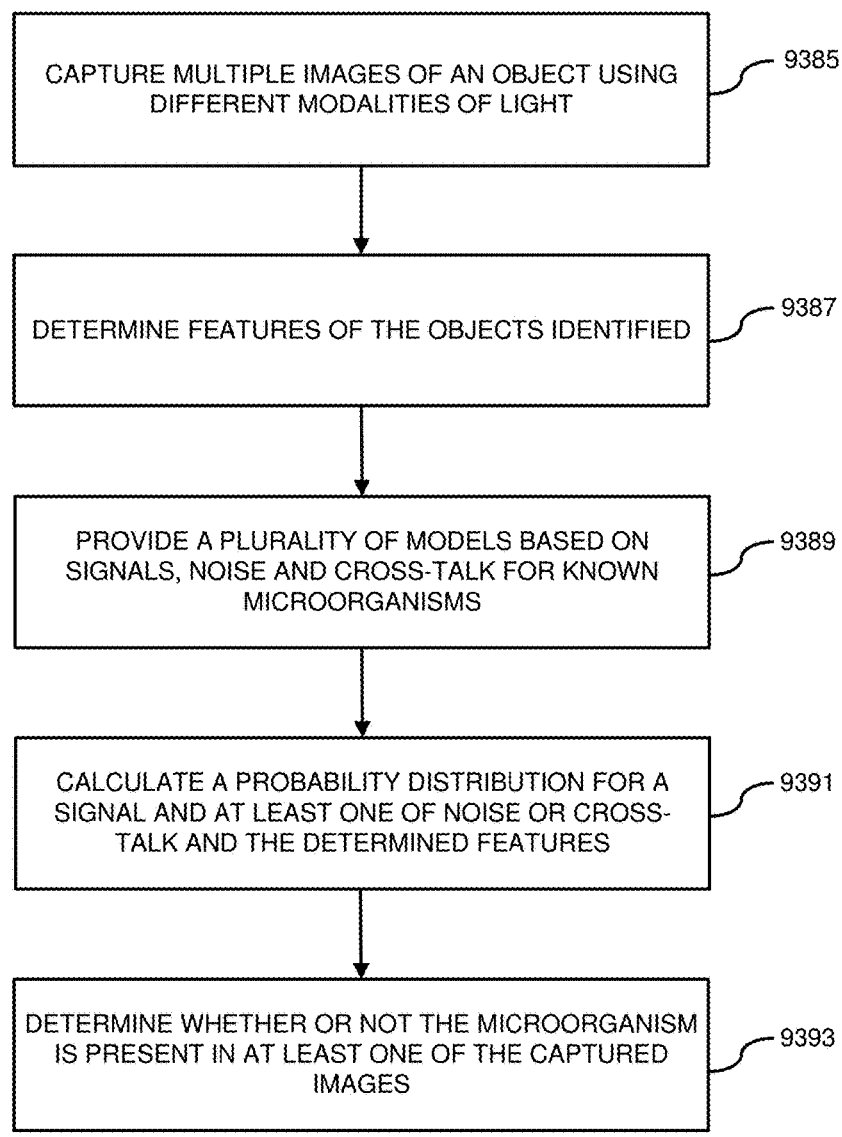

FIG. 93C is a flowchart of another embodiment for identifying microorganisms.

Figure 94:
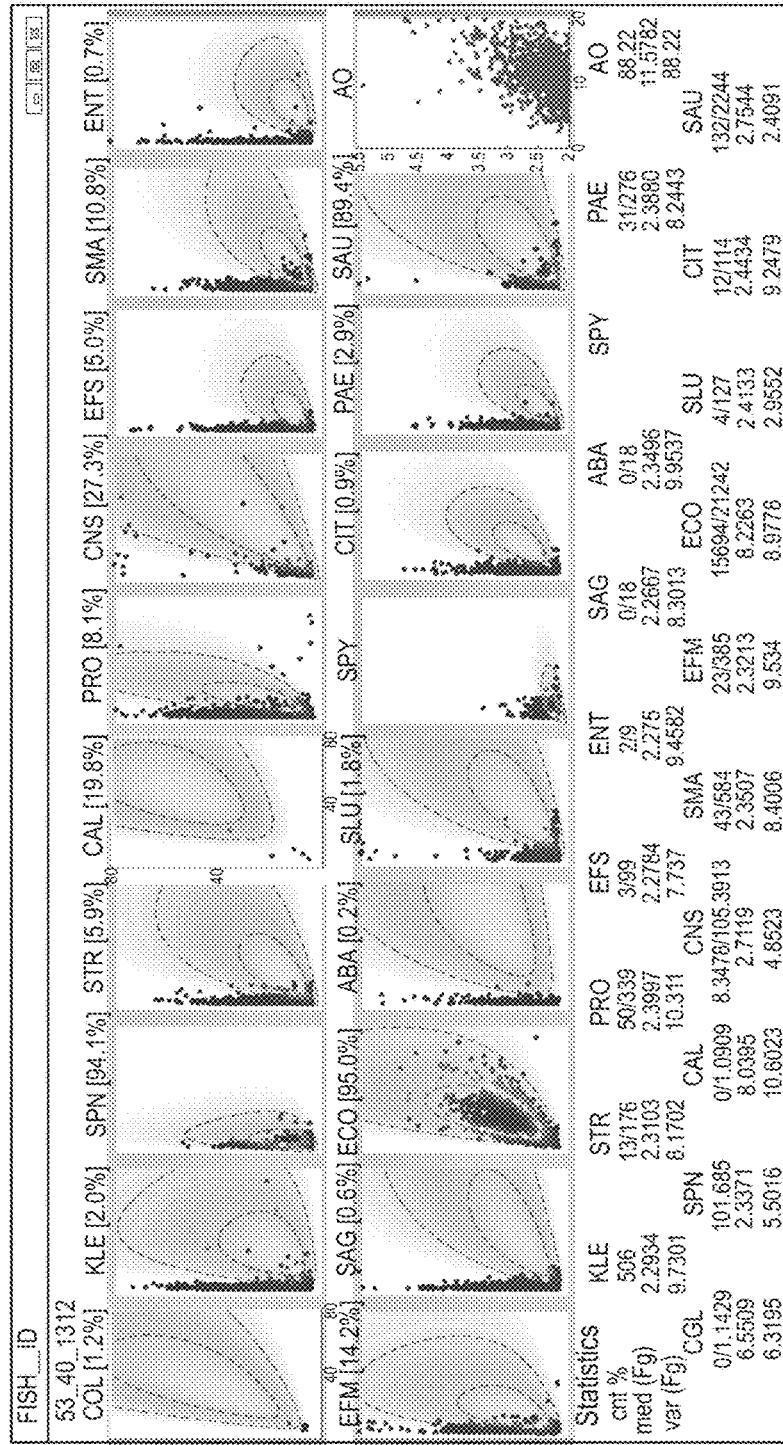

FIG. 94 illustrates the signal distribution data for the microorganisms presented in FIG. 93A, plotting target probe signal along the x-axis and universal probe signal along the y-axis. The dark dots represent signal and the light dots represent noise.

Figure 95:
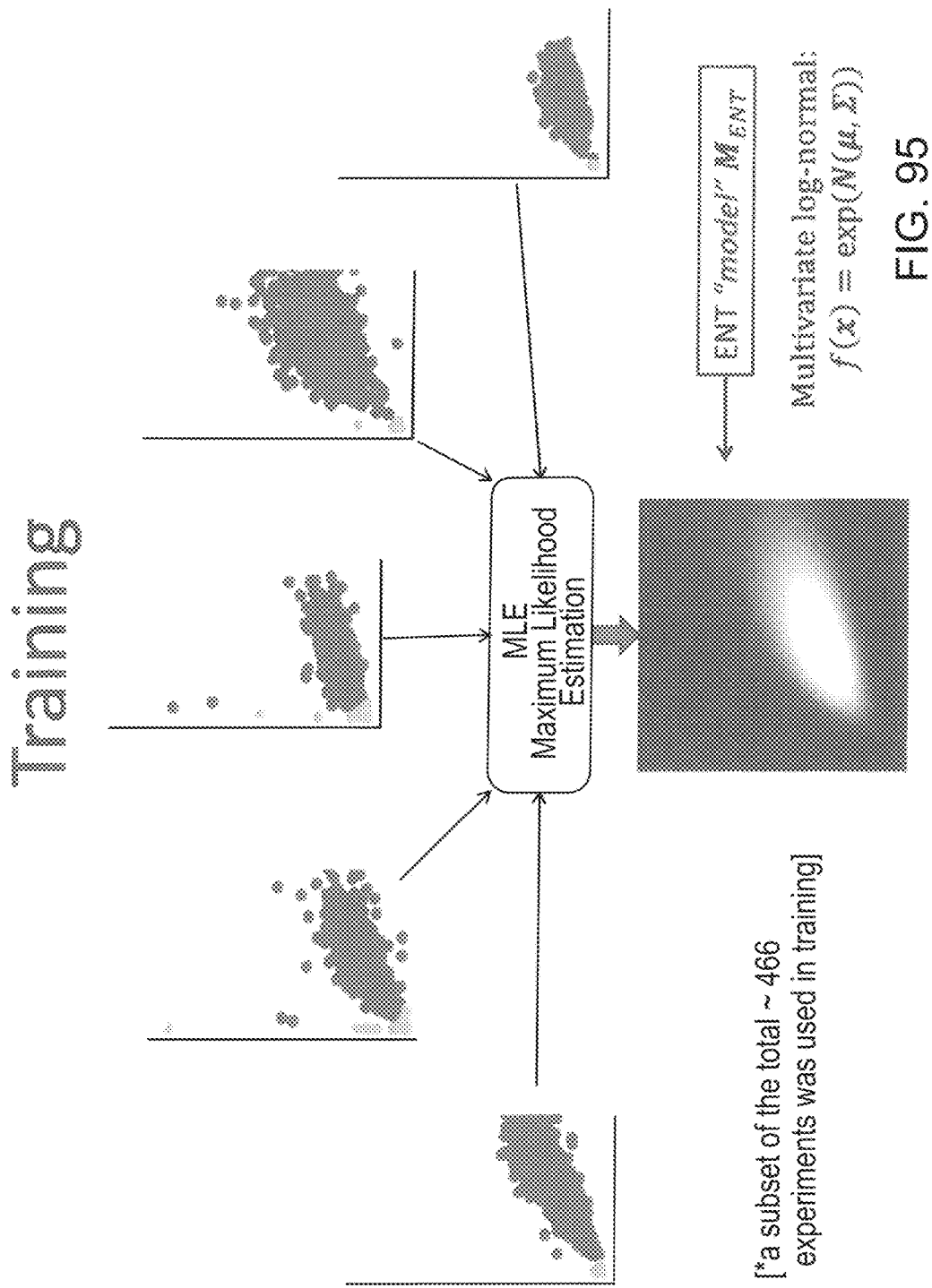

FIG. 95 illustrates the combination of five sets of *Enterobacter* distribution experiments during instrument training in order to arrive at the Maximum Likelihood Estimation model unique for this microorganism.

Figure 96:
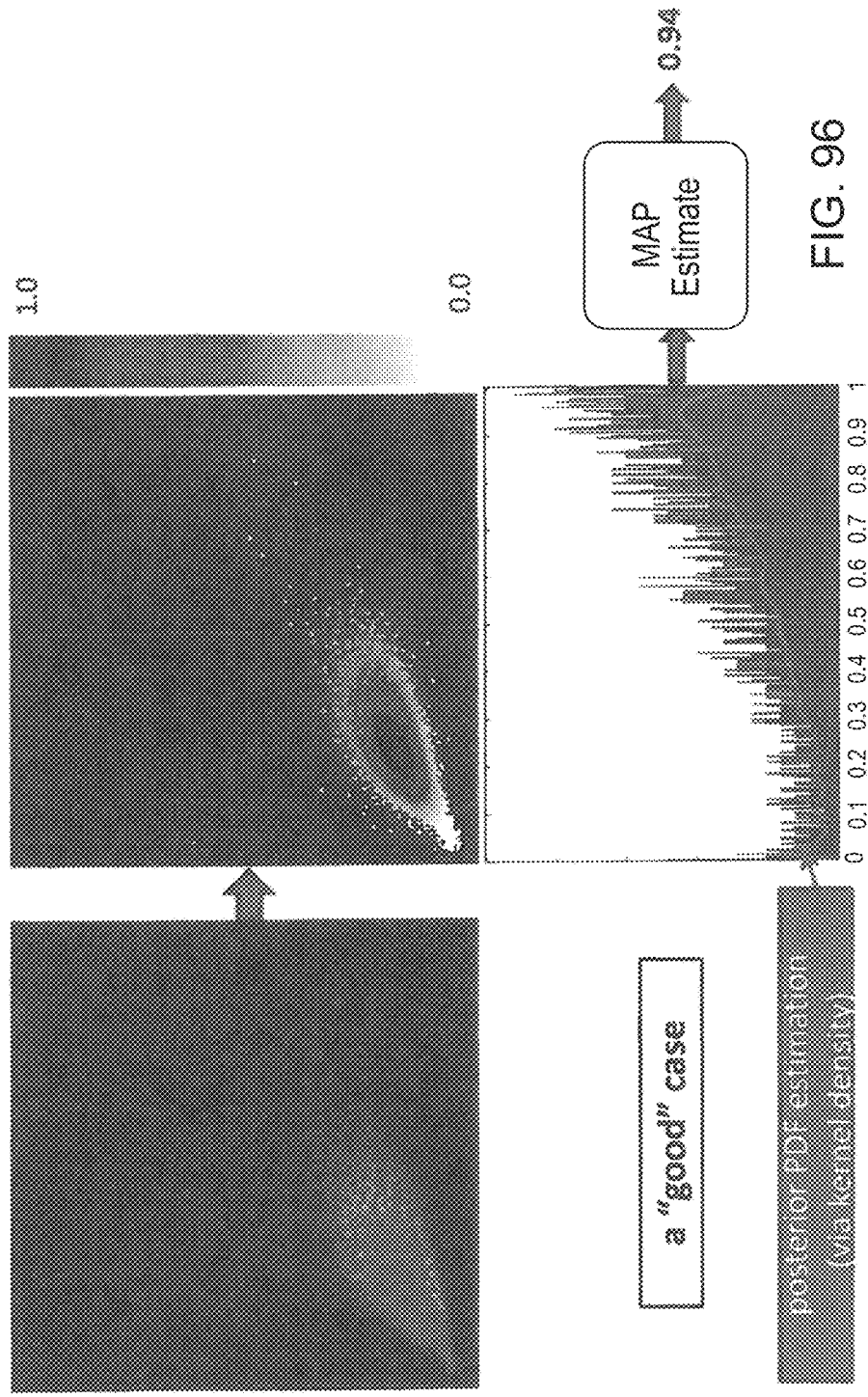

FIG. 96 illustrates a test run showing a good case for the *Enterobacter* probabilistic model.

Figure 97:
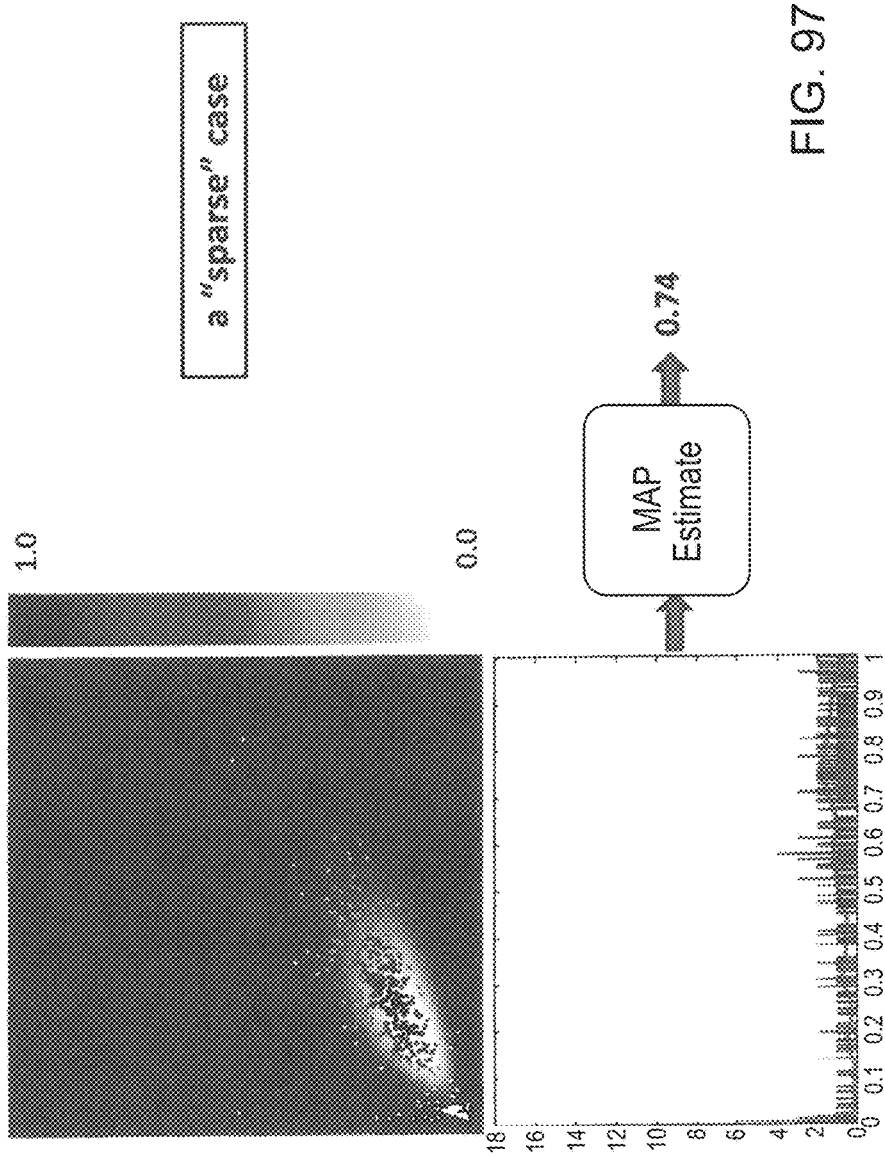

FIG. 97 illustrates a test run showing a sparse case for the *Enterobacter* probabilistic model.

Figure 98:
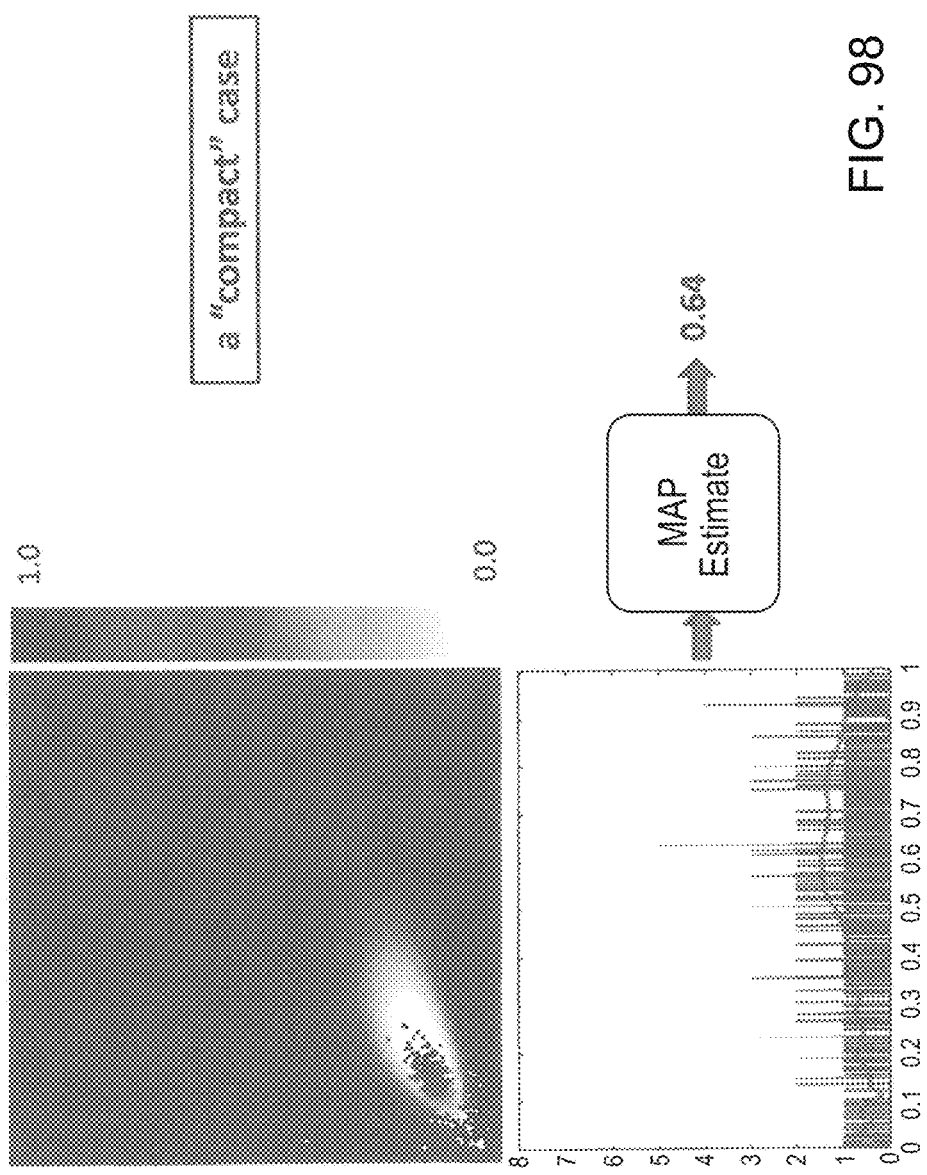

FIG. 98 illustrates a test run showing a compact case for the *Enterobacter* probabilistic model.

Figure 99:
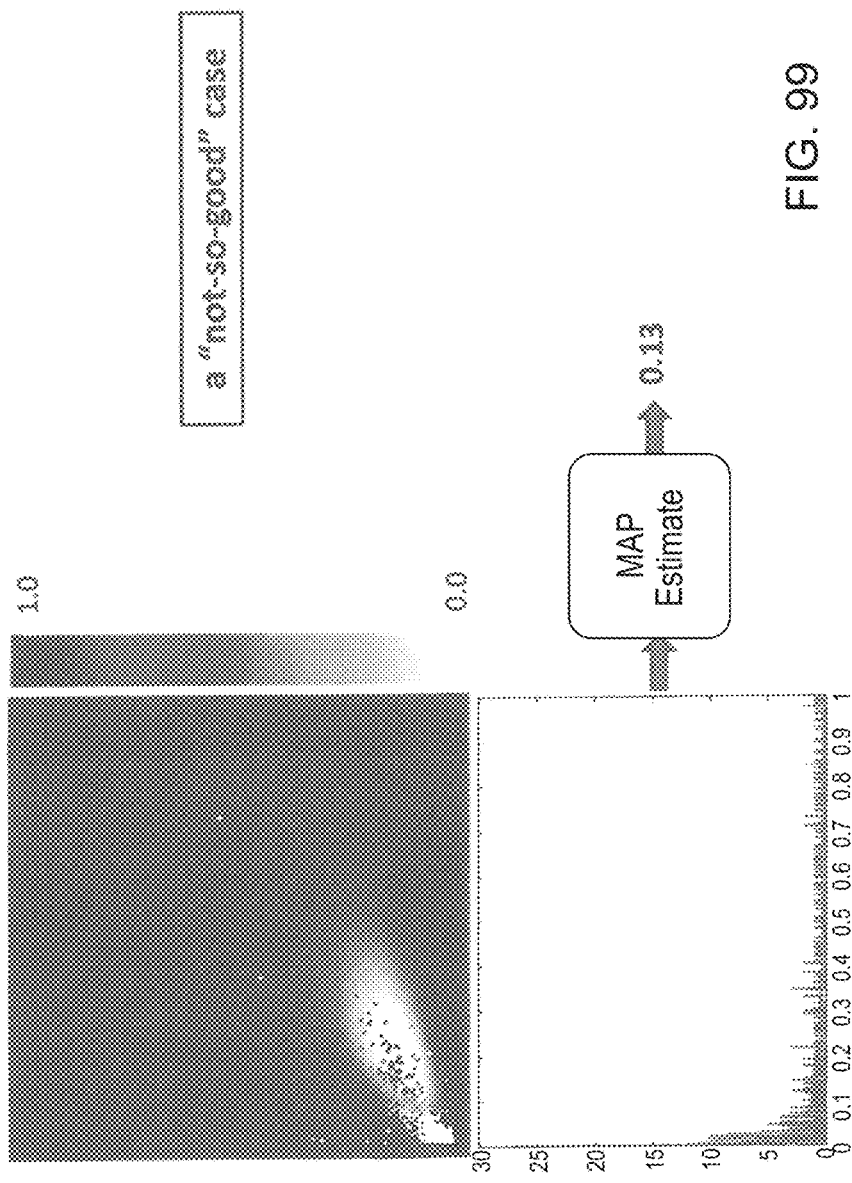

FIG. 99 illustrates a test run showing a poor case for the *Enterobacter* probabilistic model, with most of the imaging emanating from noise.

Figure 100:
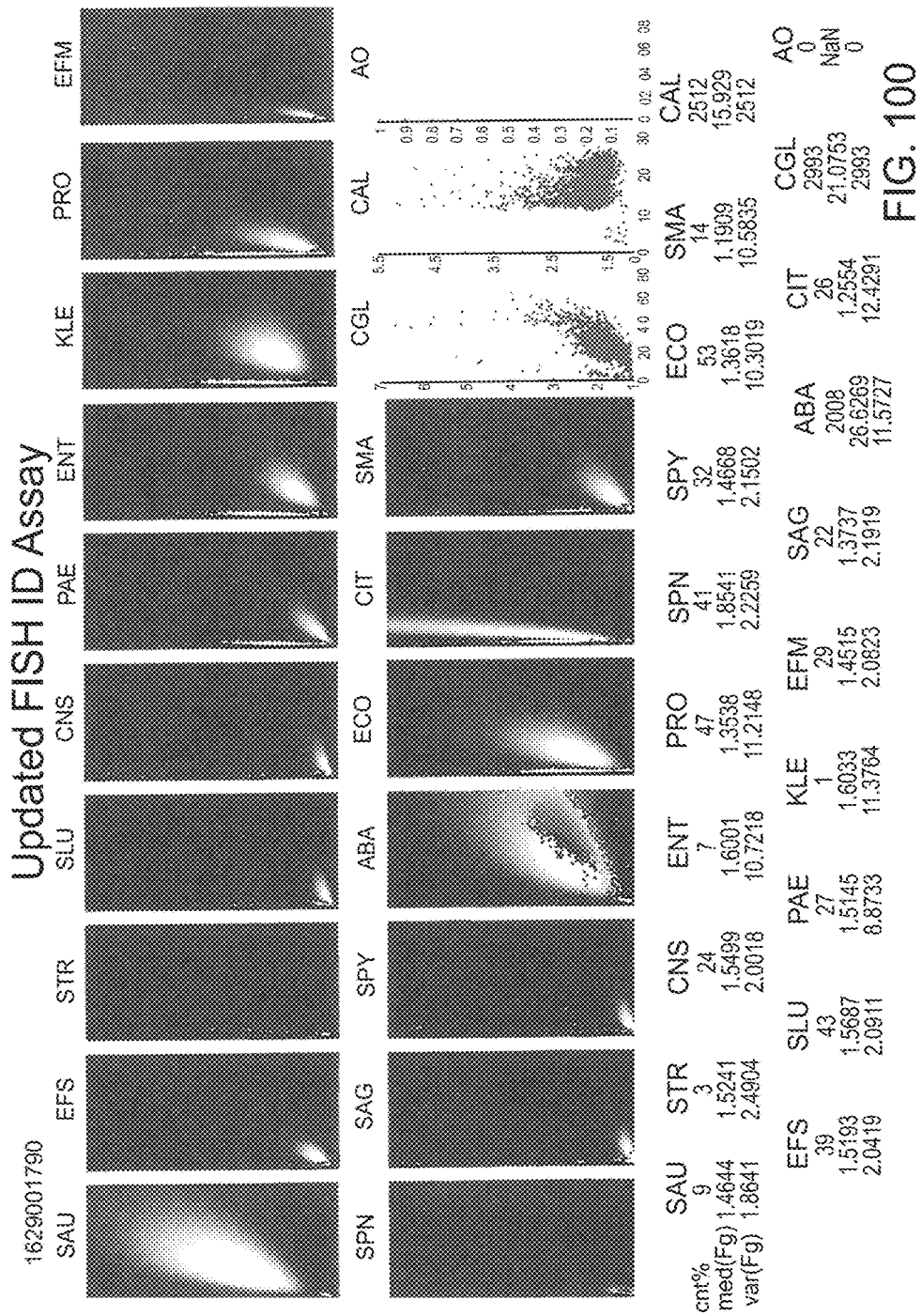

FIG. 100 illustrates an updated version of the distribution expectation model. Additional microorganisms are included in the reference panel over the prior version shown in FIG. 94.

Figure 101:
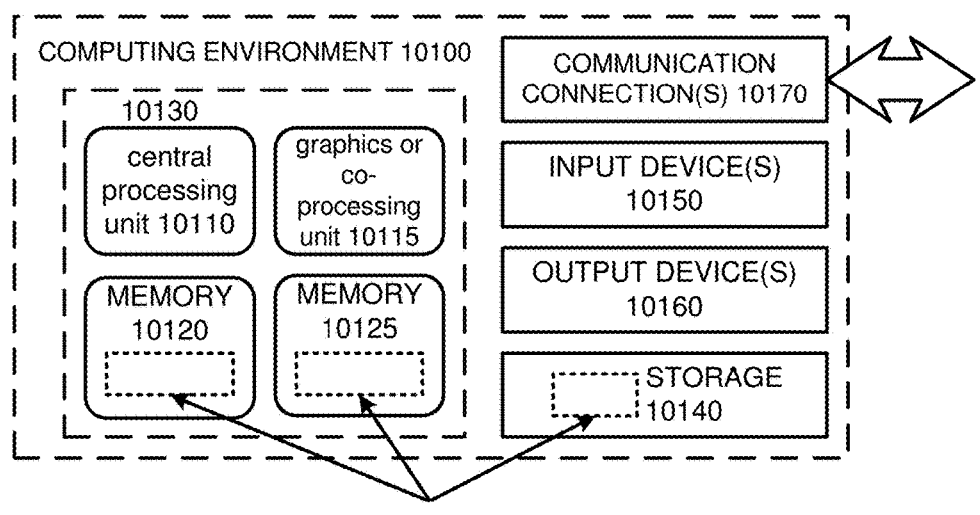

FIG. 101 depicts a generalized example of a suitable computing environment in which the described innovations may be implemented.

Figure 102:
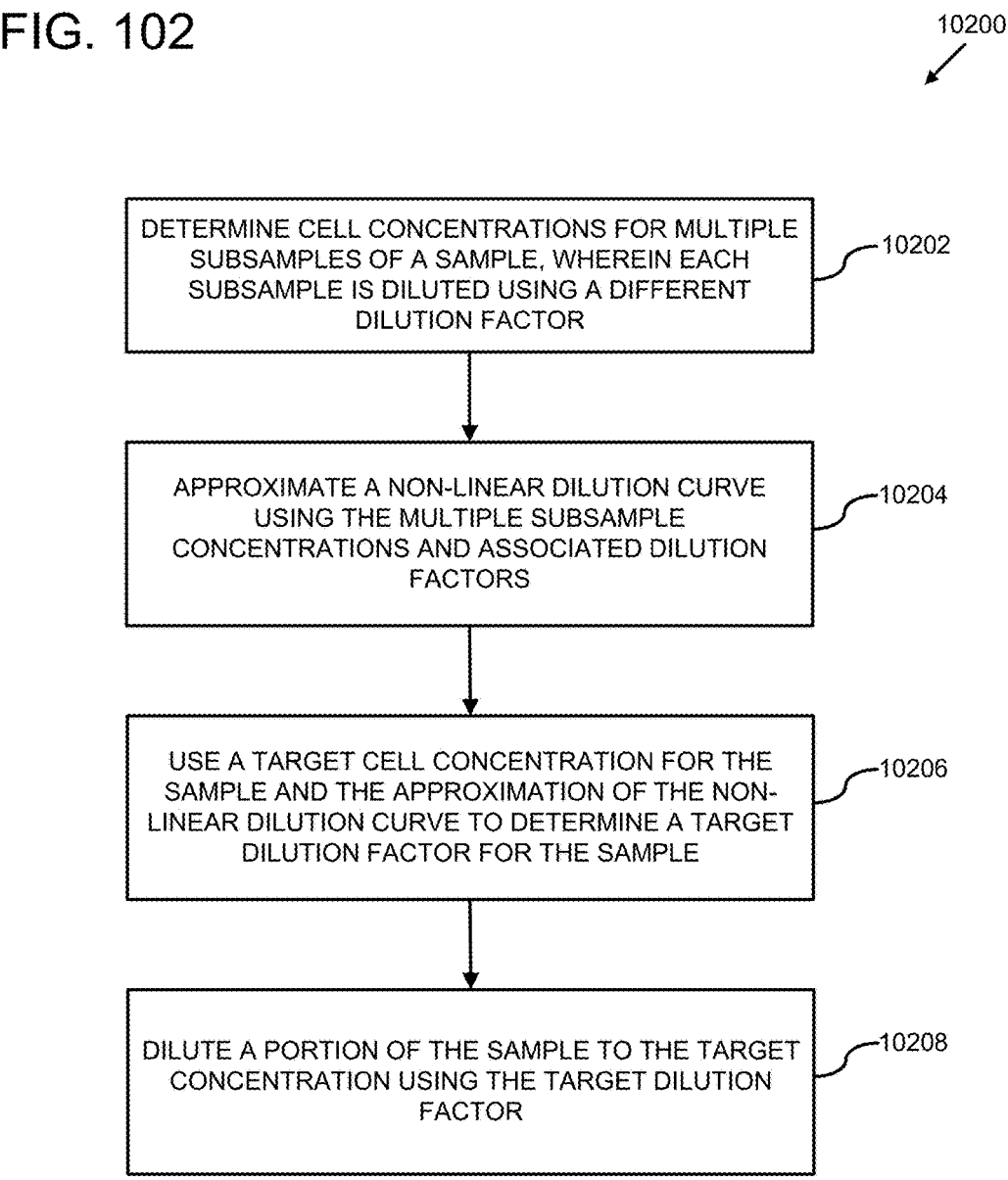

FIG. 102 is a flowchart of an example method of determining a target dilution factor using dynamic dilution and diluting a sample using the target dilution.

Figure 103:
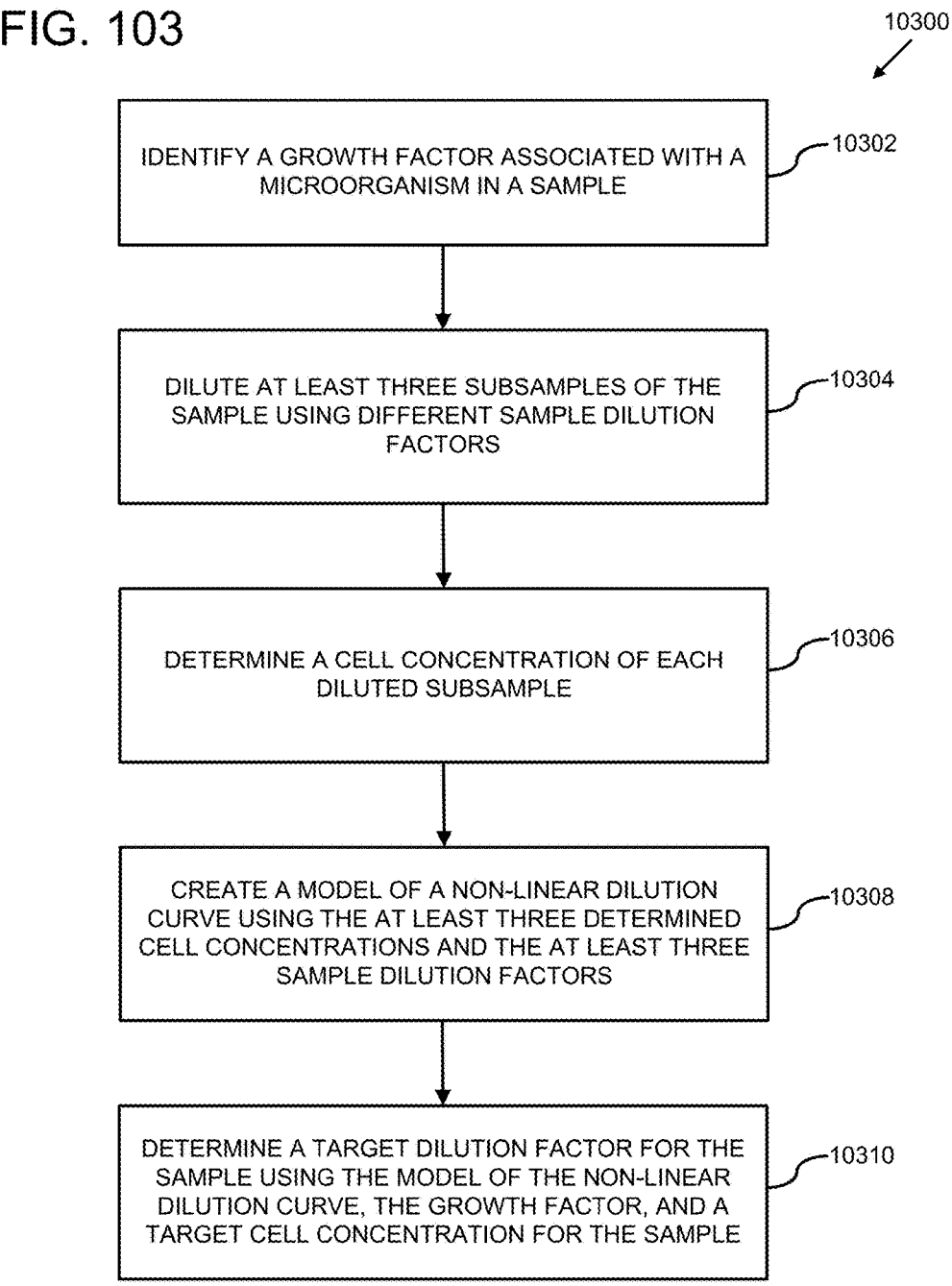

FIG. 103 is a flowchart of an example method of determining a target dilution factor for a sample using a growth factor.

Figure 104A:
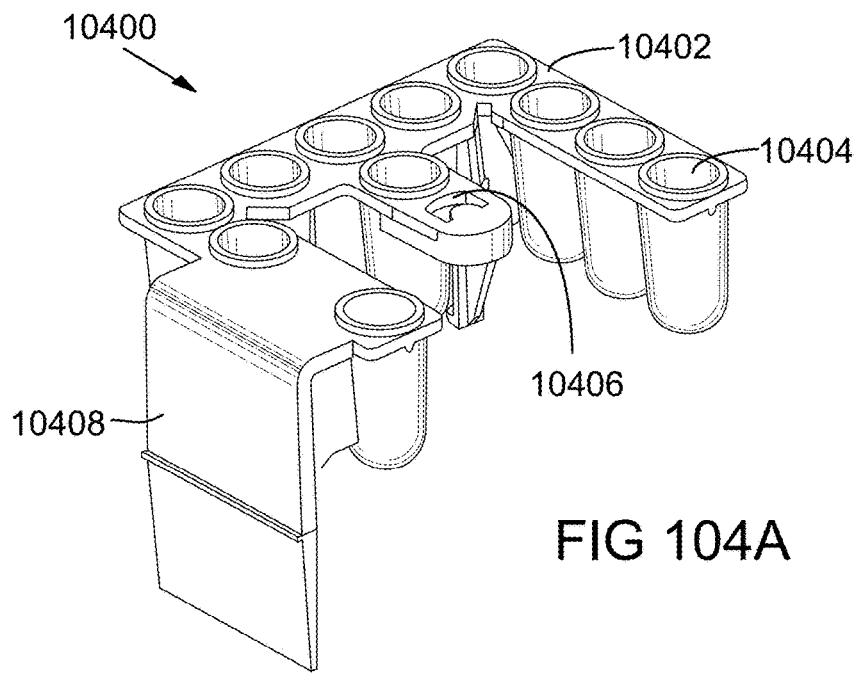

FIG. 104A is a perspective view of an exemplary ID QC test component.

Figure 104B:
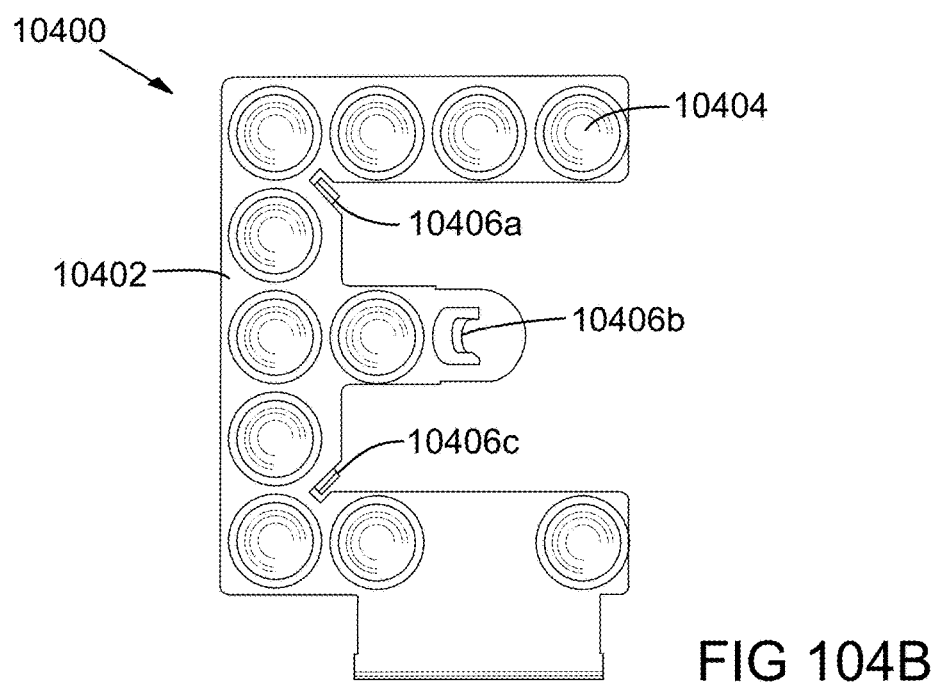

FIG. 104B is a top view of the ID QC test component shown in FIG. 104A.

Figure 104C:
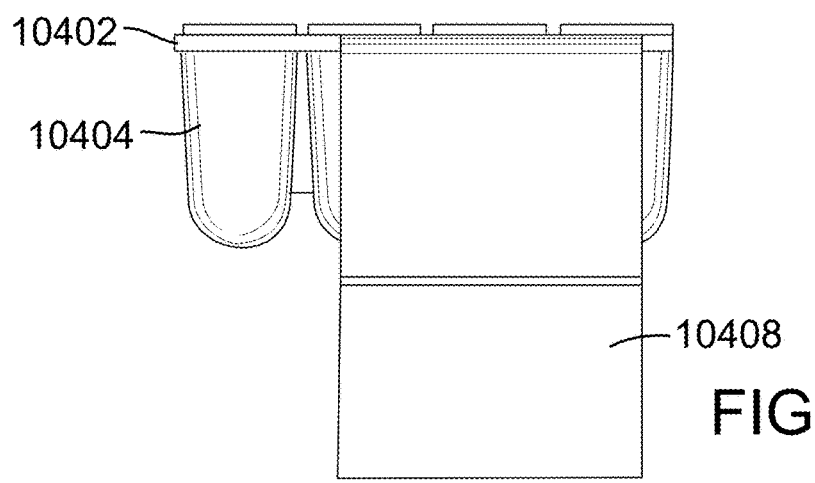

FIG. 104C is a side view of the ID QC test component shown in FIG. 104A.

Figure 104D:
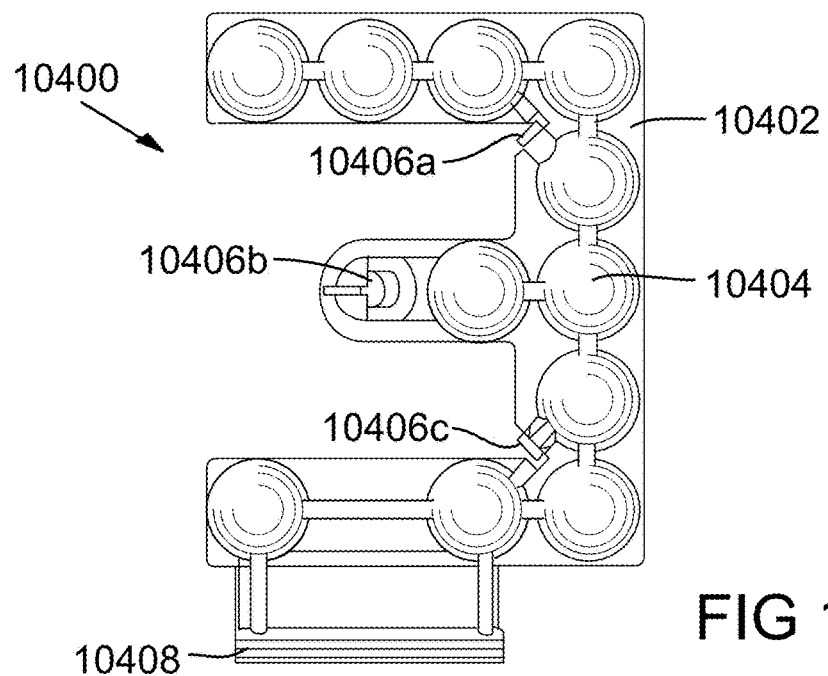

FIG. 104D is a bottom view of the ID QC test component shown in FIG. 104A.

Figure 105A:
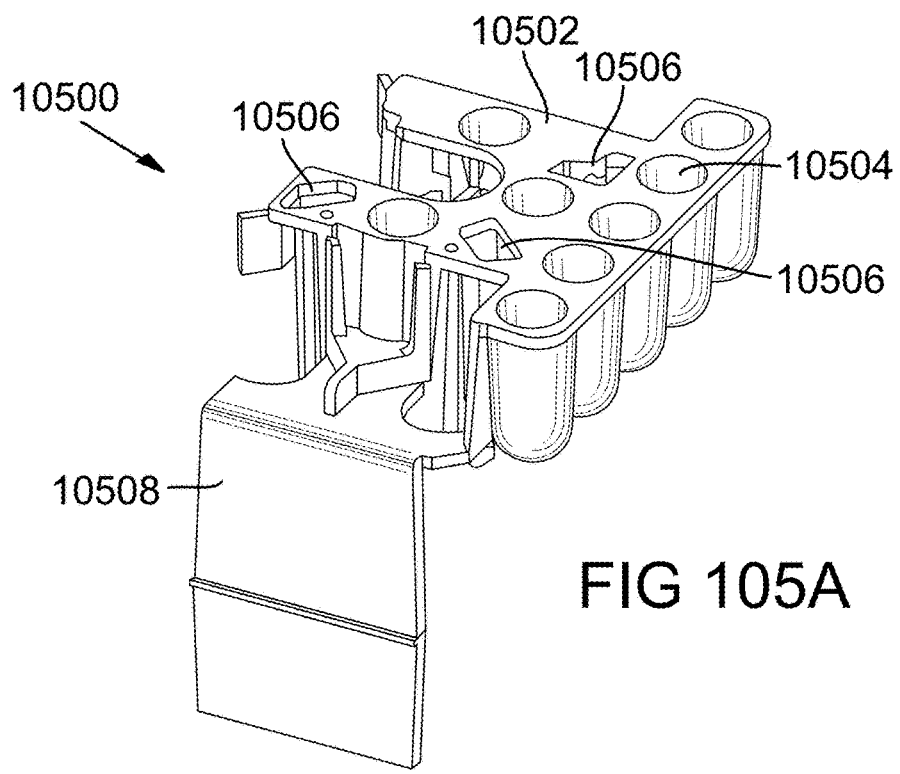

FIG. 105A is a perspective view of an exemplary AST QC test component.

Figure 105B:
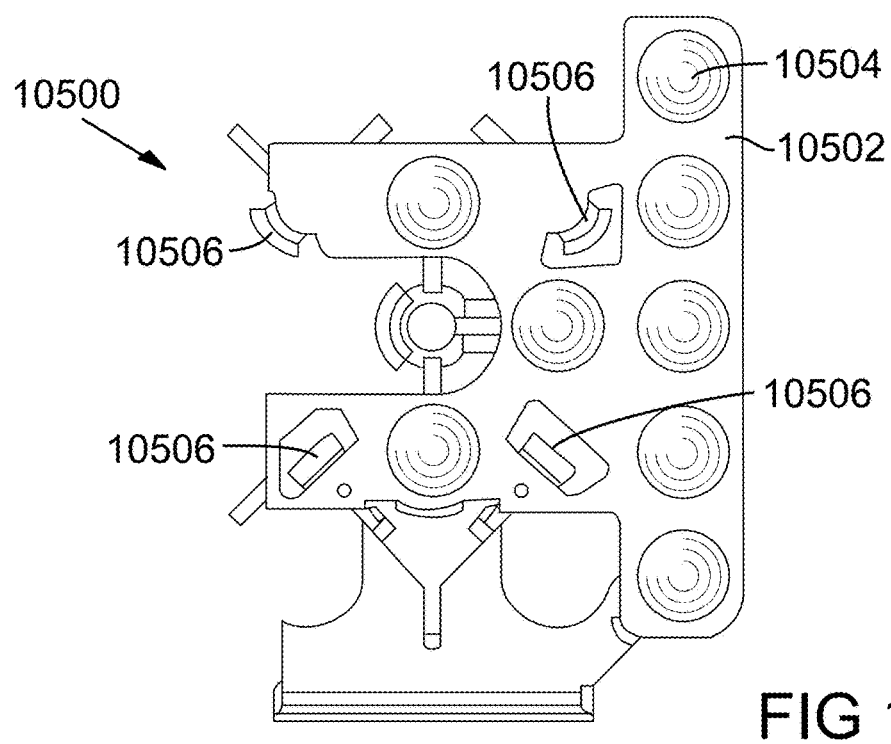

FIG. 105B is a top view of the at QC test component shown in FIG. 105A.

Figure 105C:
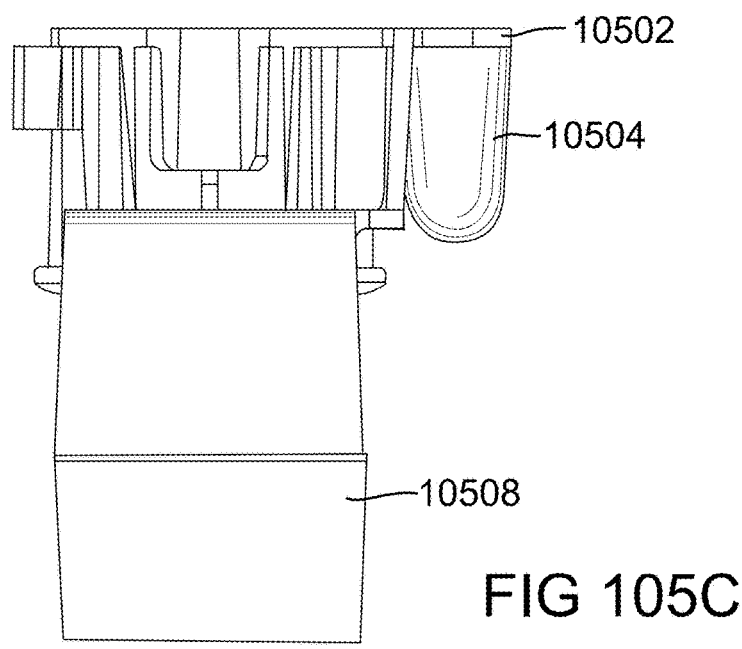

FIG. 105C is a side view of the AST QC test component shown in FIG. 105A.

Figure 105D:
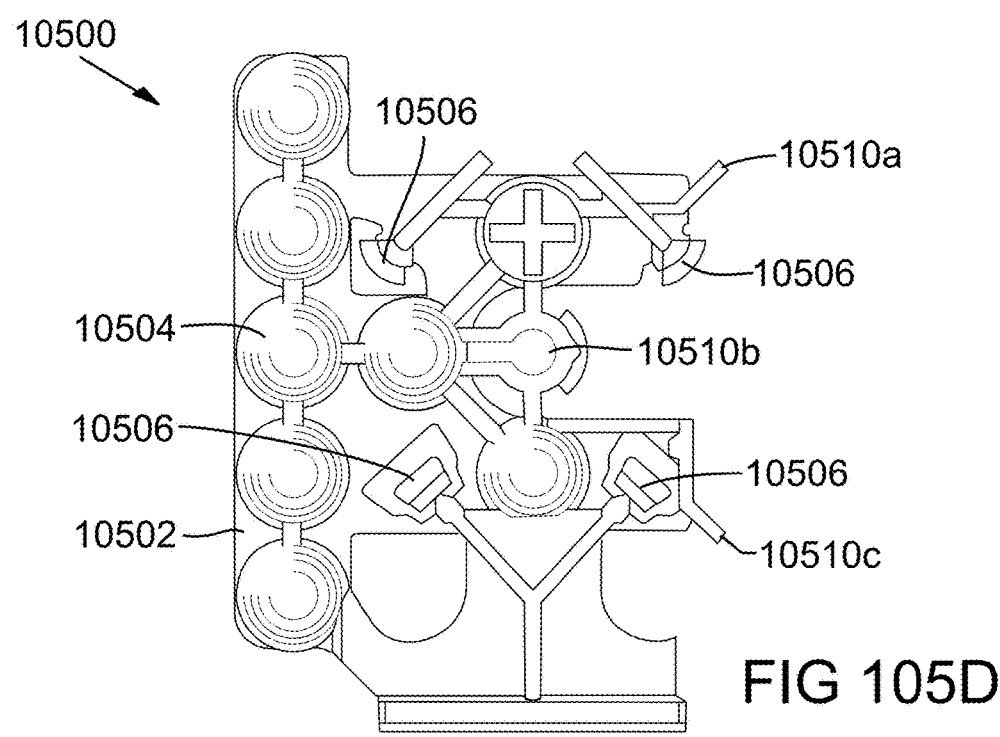

FIG. 105D is a bottom view of the AST QC test component shown in FIG. 105A.

Figure 106A:
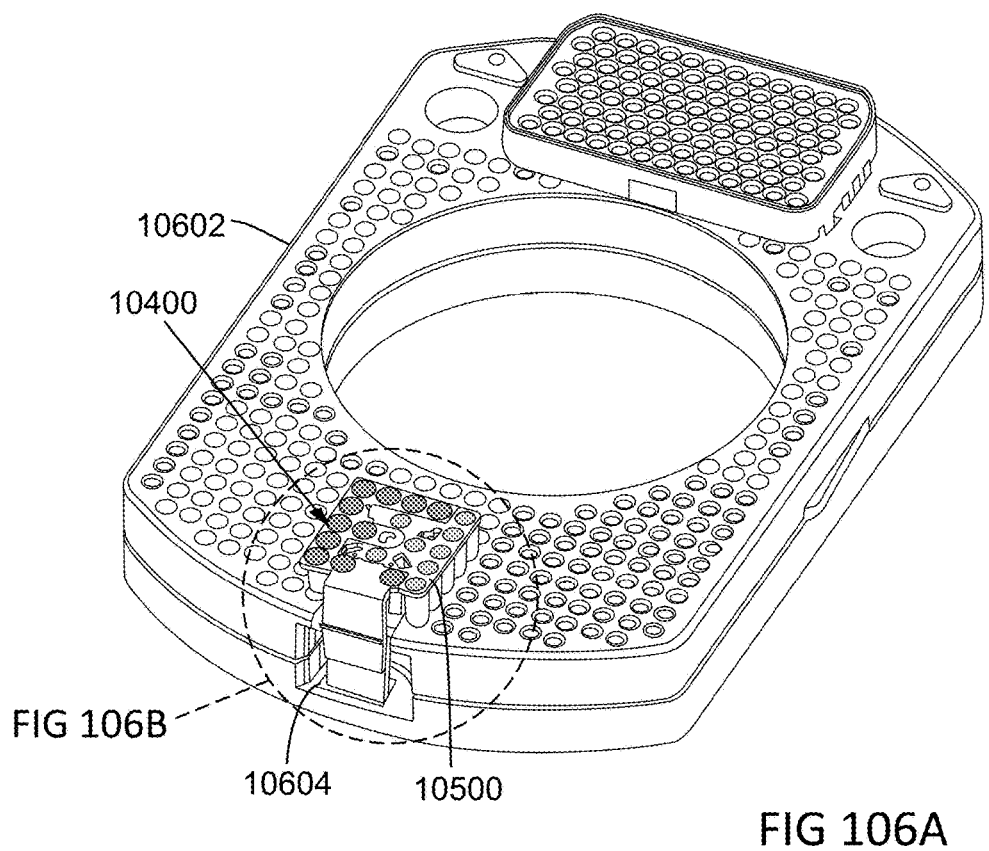

FIG. 106A is a perspective view of an exemplary reagent cartridge with the ID QC and AST QC test components inserted in place of a sample vial.

Figure 106B:
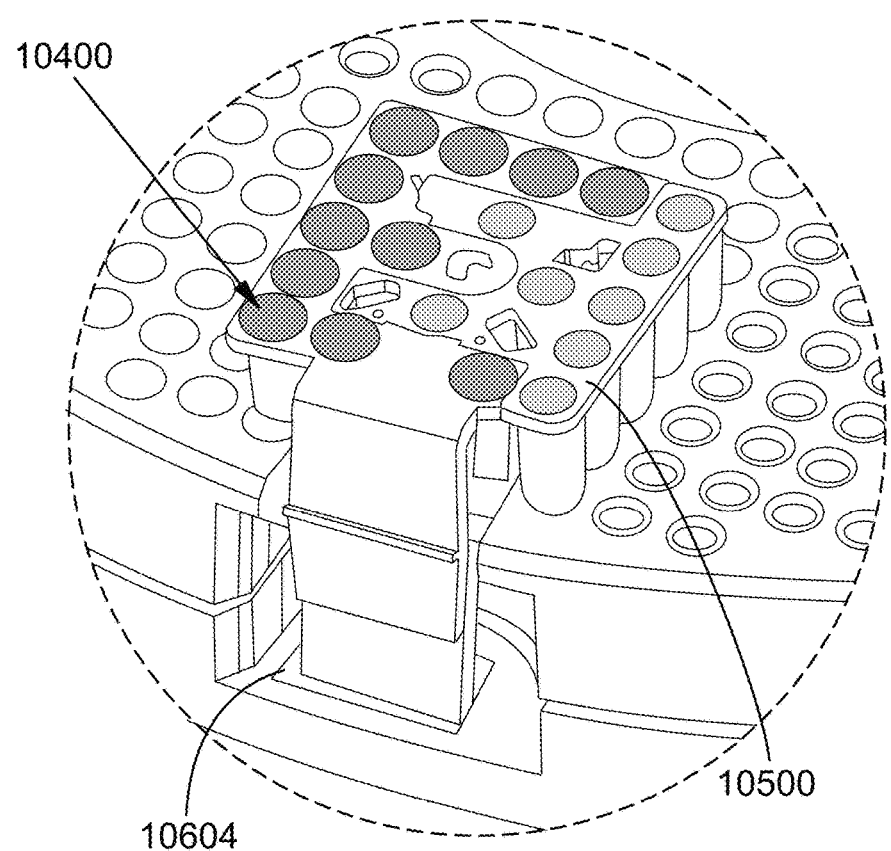

FIG. 106B is a close-up of the circled portion of FIG. 106A.

Figure 107:
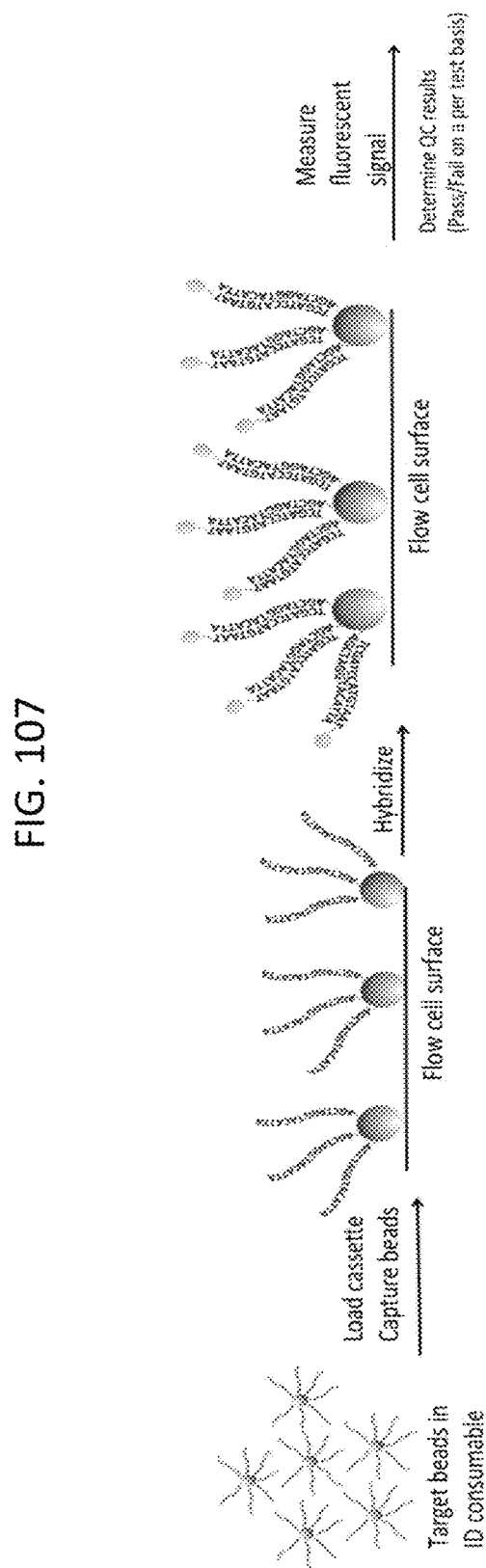

FIG. 107 is a schematic diagram showing an exemplary method of microorganism detection in an ID QC test using microbial specific sequences coupled to polymer microspheres. The schematic illustrates a random sequence as the target sequence coupled to microspheres (SEQ ID NO: 1) and which is complementary to a probe sequence (SEQ ID NO: 2). Any target sequence specific to a microbe of interest and a complementary probe sequence can be utilized in the assays disclosed herein.

FIG. 108 is a schematic diagram showing arrangement of an exemplary ID QC and AST QC test components for ID QC testing, when inserted into a reagent cartridge. Exemplary reagents for use in an ID QC test are depicted.

FIG. 109 is a schematic diagram showing arrangement of an exemplary ID QC test component in relationship to an exemplary AST QC test component when inserted into a reagent cartridge. Exemplary reagents for AST QC testing are depicted in shaded wells. When only an AST QC test is required, the AST QC insert is affixed to the reagent cartridge for use in the instrument without the ID QC insert.

SEQUENCE LISTING

Any nucleic acid and amino acid sequences listed herein or in the accompanying sequence listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Sep. 29, 2016, and is 1494 bytes, which is incorporated by reference herein.

SEQ ID NO: 1 is an exemplary target nucleic acid sequence.

SEQ ID NO: 2 is an exemplary probe nucleic acid sequence, which is complementary to SEQ ID NO: 1.

DETAILED DESCRIPTION

The detailed description of exemplary embodiments herein makes reference to the accompanying drawings, which show exemplary embodiments by way of illustration and their best mode. While these exemplary embodiments are described in sufficient detail to enable those skilled in the art to practice the inventions, it should be understood that other embodiments may be realized and that logical, chemical, and mechanical changes may be made without departing from the spirit and scope of the inventions. Thus, the detailed description herein is presented for purposes of illustration only and not of limitation. For example, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

As used herein, "AST" is antimicrobial susceptibility testing, antimicrobial agent susceptibility testing, or antibiotic susceptibility testing.

As used herein, "FISH" is fluorescence in situ hybridization.

As used herein, "EKC" is electrokinetic concentration. EKC is a process of applying an electrical field to microbial cells suspended in a fluid to produce migration of the cells toward the surface of a positive electrode.

As used herein, "GEF" is gel electrofiltration. GEF is a process of sample preparation that relies on application of an electrical field to cause sample debris present in a sample to be separated from microorganism cells.

As used herein, "ID" is identification, such as a process of determining the species identity of a microorganism, for example, using FISH.

As used herein, "ITO" is indium tin oxide.

As used herein, an "LED" is a light emitting diode.

As used herein, "MHA" is Mueller Hinton Agar.

As used herein, "MLSb" is macrolide-lincosamide-streptogramin B resistance.

As used herein, "MRS" is methicillin-resistant staphylococci.

As used herein, "MRSA" is methicillin-resistant *Staphylococcus aureus*.

Overview of Methods and System

Patient samples, such as blood samples, are the primary biological starting point for assessing the etiology of a patient's disease and determining the appropriate therapy course for treating that disease. Key to reducing morbidity and mortality is initiating the proper therapeutic treatment of a critically ill patient at the appropriate dosage regimen as soon as possible. The historically weak link in this process is sufficient cultivation of a microbial population to enable identification of pathogen(s) present and to determine which antimicrobial compounds the pathogen(s) will respond to in therapy. Reducing the assay time required to properly identify microorganism(s) in a patient sample and assess their drug sensitivity is crucial to improving patient survival odds.

In many instances, patient samples contain multiple types of microorganisms, such as mixtures of bacteria from differing genera, species, and even strains (also known as "polymicrobial" samples). Diagnostic accuracy is traditionally expressed in terms of sensitivity and specificity. Sensitivity refers to the probability of assigning a diagnostic test as positive when it is in fact, positive (the fraction of true positives), which confound the identification and antimicrobial sensitivity processes. The counter to sensitivity is specificity, which is the rate of obtaining false negative test results. Current methods of identifying unknown microorganisms are prone to failure in both false positive and false negative modes. These difficulties with sensitivity and specificity are typically fostered by factors that impede sample detection, such as noise, crosstalk, borderline resistance, and the like. Traditional analysis methods often trade sensitivity of detection for the specificity of microorganism identification. In other applications, the reverse is true, prioritizing sensitivity over accurate microorganism identification. But to maximize efficiency, and thus improve the odds of achieving a better treatment outcome for the patient, both sensitivity and specificity need to be enhanced in balance when using a rapid, automated testing system.

Traditional methods for identification (ID) and antimicrobial susceptibility testing (AST) of organisms from clinical specimens typically require overnight subculturing to isolate individual species prior to biochemical assay-based identification, followed by growing isolated organisms in the presence of various antimicrobials to determine susceptibilities. Molecular identification methods can provide organism identification in a few hours directly from clinical specimens as well as resistance marker detection, but these methods do not provide the antimicrobial susceptibility information required by clinicians to inform treatment decisions. Studies demonstrating the feasibility of using various sample types including whole blood and respiratory samples have been reported, but sample preparation techniques require further refinement. Current rapid molecular-based diagnostic methods only report identification and genotypic resistance marker results. While available in a couple of hours, these results only provide a partial answer. This leaves the clinician to prescribe overly-broad spectrum empiric therapy while waiting two to four days for conventional antibiotic susceptibility test results before adjusting therapy. The availability of an antimicrobial susceptibility test result in as few as 5 hours or less, as opposed to a few days, could potentially decrease morbidity and mortality in critically ill patients due to delays in administration of appropriate therapy. In addition, rapid de-escalation from broad-spectrum empiric therapies to targeted specific antimicrobials could assist antimicrobial stewardship efforts to decrease the emergence and spread of multi-drug resistant organisms (MDROs).

Rapid methods for identification and genotypic resistance marker detection currently exist. However, absent a rapid method for antimicrobial susceptibility testing, clinicians lack fully actionable results from such tests. Assays for the detection of additional resistance phenotypes such as heterogeneous vancomycin-intermediate *S. aureus* (hVISA), extended-spectrum beta-lactamase (ESBL), and *Klebsiella pneumoniae* carbapenemase (KPC) have been reported. Nonetheless, such processes known in the art are insufficient to efficiently and accurately identify microbial populations in a patient sample—especially polymicrobial populations—particularly when the identification process is undertaken in a direct-from-sample manner.

To address these problems, massively multiplexed automated single cell digital microscopy was developed as a fully automated, microscopy-based method that can in some embodiments perform bacterial/yeast identification in about one (1) hour and antimicrobial susceptibility testing in about five (5) or fewer hours directly from clinical specimens. Various embodiments disclosed herein set forth a massively multiplexed automated single cell digital microscopy system employing a process that applies a Fluorescence In Situ Hybridization (FISH)-based detection protocol for the identification of microorganisms in patient samples, whether the target sample is composed of a single, or mono-microbial population or a mixed, polymicrobial population. To achieve this in an automated detection system, the system uses sufficient information about typical or "expected" reference sample microbe populations (such as a reference panel of known microorganisms) in order to be "trained" to establish baseline expectations for typical patient samples subjected to FISH analysis. Once trained, the automated system can apply the baseline parameters to evaluate a patient sample of unknown composition with sufficient confidence that microbial cells can be identified from sample contaminants. The relevance between unknown microbes in a sample and members of a reference panel is assessed statistically. Thus, by application of a unique identification algorithm to FISH images, the identity of unknown microorganisms can be achieved without specific a priori knowledge of the type or types of organisms present in a patient sample. And the process can be performed on multiple samples loaded into a single disclosed instrument, making microbial identification highly accurate and efficient.

The methods and systems described herein provide for microbial identification through a process that combines FISH labeling of unknown microbes and analysis of that binding by Bayesian statistical methodology using probability distribution established by system training. This approach enables better discrimination of microorganisms of interest from interfering noise and/or other microorganisms than is afforded by more traditional methodologies. These benefits are realized without impairing detection sensitivity or specificity. This improved technology avoids many of the pitfalls that beset "Frequentist" logic, which entails setting single a discriminatory value in order to minimize Type 1 errors (rejecting the null hypothesis when it is in fact true) and Type 2 errors (not rejecting the null hypothesis when in fact the alternate hypothesis is true). The methods and systems disclosed herein provide a process by which microorganisms may be discriminated and/or identified by species and/or type. To achieve this end, various embodiments utilize FISH as a tool for visualizing targeted microorganisms. Bayesian analysis is coupled with a model derived from accumulating an extensive data set to define the characteristics/descriptors to be employed in microbial identification and sensitivity testing. The identity of unknown organisms is assessed in part by calculating a probability that determines the likelihood that sequences in an unknown organism are complementary to FISH probes directed to known reference organism sequences. The assessment includes assigning a posterior probability for one or more reference microorganisms given the observed probe binding of unknown organisms in a patient sample. This probability is Bayesian in nature, which assesses the likelihood of the identity of the unknown microorganisms. Once the microbial pathogens in a patient sample have been identified, the FISH results (both counts and actual posterior probabilities) will steer or direct AST sub-population analysis.

In aspects of the disclosure, an ID/AST System (identification/antimicrobial susceptibility testing) that provides identification and susceptibility results in a few hours directly from patient samples is provided. In some embodiments, the disclosed ID/AST system provides clinicians information to make patient treatment decisions in a timely manner In some embodiments, an ID/AST system as described herein may aid antimicrobial stewardship efforts and lead to improved patient outcomes.

In specific aspects of the disclosure, assays for detecting methicillin-resistant *Staphylococcus aureus* (MRSA), methicillin-resistant staphylococci (MRS), macrolide-lincosamide-streptogramin b resistance (MLSb), and high-level aminoglycoside resistance (HLAR) are provided.

System Overview

The system as disclosed herein may be exemplified in various embodiments by Accelerate Diagnostics Instrument Model AD-1 ("AD-1"). The disclosed AD-1 instrument analyzes samples derived from various types of biological specimens, such as blood (or a fraction thereof, such as plasma or serum), respiratory samples (such as bronchoalveolar lavage, sputum, oropharyngeal swab, or nasopharyngeal swab), urine, etc., to perform identification (ID) of the species of bacteria present in the sample as well as to determine the susceptibility of the bacteria to various antibiotics from a panel of antibiotics (e.g., antibiotic susceptibility testing, or "AST"). The disclosed instrument is configured to perform these processes rapidly in an automated fashion that does not require user intervention following preparation of the sample and initiation of an analytical run. The instrument comprises an outer housing and a base assembly. The base assembly supports a reagent stage, a cassette stage, a pipettor assembly for fluid handling, and an illumination and optics assembly for imaging the sample. An attached system controller is configured to receive input and provide output, run the instrument, and store and process image data acquired by the system. The system also comprises a reagent cartridge that contains all reagents and consumables required by the instrument during a run as well as the cassette used to perform the ID and AST steps and facilitate microorganism visualization and image acquisition by the instrument's illumination and optics assembly. In operation, a user prepares a sample to be analyzed using the system and places a portion of the sample in a sample vial provided as part of the reagent cartridge. The user places the sample vial containing the sample in position in the cartridge, inserts the cartridge into the reagent stage of the instrument, inserts a cassette into the cassette stage, and presses a button on the instrument to initiate the ID and AST analyses, which the instrument and system can generally complete within 8 hours or less, such as less than about 5 hours (such as 4 to 8 hours, 4 to 6 hours, or 5 to 6 hours).

Each of the instrument components and the separate system components as well as the method of operation of the instrument and system are described in greater detail below.

Outer Enclosure and Base Assembly

Figure 1:
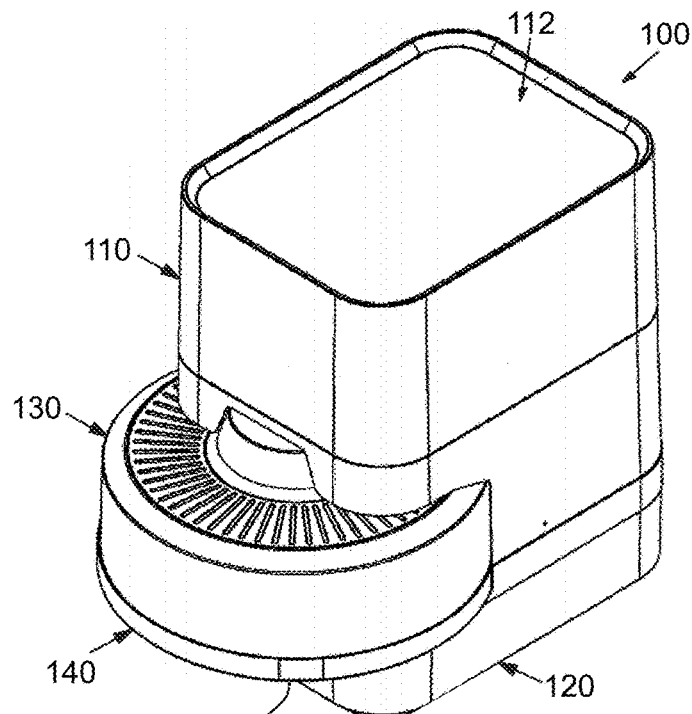
FIG. 1 is a perspective view of the instrument.

Referring to FIG. 1, a perspective view of an instrument 100 is illustrated according to various embodiments. The instrument 100 may comprise an upper enclosure 110, a lower enclosure 120, a door 130, and a base assembly 140. The upper enclosure 110 may enclose and protect many of the instrument components, such as the illuminator, the pipettor, and the controller. The upper enclosure 110 may comprise a rigid and lightweight material, such as plastic, aluminum, or a composite material. The upper enclosure 110 may be generally rectangular with rounded corners. However, those skilled in the art will appreciate that the upper enclosure 110 may be any suitable shape. The upper enclosure 110 may comprise a flat top side 112.

The upper enclosure 110 may comprise an opening for a door 130. In various embodiments, the door 130 may be generally cylindrical or frustoconical. The instrument 100 may comprise a button 150 which causes the door 130 to open or close. In the illustrated embodiment, the button 150 is located in a base assembly 140 of the instrument 100. However, the button 150 may be located at any suitable position on the instrument 100. In response to a user pushing the button 150, the door 130 may rotate to an open position.

Figure 2:
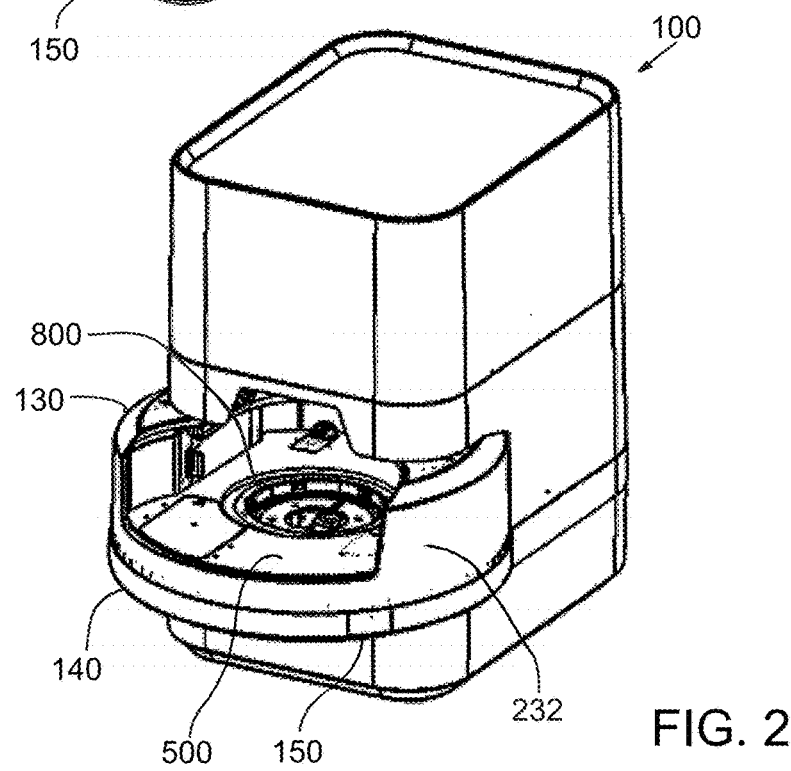
FIG. 2 is a perspective view of the instrument with a door in an open position.

Referring to FIG. 2, a perspective view of the instrument 100 with the door 130 in the open position is illustrated according to various embodiments. The door 130 may rotate to open or close. The door 130 may be driven by an electric motor. The door 130 may comprise a cut out section 232 configured to receive a cartridge which contains reagents and a specimen. A user may also insert a cassette through the open door 130. A user may insert a cartridge and cassette through the cut out section 232 of the door 130, and press the button 150 to close the door 130. In various embodiments, pressing the button 150 to close the door 130 automatically starts the ID/AST process.

Figure 3:
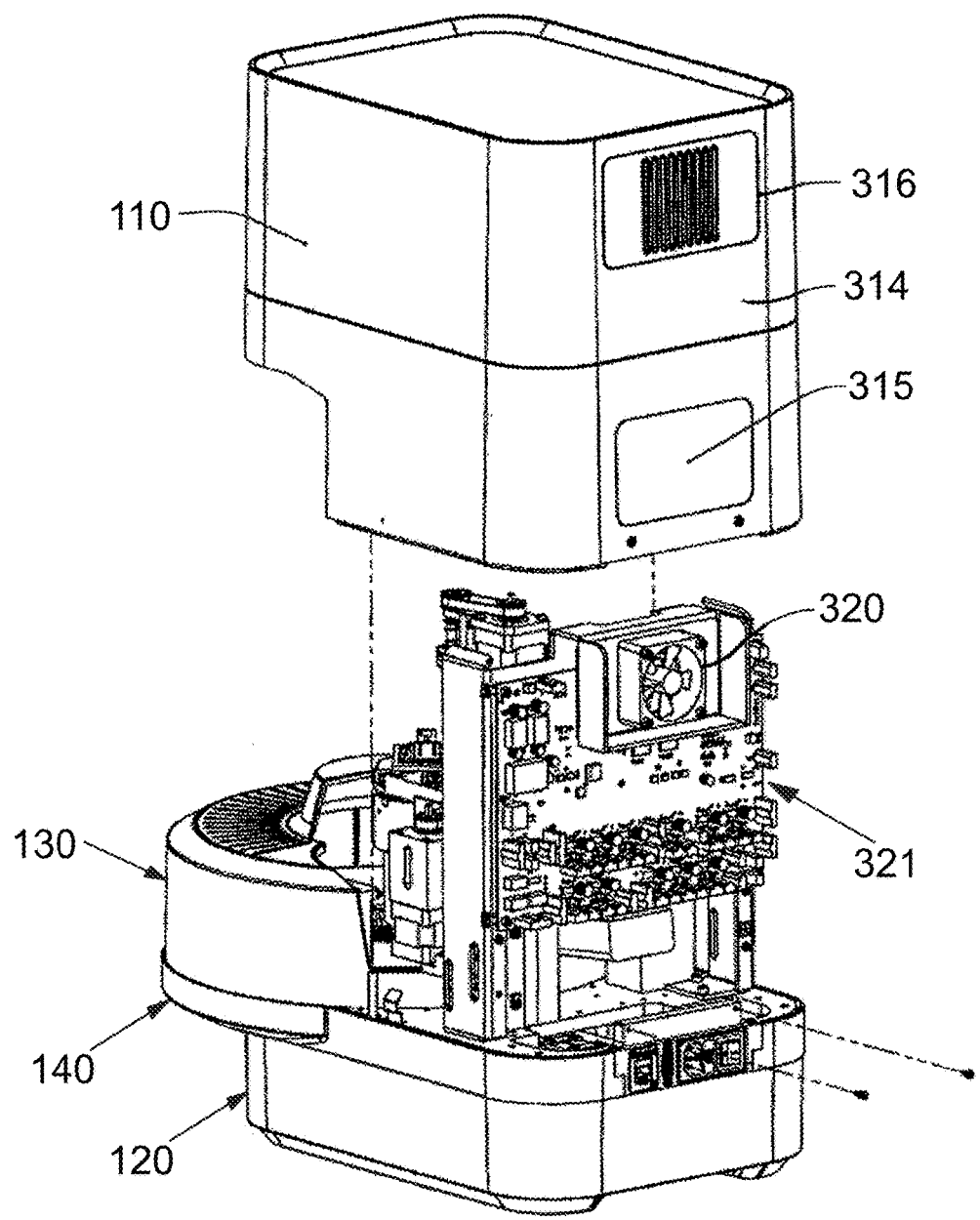
FIG. 3 is a perspective view of the instrument from a rear side and showing the upper enclosure removed from a lower portion of the instrument.

Referring to FIG. 3, a perspective view of a back side 314 of the upper enclosure 110 is illustrated according to various embodiments. The back side 314 of the upper enclosure 110 may comprise an exhaust port 316. The exhaust port 316 may allow an exhaust fan 320 to expel air from within the upper enclosure 110. The exhaust fan 320 may provide cooling to the instrument 100 as needed to maintain precise temperatures. In various embodiments, the upper enclosure 110 may comprise an insulation layer configured to decrease heat escape from the interior of the instrument 100.

Tight control of an instrument's enclosure temperature can be very difficult to achieve using only an exhaust fan, particularly in view of the substantial variations in ambient laboratory temperatures that may exist. Ambient laboratory temperatures may range, for example, from about 16° C. to about 32° C. depending upon geographic location, building heating and cooling controls, and other factors. Moreover, the presence of one or more motors and/or heaters that exude heat in an enclosed instrument generally necessitates the use of a larger exhaust fan than otherwise would be needed for cooling the instrument. Inclusion of a larger exhaust fan necessitates enlargement of the overall size of the instrument, thereby increasing manufacturing costs. Even when an instrument is adjusted to decrease its standard heat load by reducing heat-generating components to a set idle level when not in use, the internal temperature of the instrument may not be sufficiently reduced to ensure that a proper temperature is maintained. Various embodiments of the disclosed instrument provide a solution to this heat problem by dynamically adjusting the heat load of the instrument enclosure through control of waste heat emitted by components in the instrument itself.

In some embodiments, the instrument overcomes this heat problem by controlling its heat-generating components (e.g., motors and heaters) and—if desired—an exhaust fan with a proportional-integral-derivative (PID) controller algorithm. In other embodiments, only heat-generating components may be subject to dynamic control by the PID controller algorithm to alter the housing temperature of the instrument. Each heat-generating component is independent, and the PID values for each are added together to determine the overall heat control needed for the instrument. In other words, an embodiment of the disclosure provides that each heat-generating instrument component be a dynamically controlled feature, such that the combination of PID algorithms adjusts for the total heat output within the instrument housing. In essence, every component that generates heat during operation of the instrument may be subjected to PID algorithmic control. Thus, for example, when each motor in the instrument completes its task during a given sample run, control of the motors may be relinquished in view of the enclosure temperature. In this scenario, the activity of each motor may be increased or decreased as needed to help control the overall instrument housing temperature. Anything that produces waste heat may be subject to this type of control, even an instrument camera. Thus, to further refine the waste heat control of the instrument, a camera may be manipulated to exude more or less heat as needed to control the temperature within the instrument housing. This heat control factor is important, as the instrument may be left on for days or weeks at a time, and the ability to manipulate the waste heat from multiple components during idle time permits finer control of the overall housing temperature. In doing so, instrument components will typically reduce their power usage when in idle mode, which improves the overall energy efficiency of the instrument. Harnessing the waste heat of multiple instrument components in this fashion requires less cycling of motors and fans, thereby extending their useful lifespans. When exhaust fans reduce their cycling, less air intake occurs, which in turn reduces the amount of dust that accumulates inside the instrument.

When each of the motors in the instrument completes its tasks, these components return to an idle power level, where they may remain until called upon to function in a subsequent sample run. The instrument's motors use more power when moving than when idle. However, idle mode does not have to mean that power usage remain static at an arbitrary level. The instrument motors can change their power draw from about 25 watts to as much as about 45 watts at idle to cool or warm the instrument depending upon need in order to match a set point, for example a set point of 31° C. A change of 20-25 watts is equivalent to about a 100-125% increase in waste heat. In various embodiments, the PID controller algorithm employs a power range extending from +100% to −100%. For each stepper motor (or any other heat-generating component), a minimum and a maximum idle torque are established which may then be scaled to fit the 0%-100% range for heat control. In various embodiments, an exhaust fan of the instrument activates in the positive region of this range and the idle torque of a stepper motor activates in the negative region of this range. Thus, for example, in the event of a cool ambient laboratory temperature (when heating is required), the idle torque of a stepper motor activates to generate heat within instrument until the set point temperature is reached. When a desired set point temperature of the instrument is exceeded, the exhaust fan activates and expels heated air through an exhaust port.

Figure 81A:
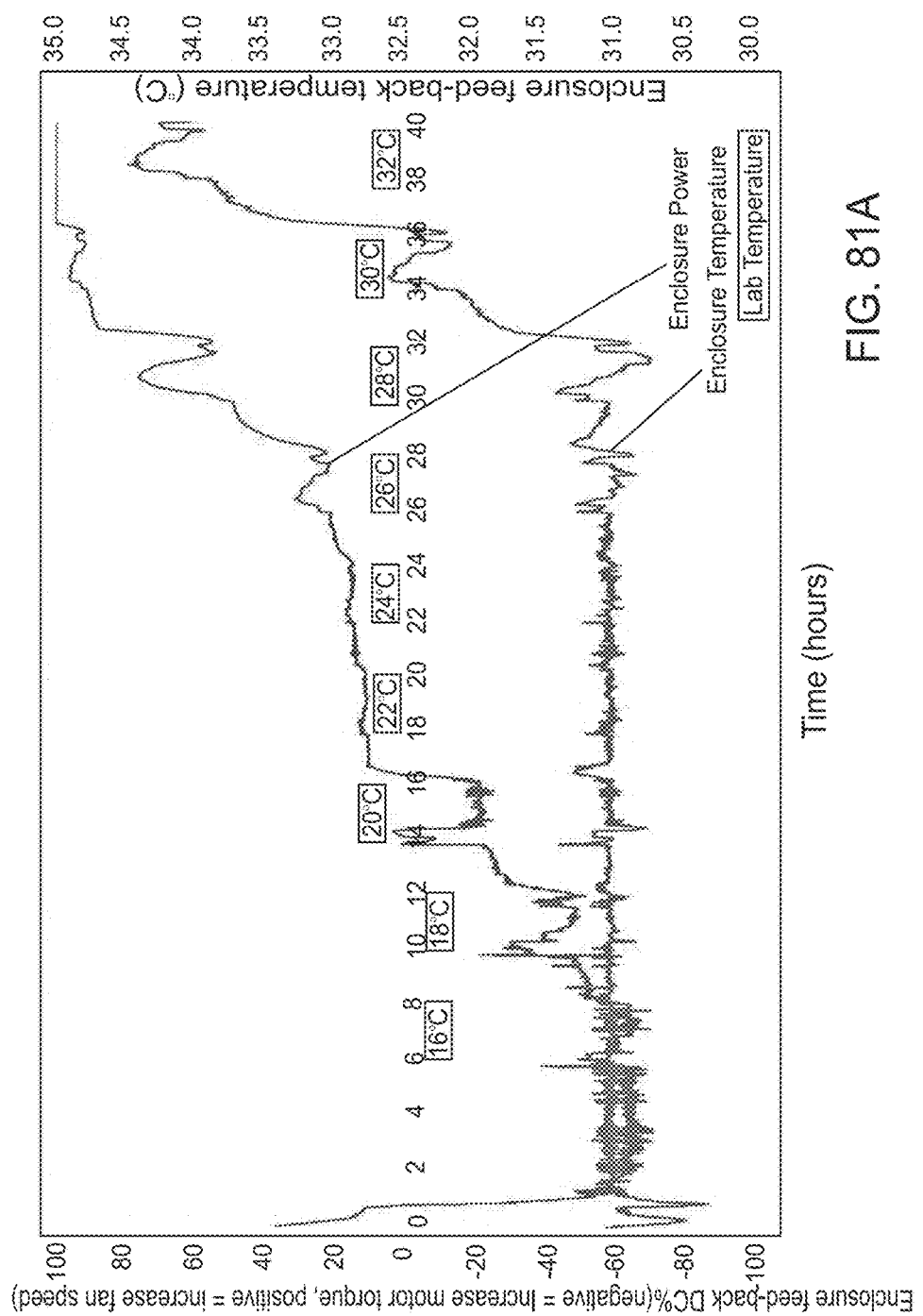
FIG. 81A is a graph showing feedback control of the enclosure temperature.

This concept is further illustrated in FIG. 81A, which graphically depicts the results of a thermal stress challenge to the instrument in an environmental chamber simulating ambient laboratory temperatures ranging between 16° C. and 32° C. The graph plots instrument enclosure power in direct current on the left y-axis against time in hours along the bottom x-axis. The right y-axis sets forth the instrument's enclosure temperature as measured and controlled throughout the experiment using feedback from a thermistor. Following an initial baseline equilibration period, a two-hour simulated assay was run at each equilibrated temperature within the range, with the test temperatures set forth in boxes in FIG. 81A. The enclosure temperature of the instrument was stably maintained at a set point value of 31° C. when exposed to simulated laboratory environment temperatures from below 18° C. to 30° C., as represented by the bottom line. Loss of enclosure temperature control occurred at a simulated laboratory temperature of 32° C., which is visualized by the upper line reaching and holding at the 100% enclosure power mark. At simulated laboratory temperatures below 22° C., the instrument enclosure temperature was controlled by modulation of stepper motor idle torque via a PID algorithm. The cooler ambient temperatures necessitated the generation of additional heat by increasing the motor idle torque (negative enclosure power on the graph), and retaining that heat by not running the exhaust fan of the instrument in order to maintain the set point temperature of 31° C. By contrast, at simulated laboratory temperatures above 22° C., the same PID algorithm drove the expulsion of heated air by increasing the speed of the instrument's exhaust fan (positive enclosure power on the graph). As is evident from the graph, for most of the tested temperatures, the exhaust fan smoothly held the enclosure set point temperature when the ambient temperature reached the threshold for reducing heat output by instrument components and increasing removal of heated air via the exhaust fan. This paired dynamic activity eliminated the need for constant switching on and off of the fan, as is observable in instruments that experience far more dramatic temperature spikes. Thus, the instrument dynamically adjusts motor torque to maintain housing temperature, thereby facilitating slower, more gradual temperature changes within a reasonable ambient temperature range. The overall result is the ability of a smaller fan to perform exhausting functions, which permits the instrument to be constructed in a smaller housing space.

By dynamically altering the waste heat generated by, for example, a motor's adjustable holding torque, fewer and/or smaller parts are incorporated into an instrument (e.g., fewer heaters and/or smaller fans), thus improving instrument reliability. Moreover, by harnessing waste heat on an as-needed basis, power consumption of the instrument decreases in comparison to instruments that do not dynamically control heat sources, thereby improving energy efficiency. Accordingly, exemplary embodiments of the instrument exercise control over enclosure temperature while minimizing the consumption of electrical power.

Figure 4:
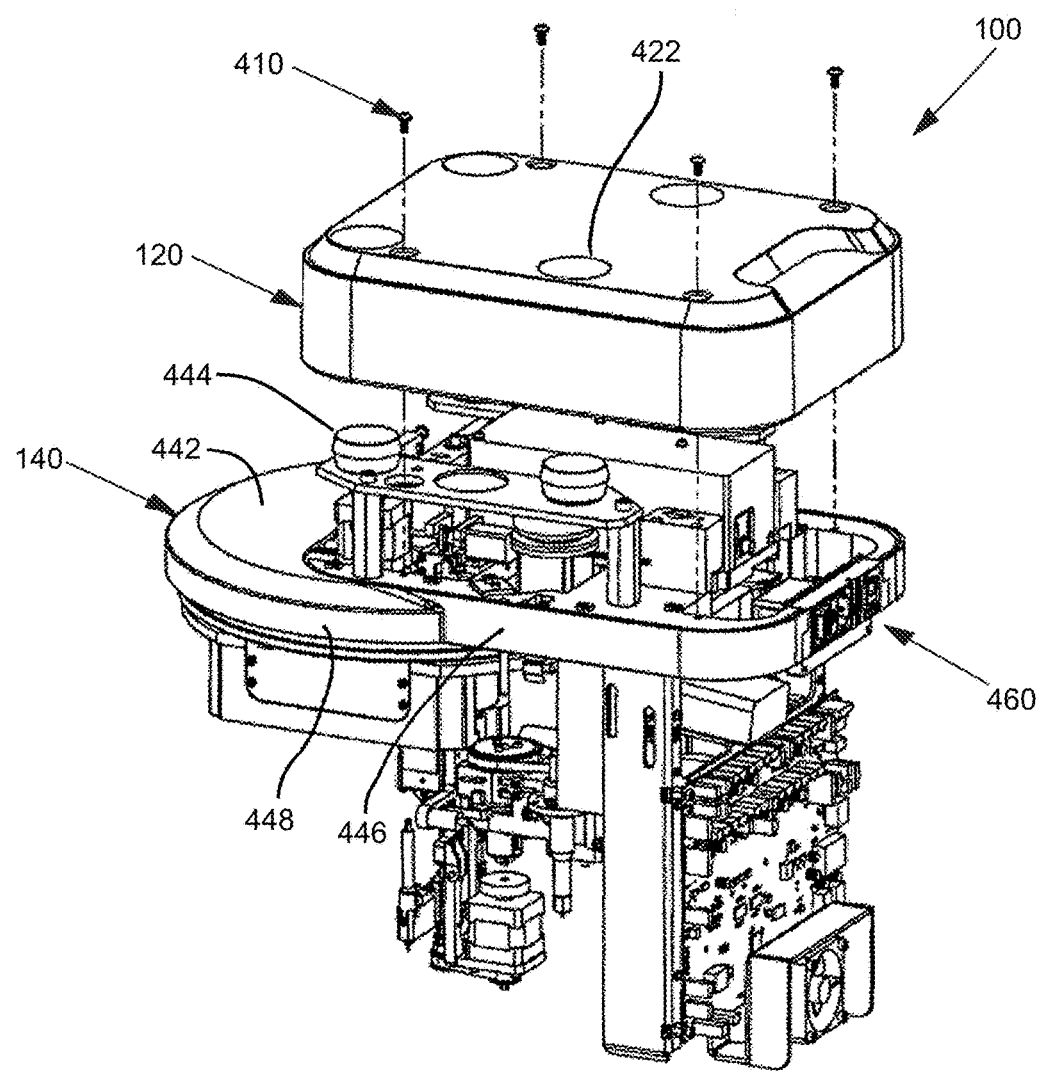
FIG. 4 is a perspective view of the lower portion of the instrument with a lower cover removed.

Referring to FIG. 4, a perspective view of the instrument 100 upside down with the lower enclosure 120 separated from the base assembly 140 is illustrated according to various embodiments. The lower enclosure 120 may enclose and protect various components, such as various optics system components. The lower enclosure 120 may be coupled to a bottom side 442 of the base assembly 140. The lower enclosure 120 may comprise a plurality of apertures 422 configured to receive damping feet 444 which support the instrument 100. The lower enclosure 120 may comprise a rigid and lightweight material, such as plastic, aluminum, or a composite material. The lower enclosure 120 may be generally rectangular with rounded corners. However, those skilled in the art will appreciate that the lower enclosure 120 may be any suitable shape. The lower enclosure 120 and the upper enclosure 110 may be coupled to the base assembly 140 via a plurality of screws 410. However, the lower enclosure 120 and the upper enclosure 110 may be coupled to the base assembly 140 by any of a variety of suitable attachment mechanisms.

A plurality of damping feet 444 may be coupled to the base assembly 140. The damping feet 444 may comprise rubber or a polymeric material which damps vibrations. The various instrument components, such as the reagent stage, cassette stage, optics system, pipettor, and illuminator may be coupled to the base assembly 140. Thus, the base assembly 140, reagent and cassette stages, optics system, pipettor, and illuminator may be vibrationally coupled, such that relative movement between components due to external vibrations is limited.

The base assembly 140 may comprise a rectangular portion 446 and a circular portion 448. The pipettor, the illuminator, and the optics system may be coupled to the rectangular portion 446. A reagent stage and a cassette stage may be coupled to the circular portion 448. The circular portion 448 may be coaxial with the door 130. Thus, when the door 130 is open, a user may insert a cartridge and a cassette through the door 130 and onto the reagent stage and the cassette stage, respectively.

The base assembly 140 may comprise various connection ports 460. For example, the base assembly 140 may comprise a power input, a communication port, and a camera output port. The connection ports 460 may allow the instrument 100 to communicate with a computer or other processor in order to receive commands and output data and other information, such as image data or instrument status information. In various embodiments, the connection ports 460 may allow multiple instruments to communicate with each other.

Reagent Stage

The instrument 100 may comprise a reagent stage which accepts a user-inserted reagent cartridge containing all reagents used during operation, including a sample. Referring to FIG. 2, the reagent stage 500 is coupled to a top side of the base assembly 140. The reagent stage 500 may be enclosed by the door 130. The reagent stage 500 is rotatable about a central axis in order to move reagents within reach of the pipettor.

Figure 5:
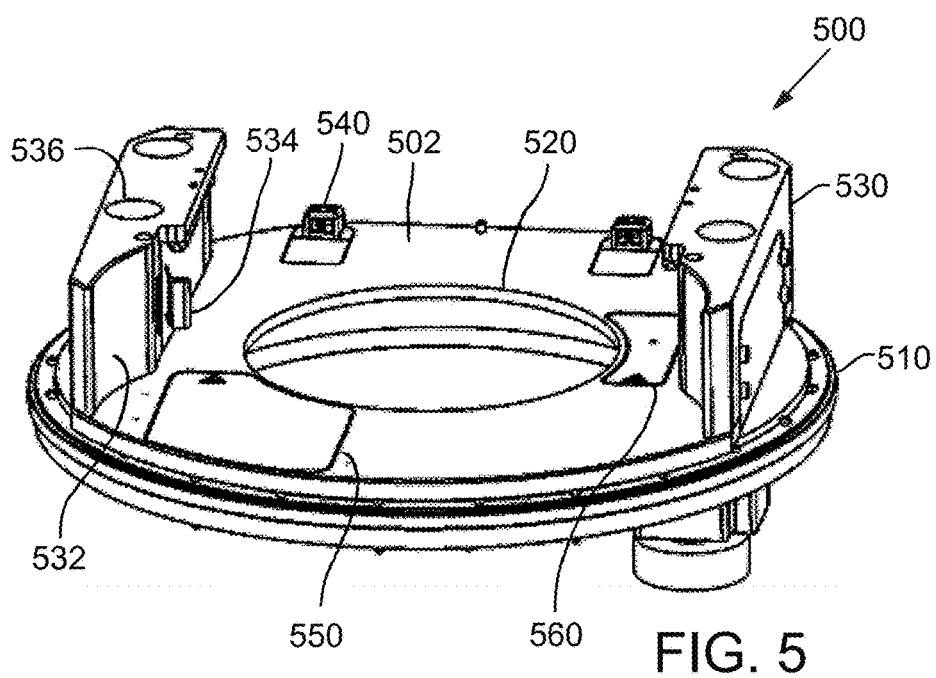
FIG. 5 and FIG. 6 are perspective views of a reagent stage.

Referring to FIG. 5, a perspective view of the reagent stage 500 removed from the instrument 100 is illustrated according to various embodiments. The reagent stage 500 may comprise a generally annular shape with an outer circumference 510 and an inner circumference 520. A pair of alignment walls 530 may be coupled to a top side 502 of the reagent stage 500. The alignment walls 530 may be configured to align a cartridge when inserted into the reagent stage 500 by a user. The alignment walls 530 may comprise curved guide surfaces 532 to direct the cartridge to the proper position as the cartridge is inserted. One or more holding features 534 may be coupled to the alignment walls 530 for precise alignment of the cartridge and to hold the cartridge in place relative to the reagent stage 500. The holding features 534 may snap the cartridge in place when the cartridge is fully inserted to provide an audible and physical indication to the user that the cartridge is fully inserted. The alignment walls 530 may comprise one or more teaching wells 536. The teaching wells 536 may be a cylindrical depression in the alignment walls 530. The teaching wells 536 may be used by the pipettor as a reference point in conjunction with the cartridge in order to allow the system to precisely locate all reagent wells in the cartridge. However, in various embodiments, the pipettor may use teaching wells only in the cartridge, only in the alignment walls, or in both the cartridge and the alignment walls.

The reagent stage 500 may comprise a plurality of GEF contacts 540. The GEF contacts 540 may be spring contacts configured to engage pairs of sliding contacts on the cartridge when the cartridge is inserted by the user. The GEF contacts 540 may supply DC voltage to the sliding contacts in order to provide electrical power for the GEF process.

The reagent stage 500 may comprise one or more heating elements or heaters. The heaters may contact areas on the cartridge to maintain reagent temperatures. Each heater may comprise a flat plate with a printed circuit type heating element bonded to its bottom surface. A precision thermistor may be embedded in the plate to provide feedback for temperature control. In various embodiments, the heaters may comprise an antibiotic heater 550 and an agar heater 560. The antibiotic heater 550 may be configured to heat an area beneath antibiotic wells in the cartridge. The antibiotic heater 550 may extend between a portion of the inner circumference 520 and a portion of the outer circumference 510 of the reagent stage 500. In various embodiments, the antibiotic heater 550 may be configured to maintain the temperature of the antibiotic wells to approximately 41° C. The agar heater 560 may be configured to heat an area beneath agar wells in the cartridge. The agar heater 560 may be located adjacent to the inner circumference 520 of the reagent stage 500. Agar is a semisolid, and it may be desirable to melt the agar prior to use. The agar heater may heat the agar to above its melting point (approximately 100° C.). Once the agar is melted, the agar heater 560 may be configured to lower the temperature of the agar to just above its solidification temperature (approximately 50° C.).

In various embodiments, the reagent stage 500 may comprise a sensor which detects the presence or absence of a cartridge. For example, the GEF contacts 540 may be used to detect the presence of sliding contacts on the cartridge. Additionally, the sensor may detect whether the cartridge was properly inserted.

Figure 6:
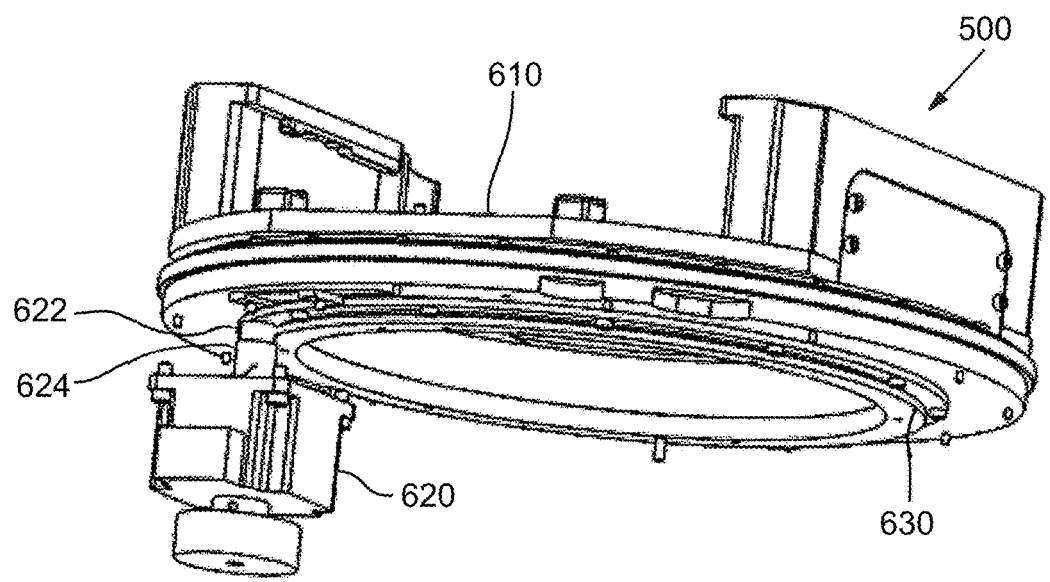

Referring to FIG. 6, a perspective view of the bottom of the reagent stage 500 is illustrated according to various embodiments. The reagent stage 500 may comprise a platform 610 which is rotatable about a central axis. The rotation of the platform 610 may allow for the pipettor to access the sample and different reagents in the cartridge. The platform 610 may be rotated by a stepper motor 620. The platform 610 may be rotated using a spur gear 622 on a motor shaft 624 of the stepper motor 620 and a ring gear 630 coupled to the platform 610.

Figure 7:
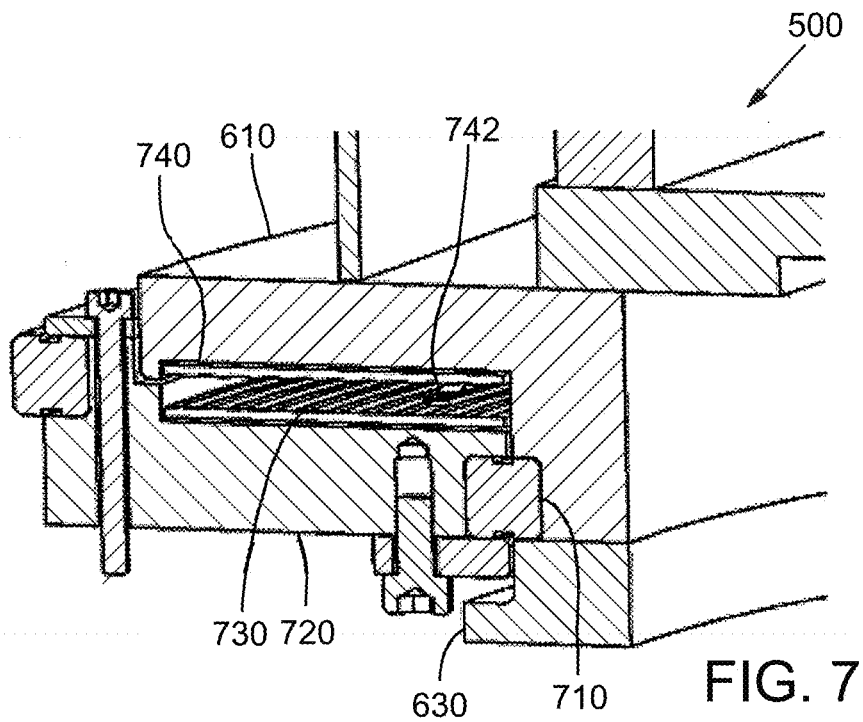
FIG. 7 is a section view of the reagent stage in elevation.

Referring to FIG. 7, a section view of the reagent stage 500 is illustrated according to various embodiments. The platform 610 may ride on a bearing 710. In various embodiments, the bearing 710 may be a stage bearing. The platform 610 may rotate relative to the ring gear 630 and a stator 720. A plurality of conductive rings 730 may be coupled to a top side of the stator 720. In various embodiments, the conductive rings 730 may comprise nickel-plated copper. A rotor 740 may be coupled to a bottom side of the platform 610. The rotor 740 may comprise a series of spring loaded contacts 742. The spring loaded contacts 742 may maintain contact with the conductive rings 730 as the platform 610 rotates. Power may be applied to the heaters, thermistors, and GEF contacts, or any other components coupled to the platform 610, via the spring loaded contacts 742 and the conductive rings 730.

Cassette Stage

The instrument 100 may comprise a cassette stage 800. Referring temporarily to FIG. 2, the cassette stage 800 may be coupled to the top side of the base assembly 140. The cassette stage 800 is configured to receive a user-inserted cassette. The cassette stage may be circumscribed by the inner circumference of the reagent stage. The cassette stage 800 is rotatable about a central axis and may also translate in order to precisely locate the cassette with respect to the illuminator and optics system objective. In various embodiments, the cassette stage 800 may translate on a y-axis. In various embodiments, the rotation of at least one of the cassette stage 800, the reagent stage, and the door 130 may be coaxial.

Figure 8A:
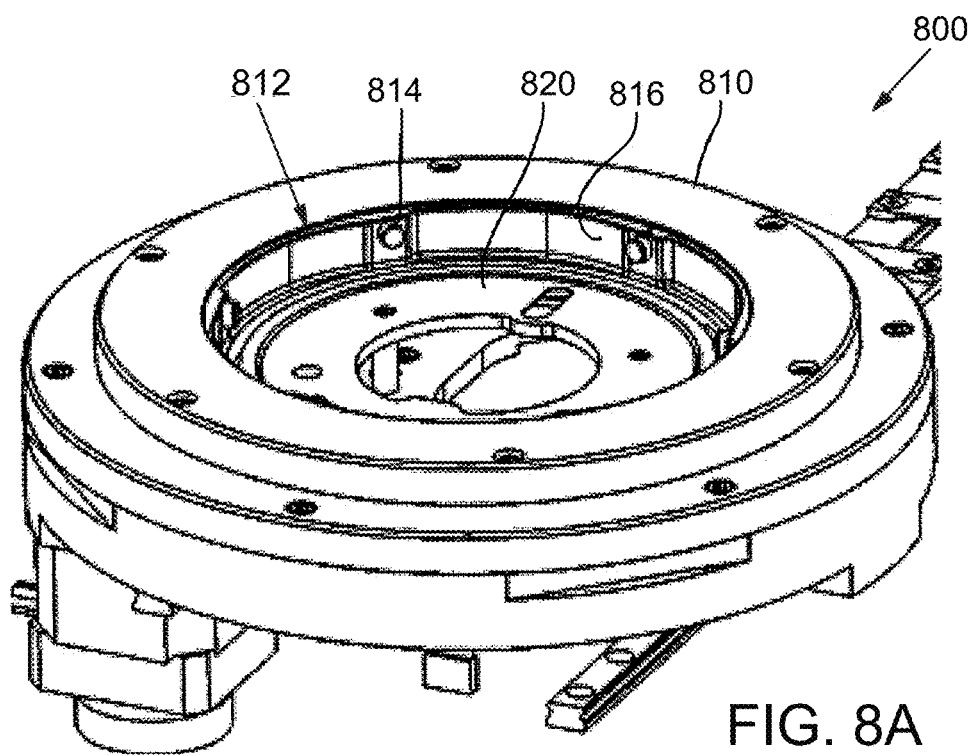
FIG. 8A is a perspective view of the reagent stage and the cassette stage.

Referring to FIG. 8A, a perspective view of the cassette stage 800 removed from the instrument 100 is illustrated according to various embodiments. The cassette stage 800 may comprise a cassette nest 810 and a heater plate 820. The cassette nest 810 may be generally annular and define a receiving well 812 configured to receive the cassette within the cassette nest 810. The heater plate 820 may define a bottom of the receiving well 812. A user may insert the cassette into the receiving well 812. The user may rotate the cassette to interface attachment features on the cassette with locating pins 814 on an inner wall 816 of the cassette nest 810. The interface between the attachment features and the locating pins 814 may align and secure the cassette within the cassette nest 810.

Figure 8B:
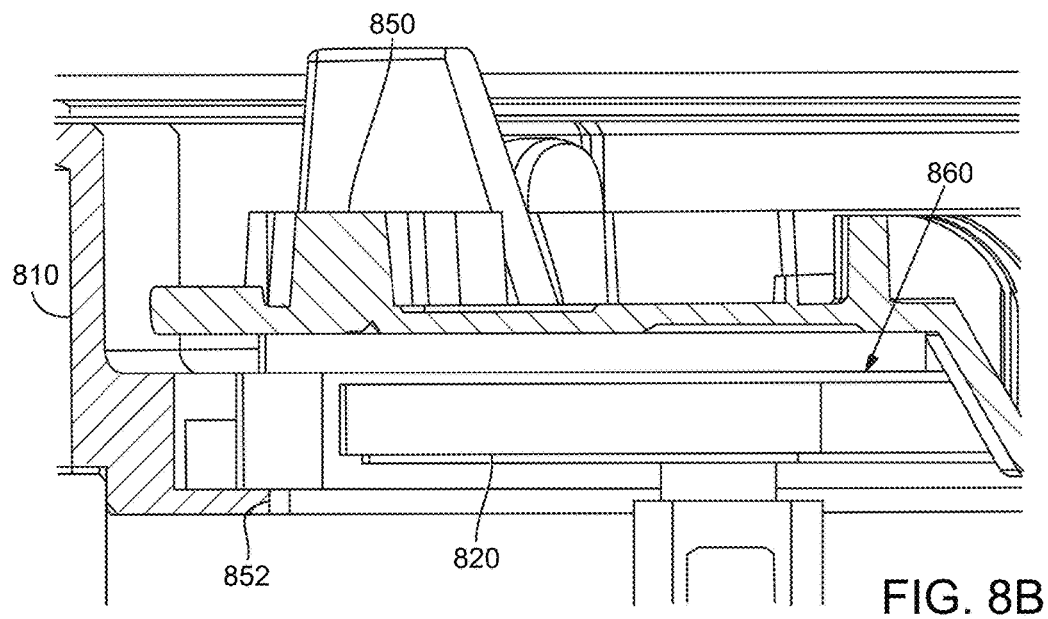
FIG. 8B is a section view of the cassette stage in elevation showing the cassette in relation to the heater.

Referring to FIG. 8B a cross-section view of a cassette 850 in the cassette nest 810 is illustrated according to various embodiments. The cassette 850 may be supported by a glass ring 852 at an outer annulus of the bottom of the cassette 850. An air gap 860 may be present between the heater plate 820 and the cassette 850.

Figure 9:
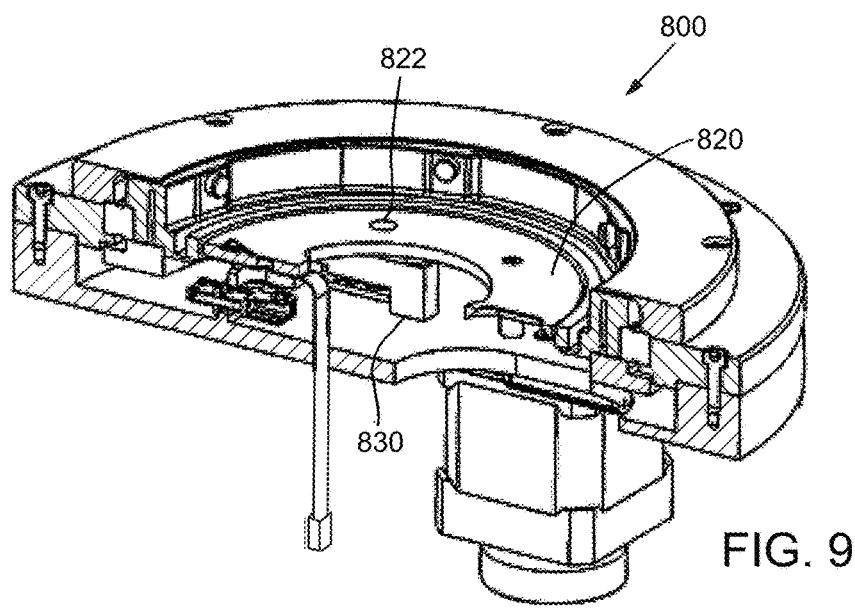

Referring to FIG. 9, a section view of the cassette stage 800 showing heating components is illustrated according to various embodiments. The heater plate 820 may be coaxial with the cassette. The heater plate 820 may comprise a flat plate with a printed circuit type heating element bonded to a bottom surface of the heater plate 820. A precision thermistor may be embedded in the heater plate 820 to provide feedback for temperature monitoring. An infrared temperature sensor 830 may be mounted to the cassette stage 800 below the heater plate 820. The infrared temperature sensor 830 may be aimed through a viewing hole 822 in the heater plate 820. The infrared temperature sensor 830 may be aimed at a bottom surface of the cassette in order to accurately measure the temperature of the cassette. The temperature of the cassette may be used to approximate the temperature of the liquid in the channels.

Referring to FIG. 10, a section view of the cassette stage 800 showing rotational features is illustrated according to various embodiments. The cassette stage 800 may rotate the cassette for pipetting, EKC, and imaging. The cassette nest 810 may ride in a bearing 1010. The cassette nest 810 may be rotated by a stepper motor 1020. The stepper motor 1020 may use a spur gear 1022 on a motor shaft 1024 and a ring gear 1030 on the cassette nest 810 to rotate the cassette nest 810. The stepper motor 1020 may rotate the cassette nest 810 to align particular channels with the pipettor or illuminator.

Referring to FIG. 11, a side view of the cassette stage 800 showing translational features is illustrated according to various embodiments. The cassette stage 800 may be mounted on one or more bearings 1010 (illustrated in FIG. 10). In various embodiments, the bearings 1010 may comprise "X-contact" ball bearings manufactured by Kaydon Corporation, Inc. (Muskegon, Mich.). However, in various embodiments, the bearings 1010 may comprise cross roller bearings or any other suitable bearings. A linear actuator 1120 may comprise a lead screw 1122, a nut 1124 and a stepper motor 1126. The linear actuator 1120 may drive the cassette stage 800 in the positive or negative y-direction. The linear actuator 1120 may work in conjunction with the stepper motor 1020 which rotates the cassette stage 800 to position the cassette for pipetting, EKC, and imaging.

Pipettor

Figure 12:
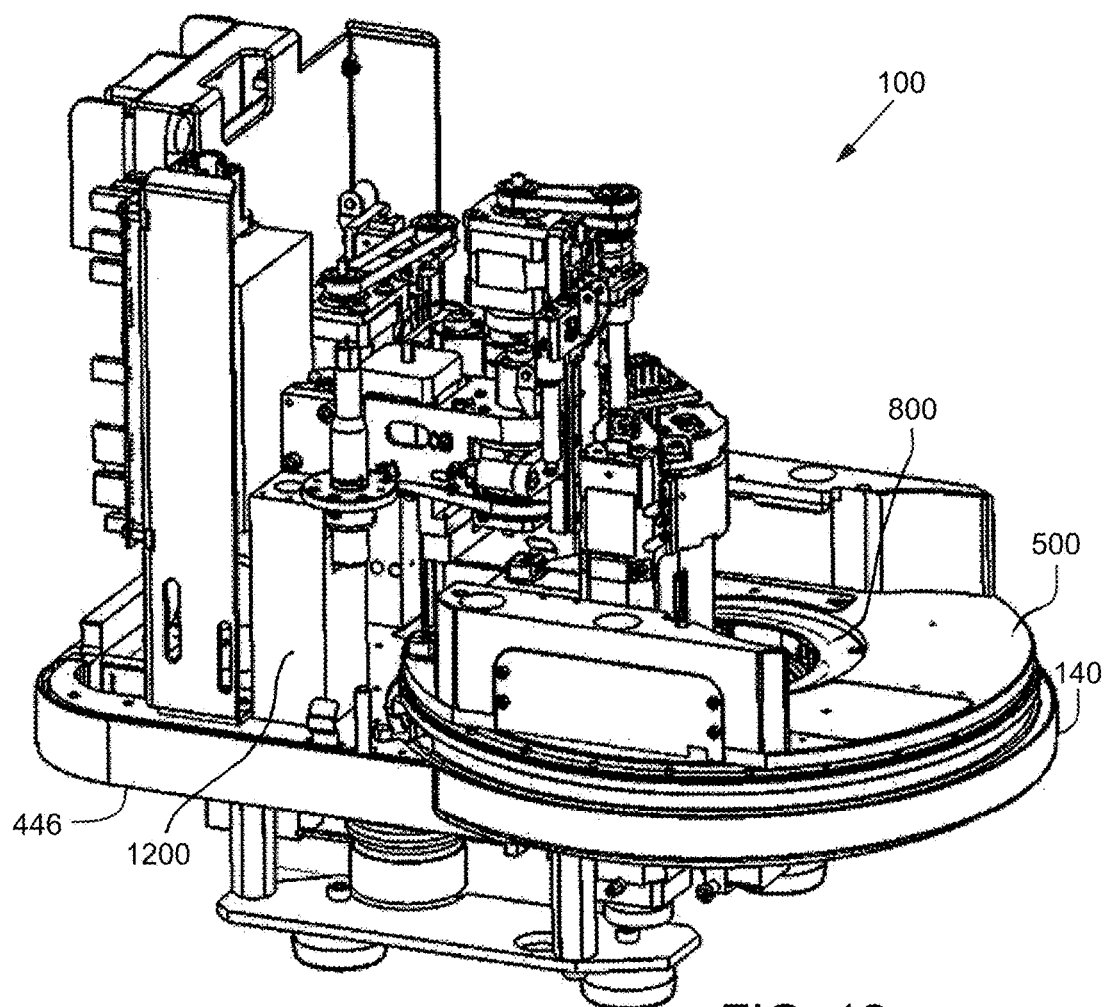
FIG. 12 is a perspective view of a portion of the instrument showing the pipettor.

Referring to FIG. 12, a perspective view of an instrument 100 with the upper enclosure and the lower enclosure removed is illustrated according to various embodiments. The instrument 100 may comprise a pipettor 1200. The pipettor 1200 may be coupled to the rectangular portion 446 of the base assembly 140. The pipettor 1200 may be cantilevered over the reagent stage 500 and the cassette stage 800 in order to access the cartridge and the cassette.

Figure 13:
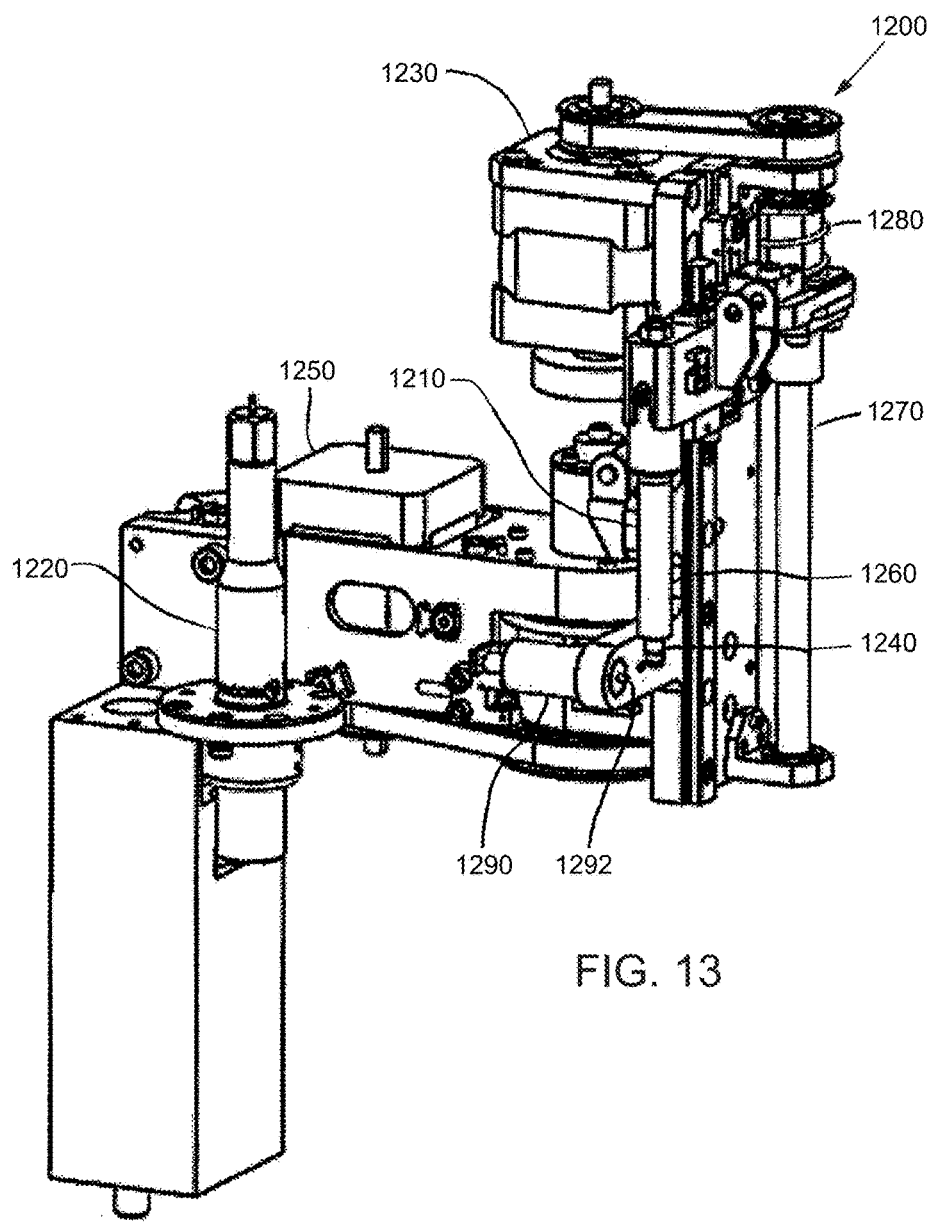
FIG. 13 is a perspective view of the pipettor.
Figure 14A:
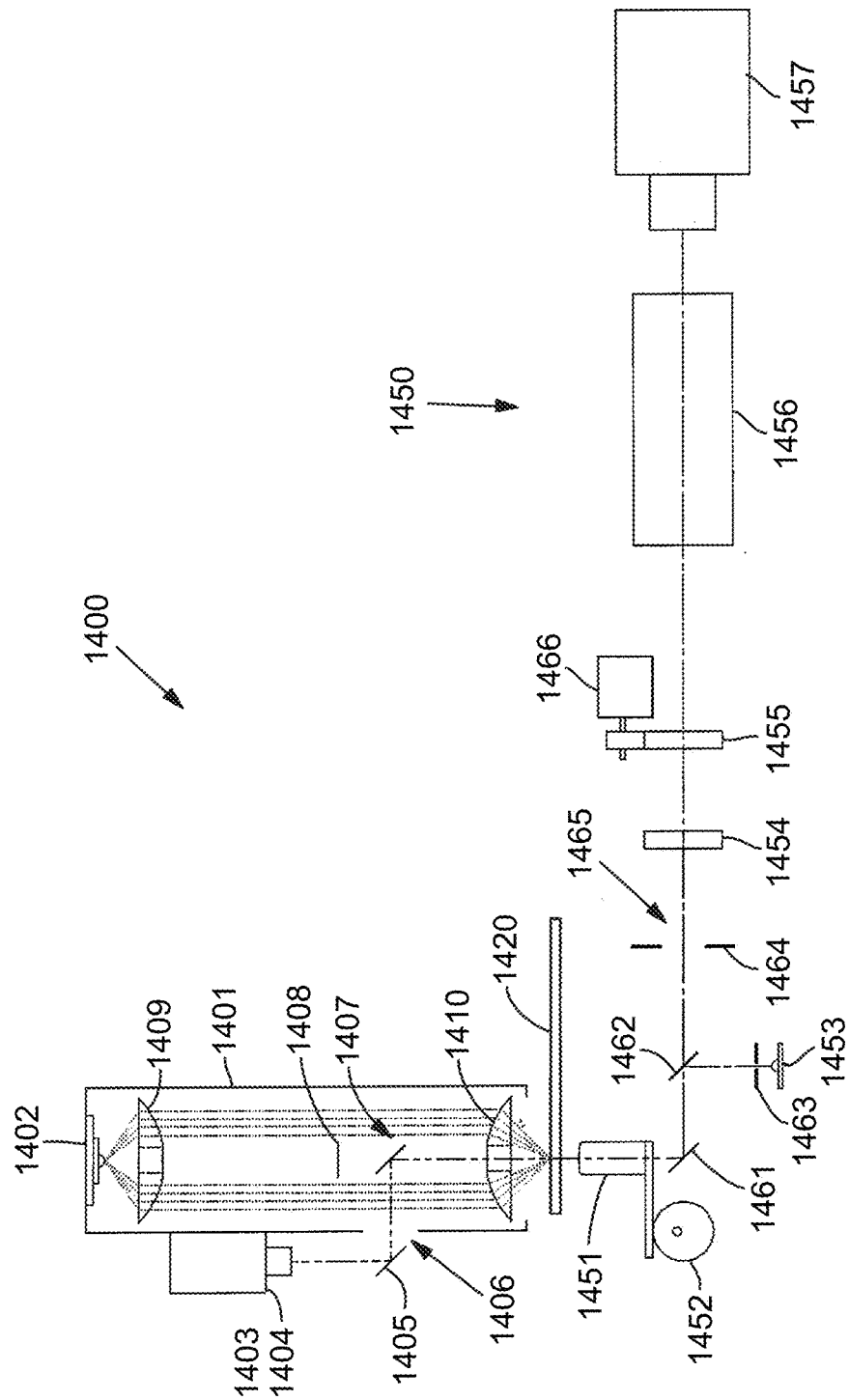
FIG. 14A is a schematic diagram of the illumination system.
Figure 14B:
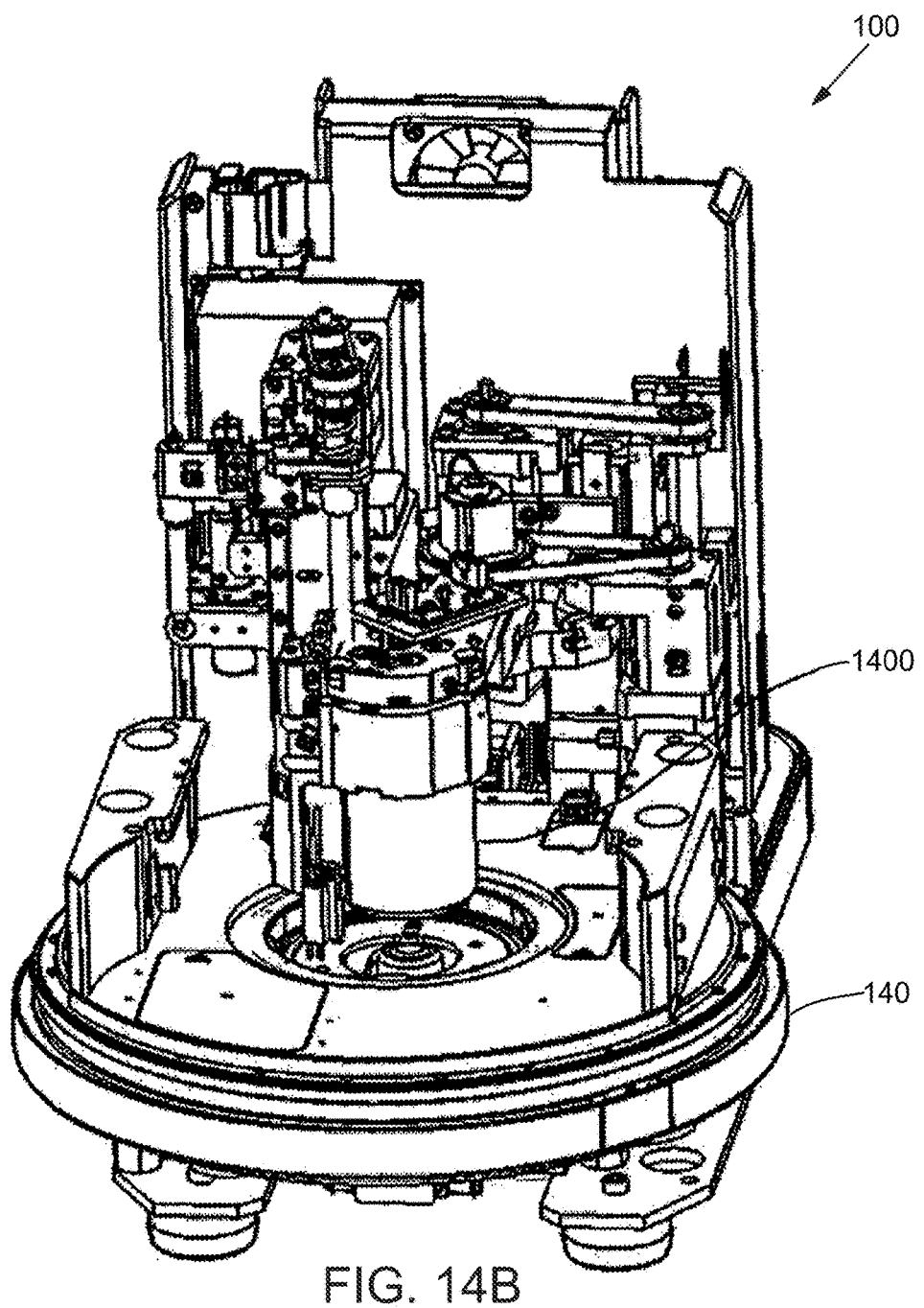
FIG. 14B is a perspective view of the instrument showing an illuminator.

Referring to FIG. 13, a perspective view of the pipettor 1200 removed from the instrument is illustrated according to various embodiments. The pipettor 1200 may comprise a fluid transfer pipette 1210 which uses a positive displacement air pump 1220 connected with a tube to a disposable pipette tip (not shown). The pipettor 1200 may comprise two motor driven axes. A z-axis motor 1230 may drive a pipettor mandrel 1240 in the positive or negative z-direction to raise or lower the pipettor mandrel 1240. A theta-axis motor 1250 may rotate the pipettor mandrel 1240 in the theta direction. The z-axis motor 1230 and the theta-axis motor 1250 may work in conjunction with the reagent stage motor and the cassette stage motors to accomplish the instrument's pipetting tasks during ID and AST processes.

The pipettor 1200 may be used to determine the precise location and orientation of the cartridge after insertion. In some cases, the cartridge may not be inserted in exactly the same position each time. The pipettor 1200 may comprise a tip stripper collar 1260. The tip stripper collar 1260 may be substantially cylindrical. The tip stripper collar 1260 may be concentric around the pipettor mandrel 1240. The tip stripper collar 1260 may contact the edges of the teaching wells in the cartridge and/or the reagent stage. The instrument may calculate the position of the cartridge based on the location of the edges of the teaching wells.

The pipettor mandrel 1240 may be the interface between the pipettor 1200 and pipette tips included in the cartridge. The pipettor 1200 may comprise a z-contact sensor and a tip presence sensor. The z-contact sensor may indicate that the z-axis drive has moved down (negative z-direction) without a corresponding movement of the pipette arm 1270. The tip presence sensor may indicate that the tip stripper collar 1260 has been raised (positive z-direction) relative to the pipettor mandrel 1240. The presence of a pipette tip is expected within a height range to indicate that a sealing portion of the pipette tip has been contacted by the pipettor mandrel 1240. Once contact is made between the pipette tip and the pipettor mandrel 1240, the z-axis motor 1230 drives the pipettor mandrel 1240 down. The downward motion may be translated to a predictable and repeatable sealing force through a lost motion spring's 1280 spring constant. The tip presence sensor may indicate that the pipette tip is coupled to the pipettor mandrel 1240. In response to the tip presence sensor detecting the pipette tip earlier than expected or not at all, the instrument may determine that the seal between the pipettor mandrel 1240 and the pipette tip is unsatisfactory, and the pipettor 1200 may remove the pipette tip and select a different pipette tip.

The pipettor 1200 may move in the theta and z-directions to remove reagents or specimens from the cartridge. The pipettor 1200 may use a pipette tip to pierce a film seal in a reagent well and obtain a reagent. The pipettor 1200 may move to a desired input port in the cassette and form a seal between the pipette tip and the input port. The pipettor 1200 may deposit the reagent into the input port and force the reagent into the sample channel. The pipettor 1200 may then remove the pipette tip and replace the pipette tip into the cartridge.

The pipettor 1200 may comprise a solenoid 1290 coupled to the theta-axis of the pipettor 1200. To remove a pipette tip, the solenoid 1290 may extend and insert a removal pin 1292 into a removal receiver in the tip stripper collar 1260. Contact between the removal pin 1292 and the removal receiver may prevent upward (positive z-direction) movement of the tip stripper collar 1260. The z-axis motor 1230 may lift the pipettor mandrel 1240 upward, and the pipette tip may contact the tip stripper collar 1260. The tip stripper collar 1260 may force the pipette tip away from the pipettor mandrel 1240, and the pipette tip may free fall into the cartridge. The pipettor 1200 may subsequently force the pipette tip downward in the event that the pipette tip does not fall completely into the desired position in the cartridge.

Illumination and Optics

A system may comprise an illumination system and an optics system. An illumination system 1400 and optics system 1450 in accordance with various embodiments are illustrated in FIGS. 14-32. The illumination system 1400 is primarily described with reference to FIGS. 14A-18E. The optics system 1450 is primarily described with reference to FIG. 14A and FIGS. 19-29. An illumination system 1400 (also referred to as an "illuminator") can comprise a housing 1401, a stage configured to provide movement of the illumination system 1400, one or more light sources, mirrors, and condensers. In various embodiments, an illuminator 1400 may also comprise an EKC electrode assembly. An optics system 1450 can include an objective 1451, a focuser 1452, a fold mirror 1461, a focus LED 1453, a beam splitter 1462, a dual band filter 1454, a single band filter changer 1466, a tube lens 1456, and a camera 1457. Each of these optics system components is described in greater detail below.

An illuminator 1400 in accordance with various embodiments provides sample illumination for image acquisition. An illuminator 1400 may be configured to provide a plurality of light sources, such as white light 1402 and laser diode light sources 1403, 1404. Each of the plurality of light sources may provide illumination along a single optical path from the sample in cassette 1420 to the objective 1451 and camera 1457. For example, an illuminator 1400 may be configured to provide three illumination sources to permit image acquisition of the sample in cassette 1420, such as a green laser diode 1403 (excitation wavelength=520 nm) and a red laser diode 1404 (excitation wavelength=637 nm) for illumination used during the ID (FISH) process and a white light LED 1402 for dark field illumination (the "dark field LED") used during both the ID and AST processes. An illuminator 1400 comprising a plurality of light sources having the same optical path can facilitate overlaying images containing the same image features (i.e., a field of view containing the same sample objects at the same sample object locations within the field of view) acquired using different illumination, such as overlaying a dark field image of a field of view with green and red fluorescence imaging to determine which image features are debris (i.e., not marked with a hybridized FISH probe) and which are microorganism cells.

In various embodiments, the illuminator 1400 can comprise an aluminum cylindrical tube housing 1401, the red 1404 and green 1403 laser diodes, and the dark field LED 1402. The illuminator housing 1401 may be mounted to the base assembly 140 by an illuminator stage configured to provide z-axis and theta-axis movement suitable to position the illuminator 1400 directly above the cassette and in coaxial alignment with the objective 1451. Z-axis movement permits the laser 1403, 1404 and dark field 1402 light sources to be positioned at different vertical positions above the cassette to enable proper focusing of the light emitted by the light source relative to the sample contained in a cassette sample channel flowcell. Z-axis movement together with theta-axis movement allows rotation of the illuminator 1400 away from the area above the cassette permitting pipettor access to the cassette.

The green 1403 and red 1404 laser diodes can be mounted on the outside of the aluminum illuminator housing 1401 described above. The lasers 1403 and 1404 may be aimed downward and reflected off a 45 degree diagonal mirror 1405 mounted midway along the housing 1401. The laser light passes through a hole 1406 in the side of the housing 1401 and is reflected downward off another 45 degree diagonal mirror 1407 (located below the optical stop 1408, described below) so that the light is coincident with the axis of the objective 1451 (i.e., coaxial with the objective 1451).

White light from the dark field LED 1402 exits the LED and passes through an upper collimating lens 1409 mounted at the top of the illuminator 1400 just below the dark field LED 1402. The upper collimating lens 1409 shapes the light into a cylinder. Light in the center of the housing 1401, 20 mm in diameter, is blocked with an optical stop 1408. At the bottom of the housing 1401 a lower condenser lens 1410 re-shapes the light into a cone with a focal point suitable for dark field illumination.

Figure 15:
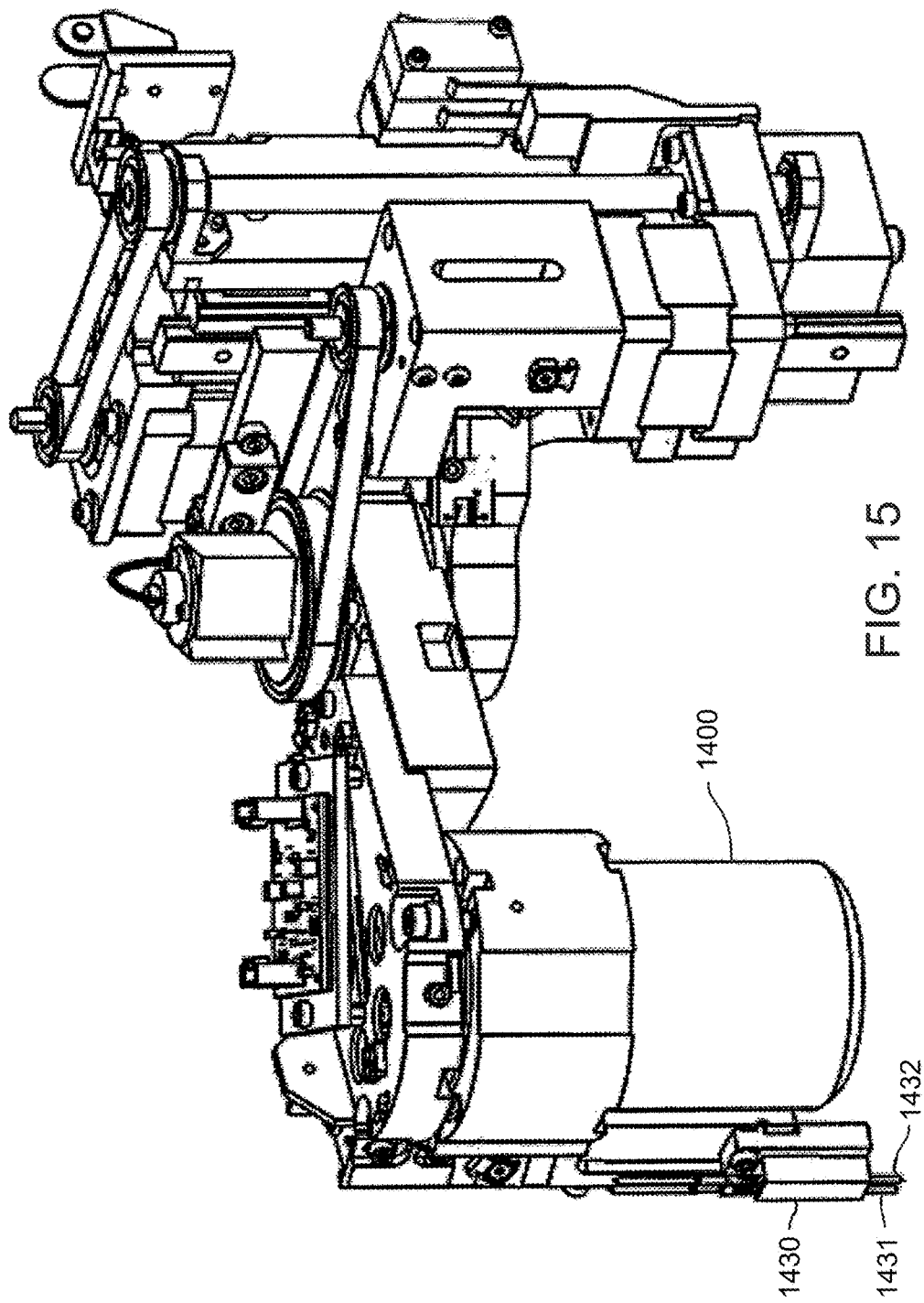
FIG. 15 is a perspective view of the illuminator and drives.
Figure 16:
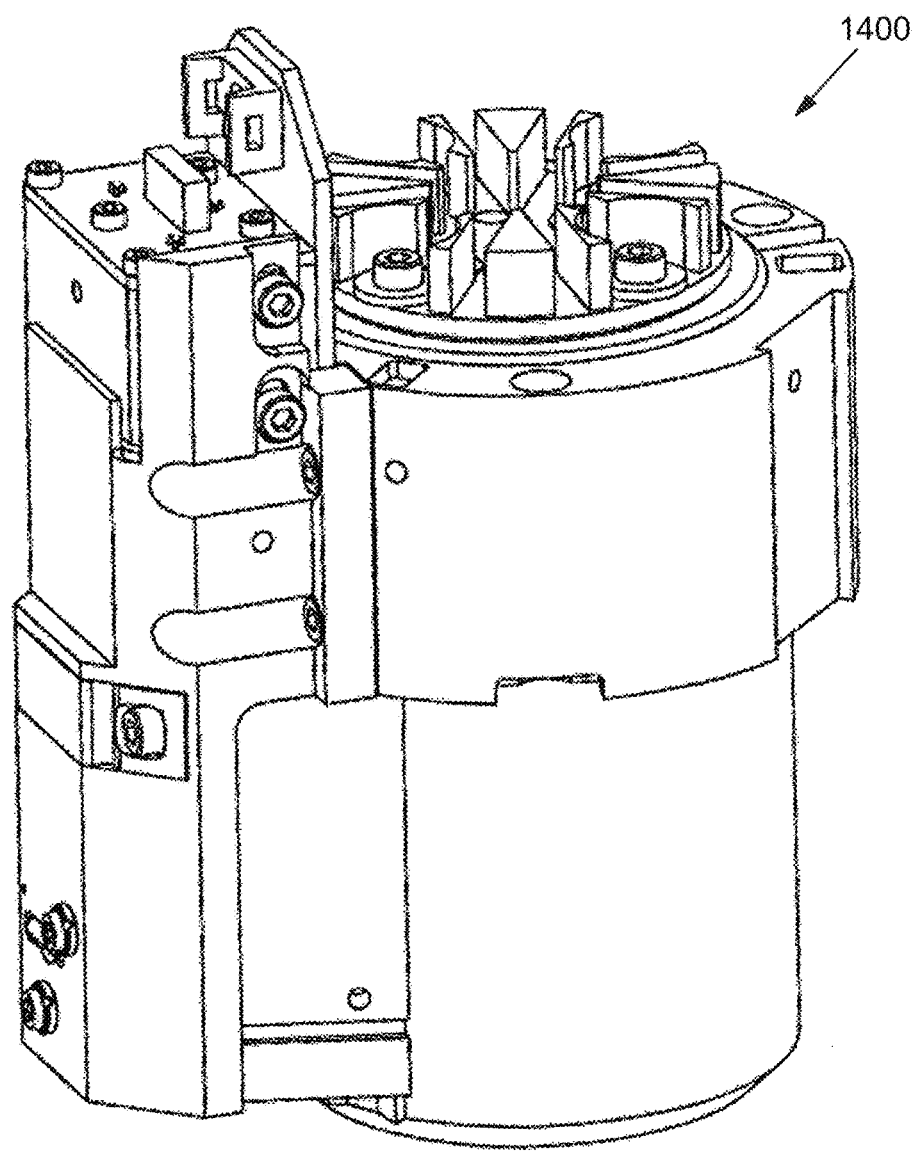
FIG. 16 is a perspective view of the illuminator.
Figure 17:
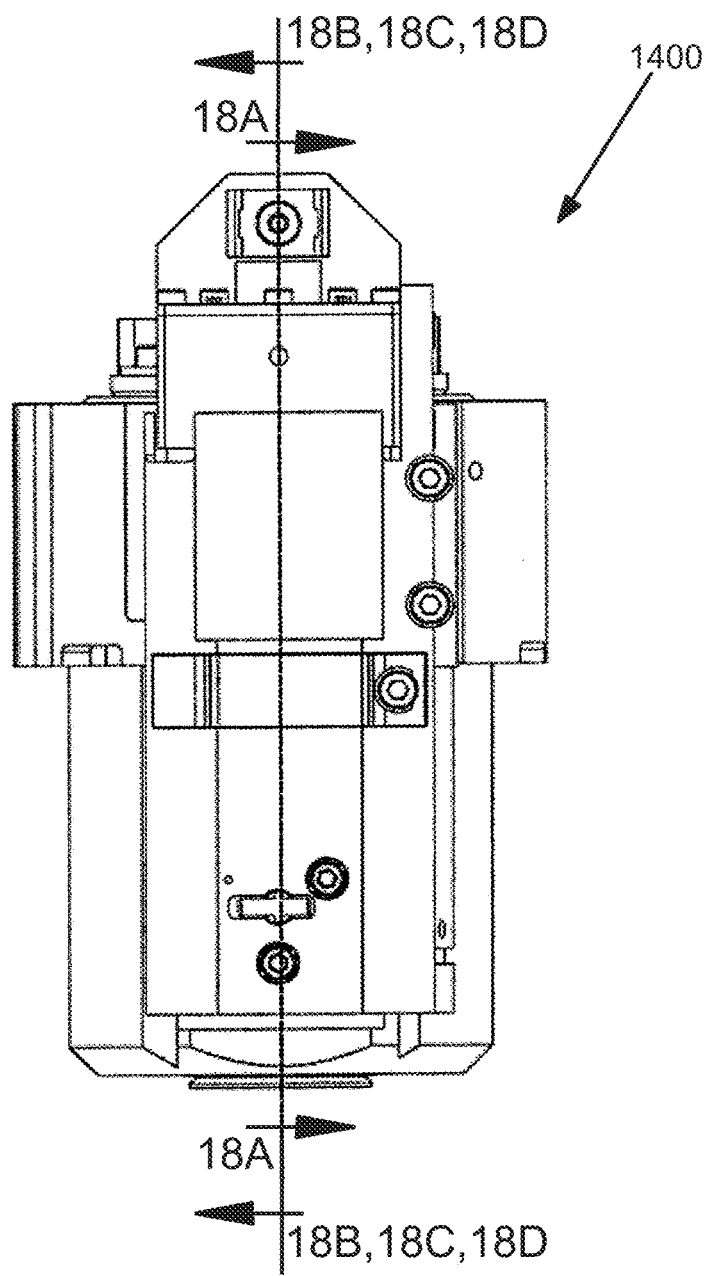
FIG. 17 is a side elevation view of the illuminator.
Figure 18A:
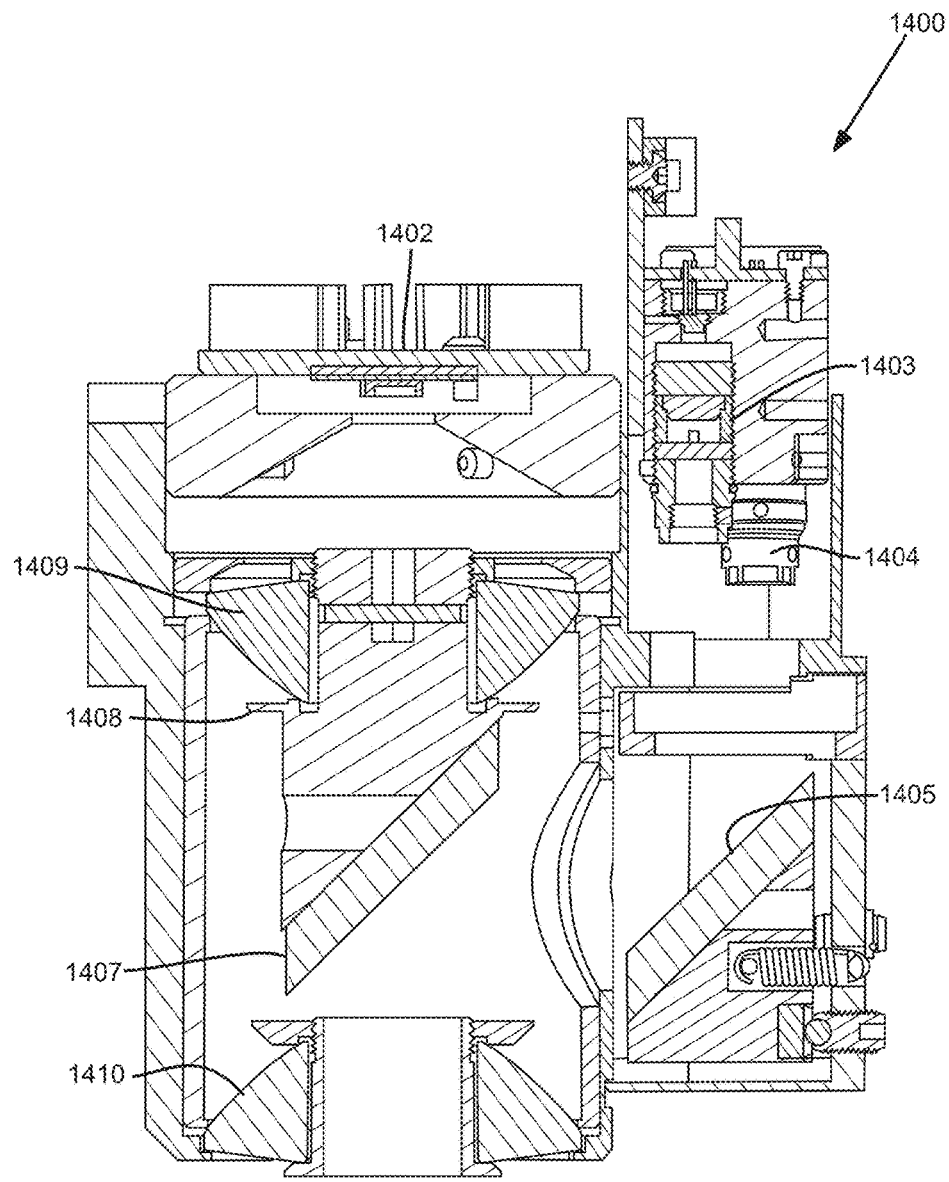
FIG. 18A is a section view of the illuminator in elevation taken along the line 18A-18A in FIG. 17.
Figure 18B:
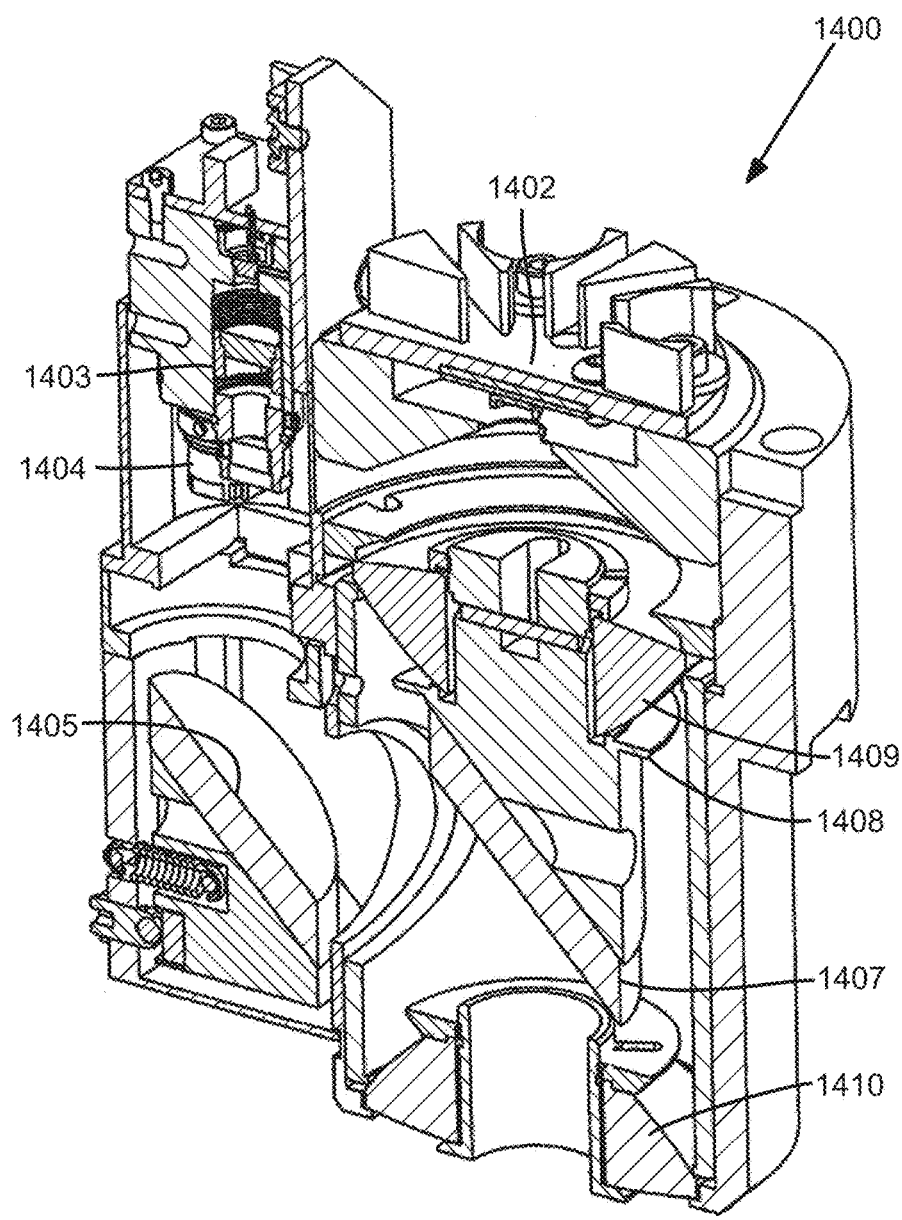
FIGS. 18B, 18C and 18D are perspective views of another section of the illuminator in elevation, which is taken along the respective lines in FIG. 17 and shown at different angles.
Figure 18C:
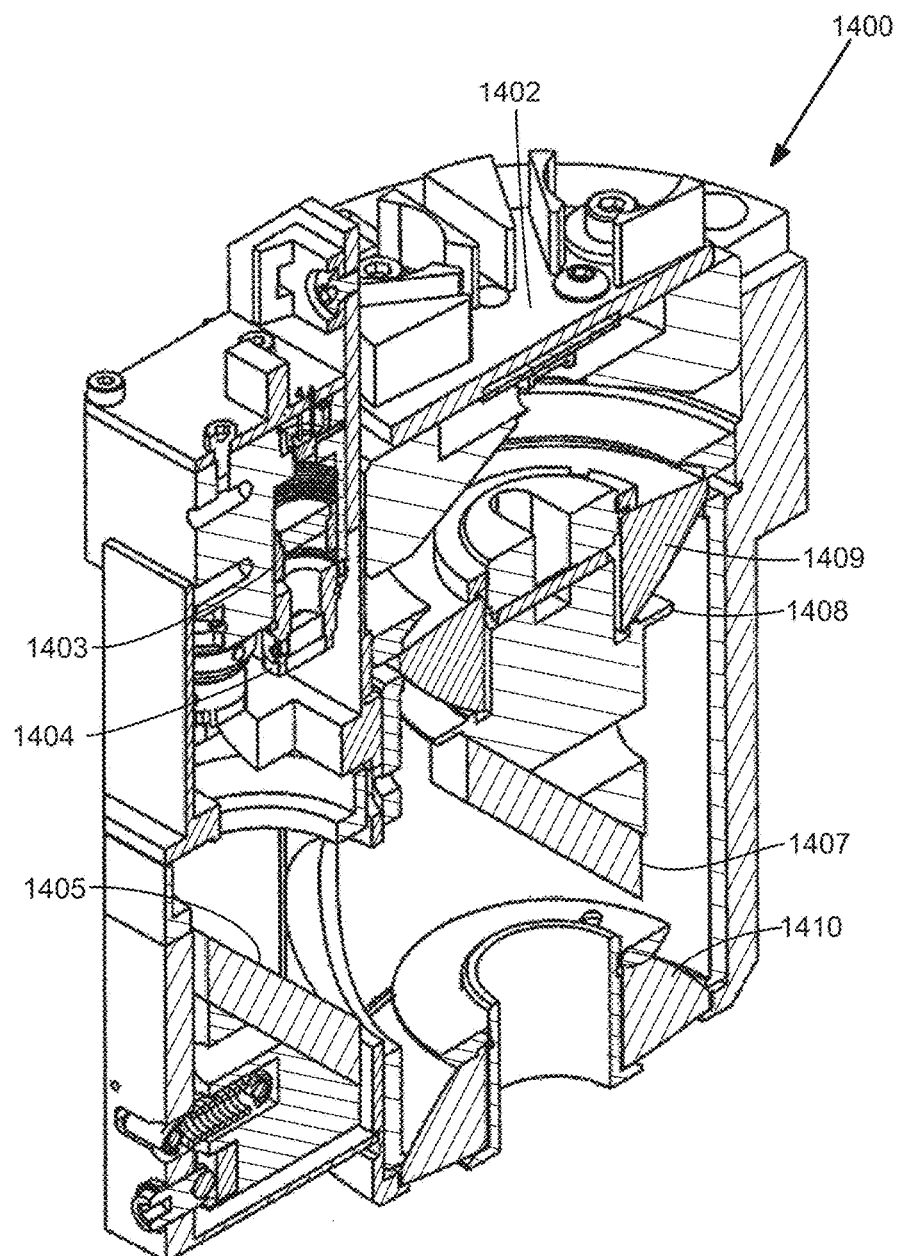
Figure 18D:
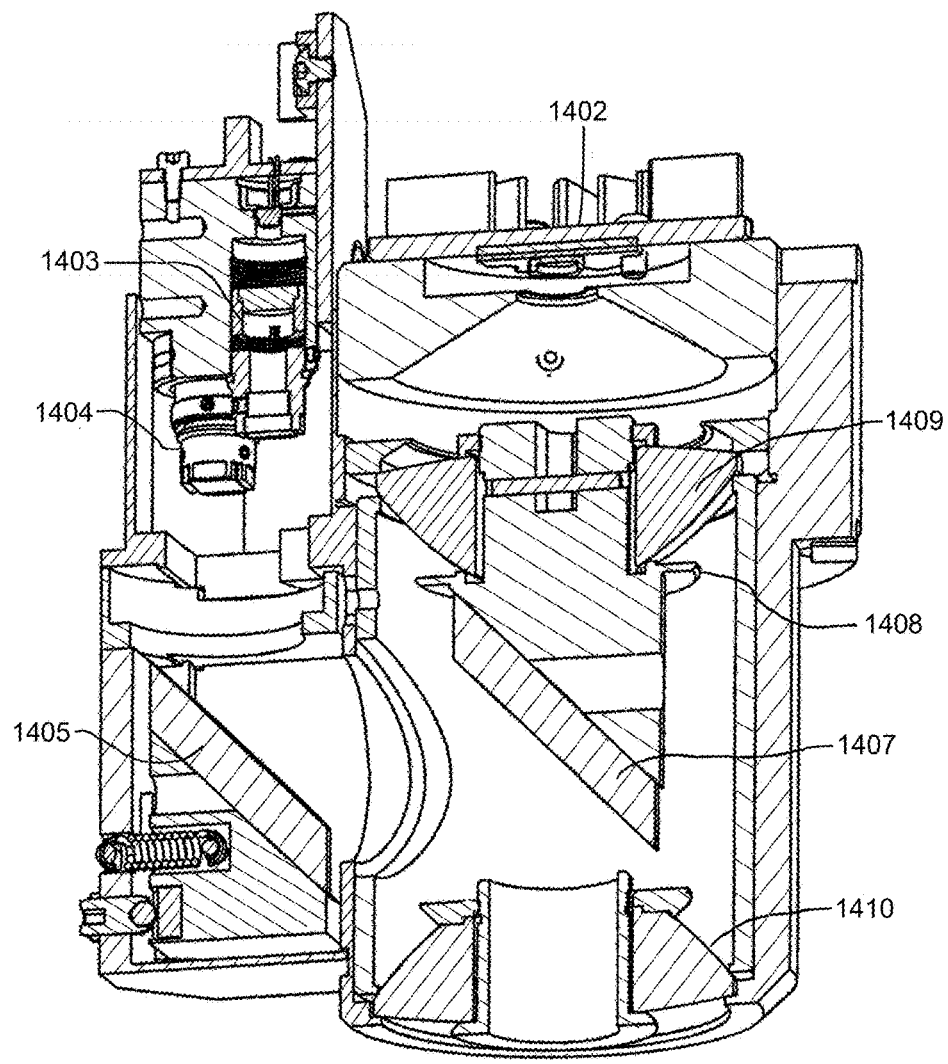
Figure 19:
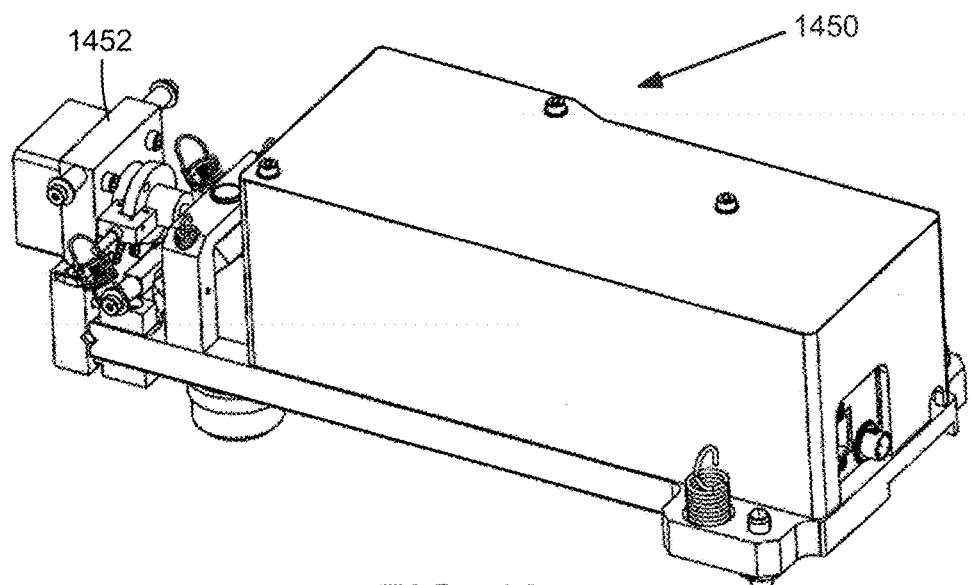
FIG. 19 is a perspective view of the optic system.
Figure 22:
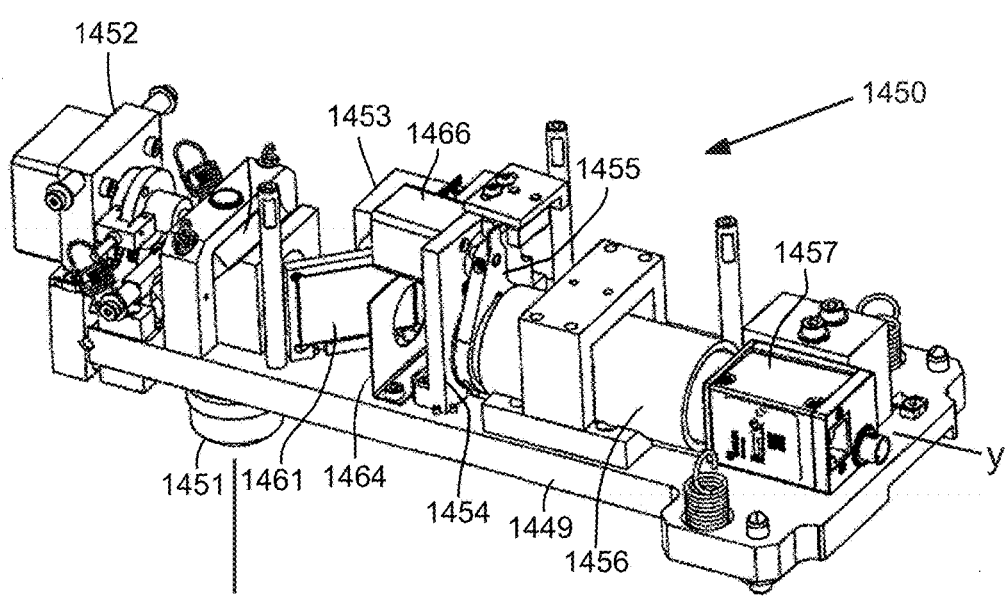
FIG. 22 is a perspective view of the optic system with the housing removed.
Figure 20:
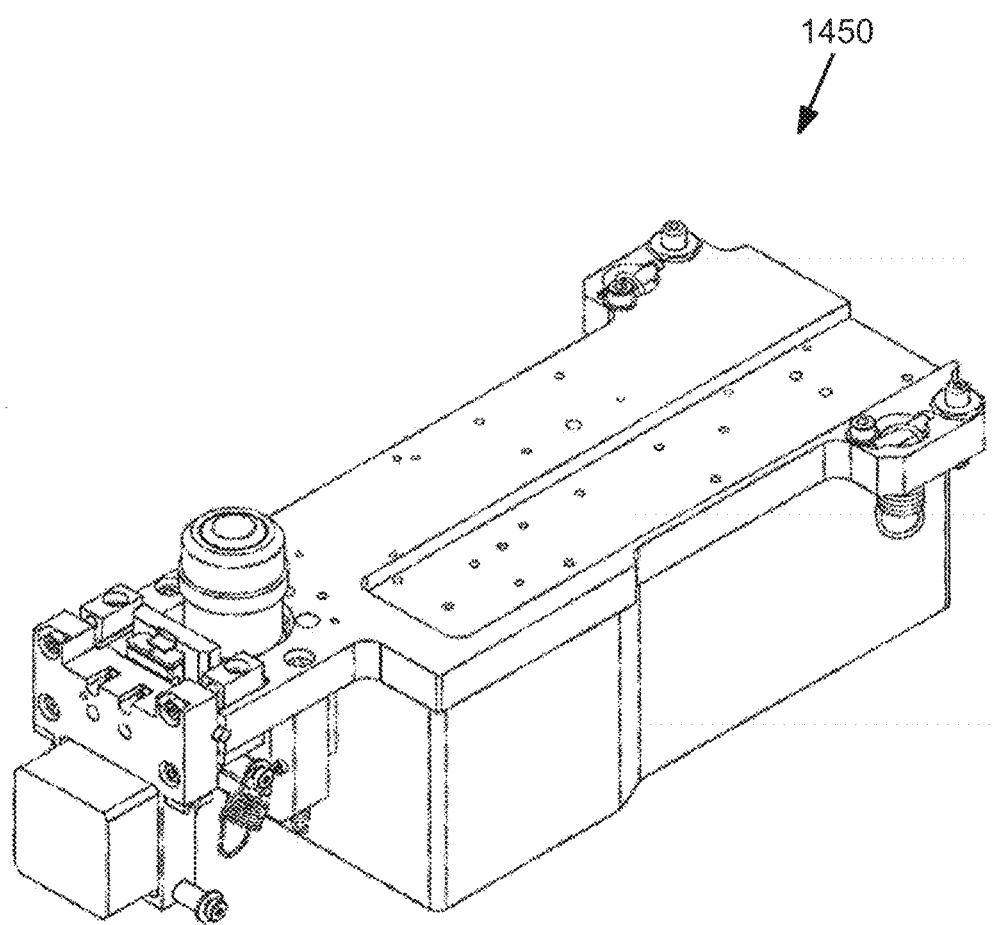
FIG. 20 is another perspective view of the optic system showing a lower side.
Figure 21:
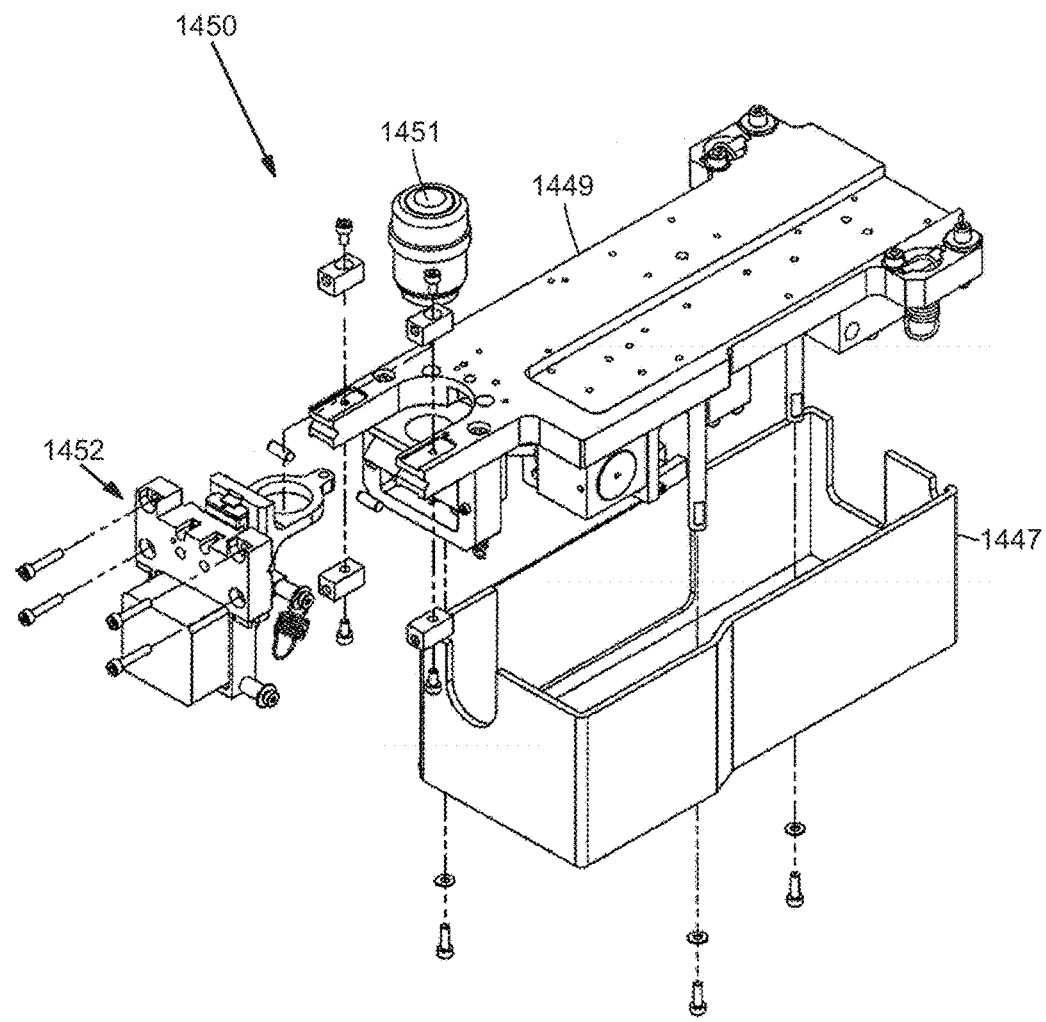
FIG. 21 is an exploded perspective view of the optic system.
Figure 23:
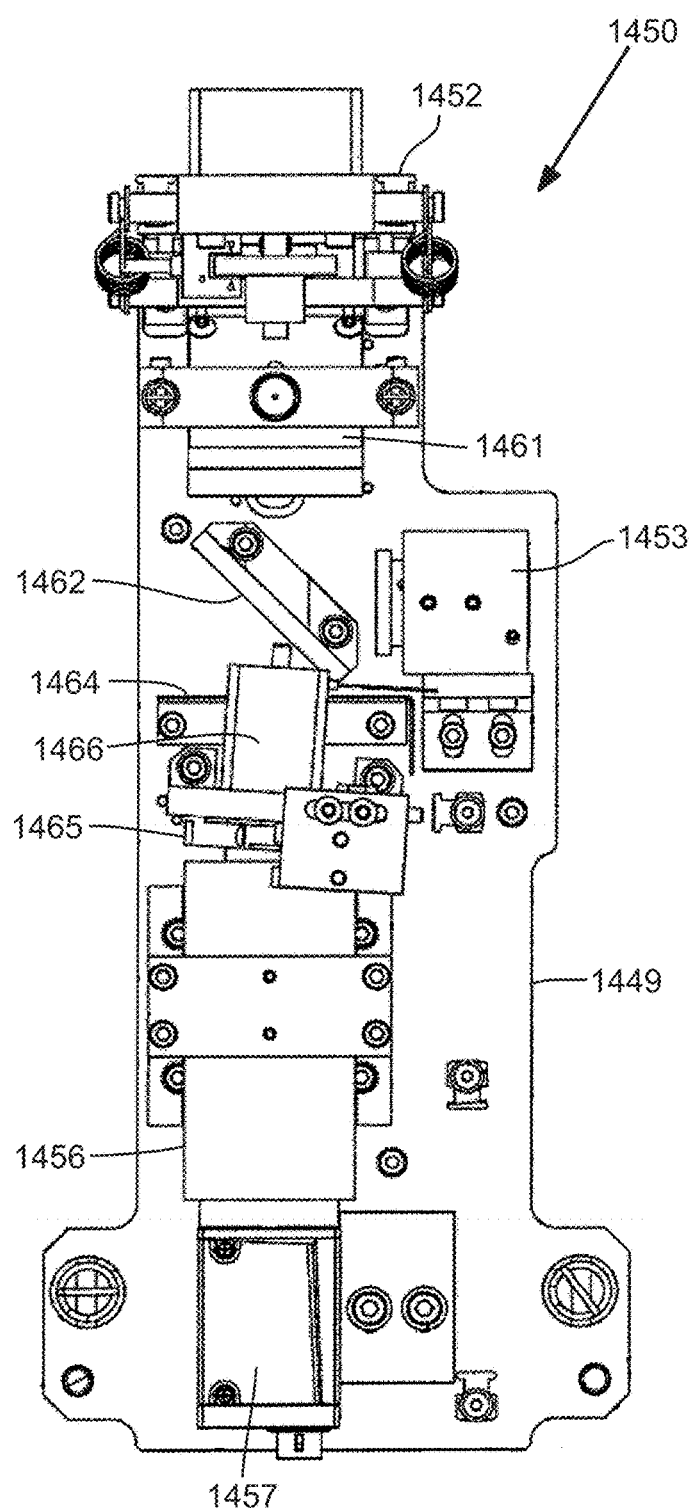
FIG. 23 is a top plan view of the optic system of FIG. 22.
Figure 24:
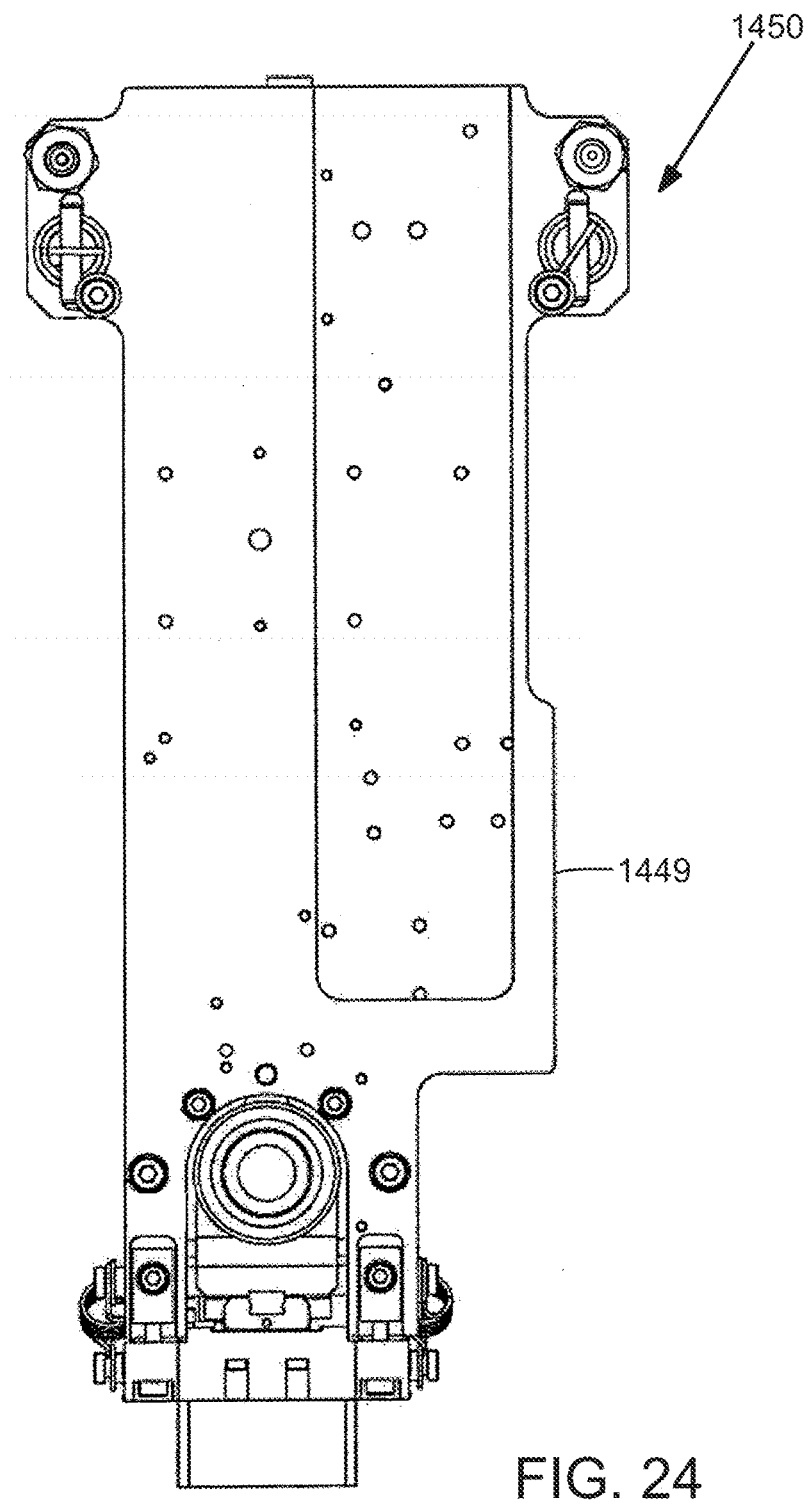
FIG. 24 is a bottom plan view of the optic system.
Figure 25:
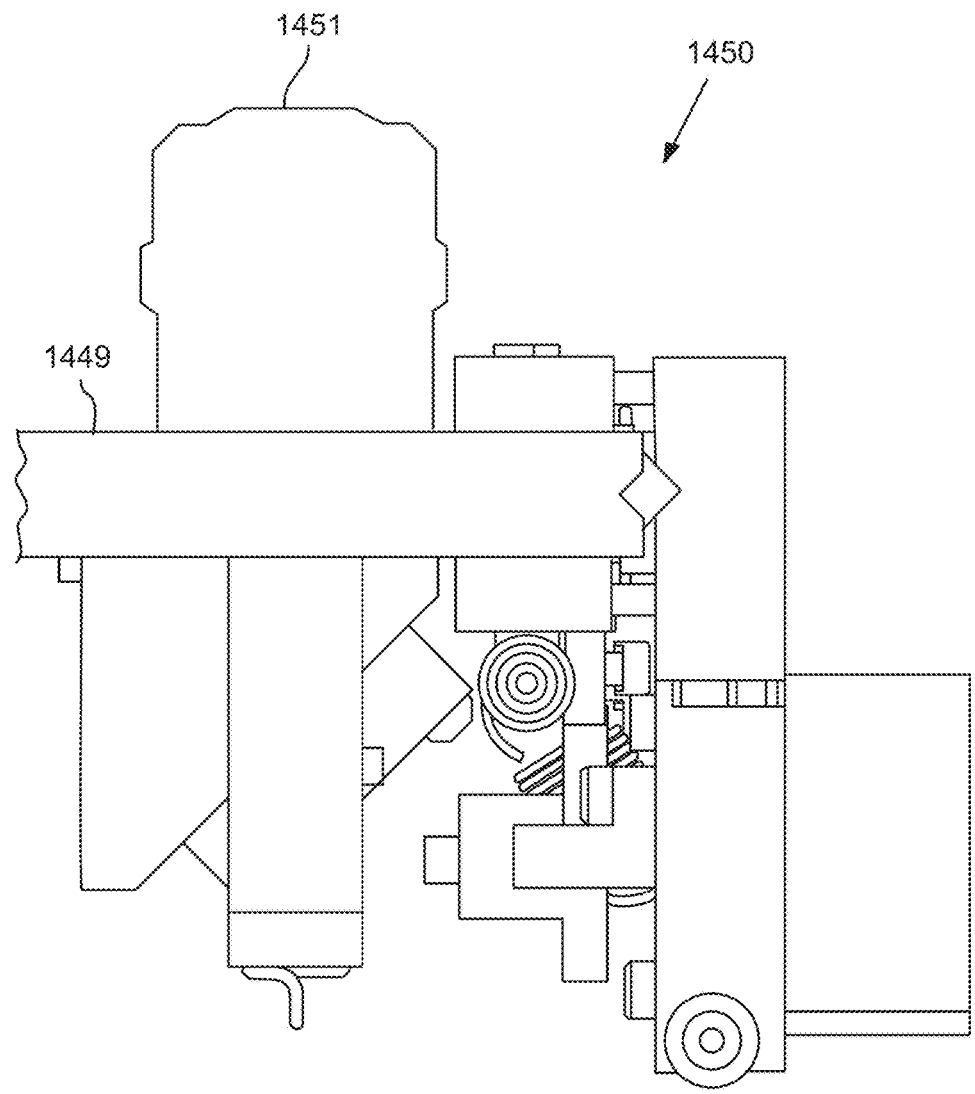
FIG. 25 is an end view of the optic system.

In various embodiments, an illuminator subassembly may be configured with an EKC electrode assembly. For example, as shown in FIG. 15, an EKC electrode assembly 1430 can comprise two spring-loaded, rhodium-plated pins that are mounted in a non-conductive (polymer) block on the side of the illuminator 1400. The system may perform an EKC procedure by positioning the illuminator so that the EKC-electrode assembly pins are received by corresponding EKC-electrode ports in the cassette and contact electrodes located in the EKC-electrode ports. A first pin 1431 contacts an electrode located on and operatively connected to the top surface of the glass layer of the cassette. A second pin 1432 contacts an electrode located on and operatively connected to the lower surface of the molded plastic upper housing of the cassette. The EKC electrode assembly 1430 may be used to deliver an electrical potential to the sample channels in the cassette. For example, a low voltage (0.6 to 1.6 volts DC) may be applied to the cassette sample channels by the instrument using the EKC electrode assembly 1430 located on the illuminator subassembly 1400. The electrical potential may be applied for a defined period of time, such as several minutes, as described in greater detail elsewhere herein.

The sample cassette 1420 placed in the system by a user may be positioned by the cassette stage so that a sample channel (or flowcell) is located just below the illuminator 1400 and just above the objective 1451 (i.e., so that a portion of the sample channel comprising an objective field-of-view is positioned in-line between the illuminator 1400 and the objective 1451).

In accordance with various embodiments, an optics system 1450 may comprise an objective 1451. The objective 1451 may be mounted to the base assembly 140 and located below the base assembly 140 such that the objective 1451 is positioned beneath the cassette stage. An objective 1451 can comprise a standard "off the shelf" microscope objective suitable to collimate an image. For example, in various embodiments, an objective with a numerical aperture of 0.45, a field number of 22 mm, and a magnification of 20× may be used. Objectives with other specifications may be used in accordance with various embodiments of the present disclosure.

The objective 1451 may be mounted to a focuser mechanism 1452. The focuser mechanism 1452 may be configured to move the objective 1451 along a z-axis (i.e., substantially normal to the horizontally-oriented sample channel holding the sample) to focus the image. In various embodiments, the objective 1451 may be moved in the z-axis by means of a stepper motor with a precision cam mounted on its shaft. The cam can comprise a round disk with an offset mounting hole. A stepper motor with a microstepping mode may be used to drive the cam. The stepper motor may provide, for example, a 200 step/revolution movement in standard mode, with a microstepping mode yielding 25,600 microsteps per revolution to provide sub-micron resolution movement of the objective 1451.

The optics system 1450 may further comprise a fold mirror 1461. The fold mirror 1461 may be used to fold the optical path 90 degrees to redirect the optical path from the z-axis (i.e., coaxial to the illuminator 1400 and objective 1451) to the y-axis direction beneath the base plate and toward a tube lens 1456 and camera 1457 used for image acquisition, described below.

The optics system 1450 may comprise a focus light system. A focus light system can comprise a focus LED 1453 and a beam splitter 1462. In various embodiments, a focus LED 1453 may be used to provide a separate light source that is reflected off the top (glass) surface of the cassette to facilitate focusing the objective 1451. The focus LED 1453, a pinhole aperture 1463, and a collimating lens may be positioned at a right angle to the main optical path. A beam splitter 1462 can be placed in the optical path and used to fold the focusing light source into the optical path. The focus light system may be used in conjunction with a rapid focus method performed by the system in response to directions provided by the controller, wherein the rapid focus method is configured to acquire and process image information based on focus light illumination reflected off of the cassette 1420 and to adjust the position of the objective 1451 accordingly.

The optics system 1450 may comprise a field stop 1464. The field stop 1464 may comprise a circular aperture 1465 configured to block stray light from reaching the camera 1457.

The optics system 1450 may further comprise a filter or a plurality of filters. The filter or plurality of filters may be placed in a fixed position in the optical path. The filter or plurality of filters may be configured to block one or more wavelength of light, such as wavelengths of light used for fluorescence excitation (e.g., the red laser diode excitation wavelength 637 nm) and pass dark field light and emission wavelengths (e.g., a 669 nm red wavelength and a 553 nm green wavelength) used for a FISH ID procedure.

The optics system may further comprise a single band filter 1455. The single band filter 1455 may be located on a single band filter changer 1466. The single band filter changer 1466 may be configured to reversibly interpose the single band filter 1455 in the light path to permit the emission green wavelength (553 nm) and block all other wavelengths during the FISH ID procedure. The single band filter changer 1466 may use a stepper motor to move the single band filter 1455 in or out of the optical path. The single band filter 1455 is introduced into the path only when imaging the emitted green light (553 nm).

Other filter configurations may be used in accordance with various embodiments. For example, an optics system can comprise any suitable number of filters, including a plurality of reversibly interposable filters. The filters may be selected based on the combinations of light sources and fluorophores used, and various combinations of light sources, fluorophores, and stationary and movable filters are possible and within the scope of the present disclosure.

The optics system may further comprise a tube lens 1456. The tube lens 1456 can be a multi-element lens configured to reimage light in the optical path onto a camera sensor surface. In conjunction with the objective 1451, the optics system 1450 provides a 6.1-fold magnification of the field of view (i.e., a 20× magnification objective and a 0.305× magnification tube lens). In some embodiments, the optics system comprises a telecentric lens providing orthographic projection, thereby permitting measurements to be taken without scaling, although other lens types may be suitable.

The optics system 1450 may further comprise an image sensor (not separately shown, but embedded within the camera 1457). An image sensor may be used to acquire images of the sample. In various embodiments, an image sensor can comprise a complementary metal-oxide semiconductor ("CMOS") sensor or active pixel sensor camera. For example, a CMOS sensor camera can be a five megapixel grayscale camera used to acquire images for processing. In various embodiments, a passive pixel sensor camera, such as a charge-coupled device image sensor, may be used. In accordance with various embodiments, an image sensor is operatively connected to a controller and transmits acquired images to the controller for storage and data processing.

Automated high speed microscopy requires a system configured to rapidly adjust the relative distance between a microscope objective lens and a sample in order to arrive at a correct distance between the two. Establishing this correct distance ensures that sample features of interest are imaged in the proper focal plane for accurate sample analysis. The optics system 1450 of the present disclosure may be configured to enable very rapid focusing of a series of successive images (frames) of microorganisms in a given sample during an analytical run of the instrument. To achieve this, the instrument undertakes a method for quickly focusing the optics system 1450 on an object of interest, (e.g., a microorganism) in less than about 500 ms. The optics system 1450 can establish a focal plane with as few as only two trial images coupled with a learning algorithm that may allow as few as two test images to be used in this process. Image data can be stored digitally and compared over time for changes in one or more sample features. Not only does the disclosed process provide a very fast method for rapid focusing in a series of successive frames captured at a specific location in a field of view, the process does not require expensive or specially manufactured components to be accomplished.

Fast Focusing of Optical System

Figure 77:
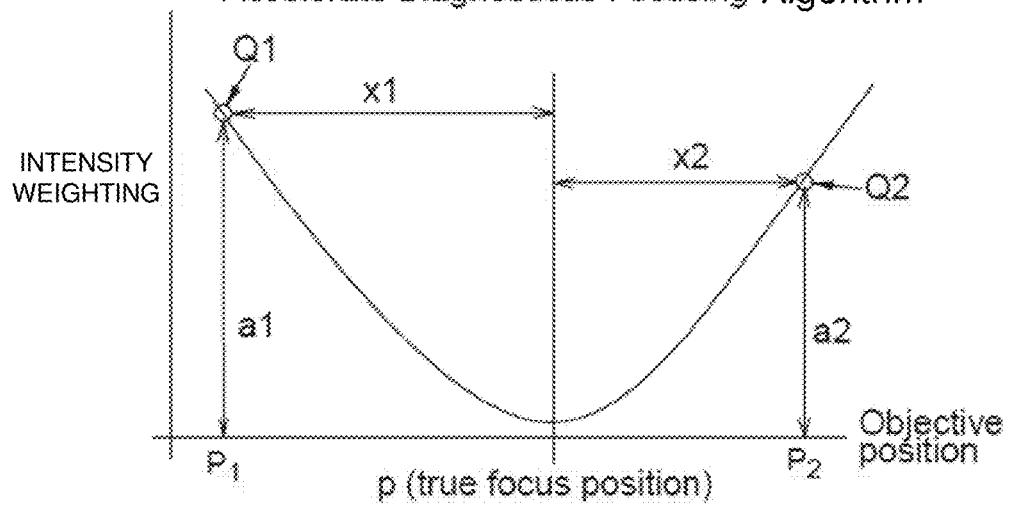
FIG. 77 is a graph of resolution plotted against objective position.
Figure 78:
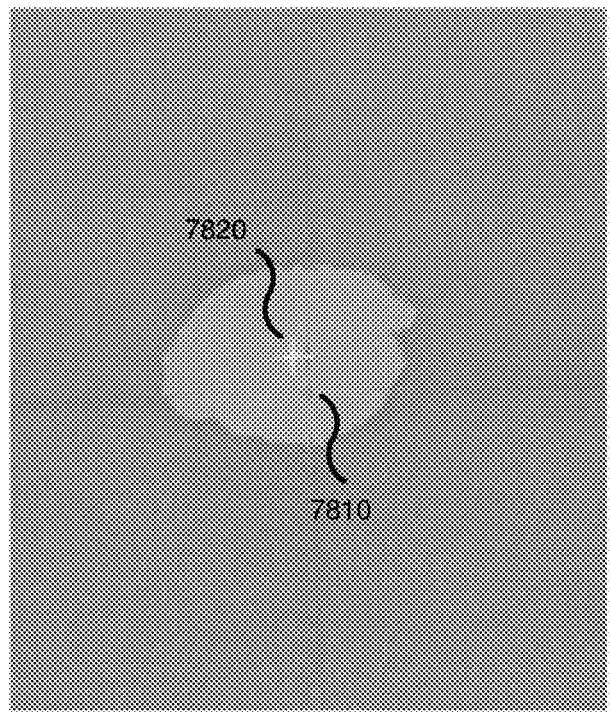
FIG. 78 is a drawing showing a point source image on one side of the image plane for a sample feature of interest (e.g., a microbe).
Figure 79:
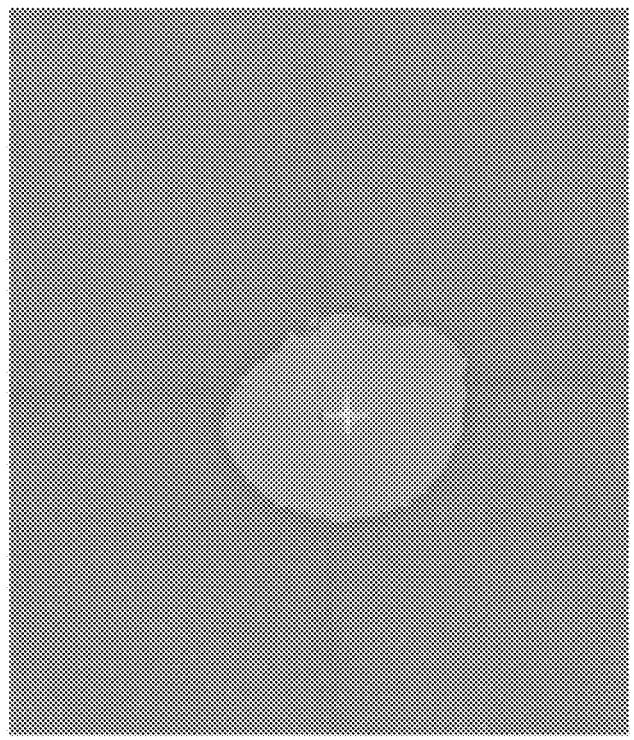
FIG. 79 is a drawing similar to FIG. 78, but showing a point source image on an opposite side of the image plane for the sample feature.

Unlike focus methods known in the art (e.g., "hunting and estimation" algorithms), the optics system 1450 may employ a rapid focusing algorithm to mathematically calculate the true focus position for an individual microorganism or an individual colony in a sample, as illustrated in FIGS. 76-80B and FIGS. 82A-82C. One skilled in the art will recognize that this disclosed fast focusing method can be used with other systems and methods (such as those used to detect cells or microorganisms), in addition to those disclosed herein. Control of movement of the objective and processing of the algorithms described below can be accomplished using hardware components shown in FIG. 101, which can be imbedded on the control board 321. Movement of the objective causes defocus of a reflected point source image on both sides of the image plane for a sample feature of interest (e.g., a microbe), as shown in FIGS. 78 and 79. The rapid focusing algorithm derives a virtual true focus position (pt) by acquiring two focus data points p1 and p2, which lie on either side of the true focus position delineated by plotting point source spot areas in pixels on the x-coordinate against the positions of the instrument's objective, as set forth in FIGS. 77, 80A and 80B. The true focus point pt is the local minimum of the curve created by computing the linear proportional position between p1 and p2. Optimally, the best image will have the smallest spot which is nearly the same as the diameter of pinhole 1463 (e.g., about 25 microns). To this end, the instrument may comprise software that directs objective 1451 through the following algorithmic steps:

Move objective to an out of focus—far position;
Acquire image of point source spot;
Move objective to out-of-focus—near position;
Acquire image of point source spot;
Use center of spot locations and spot sizes to compute correct focus position for objective;
Move objective to computed location and acquire actual image.

The center spot locations can be computed for a grayscale focus image, the content of which can be irregular and of varying intensities. Knowing the center of the focus image spot provides the focusing algorithm with the directional components required for fast focusing. Pixels in the image are indexed by row and column, and have intensity values from 0-4095 (12 bit grayscale) in one implementation. All pixels in the image are examined. Each pixel intensity value is multiplied by its row and added to a 'row sum'. Each pixel intensity value is multiplied by its column and added to a 'column sum'. Also, each pixel intensity value is added to a 'full image sum'.

Once all pixels have been examined and the sums accumulated, the intensity weighted center row and column of the image centroid are computed as:

Row sum/Full image sum
Column sum/Full image sum

Using this method, brighter pixels contribute more weight to the computed position, while darker pixels contribute less. Thus, the results represent a good measure of the center position of the image content.

In some embodiments, the order of the steps may be altered for this learning algorithm (by which the instrument learns or identifies the specific location in the field of view of a given microorganism). For example movement of the objective to the out-of-focus—near position and imaging of the near point source spot may be performed before the objective is moved to an out-of-focus far position and imaging of the far point source spot is performed. Site-to-site variations in reflectance and other such parameters may change the absolute values of the focal curve (e.g., raising or lowering the curve along the x-axis) but this type of variation does not alter the resultant computed true focus position. The initial pass of focusing at a given site can take more than two focus images before two "qualified" focus images are achieved and true focus can be computed. During the first imaging pass, the learning algorithm uses neighboring sites that are close to the same height as initial starting points for focus trial images. During successive passes, the learning algorithm uses the previous pass focus trial image positions for the site to guide the focus trial images. In all cases, the focus trial images must not be "too near" or "too far" away from the true focus point. If they are, then new focus trial images are taken. Mathematically, the true focus position can be identified as follows.

$$\frac{x1}{a1} = \frac{x2}{a2} \quad \text{Equation 1}$$

or $$\frac{x1}{x2} = \frac{a1}{a2}$$

$$p2-p1=x1+x2 \text{ or } x1=p2-p1-x2 \quad \text{Equation 2:}$$

$$p_t=p2-x2 \quad \text{Equation 3:}$$

Substituting x1 from Equation 2 into x1 of Equation 1:

$$\frac{p2-p1-x2}{x2} = \frac{a1}{a2}$$

$$\frac{p2-p1}{x2} - 1 = \frac{a1}{a2}$$

$$\frac{p2-p1}{x2} = \frac{a1}{a2} + 1$$

$$p2 - p1 = \left(\frac{a1}{a2} + 1\right)x2$$

$$x2 = \frac{p2-p1}{\frac{a1}{a2}+1} =$$

Substituting x2 from the above into Equation 3 yields final equation:

$$p = p2 - \frac{p2-p1}{\frac{a1}{a2}+1}$$

Using these equations, for example, if:
p1=4.581, a1=1819, p2=5.823 and a2=1623 then, the resultant pt=5.237.

Figure 80A:
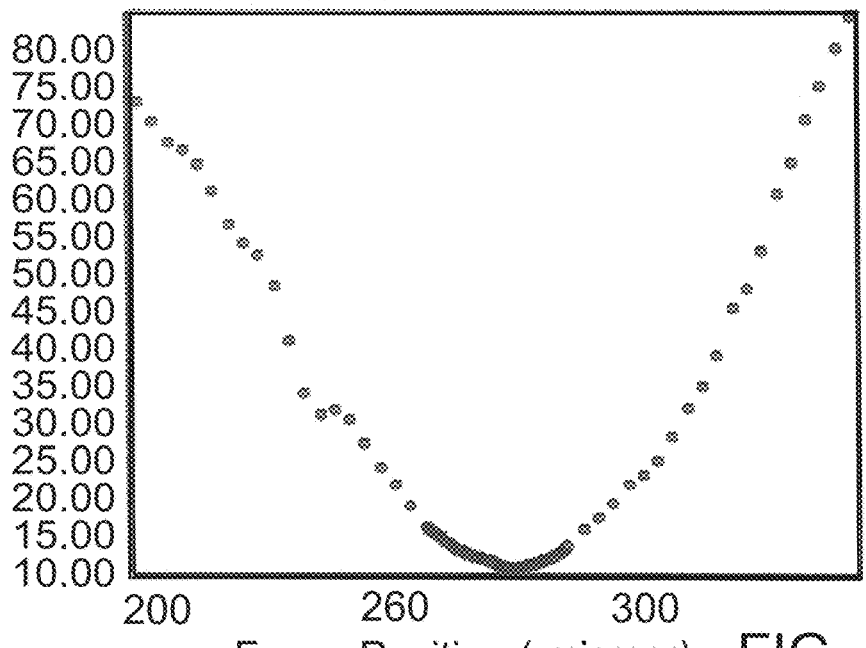
FIGS. 80A and 80B are graphs of Spot Area versus focus position and intensity weighting versus focus position.
Figure 80B:
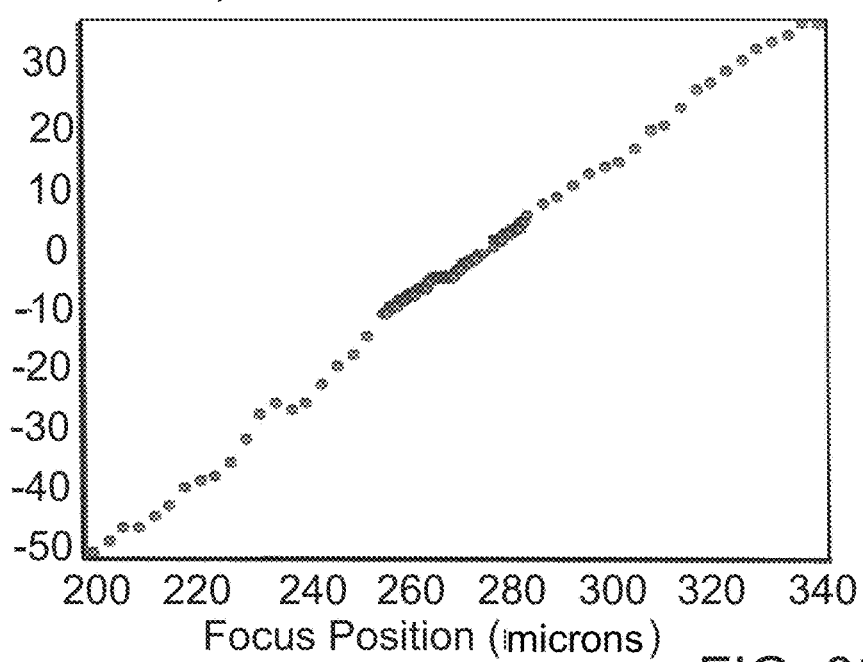
Figure 80C:
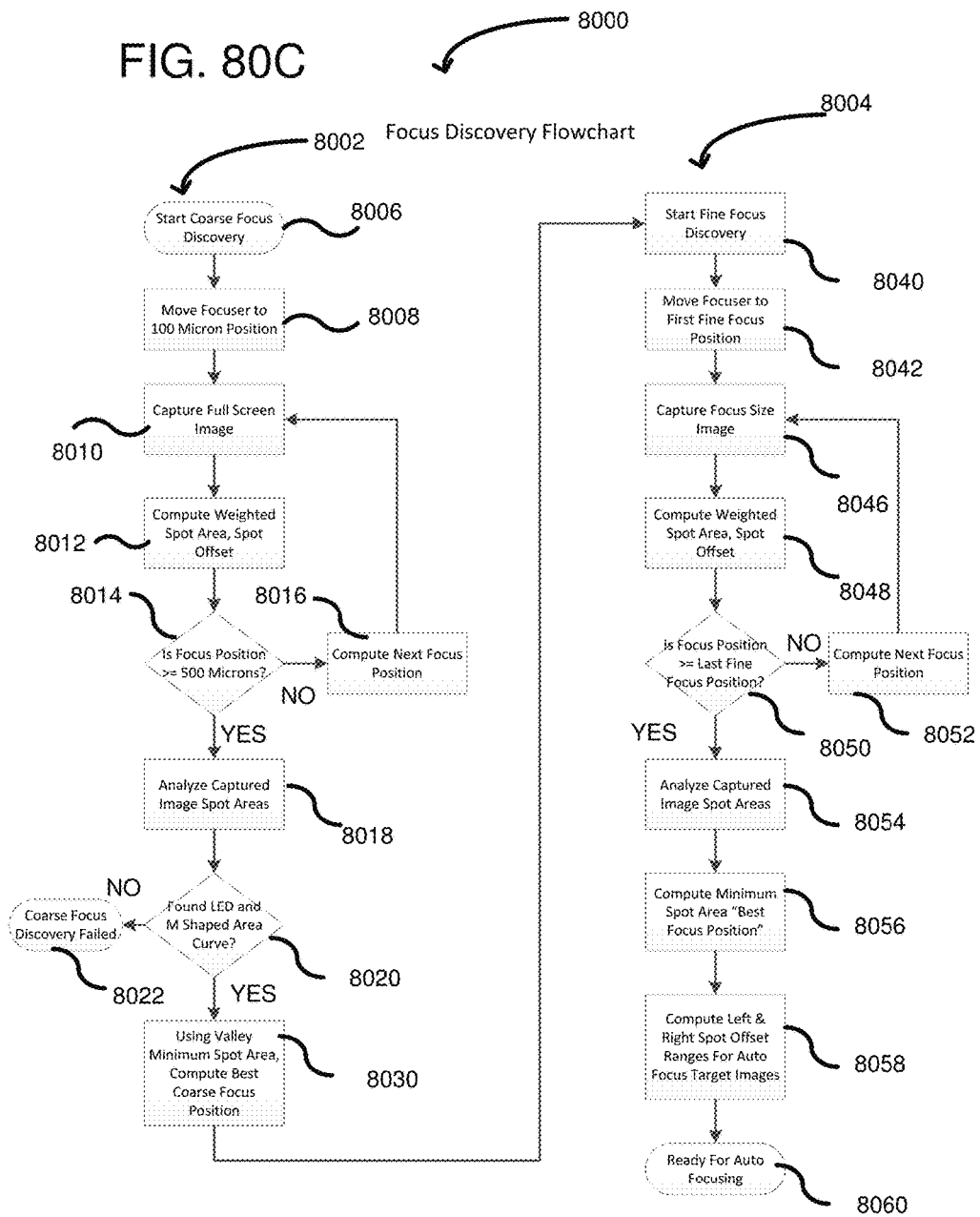
FIG. 80C is a flowchart of a method for a discovery phase for generating data used for autofocusing.

A prescan 8000 is performed in FIG. 80C in order to obtain the graphs shown in FIGS. 80A and 80B. In process block 8002, a coarse focus discovery is initiated. The focus discovery is accomplished in two passes: a coarse focus discovery pass 8002 and then a fine focus discovery pass 8004. The coarse focus discovery pass is used to locate a position of the light source (e.g., LED). The focus LED appears in the camera image in a different location for every instrument, and if an instrument has been serviced, it may change. Thus, during the coarse focus discovery pass, a location of a reflection generated by the light source needs to be determined. To accomplish this, full-screen images (e.g., 2592×1944 pixels) are taken during the coarse pass. The coarse pass is repeated for multiple iterations of different focus positions, such as different focus positions between 100 to 500 microns (50 micron increments, for example). At process block 8006, the coarse focus discovery is started. In process block 8008, the objective is moved to a position of 100 microns (though one will recognize that other starting positions can be used). In process block 8010, a full screen image is captured. In process block 8012, a weighted spot area and spot offset are determined using the techniques described herein. Computing the weighted spot area involves computing the area for just a single image. The weighted spot area is computed using grey-scale values (light intensity) for the pixels and relative row and column position of the pixels. The spot offset is calculated as an offset from image center. In decision block 8014, a check is made whether the focus position has reached a predetermined distance (e.g., 500 microns, in this example, but other distances can be used). If not, then in process block 8016, the next focus position is computed, and process blocks 8010 and 8012 are repeated so that the image is re-captured. Once decision block 8014 is answered in the affirmative, then in process block 8018, the captured image spot areas are analyzed. Analyzing the captured image spot areas involves using the computed weighted spot areas of all of the images together (the curve), and looking for the best focus position. The spot areas are used to find the curve bottom. Once the bottom is found, fixed delta positions on either side of the best focus position are used to lookup the spot offset ranges to later use when focusing.

FIG. 77 shows a portion of an M-shaped graph that can be obtained through performance of process blocks 8010, 8012, and 8018. The figure shows the M-shaped curve in a trough between the two legs (not shown) of the "M." A good focus position is at the valley at the center of the M-shaped curve. During the coarse focus discovery phase a determination is made whether the spot moves left or if it moves right when the focus position increases. The algorithm learns the direction of movement and uses such direction for future calculations.

At decision block 8020, a check is made whether the proper LED position was found and the trough in the M-shaped curve. If not, then at process block 8022, the coarse focus discovery terminates. An error can be reported to the user interface. On the other hand, if decision block 8020 is answered in the affirmative, then in process block 8030, a good focus position can be determined using the bottom-most point of the M-shaped curve in the area of the trough.

This coarse phase 8002 results in targeting where to perform the fine focus discovery pass 8004. The fine focus discovery pass uses much finer focus position steps, centered around the best coarse focus position, and uses smaller (e.g., 401×401 pixels) images, because it is known at which part of the image the LED appears.

Fine focus discovery 8004 starts at process block 8040. In process block 8042, the focuser (objective) is moved to a first position. In process block 8046, a spot can be displayed on the image from a light source and a camera can be used to capture the spot. In process block 8048, intensity weightings and spot offset are computed in a similar fashion as was described above. In decision block 8050, a check is made whether the focus position is greater than a last focus position, which is a predetermined number. If not, then in process block 8052, a next focus position is computed, such as by adding a predetermined distance to the focus position (e.g., 10 microns). If decision block 8050 is answered in the affirmative, then in process block 8054, the captured image spot areas are analyzed. For example, the spot areas can be computed, such as by measuring a distance across the spot. Additionally, an offset from the center of the image can be computed. In process block 8056, a minimum spot area is determined. The minimum spot area is associated with the best focus position. In process block 8058, left and right offset ranges are determined for the autofocus feature. The ranges dictate whether a captured image of a spot is acceptable or not. Once the ranges are chosen, then the prescan phase ends in process block 8060.

With the prescan completed, autofocus can be accomplished using as little as two images. Generally, an image is captured with the focus position in front of and behind the image plane by predetermined amounts. Assuming that the spot is within the spot offset range determined during the prescan, an intensity weighting can be computed for each spot and mapped onto the prescan data to determine the best focus position for the objective. The overall decision path followed by the instrument can be visualized in the process flow depicted in FIG. 82A. The process begins at process block 8202. At process block 8204, a first image is captured or acquired for a first curve side. An attempt by the system is made to acquire a focus image for an object of interest (e.g., a microorganism) on one side of the focus point curve (the first side). Accordingly, a predetermined focus position (P1, FIG. 77) is used wherein the objective is moved in order to estimate a first spot offset. Using that positional information, the objective 1451 is moved so that the focus point is a predetermined distance in front of the image plane. For example, in FIG. 76, an image plane 7620 that includes a glass/liquid interface (i.e., the microorganism positioned upon a glass substrate) is shown as being the best focus position for the objective 1451. However, the objective 1451 is moved to the left, as shown by arrow 7640 so as to change the focus point to a predetermined distance in front of the image plane 7620. Consequently, the focus point is changed to a position shown at 7610, purposely a predetermined distance in front of the image plane. If the image initially obtained from the first side of the curve is outside of the required range, then the instrument makes slight parameter adjustments and acquires an image of that position again. Thus, in decision block 8206 of FIG. 82A, a check is made whether the image is within the required range. Specifically, a range was determined in process block 8058 of FIG. 80C during the prescan. That range relates to spot offset versus focus position information obtained during the prescan and shown in FIG. 80B. A spot offset is an offset of the center of the spot from dead center, which is a known center. For example, in FIG. 78, a known center of the image is shown at 7810. The center of the spot is shown at 7820 and is calculated by measuring from one point on the edge of the spot to an opposite edge at several locations. The offset is a distance between the center of the image 7810 and the center of the spot 7820. That distance is used in decision block

8206 to determine whether the captured image includes a spot that is within the required range. If decision block 8206 is answered in the negative, then in decision block 8208, a check is made whether the number of attempts made to capture the image exceeds a threshold. If so, then a failure occurs in process block 8210. Otherwise, a position of the objective is changed in a direction necessary to move the spot offset within the desired range in process block 8212. The proper direction can be determined using the prescan spot offset data of FIG. 80B. After the objective is modified in process block 8212, an image of the spot can be reacquired. Thus, the process includes repeatedly moving the objective and re-capturing the first image until the offset distance is within the predetermined limits. If this image is within the required range, then the same procedure is followed on the opposite (second) side of the curve in process block 8220. Thus, the objective position is moved to point P2 (FIG. 77). The focus point is thus changed to a new out-of-focus position 7630 (FIG. 76) at a distance behind the image plane, as shown at 7630. In process block 8222, an image is acquired for the newly selected out-of-focus position.

Process blocks 8224, 8226, 8228, and 8230, are similar to those described above for the first image acquisition and will not be re-described for purposes of brevity. The true focus position is calculated from the out-of-focus images from the first and second sides of the focus point curve in process block 8250. In order to calculate the true focus position, the prescan curve of FIG. 77 can be used. An intensity weighting is determined for each image and mapped onto the prescan information as shown at points Q1 and Q2 (FIG. 77). The intensity weighting can be determined by taking a 12 bit grayscale image of the reflected light from the focus LED, and computing a representative spot area. Each pixel in the image has an intensity value of between 0-4095. The computing of the spot area is determined knowing that actual focus images can be quite bright or quite dim, so an algorithm that operates on it should be insensitive to actual image brightness. To accomplish that, first the average pixel value for all pixels in the image is computed. Then, a pixel intensity threshold is computed by taking 80% of that average. All pixels meeting or exceeding that pixel intensity threshold are counted to produce the spot area. The resultant spot area is thus insensitive to absolute image intensity.

A determination can then be made where the bottom of the parabola is located and the objective position associated with the bottom of the parabola is used as the true focus position. While the true focus position is fairly accurate, in process block 8252, a visual focus position is calculated by adding a predetermined offset (a known offset) to the true focus position. The visual focus position is merely a calibration adjustment to take into account the particular application, which is focusing for capturing images of microorganisms (e.g., bacteria or fungi). Once the offset is applied, the objective is moved to the computed position for imaging the microorganism. In process block 8260, an image is captured of the microorganism.

Thus, the visual focus position is computed and the instrument employs this information to move to the true focus position of the microorganism of interest and then acquires an image. If during the learning process a particular image is unable to be obtained in the required range within a certain number of attempts (for example, 20 attempts), then the instrument will deem that position to be unfocusable, abandon the image location, and move on to another object of interest to begin the process anew. In some embodiments, two or slightly more than two—but rarely more than five—focus images may be required to establish the true focus point of an image. The instrument utilizes offset spots (pixels of offset) to set zones on either side of a focus point that permit mathematical calculation of the true focus point. After the initial pass at the first site, the instrument "learns" from the initial data and may reduce the number of images needed for calculation of the true focus point to only two per site at additional locations in the field of view. This learning process substantially reduces the amount of time needed to focus upon and repeatedly capture images of multiple microorganisms in a microfluidic sample channel 5702. The ability to mathematically calculate the precise location of the true focus point of an object—without the instrument's objective having to actually go to that site to home in on the location by trial and error—is desirable to obtaining images in a fast, accurate manner.

Once a true focus position is located for a particular microorganism, the instrument will store location data for that microorganism, thereby permitting the instrument to move on to the next microorganism in a sample within a microfluidic sample channel 5702 of the cassette 4500 and repeat the process, thus imaging this next microorganism. The instrument may retrieve stored image location data and repeatedly return to a specific microorganism in a given field of view to capture multiple images over time, thereby memorializing any responses or changes the microorganism exhibits under a test condition (e.g., growth in the presence or absence of an antibiotic). The rapidity with which this step-wise determination of the true focus position of a microbe in a biological sample is achieved is key to facilitating within a matter of a few hours (preferably less than eight hours, more preferably less than seven hours, and even more preferably less than four hours, such as 3-8 hours, 4-8 hours, 4-7 hours, or 4-6 hours) the identification of microorganisms in the sample as well as their sensitivity to treatments, such as the sensitivity of bacteria to particular antibiotics.

In some embodiments, a light source 1453 illuminates a sample. Objective 1451 is moved through the z-plane to locate the best image locale. Once identified, the targeted reflective spot may be revisited multiple times, the first time establishing a baseline against which additional images may be compared for changes or modifications. The z-height of focuser 1452 does not change much from site-to-site on a given glass support, although there will be slight variations due to imperfections introduced to the glass support during manufacture. Thus, initial data obtained from a first image pass can be used to inform the instrument about where to target a second site on glass support 4400 for imaging a second object (microorganism) of interest.

Because microorganisms are three-dimensional entities, and because the contours of a microorganism may change with growth or exposure to environmental challenges (temperature alterations, nutritional conditions, antibiotics, etc.) during an analysis period, objective 1451 targets the bottom or glass contacting area of a microorganism for consistency in measurement over time. By contrast, focusing on the top of a microorganism during baseline measurement would make it difficult to locate the exact same spot some minutes to hours later after the microorganism has grown in size or multiplied. Under this scenario, the depth of the original focal spot would differ at each return visit by the objective due to additional cell mass, introducing the potential for error in measuring from the originally targeted position. The rapid focus algorithm described herein overcomes this deficiency.

In certain embodiments, microorganisms are immobilized in a medium (such as one including agar or agarose) and therefore remain in the same location during the analysis time period, permitting repeated imaging via the bottom or glass contacting area of a microorganism which the tracks features that change in response to changes in environmental conditions. For example, the microorganism can be retained on a surface of the support (such as a flowcell or glass support), thereby producing a retained microorganism.

In certain embodiments, camera 1457 communicates with a system controller, which may be a host computer. The system controller comprises software that instructs instrument 100 where to move focuser 1452. The system controller instructs LED light source 1453 to turn on and camera 1457 to capture an image. In some examples, no image data is stored in the instrument module; image data is stored in—and later retrieved from—the system controller.

Figure 82A:
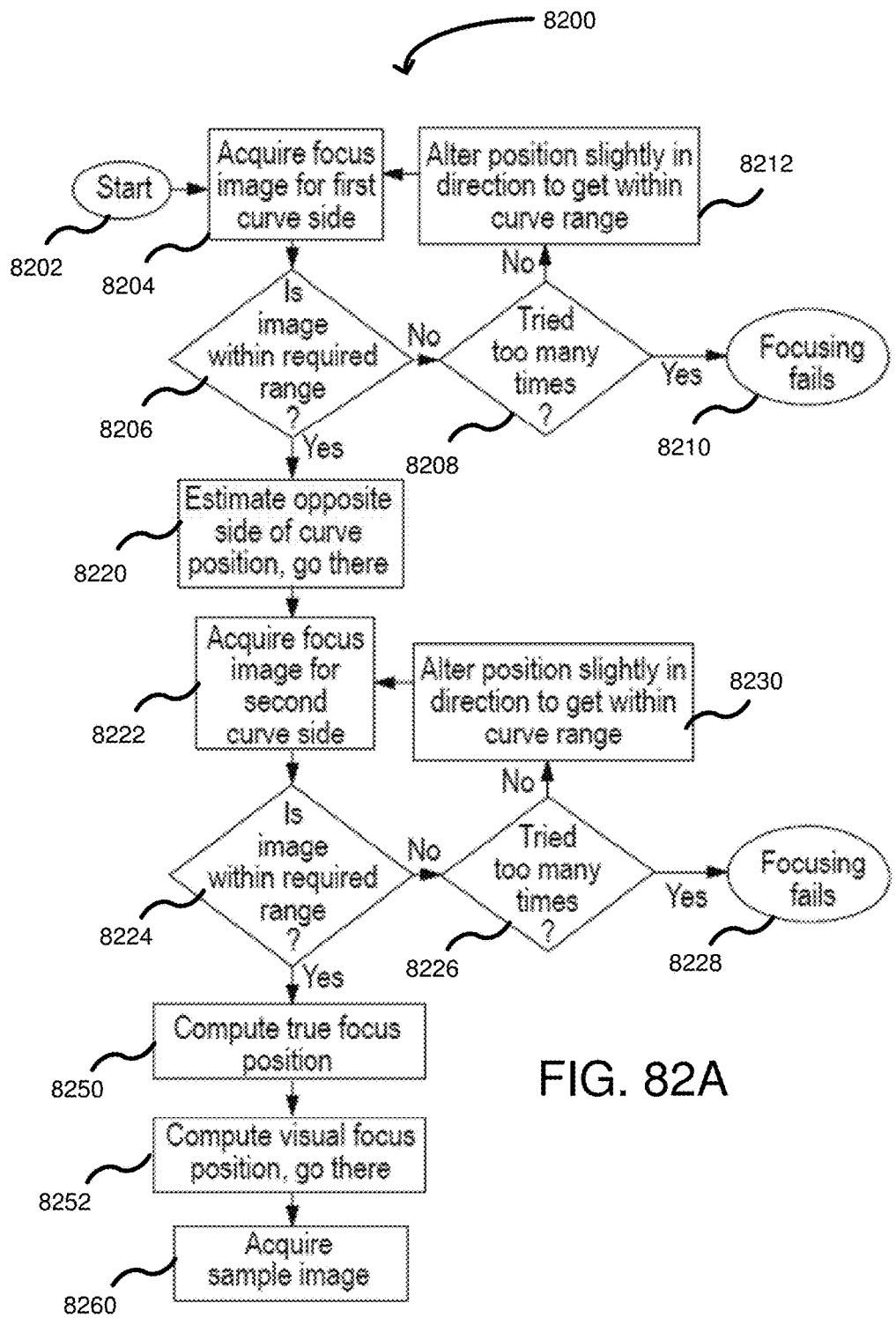
FIG. 82A is a flowchart of the focusing algorithm according to one embodiment.
Figure 82B:
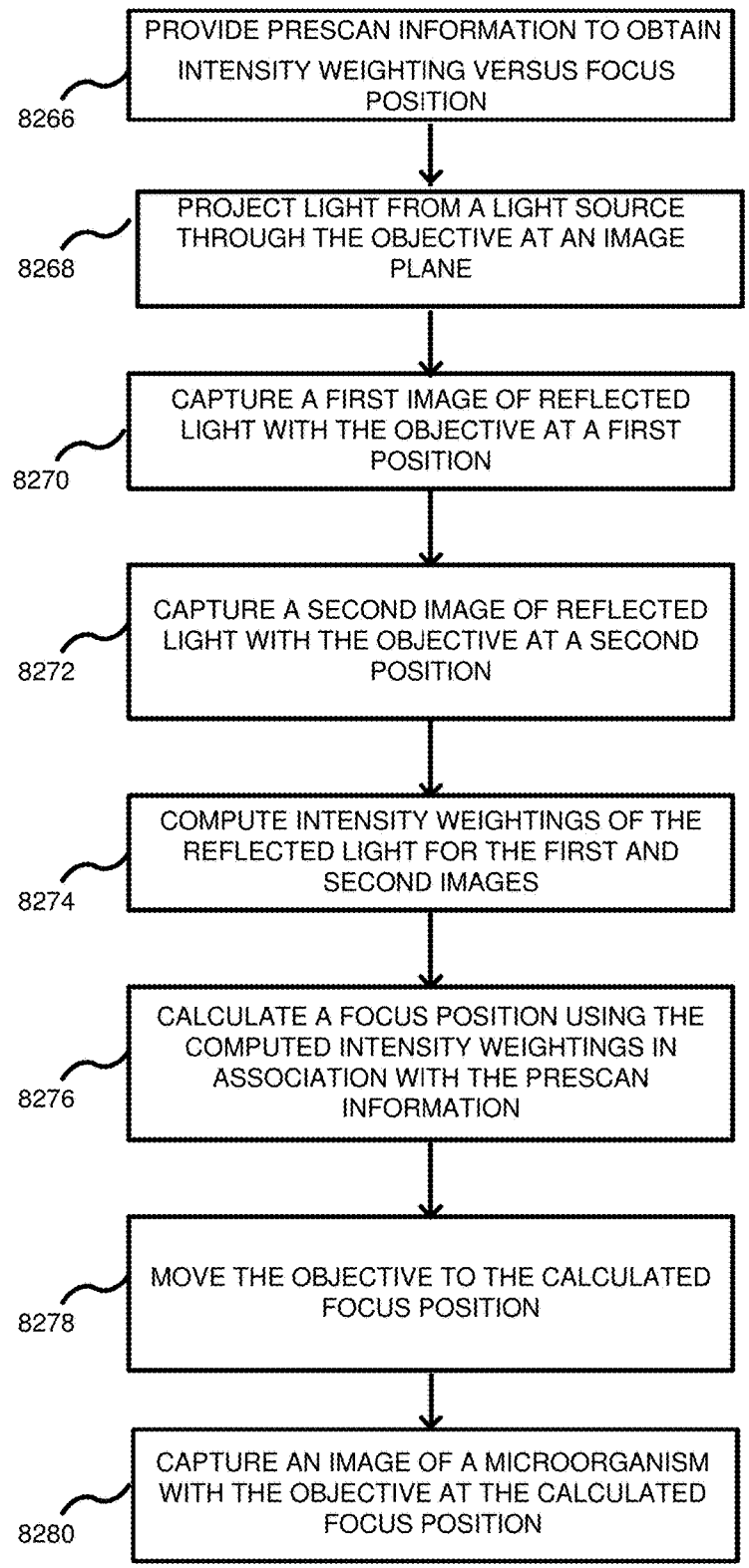
FIG. 82B is a flowchart of the focusing algorithm according to another embodiment.

FIG. 82B is a flowchart according to one embodiment for autofocusing on a microorganism. In process block 8266, prescan information is provided that includes intensity weightings versus focus position. The prescan flow was described in FIG. 80C, above. During the prescan, a plurality of intensity weighting versus focus position information is obtained for a range of different focus positions. The results can be plotted as shown in FIG. 80A. Likewise, spot offset versus focus position can be obtained in some embodiments over a plurality of focus points as shown in FIG. 80B. In process block 8268, a light can be projected from a light source through the objective at an image plane. For example, the light source can be a first light source designed to project a beam of light that generates a reflection off of a glass/liquid interface. Example light sources include an LED, laser diode, etc. (such as diode 1403 or 1404). The light source can be a colored light source so that the reflection is easily visible. However, using greyscale analysis, greyscale values are used to measure the reflection, so colored light is not required. The light source used to generate the reflection is a different light source than that used for imaging the microorganism. In process block 8270, a first image is captured of the reflected light with the objective (e.g., 1451) at a first position. The first position is an intentionally out-of-focus position with a focal point in front of the true focal point. An example of such an out-of-focus position is shown by focus point 7610 in FIG. 76. In process block 8272, a second image is captured of reflective light with the objective at a second position. In this case, the second position is an intentionally out-of-focus position behind the true focal point. An example of such an out-of-focus position is shown by focus point 7630 in FIG. 76. In process block 8274, intensity weightings are computed for the reflected light of the first and second images. As described above, the intensity weightings take into account the greyscale values and row/column information to provide a weighting to each pixel in the image. In process block 8276, a focus position is calculated using the computed intensity weightings in association with the prescan information. The computed intensity weighting can be mapped onto the prescan information and a lowest point (lowest intensity weighting) of the prescan information can be determined. The focus position associated with that determined point is the desired focus position (although some additional calibration may be required). In process block 8278, the objective is moved to the calculated focus position. At this point, the focus position should be the true focus position on the image plane, as shown at 7620 in FIG. 76. In process block, 8280, with the objective properly positioned, an image of the microorganism can be captured.

Using the process described above, the autofocus feature can be accomplished in as little as two images, making it faster than other solutions.

Figure 82C:
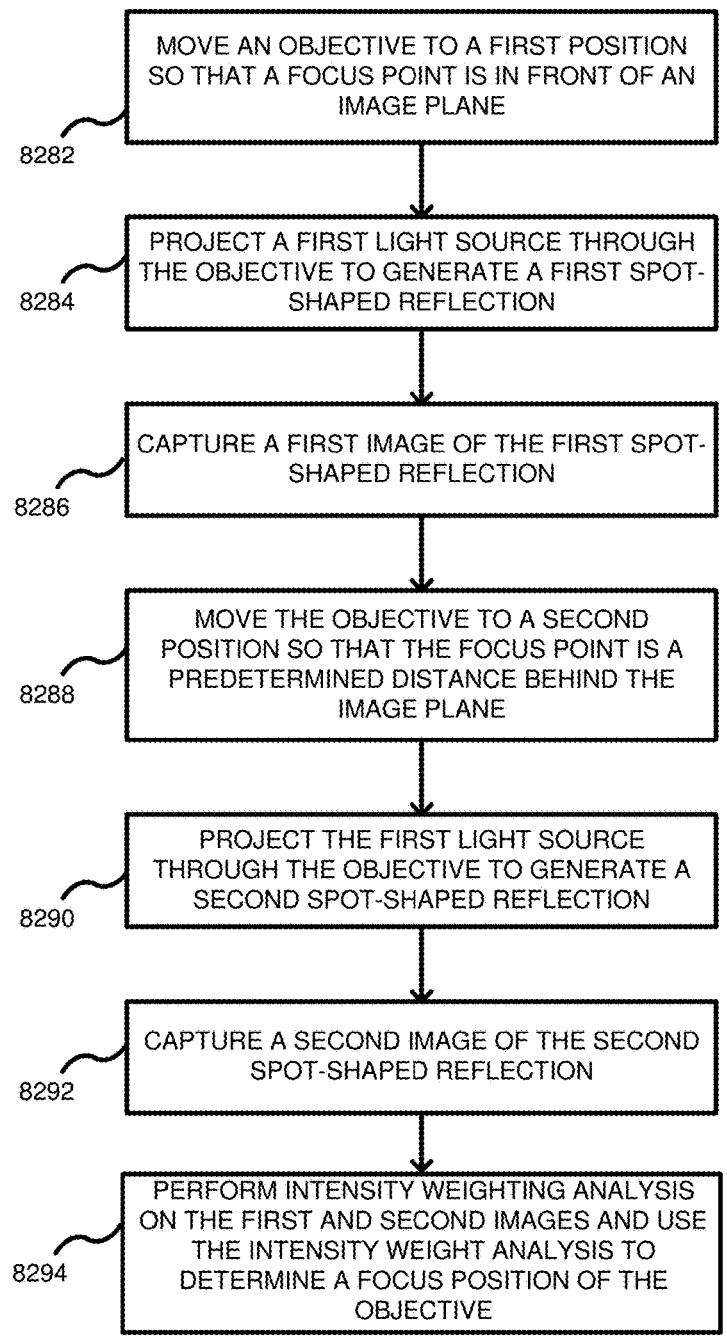
FIG. 82C is a flowchart of the focusing algorithm according to still another embodiment.

FIG. 82C shows a flowchart according to another embodiment. In process block 8282, an objective (e.g., 1451) is moved to a first position so that a focus point is in front of an image plane. The image plane (e.g., 7620) is typically a glass substrate with a microorganism-based liquid thereon. By "in front" of the image plane, it is meant that the focus point is in-between the image plane and the objective. Thus, the objective is moved in a direction away from the image plane to make the focus position intentionally out-of-focus. By so doing, a point Q1 (FIG. 77) can be determined and mapped onto an existing graph obtained during the prescan phase. In process block 8284, a first spot-shaped reflection is generated using the objective at the out-of-focus position. A first light source, such as diode 1403 or 1404, can be used. Based on the objective position, different greyscale values and offsets will be generated. In process block 8286, a first image is captured of the first spot-shaped reflection. For example, the camera 1457 is used to capture the first image under direction of the controller. In process block 8288, the objective is moved to a second position (see P2, FIG. 77) so that a focus point is a predetermined distance behind the image plane. By being behind the image plane it is meant that the image plane is in-between the focus point and the objective. In process block 8290, the first light source is projected through the objective to generate a second spot-shaped reflection. By "first" light source, it is meant a first type of light source. Thus, laser diodes 1403 and 1404 are both considered a first light source as they are used for generating reflections. In process block 8292, a second image is captured of the second spot-shaped reflection. In process block 8294, an intensity weighting analysis is performed on the first and second images. The intensity weighting analysis is used to determine a focus position of the objective. For example, the intensity weighting values Q1 and Q2 can be determined (FIG. 77) and the prescan graph adjusted to fit Q1 and Q2. Then the focus position P can be calculated as being in line with the lowest point on the parabola. It should be noted that while a linear curve aspect of a parabola has been used for focus mapping in certain embodiments, the process described herein may be applied to other curves using a different underlying equation.

Enclosure Temperature Control

Figure 81B:
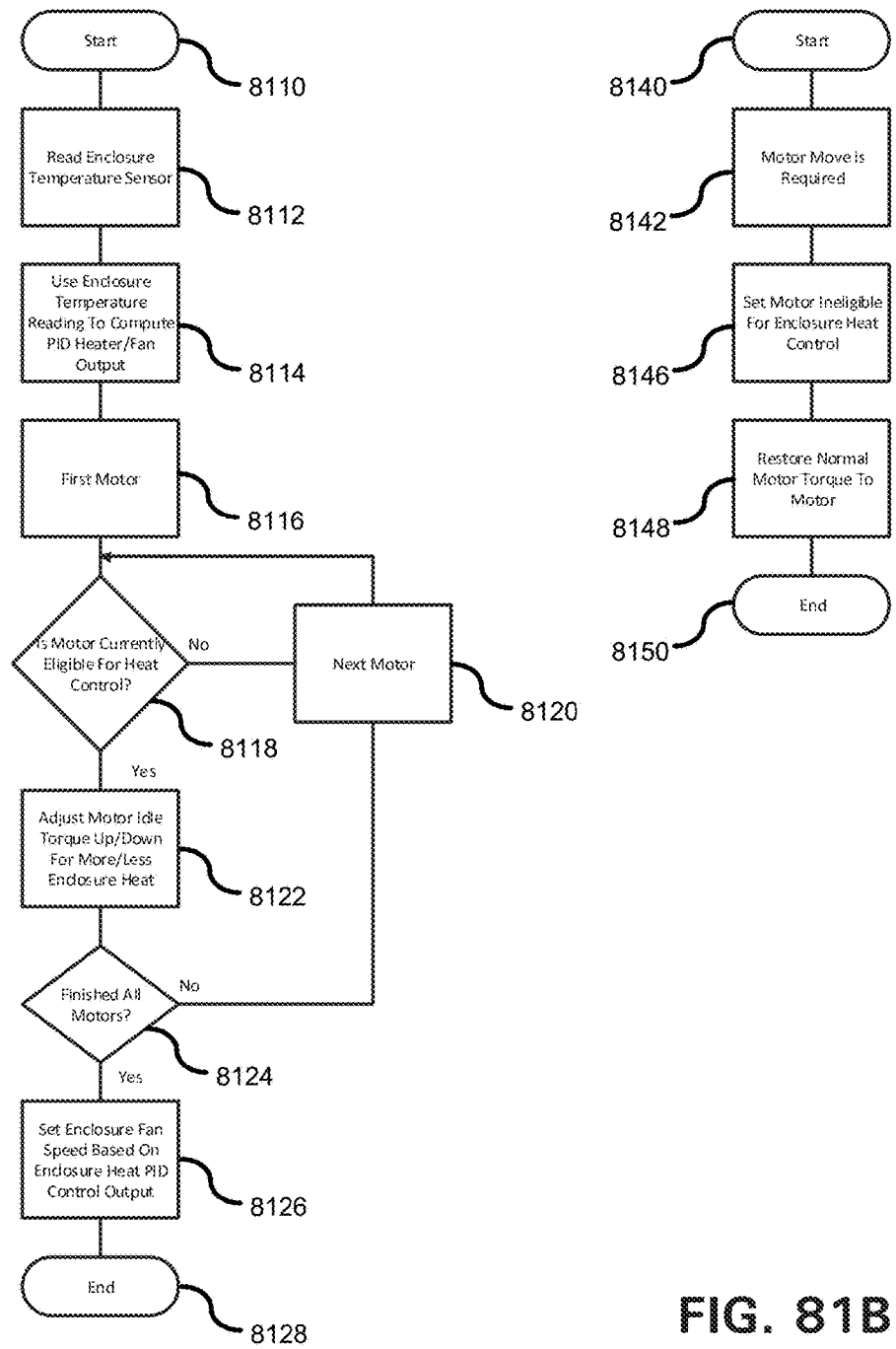
FIG. 81B is a flowchart according to one embodiment for controlling enclosure temperature using stepper motors.

FIGS. 81A and 81B relate to controlling temperature within the upper enclosure 110 above the cassette. One skilled in the art will recognize that the disclosed temperature control method can be used with other systems and methods (such as other enclosed systems), such as other enclosed systems, in addition to those disclosed herein. Referring to FIG. 3, the enclosure 110 is shown removed to expose a control board 321. The control board 321 can include one or more temperature sensors and a controller (e.g., processor, microcontroller, ASIC, etc.) for controlling a temperature control algorithm. The control board 321 can further include one or more of the components described in FIG. 101. It is desirable to maintain a constant air temperature within the enclosure 110 so that the biological samples are not adversely impacted by temperature variations. However, due to space limitations, additional heating and/or cooling components can prove to be difficult to incorporate into the design. Accordingly, the controller controls existing components that have a function unrelated to heating, in order to heat the enclosure. For example, stepper motors that are not actively being used can have their idle currents increased so as to generate additional heat to heat the enclosure.

A simple flow diagram is shown in FIG. 81B for dynamically controlling waste heat. In process block 8110, the enclosure temperature control flow diagram begins Although described for stepper motors, the flow diagram can be extended to other components that have a primary purpose unrelated to heating. In process block 8112, a temperature of the enclosure is read. For example, a temperature sensor, such as a thermistor or thermocouple, can be used to provide temperature information of a temperature within the enclosure. Such as temperature sensor can be mounted on the control board 321. In process block 8114, the temperature reading can be used to compute a proportional-integral-derivative (PID) heater or fan output. The controller on board 321 can use PID algorithms to compute an output number. That output number can be a percentage of a maximum potential output. PID algorithms are known in the art and any desired PID algorithm can be used. PID parameters may be provided—namely the P, I and D terms, which act as multipliers in the PID algorithm to allow tuning of the algorithm to the application at hand. The PID algorithm can be used to determine whether heating or cooling is needed, and, in addition, what amount of heating or cooling is to be performed. For example, if the PID algorithm produces a control output that is a negative number then heating of the enclosure temperature is needed. On the other hand, if the PID algorithm outputs a positive number then cooling is needed. In addition, the output of the PID algorithm can have a range between a negative maximum and a positive maximum and the output can be a percentage of a maximum to further control heating or cooling. For example, the computed percentage can be used to adjust the speed of the fan with a corresponding percentage of the maximum fan speed. In a simple example, if the PID output is 70% of its maximum output, then the fan speed can be set at 70% of its maximum speed. Conversely, if heating is required, then a number of components or percentage power increase associated with those components can be computed based on the percentage of the maximum PID output.

The stepper motors can have a minimum current requirement for hold torque (when stepping motion is not occurring). However, additional current to the stepper motors is acceptable and will generate additional waste heat up to a maximum current as specified by the manufacturer of the stepper motor. Using the maximum and minimum values for the stepper motors as a 100% and 0%, a scale can be generated based on the PID algorithm output. If cooling is required, the stepper motors can have the hold torque set to a minimum so that a minimum amount of waste heat is generated.

In process block 8116, a check is made of a state of a first stepper motor. The stepper motor can either be active (moving) or inactive (not moving and maintaining its current position) for a predetermined threshold period of time (e.g., 5 seconds). When active, the stepper motor can be considered in an active mode. The controller can maintain a timer on each stepper motor and simply reset the timer when the motor becomes active, which is also under the control of the controller. In this way, the controller can monitor the status of all of the stepper motors. Stepper motors that are not being used actively can be utilized for heat control, which is unrelated to movement. In decision block 8118, a determination is made whether a motor is eligible for heat control. If not, then a next motor is checked in process block 8120. An example of when a motor is not eligible is when the motor is active and performing rotational motion of components in the system. In such a state, the stepper motor uses motion control parameters for its torque. If decision block 8118 is answered in the affirmative, then in process block 8122, the motor idle torque is adjusted up or down according to whether the PID output indicated heating or cooling. For example, if the PID algorithm indicated that the temperature of the enclosure should be heated, then the controller can transmit a command to the stepper motor to increase its idle torque current to a desired value. In one particular implementation, an Application Programming Interface (API) request can be sent from the controller to the stepper motor with a parameter used to set the idle torque current. A check can be made on a maximum current of the stepper motor and a percentage of the maximum current can be used based on the PID output. In the case the enclosure should be cooled, the idle torque current can be set to the minimum, which is the minimum required to hold the current position. Thus, power is decreased to the components, which includes setting currents associated with the components to minimum allowable currents. After the current stepper motor has its idle torque current set, in decision block 8124, a check is made whether all motors have had their idle torque current set. If not, the process returns to process block 8120 to select a next motor. Decision blocks 8118 and 8122 are then repeated. After all the motors have had their idle torque current adjusted, then in process block 8126, the enclosure fan 320 can have its speed adjusted. For example, if the PID output indicates that heating of the enclosure is needed, then the fan 320 can be turned off. Alternatively, if cooling of the enclosure is needed, the fan can be activated and the holding torque on each idle stepper motor is set to a minimum (the current needed to maintain the motor position). The speed (RPM) of the fan is variable and can be controlled based on the PID output. In process block 8128, the enclosure temperature routine ends. The routine can be rerun at predetermined intervals so as to consistently control temperature within the enclosure.

A separate flowchart shows the process used when a stepper motor is activated to perform its normal stepper functionality. In process block 8140, the routine starts. In process block 8142, a determination is made by the controller that motor movement is required. In process block 8146, the controller can then set the motor as ineligible for enclosure heat control. Typically, the motor is only eligible when it becomes inactive for a predetermined period of time. In process block 8148, normal motor torque is restored to the motor. In process block 8150, the flow terminates. If the motor is later stopped, it can become eligible again for heat control after a predetermined period of time has passed.

Thus, components that have a function that is typically not related to heating (e.g., motors) can have their current altered so as to maximize heat generation. Alternatively, their current can be lowered and fan speed increased to lower temperature.

A graph shown in FIG. 81A shows the enclosure temperature as a function of power consumption. In order to raise the overall temperature, the controller increases power to various components so that the temperature of the enclosure increases. Increasing power can be unrelated to improving functionality of the individual components, but rather to simply increase heat generation. Alternatively, when the controller attempts to cool the enclosure, power consumption can be reduced.

Controller

In various embodiments, a system can comprise a computer operably connected to the instrument and configured to control instrument operations and/or receive, store and process data received from the instrument. A computer can be a special purpose computer or a general purpose computer configured to run custom software. In various embodiments, a computer can include a display. A display configured to receive user inputs may be used, such as a touchscreen display. An example controller is shown in FIG. 101.

Reagent Cartridge

Figure 26:
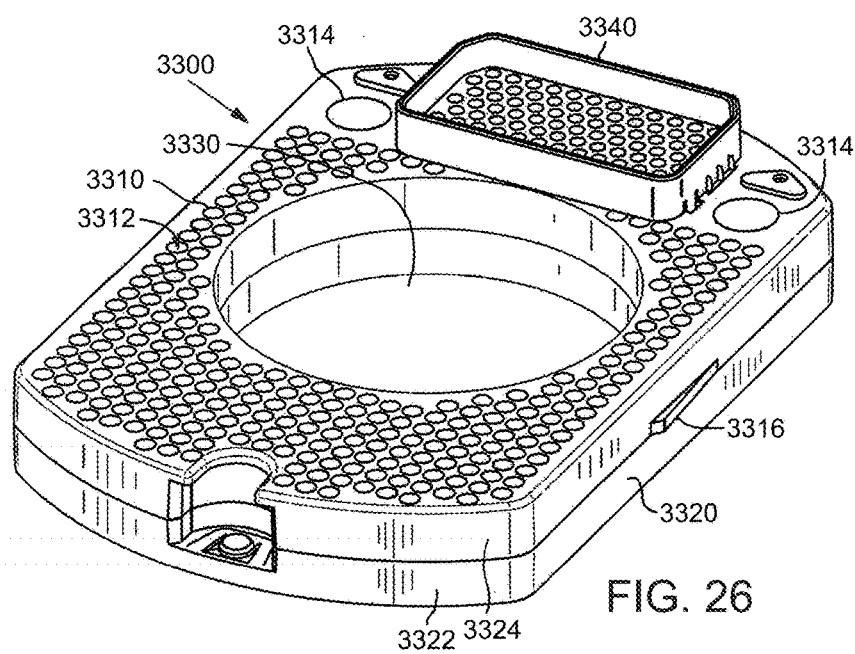
FIG. 26 is a perspective view of a reagent cartridge.
Figure 27:
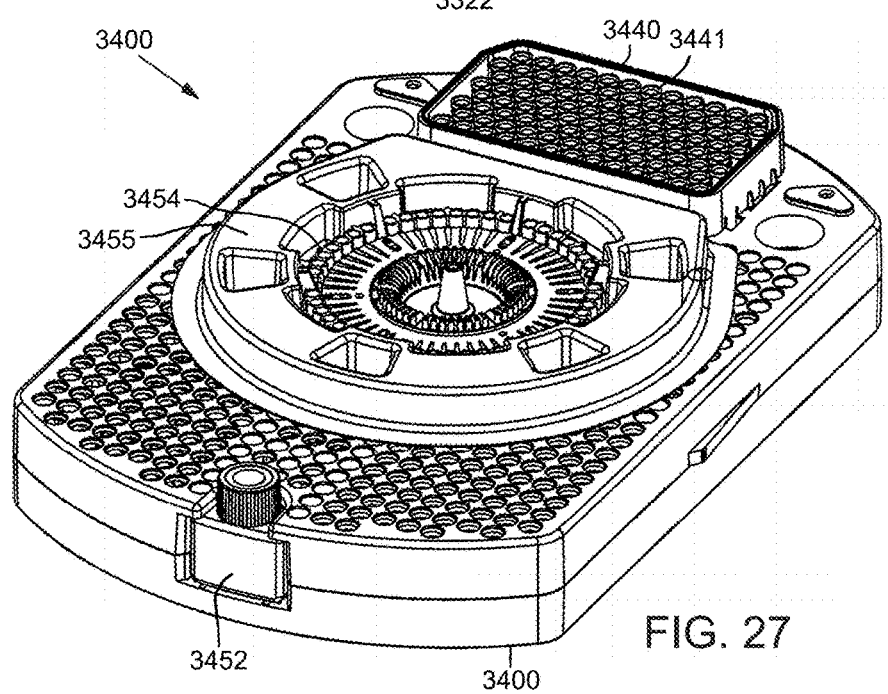
FIG. 27 is a perspective view of a reagent cartridge kit that includes a reagent cartridge.
Figure 28:
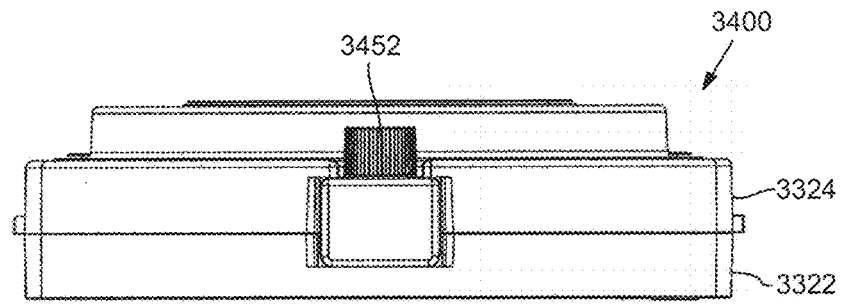
FIG. 28 is an end elevation view of the reagent cartridge kit.
Figure 29:
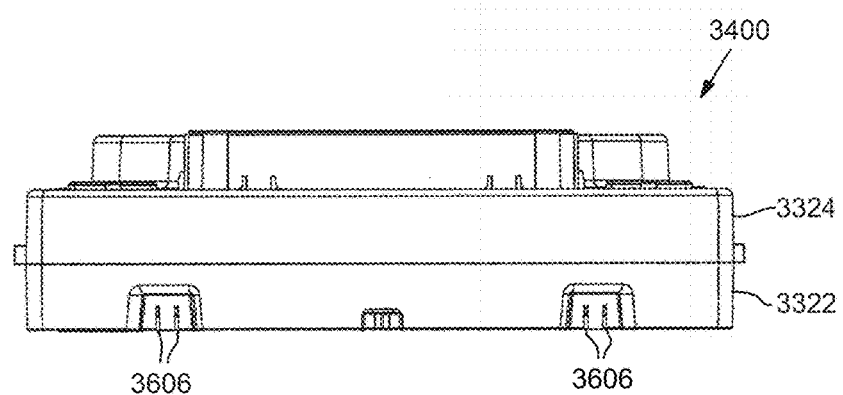
FIG. 29 is an opposite end elevation view of the reagent cartridge kit.
Figure 30:
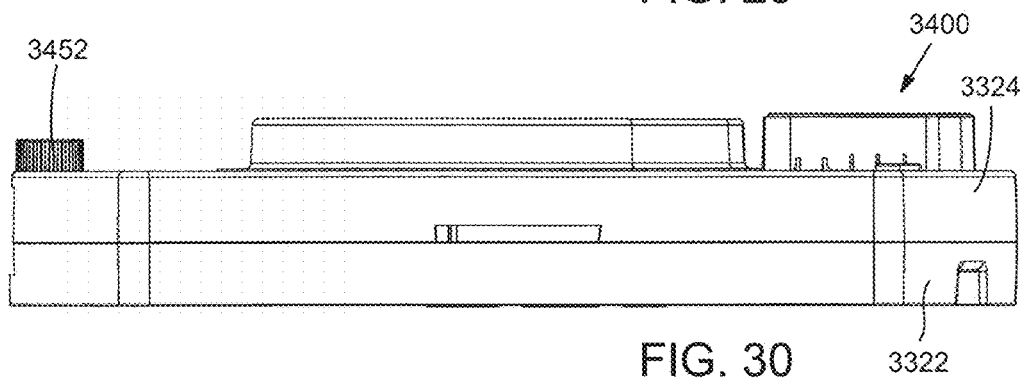
FIG. 30 is a side elevation view of the reagent cartridge kit.

In various embodiments, a system can comprise a reagent cartridge. A reagent cartridge 3300 in accordance with various embodiments is illustrated in FIGS. 26-34. The reagent cartridge can be configured to hold and/or store one, two, three, four, five, or more (or even all) reagents and consumables required for an ID/AST operation in a predefined reagent arrangement within the cartridge. For example, reagents can include sterile deionized water, antimicrobial agents, buffers such as GEF buffer and EKC buffer, growth media, FISH-related reagents such as nucleic acid probes, permeabilization agents, stringency wash solutions, cell stains or dyes, and the like. Reagents may be included as solutions or as dried or lyophilized reagents that are reconstituted by the instrument during operation. With reference now to FIGS. 26 and 27, reagents may be sealed in a plurality of reagent wells 3310 distributed around the reagent cartridge. The reagent wells may be sealed with a foil seal pierceable by the instrument pipettor fitted with a pipette tip, such as a pipette tip 3441. Consumables can include suitable pipette tips 3441 for use with the instrument pipettor, such as aerosol barrier filter tips. In various embodiments, the cartridge may also comprise subassemblies for performing various sample preparation functions, such as one or more GEF apparatuses, groups of reagent wells, or consumables racks (e.g., a pipette tip rack). Cartridge subassemblies may be operatively connected to or exposed to portions of the reagent stage, such as heating elements and electrical contacts (e.g., GEF contacts).

The reagent cartridge 3300 may be constructed of a polymer or other suitable material. The reagent cartridge may comprise polymer housing (or other suitable material) 3320. The housing may have a generally rectangular shape (with rounded corners and curved ends) and may define a circular opening 3330 within the housing configured to accommodate independent operation of the cassette stage with an attached cassette and access to the cassette by other components of the instrument, such as the pipettor, the illuminator, and the optics system. The housing 3320 may be configured with a plurality of ports 3312 in the upper surface of the housing, with the ports providing access by the pipettor to wells containing various reagents or cartridge subcomponents. The upper surface of the housing may also comprise one or more teaching wells 3314. A teaching well 3314 can be an opening in the cartridge housing, such as a circular opening, that the pipettor may use to spatially orient itself to the cartridge, such as in an initial pipettor orientation step after user insertion of the cartridge and initiation of an ID/AST process and/or in periodic pipettor orientation steps throughout instrument operation. In various embodiments, a teaching post or other structural feature that extends from the reagent cartridge may be used as a teaching feature for pipettor orientation. The locations of all cartridge ports or other openings may be known (i.e., addressed, such as using a coordinate system) relative to the location of the teaching well(s) or other teaching feature. Likewise, the contents of the cartridge at each cartridge port or opening may be associated with the port or opening location by the system based on one of user input regarding the reagent cartridge used for an ID/AST process or information acquired by the instrument from the cartridge itself, such as a barcode or other identifier that may be sensed by the instrument.

The reagent cartridge housing may be configured to provide a friction fit with alignment walls of the instrument reagent stage. For example, the width of the reagent cartridge may be configured to interface with the alignment walls on either side of the cartridge. The reagent cartridge housing may further include on or more features such as a cleat 3316 that interfaces with holding features coupled to the alignment walls of the reagent stage, further providing for secure insertion and precise positioning of the reagent cartridge in the reagent stage, such as by providing a positive stop for reagent cartridge insertion into the reagent stage and/or a snap friction fit.

The reagent cartridge may include a pipette tip rack 3340. The pipette tip rack 3340 may be integral to the reagent cartridge housing, or the pipette tip rack may be a separate component that is assembled into the reagent cartridge housing by a friction fit or by any other suitable attachment mechanism.

The reagent cartridge housing may comprise two or more separate housing components. For example, a housing may comprise a lower housing component 3322 and an upper housing component 3324. The lower and upper housing components may be attached to one another by a friction fit or by any other suitable attachment housing.

Figure 31:
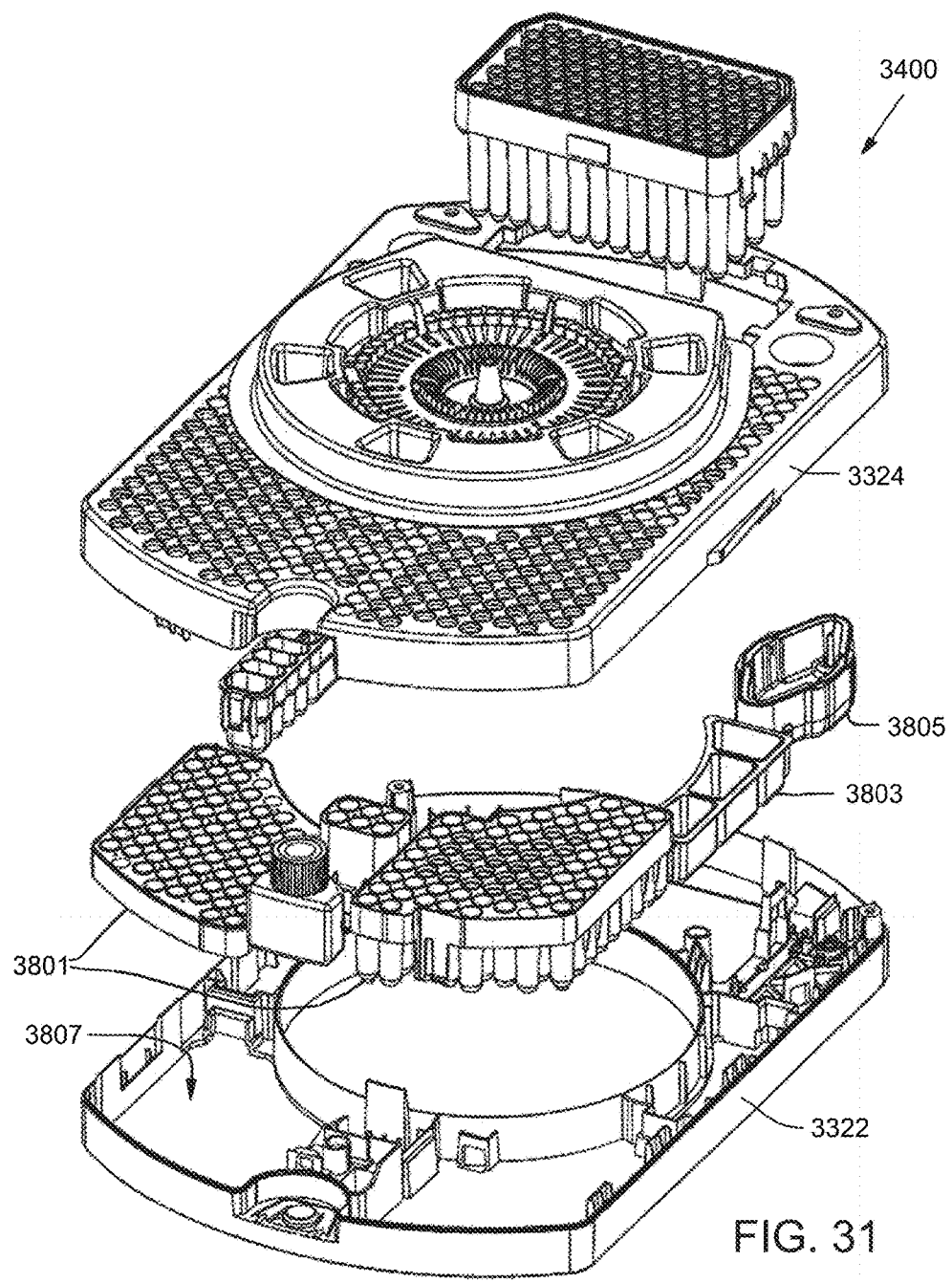
FIG. 31 is an exploded view of the reagent cartridge kit showing various reagent cartridge components, including reagent wells, GEF wells and other components.
Figure 32:
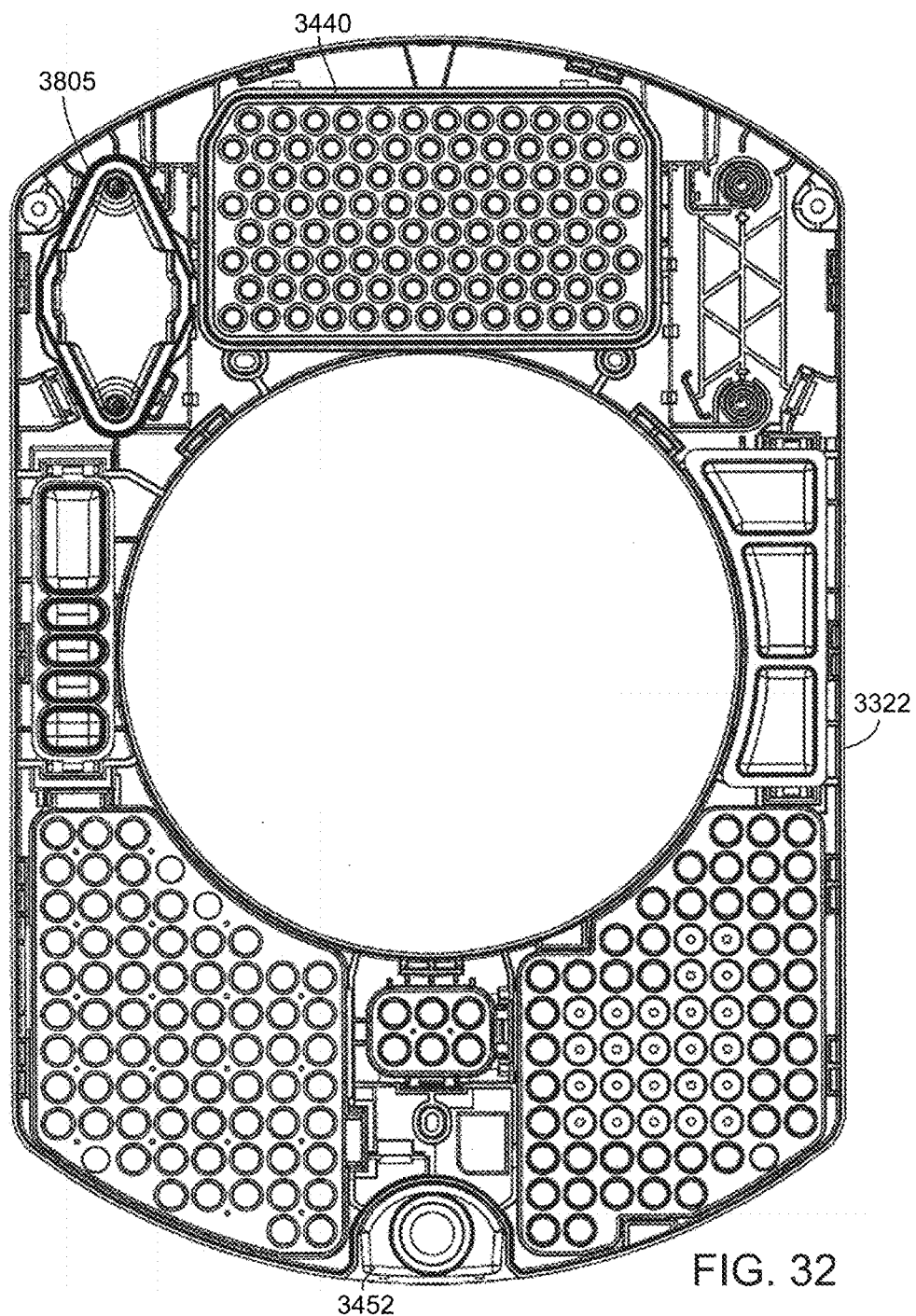
FIG. 32 is a top plan view of a lower housing component of the reagent cartridge.
Figure 33:
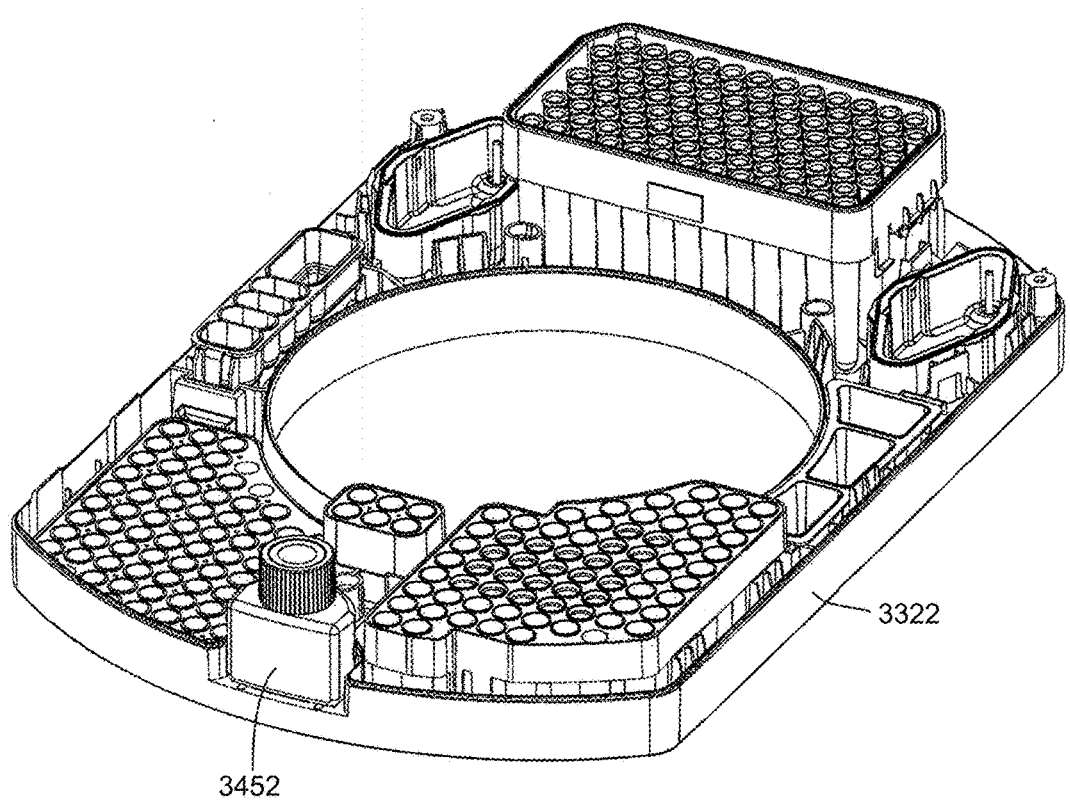
FIG. 33 is a perspective view of the reagent cartridge with an upper housing component removed.
Figure 34:
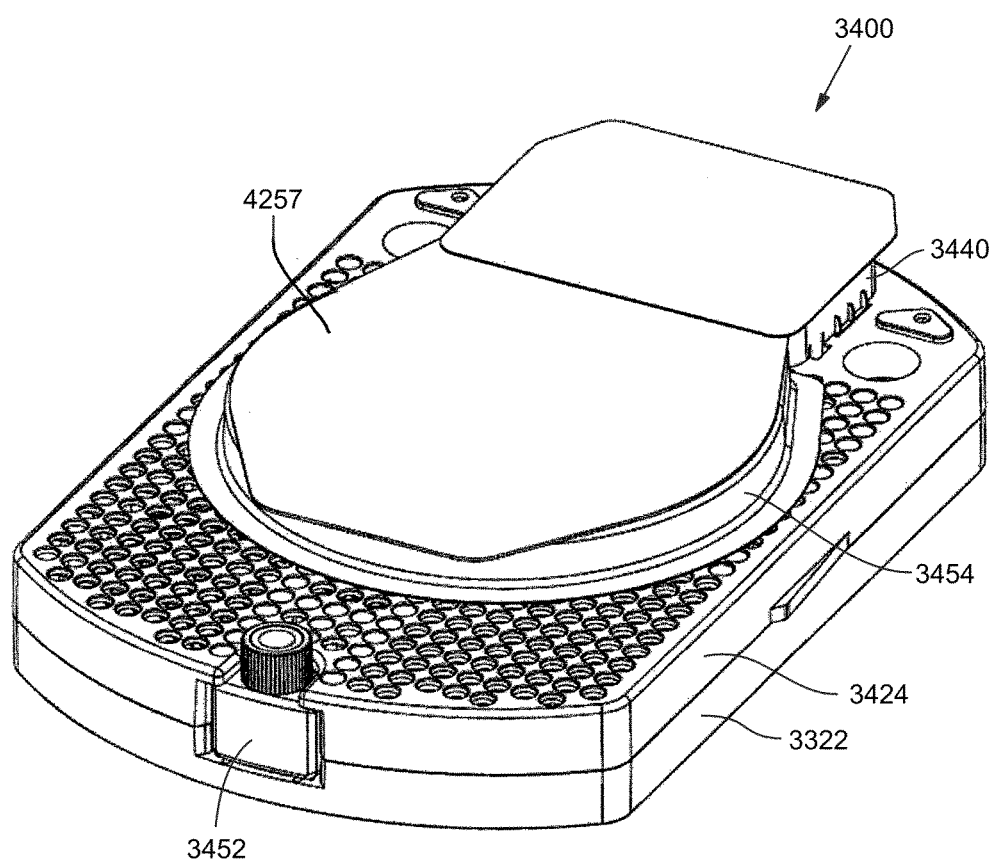
FIG. 34 is a perspective view of the reagent cartridge showing a seal in place over the cassette and pipette tip rack.
Figure 35:
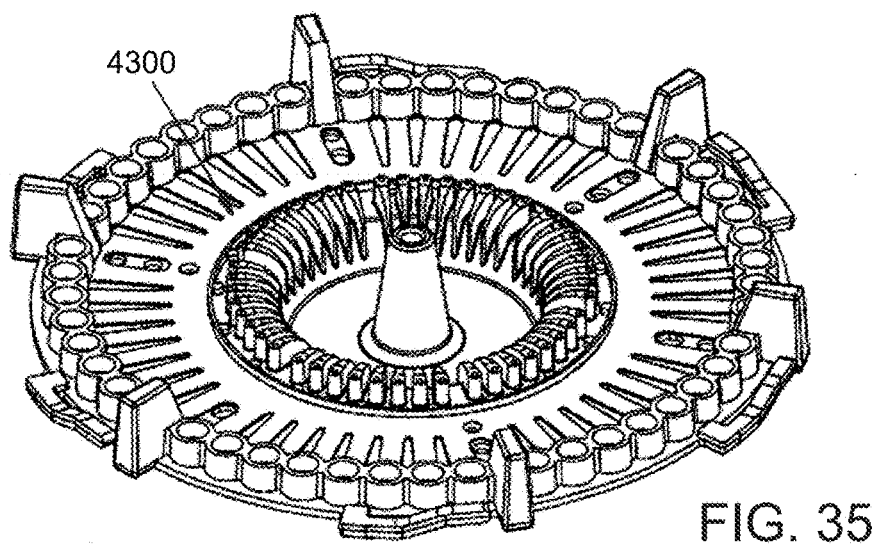
FIG. 35 is a perspective view of a cassette top.
Figure 36:
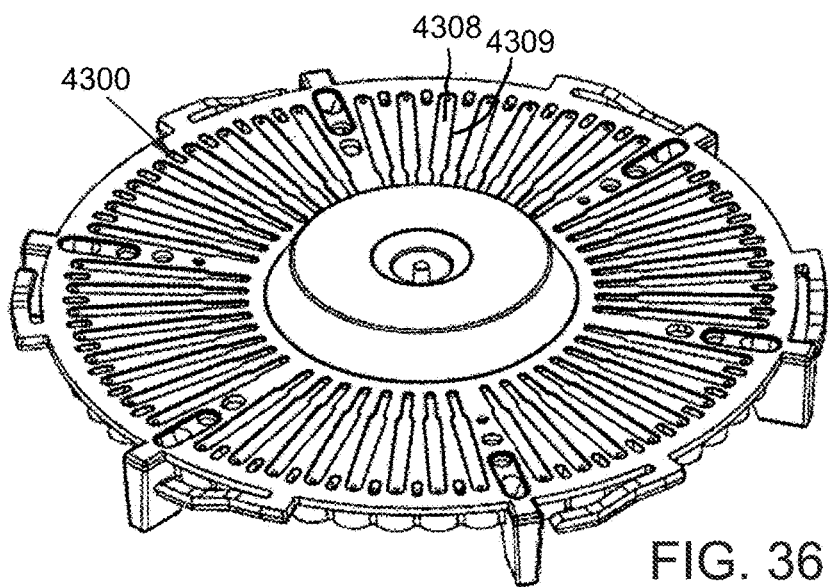
FIG. 36 is a perspective view of the cassette top showing a bottom surface.

In various embodiments, the housing may define an interior space. Referring now to FIG. 31, the interior space may be configured to house a plurality of reagent cartridge components such as reagent racks 3801 comprising reagent wells in various configurations, reagent tubs (e.g., tub 3803), GEF wells 3805 configured to house GEF apparatus, and the like. The lower housing component 3322 may include openings for access and/or contact between the reagent stage and reagent cartridge components, such as between reagent stage heating elements and reagent racks (e.g., opening 3807). Likewise, the lower housing component 3322 may also include components such as electrical contacts to provide an electrical interface between the reagent stage and one or more reagent cartridge components. For example, the reagent cartridge may include electrical contacts 3606 (FIG. 29) in a portion of the reagent cartridge housing configured to engage GEF contacts 540 (FIG. 5) located on the reagent stage when the cartridge is inserted by a user. For example, at least one electrical contact is accessible from an exterior of the reagent cartridge. In some examples, the at least one contact includes a pair of spaced apart contacts positioned at one end of the reagent cartridge and configured for engagement by causing the reagent cartridge to translate and engage other electrical contacts of the system.

At least some of the various wells and tubs included in the reagent cartridge may be sealed with a film, such as a film that may be pierced by a pipette tip mounted on the pipettor. The film may be located on the ports of the reagent cartridge housing, or the film may be located on the reagent wells and reagent tubs housed by the reagent cartridge housing.

In various embodiments, certain reagents included in the reagent cartridge may be dried or lyophilized. For example, an antimicrobial agent may be dried into a film on the interior surface of a reagent well. Dried or lyophilized reagents may be reconstituted by the instrument by addition of water or buffers included in the reagent cartridge.

Reagents included in the reagent cartridge may include any of a variety of reagents that may be used to perform microorganism ID and AST. For example, reagents can include water, various detergents or buffers, growth media, permeabilization agents, probes, dyes or stains, solvents, and the like.

The reagent cartridge may comprise a part of a reagent cartridge kit 3400 (FIGS. 27-31 and 34). The reagent cartridge kit may be packaged in a sealed package, with each of the reagent cartridge kit components intended to be used for a single ID/AST operation. The reagent cartridge kit may further include a sample vial 3452 (for example, a sample vial insertable in the reagent cartridge) and a cassette 3454. The cassette may be housed or set in a disposable cassette holder 3455 configured to sit within a circular opening in the body of the reagent cartridge 3300 configured to accommodate operation of the cassette and cassette stage when the reagent cartridge is inserted in the instrument. For example, the cassette holder may be shaped to receive the cassette, for example, having an outer dimension shaped for coupling the cassette holder over or in the opening in the reagent cartridge. The cassette and the pipette tip rack 3440 containing pipette tips 3441 may further be covered with a removable seal 4257 (FIG. 34) within the sealed cartridge kit package.

In operation, an instrument user may obtain a reagent cartridge kit, remove the reagent cartridge from the sealed package, remove the sample vial from the cartridge to place a clinical or research specimen in the sample vial, remove the film seal cover from the cassette housing and pipette tip rack, remove the cassette and/or cassette housing from the cartridge, and place the cartridge in the instrument, placing the cartridge in the reagent stage. In accordance with various embodiments, different reagents may be included in a reagent cartridge and cartridges comprising different sets of reagents may be offered as kits for different research and diagnostic purposes. Different cartridge kits may be offered for different clinical specimen types or different differential diagnoses. For example, different cartridge kits may be offered for ID/AST of blood cultures, bronchiolar lavage specimens, sputum, wound infections, urine samples, and the like. The reagents included in the reagent cartridge may vary according to kit type, with different FISH probes, sample preparation reagents, and antimicrobial agents included in different kits in accordance with the specimen type and anticipated pathogens that may be present the specimen type. For example, various Gram-positive and Gram-negative bacteria and fungi (e.g., yeasts) can be identified using an ID/AST cartridge kit for a positive blood culture assay, including but not limited to: *Staphylococcus aureus, Staphylococcus lugdunensis*, coagulase-negative *Staphylococcus* species (*Staphylococcus epidermidis, Staphylococcus haemolyticus, Staphylococcus hominis, Staphylococcus capitis*, not differentiated), *Enterococcus faecalis, Enterococcus faecium* (*Enterococcus faecium* and other *Enterococcus* spp., not differentiated, excluding *Enterococcus faecalis*), *Streptococcus pneumoniae, Streptococcus pyogenes, Streptococcus agalactiae, Streptococcus* spp., (*Streptococcus mitis, Streptococcus pyogenes, Streptococcus gallolyticus, Streptococcus agalactiae, Streptococcus pneumoniae*, not differentiated), *Pseudomonas aeruginosa, Acinetobacter baumannii, Klebsiella* spp. (*Klebsiella pneumoniae, Klebsiella oxytoca*, not differentiated), *Escherichia coli, Enterobacter* spp. (*Enterobacter cloacae, Enterobacter aerogenes*, not differentiated), *Proteus* spp. (*Proteus mirabilis, Proteus vulgaris*, not differentiated), *Citrobacter* spp. (*Citrobacter freundii, Citrobacter koseri*, not differentiated), *Serratia marcescens, Candida albicans*, and *Candida glabrata*.

Other specific bacteria that can be detected with the disclosed systems and methods, include without limitation: *Acinetobacter baumannii, Actinobacillus* spp., *Actinomycetes, Actinomyces* spp. (such as *Actinomyces israelii* and *Actinomyces naeslundii*), *Aeromonas* spp. (such as *Aeromonas hydrophila, Aeromonas veronii* biovar *sobria* (*Aeromonas sobria*), and *Aeromonas caviae*), *Anaplasma phagocytophilum, Alcaligenes xylosoxidans, Actinobacillus actinomycetemcomitans, Bacillus* spp. (such as *Bacillus anthracis, Bacillus cereus, Bacillus subtilis, Bacillus thuringiensis*, and *Bacillus stearothermophilus*), *Bacteroides* spp. (such as *Bacteroides fragilis*), *Bartonella* spp. (such as *Bartonella bacilliformis* and *Bartonella henselae, Bifidobacterium* spp., *Bordetella* spp. (such as *Bordetella pertussis, Bordetella parapertussis*, and *Bordetella bronchiseptica*), *Borrelia* spp. (such as *Borrelia recurrentis*, and *Borrelia burgdorferi*), *Brucella* sp. (such as *Brucella abortus, Brucella canis, Brucella melintensis* and *Brucella suis*), *Burkholderia* spp. (such as *Burkholderia pseudomallei* and *Burkholderia cepacia*), *Campylobacter* spp. (such as *Campylobacter jejuni, Campylobacter coli, Campylobacter lari* and *Campylobacter fetus*), *Capnocytophaga* spp., *Cardiobacterium hominis, Chlamydia trachomatis, Chlamydophila pneumoniae, Chlamydophila psittaci, Citrobacter* spp. *Coxiella burnetii, Corynebacterium* spp. (such as, *Corynebacterium diphtheriae, Corynebacterium jeikeum* and *Corynebacterium*), *Clostridium* spp. (such as *Clostridium perfringens, Clostridium difficile, Clostridium botulinum* and *Clostridium tetani*), *Eikenella corrodens, Enterobacter* spp. (such as *Enterobacter aerogenes, Enterobacter agglomerans, Enterobacter cloacae* and *Escherichia coli*, including opportunistic *Escherichia coli*, such as enterotoxigenic *E. coli*, enteroinvasive *E. coli*, enteropathogenic *E. coli*, enterohemorrhagic *E. coli*, enteroaggregative *E. coli* and uropathogenic *E. coli*) *Enterococcus* spp. (such as *Enterococcus faecalis* and *Enterococcus faecium*) *Ehrlichia* spp. (such as *Ehrlichia chafeensia* and *Ehrlichia canis*), *Erysipelothrix rhusiopathiae, Eubacterium* spp., *Francisella tularensis, Fusobacterium nucleatum, Gardnerella vaginalis, Gemella morbillorum, Haemophilus* spp. (such as *Haemophilus influenzae, Haemophilus ducreyi, Haemophilus aegyptius, Haemophilus parainfluenzae, Haemophilus haemolyticus* and *Haemophilus parahaemolyticus*), *Helicobacter* spp. (such as *Helicobacter pylori, Helicobacter cinaedi* and *Helicobacter fennelliae*), *Kingella kingii, Klebsiella* spp. (such as *Klebsiella pneumoniae, Klebsiella granulomatis* and *Klebsiella oxytoca*), *Lactobacillus* spp., *Listeria monocytogenes, Leptospira interrogans, Legionella pneumophila, Leptospira interrogans, Peptostreptococcus* spp., *Moraxella catarrhalis, Morganella* spp., *Mobiluncus* spp., *Micrococcus* spp., *Mycobacterium* spp. (such as *Mycobacterium leprae, Mycobacterium tuberculosis, Mycobacterium intracellulare, Mycobacterium avium, Mycobacterium bovis*, and *Mycobacterium marinum*), *Mycoplasm* spp. (such as *Mycoplasma pneumoniae, Mycoplasma hominis*, and *Mycoplasma genitalium*), *Nocardia* spp. (such as *Nocardia asteroides, Nocardia cyriacigeorgica* and *Nocardia brasiliensis*), *Neisseria* spp. (such as *Neisseria gonorrhoeae* and *Neisseria meningitidis*), *Pasteurella multocida, Plesiomonas shigelloides. Prevotella* spp., *Porphyromonas* spp., *Prevotella melaninogenica, Proteus* spp. (such as *Proteus vulgaris* and *Proteus mirabilis*), *Providencia* spp. (such as *Providencia alcalifaciens, Providencia rettgeri* and *Providencia stuartii*), *Pseudomonas aeruginosa, Propionibacterium acnes, Rhodococcus equi, Rickettsia* spp. (such as *Rickettsia rickettsii, Rickettsia akari* and *Rickettsia prowazekii, Orientia tsutsugamushi* (formerly: *Rickettsia tsutsugamushi*) and *Rickettsia typhi*), *Rhodococcus* spp., *Serratia marcescens, Stenotrophomonas maltophilia, Salmonella* spp. (such as *Salmonella enterica, Salmonella typhi, Salmonella paratyphi, Salmonella enteritidis, Salmonella cholerasuis* and *Salmonella typhimurium*), *Serratia* spp. (such as *Serratia marcesans* and *Serratia liquifaciens*), *Shigella* spp. (such as *Shigella dysenteriae, Shigella flexneri, Shigella boydii* and *Shigella sonnei*), *Staphylococcus* spp. (such as *Staphylococcus aureus, Staphylococcus epidermidis, Staphylococcus hemolyticus, Staphylococcus saprophyticus*), *Streptococcus* spp. (such as *Streptococcus pneumoniae* (for example chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, tetracycline-resistant serotype 19F *Streptococcus pneumoniae*, penicillin-resistant serotype 19F *Streptococcus pneumoniae*, and trimethoprim-resistant serotype 23F *Streptococcus pneumoniae*, chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, optochin-resistant serotype 14 *Streptococcus pneumoniae*, rifampicin-resistant serotype 18C *Streptococcus pneumoniae*, penicillin-resistant serotype 19F *Streptococcus pneumoniae*, or trimethoprim-resistant serotype 23F *Streptococcus pneumoniae*), *Streptococcus agalactiae, Streptococcus mutans, Streptococcus pyogenes*, Group A streptococci, *Streptococcus pyogenes*, Group B streptococci, *Streptococcus agalactiae*, Group C streptococci, *Streptococcus anginosus, Streptococcus equismilis*, Group D streptococci, *Streptococcus bovis*, Group F streptococci, and *Streptococcus anginosus* Group G streptococci), *Spirillum minus, Streptobacillus moniliformi, Treponema* spp. (such as *Treponema carateum, Treponema petenue, Treponema pallidum* and *Treponema endemicum, Tropheryma whippelii, Ureaplasma urealyticum, Veillonella* sp., *Vibrio* spp. (such as *Vibrio cholerae, Vibrio parahemolyticus, Vibrio vulnificus, Vibrio parahaemolyticus, Vibrio vulnificus, Vibrio alginolyticus, Vibrio mimicus, Vibrio hollisae, Vibrio fluvialis, Vibrio metchnikovii, Vibrio damsela* and *Vibrio furnisii*), *Yersinia* spp. (such as *Yersinia enterocolitica, Yersinia pestis*, and *Yersinia pseudotuberculosis*) and *Xanthomonas maltophilia* among others.

Other specific fungi that can be detected with the disclosed systems and methods, include without limitation: *Candida* spp. (such as *Candida albicans, Candida glabrata, Candida tropicalis, Candida parapsilosis*, and *Candida krusei*), *Aspergillus* spp. (such as *Aspergillus fumigatous, Aspergillus flavus, Aspergillus clavatus*), *Cryptococcus* spp. (such as *Cryptococcus neoformans, Cryptococcus gattii, Cryptococcus laurentii*, and *Cryptococcus albidus*), *Fusarium* spp. (such as *Fusarium oxysporum, Fusarium solani, Fusarium verticillioides*, and *Fusarium proliferatum*), *Rhizopus oryzae, Penicillium marneffei, Coccidiodes immitis*, and *Blastomyces dermatitidis*.

The ID/AST cartridge kit for a positive blood culture assay may be indicated as an aid in the diagnosis of bacteremia and fungemia. It may also be indicated for susceptibility testing of specific pathogenic bacteria commonly associated with or causing bacteremia. Results optimally should be used in conjunction with other clinical and laboratory findings.

An ID/AST cartridge kit (such as one for use with a blood culture assay) may include the following antimicrobial agents: amikacin, ampicillin, ampicillin-sulbactam, aztreonam, ceftazidime, ceftaroline, cefazolin, cefepime, ceftriaxone, ciprofloxacin, colistin, daptomycin, oxycycline, erythromycin, ertapenem, gentamicin, imipenem, linezolid, meropenem, minocycline, piperacillin-tazobactam, trimethoprim-sulfamethoxazole, tobramycin, vancomycin, or combinations of two or more thereof. Additional antimicrobial agents that may be used in the systems and methods disclosed herein also include aminoglycosides (including but not limited to kanamycin, neomycin, netilmicin, paromomycin, streptomycin, and spectinomycin), ansamycins (including but not limited to rifaximin), carbapenems (including but not limited to doripenem), cephalosporins (including but not limited to cefadroxil, cefalotin, cephalexin, cefaclor, cefprozil, fecluroxime, cefixime, cefdinir, cefditoren, cefotaxime, cefpodoxime, ceftibuten, and ceftobiprole), glycopeptides (including but not limited to teicoplanin, telavancin, dalbavancin, and oritavancin), lincosamides (including but not limited to clindamycin and lincomycin), macrolides (including but not limited to azithromycin, clarithromycin, dirithromycin, roxithromycin, telithromycin, and spiramycin), nitrofurans (including but not limited to furazolidone and nitrofurantoin), oxazolidinones (including but not limited to posizolid, radezolid, and torezolid), penicillins (including but not limited to amoxicillin, flucloxacillin, penicillin, amoxicillin/clavulanate, and ticarcillin/clavulanate), polypeptides (including but not limited to bacitracin and polymyxin B), quinolones (including but not limited to enoxacin, gatifloxacin, gemifloxacin, levofloxacin, lomefloxacin, moxifloxacin, naldixic acid, norfloxacin, trovafloxacin, grepafloxacin, sparfloxacin, and temafloxacin), suflonamides (including but not limited to mafenide, sulfacetamide, sulfadiazine, sulfadimethoxine, sulfamethizole, sulfamethoxazole, sulfasalazine, and sulfisoxazole), tetracyclines (including but not limited to demeclocycline, doxycycline, oxytetracycline, and tetracycline), and others (including but not limited to clofazimine, ethambutol, isoniazid, rifampicin, arsphenamine, chloramphenicol, fosfomycin, metronidazole, tigecycline, and trimethoprim), or any combination of two or more thereof. Further antimicrobial agents include amphotericin B, ketoconazole, fluconazole, itraconazole, posaconazole, voriconazole, anidulafungin, caspofungin, micafungin, flucytosine, or any combination of two or more thereof.

In one specific example, the reagent cartridge includes at least one probe (such as 1, 2, 3, 4, 5, 6, 7, 8, 9, 10, 11, 12, 13, 14, 15, 16, 17, 18, 19, 20, or more) and at least one antimicrobial agent (such as 1, 2, 3, 4, 5, 6, 7, 8, 9, 10, 11, 12, 13, 14, 15, 16, 17, 18, 19, 20, or more) in one or more wells of the reagent cartridge. In a particular non-limiting embodiment, the reagent cartridge includes at least one well including a *Staphylococcus aureus* probe, a well including a coagulase-negative staphylococci probe (for example, a probe hybridizing to *S. epidermidis, S. haemolyticus, S. hominis, S. captis*, not differentiated), a well including a *Staphylococcus lugdunensis* probe, a well including an *Enterococcus faecalis* probe, a well including an *Enterococcus faecium* probe, a well including a *Streptococcus agalactiae* probe, a well including a *Streptococcus* spp. probe (for example, a probe hybridizing to *S. mitis, S. gallolyticus, S. agalactiae, S. pneumoniae*, not differentiated), a well including an *Escherichia coli* probe, a well including a *Klebsiella* spp. probe (for example, a probe hybridizing to *K. pneumoniae* and *K. oxytoca*, not differentiated), a well including an *Enterobacter* spp. probe (for example, a probe hybridizing to *E. aerogenes* and *E. cloacae*, not differentiated), a well including a *Citrobacter* spp. probe (for example, a probe hybridizing to *C. freundii* and *C. koseri*, not differentiated), a well including a *Proteus* spp. probe (for example, a probe hybridizing to *P. mirabilis* and *P. vulgaris*, not differentiated), a well including a *Serratia marcescens* probe, a well including a *Pseudomonas aeruginosa* probe, a well including an *Acinetobacter baumannii* probe, a well including a *Candida albicans* probe, a well including a *Candida glabrata* probe, a well including amikacin, a well including ampicillin, a well including ampicillin/sulbactam, a well including aztreonam, a well including cefazolin, a well including cefepime, a well including cefaroline, a well including cefazidime, a well including ciprofloxacin, a well including colistin, a well including daptomycin, a well including doxycycline, a well including ertapenem, a well including erythromycin, a well including gentamicin, a well including imipenem, a well including linezolid, a well including meropenem, a well including minocycline, a well including macrolide-lincosamide-streptogramin B, a well including cefoxitin, a well including piperacillin/tazobactam, a well including streptomycin, a well including tobramycin, a well including trimethoprim/sulfamethoxazole, and a well including vancomycin. In some examples, each of the wells including a probe also includes a universal microbial or cell stain, such as acridine orange or propidium iodide.

Quality Control Test Components

In some embodiments, disclosed herein are quality control (QC) components that may be utilized with the reagent cartridge and systems disclosed herein, such as an AST QC component and/or an ID QC component. The AST QC component is configured to fit in the reagent cartridge in place of the patient sample vial. If used, the ID QC component is configured to fit in the reagent cartridge sample vial position along with the AST QC component, for example, the ID QC component has a complementary shape to the AST QC component.

The Quality Control assay tests may be packaged in the form of disposable kits containing all reagents and tools necessary to perform the assays. The disposable units may be configured to fit onto the reagent cartridge used to run patient samples tested in the AD-1 Instrument System. In one embodiment, QC test components may take the form of an insert having a multiwell format. The insert may be formed of any suitable material, such as plastic or other suitable polymer, and may be constructed to snap onto the reagent cartridge over the open well that typically houses patient samples. The inserts housing the QC test materials may take any shape. For example, the AST QC test component may be fashioned and configured in the shape of the Greek letter pi (Π). Assay reagents may be located in the wells of the insert that form the "pi" shape. The wells may be covered with a film, foil, or other barrier to protect the QC assay reagents during transport and storage. In some embodiments, the protective barrier optionally is removable.

The ID QC test component may comprise wells formed into a shape complementary to the AST insert. For example, the ID QC test insert may be configured in the shape of the letter "E" such that it snaps into place on the reagent cartridge of the AD-1 Instrument System as a mate to the "pi"-shaped AST QC test insert. ID QC assay reagents may be contained in wells of the insert formed in an "E" shape. The tops of the reagent wells may be covered by a film, foil, or other barrier to protect the reagents during transport and storage. In some embodiments, the protective barrier optionally is removable. In some examples, both the AST and ID QC disposable inserts are flush with one another when seated correctly on the reagent cartridge of the AD-1 Instrument System. Each QC assay test kit insert may have a label for identification purposes, such as a one-dimensional bar code, a two-dimensional bar code (such as a datamatrix code), an RFID tag, and the like. In some embodiments, each component QC kit may have a tab onto which the label is affixed for recognition by the instrument. In some embodiments, an optical scanning device within the instrument system scans the label on a QC insert and reads the information embedded in the label to identify the type of quality control test to be run in connection with the reagents contained in the insert, e.g., ID QC or AST QC.

Referring to FIGS. 104A-D, an exemplary ID QC test component 10400 is shown, including a frame 10402 generally in the shape of the letter "E" and having a plurality of wells 10404 and one or more clips 10406 attached to the frame 10402, which can interact with complementary clips on the AST QC test component (discussed below, e.g., FIGS. 105A-105D, 10500). FIGS. 104A-104D illustrate an embodiment with three clips 10404*a*, 10404*b*, and 10404*c* that interlock with complementary clips in the AST QC test component. The exemplary ID QC test component shown in FIGS. 104A-104D has 11 wells; however ID QC test components with more or fewer wells (such as 1, 2, 3, 4, 5, 6, 7, 8, 9, 10, 11, 12, 13, 14, 15, 16, 17, 18, 19, 20, or more) are also contemplated. The ID QC test component 10400 also includes a tab 10408 that is attached to frame 10402 and extends below the level of wells 10404. In some embodiments, an identification label, such as a bar code is affixed to the tab 10408. Although the ID QC test component is shown in FIGS. 104A-D as being in the shape of the letter "E" additional configurations are also contemplated. In addition to clips, other suitable structures to permit coupling of the ID QC component to the AST QC component can be used.

Reagents for ID QC testing are placed in one or more wells of the ID QC test component. In some embodiments, the ID QC test component includes one or more target nucleic acids having a sequence complementary to at least one probe in the probe cocktail(s) to be tested. In some examples, each well contains a plurality of beads (such as microspheres) coupled to a nucleic acid complementary to a single probe in the probe cocktail. In other examples, at least one well includes a plurality of beads coupled to a nucleic acid complementary to a first probe in the probe cocktail and a plurality of beads coupled to a nucleic acid complementary to a second probe in the probe cocktail. In further examples, at least one well includes at least three sets of beads (such as at least 4, at least 5, at least 6, or more) wherein each set of beads includes a plurality of beads coupled to a nucleic acid complementary to a different probe in the probe cocktail. The number of target beads that may occupy a single well ultimately depends upon a given test design.

In some examples, the ID QC test component is kept in refrigerated storage (such as about 1-12° C., about 2-8° C., or about 3-6° C.) prior to use. In one non-limiting example, an ID QC test component includes in at least one well beads conjugated to a target sequence complementary to a probe in a probe cocktail, where the target sequence is from *Acinetobacter baumannii*, *Citrobacter* spp., *Enterobacter* spp., *Escherichia coli*, *Klebsiella* spp., *Proteus* spp., *Pseudomonas aeruginosa*, *Serratia marcescens*, Coagulase-negative *Staphylococcus* spp., *Enterococcus faecalis*, *Enterococcus faecium*, *Staphylococcus aureus*, *Staphylococcus lugdunensis*, *Streptococcus* spp., *Candida albicans*, or *Candida glabrata*. Other microbial targets may be included in the ID QC test component, either in addition to, or in place of these microbes. One of skill in the art can select other microbial targets for ID QC testing, including any of the microbes described herein, based on the assay for which the ID QC test component is designed, to provide appropriate QC testing. One exemplary embodiment of a QC ID test component having at least one set of beads in 10 of 13 wells is shown in FIG. 108.

Referring to FIGS. 105A-105D, an exemplary AST QC test component 10500 is shown, including a frame 10502 generally in the shape of the Greek letter "pi" and having a plurality of wells 10504, one or more clips 10506 attached to the frame 10502 that can interact with complementary clips on the reagent cartridge (discussed below), and one or more clips 10510 attached to the frame 10502 that can interact with complementary clips on the ID QC test component. In the embodiment illustrated in FIG. 105D, clips 10510a, 10510b, and 10510c interact with clips 10406a, 10406b, and 10406c of the ID QC test component shown in FIG. 104B, respectively. The exemplary AST QC test component shown in FIGS. 105A-105D has 8 wells; however AST QC test components with more or fewer wells (such as 1, 2, 3, 4, 5, 6, 7, 8, 9, 10, 11, 12, 13, 14, 15, 16, 17, 18, 19, 20, or more) are also contemplated. The AST QC test component 10500 also includes a tab 10508 that is attached to frame 10502 and extends below the level of wells 10504. In some embodiments, an identification label, such as a bar code, is affixed to the tab 10508. Although the AST QC test component is shown in FIGS. 105A-105D as being in the shape of the letter "pi," additional configurations are also contemplated. In addition to clips, other suitable structures to permit coupling of the AST QC component to the reagent cartridge and/or the ID QC component can be used.

Reagents for AST QC testing are placed in one or more wells of the AST QC test component. In some embodiments, the AST QC test component includes one or more microbial isolates to be tested in one or more of the wells. In some examples, each well contains one microbial isolate. In other embodiments, polymicrobial isolate mixtures may be used, depending upon the test design. The microbial isolates are included in the AST QC test component in a pre-selected amount, such as a McFarland standard of 1-2. Higher or lower McFarland standards (such as 0.5-5) may be employed, as needed based on assay design. In some examples, the AST QC test component is kept in frozen storage (such as about –60 to –85° C., about –65 to –80° C. or about –70 to –80° C.) until use. The AST QC test component may include microbial isolates from both antibiotic susceptible and antibiotic resistant strains of the same microbial species (such as one *Staphylococcus aureus* susceptible strain and one *Staphylococcus aureus* resistant strain). In one non-limiting embodiment, the AST QC test component includes one or more microbial isolates in different wells, for example, one or more of *E. coli* (such as *E. coli* ATCC 25922 and/or *E. coli* ATCC 35218), *Pseudomonas aeruginosa* (such as *P. aeruginosa* ATCC 27853), *Enterococcus faecalis* (such as *E. faecalis* ATCC 29212), *Staphylococcus aureus* (such as *S. aureus* ATCC 29213, *S. aureus* ATCC 43300, and/or *S. aureus* ATCC BAA-977), and/or *Candida albicans* (such as *C. albicans* ATCC 96268). One of skill in the art can select other microbial isolates for AST QC testing, including any of the microbes described herein, based on the assay for which the AST QC test component is designed, to provide appropriate QC testing. One exemplary embodiment of an AST QC test component having at least one microbial isolate in 8 of 12 wells is shown in FIG. 109.

In some embodiments, the ID QC test component interlocks with the AST QC component when both components are utilized together and placed in a reagent cartridge (for example, as shown in FIG. 106, discussed below). Therefore, in some embodiments, the ID QC test component includes one or more clips that interlock with clips on the AST QC test component and/or the reagent cartridge, or other suitable structures to permit their coupling. Referring to FIG. 104B, clips 10406 interlock with clips 10510 shown in FIG. 105D. In additional embodiments, the AST QC test component also can include one or more clips that interlock with clips on the reagent cartridge, such as one or more components in the sample vial position of the reagent cartridge. Referring to FIG. 105B, clips 10506 interlock with the reagent cartridge (not shown). In some examples, clips 10506 are substantially straight vertical projections extending downward from frame 10502. These vertical projections snap into corresponding holes on the reagent cartridge close to or adjacent to the sample vial position. In other examples, clips 10510 are lateral projections that snap in place sideways to the ID QC insert clips 10406.

FIGS. 106A and 106B illustrate embodiments of a reagent cartridge showing the AST QC and ID QC test components inserted in place of the sample vial. In this embodiment ID QC test component 10400 and AST QC test component 10500 are inserted in reagent cartridge 10602 at sample vial holder 10604. When the reagent cartridge is used for patient sample testing, the patient sample is inserted at sample vial holder 10604. In the illustrated embodiment, the "E" shaped ID QC test component 10400 and the "pi" shaped AST QC test component 10500 interlock to fit in the sample vial position.

Cassette

In accordance with various embodiments, a system can comprise a cassette. The cassette may be configured to receive portions of the sample and other reagents in microfluidic sample channels. The cassette and sample channels facilitate performing EKC, FISH ID, AST, pharmacodynamics testing, and other assays and imaging microorganism cells with the instrument illumination and optics systems. Cassettes in accordance with various embodiments are illustrated in FIGS. 35-65 and described in greater detail below.

In various embodiments and with reference to FIGS. 35-46, a cassette 4500 may be a disk-shaped device comprising a glass support 4400, a laminate layer 4601, and a cassette top 4300 (see FIG. 46), also referred to as a cassette component. The laminate layer 4601 may comprise a polymer material with an adhesive layer or adhesive treatment on both sides of the laminate layer polymer material. The glass support 4400 may be adhered to the cassette top 4300 by the adhesive-treated laminate layer 4601. The three components may be pressed together to form the assembled cassette 4500. The assembled cassette 4500 can feature a plurality of microfluidic sample channels 5702 (e.g., 48 sample channels) (see FIGS. 37B and 57) arranged in a radial configuration in the cassette, with each sample channel having an inlet port 4503 and an outlet port 4504 (FIG. 41), described in greater detail below. In some examples, the microfluidic channels are formed in the laminate layer or in the laminate layer and in the cassette component. In various embodiments, the sample channels are oriented with the inlet ports 4503 toward the outer perimeter of the cassette and the outlet ports 4504 oriented toward the center of the cassette. In various other embodiments, the inlet ports may be near the center of the cassette and the outlet ports near the perimeter of the cassette. In some embodiments, the cassette includes a glass support adhered to a molded polymer disc and a plurality of microfluidic channels arranged in a radial configuration across the cassette.

Figure 41:
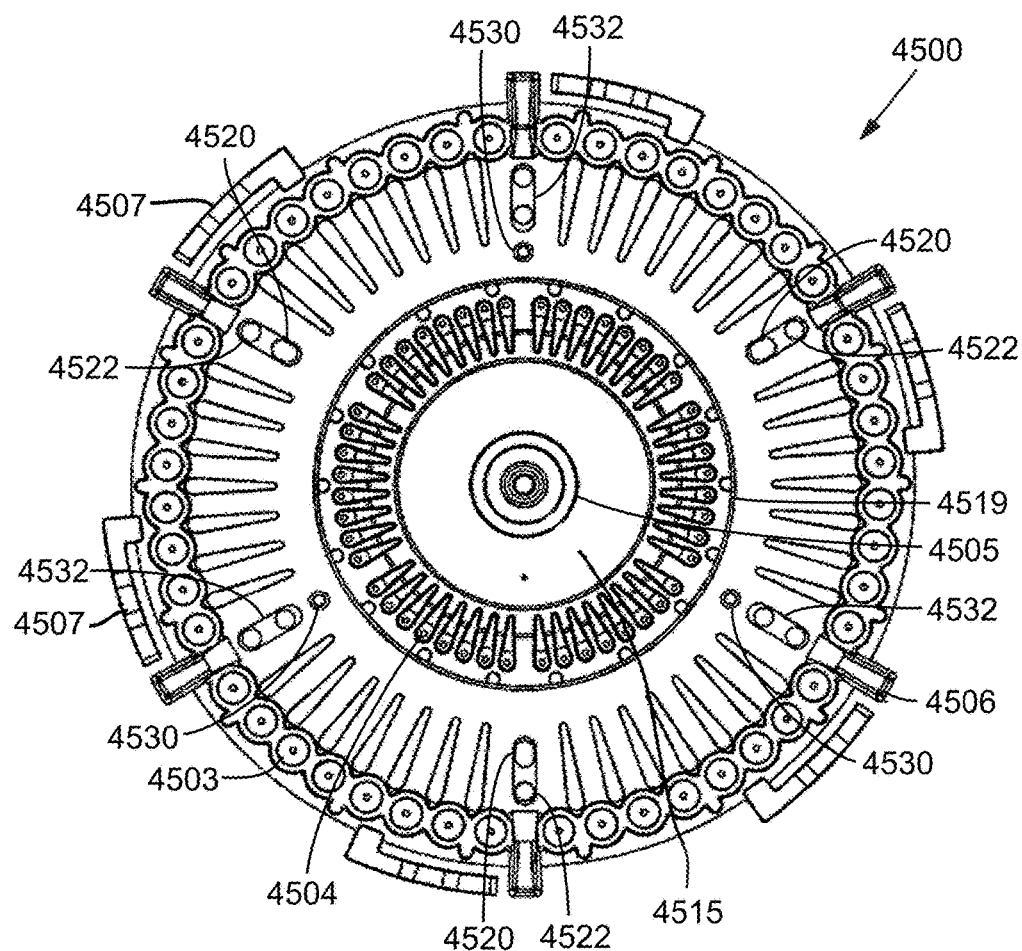
FIG. 41 is a top plan view of the cassette.
Figure 42:
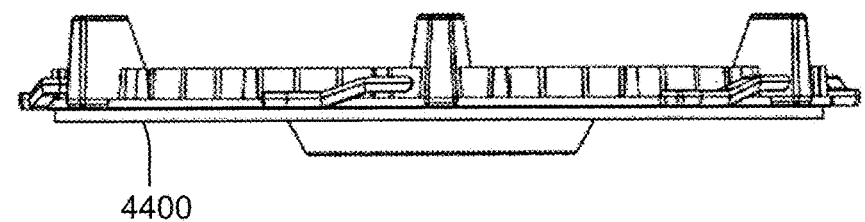
FIG. 42 is a side elevation view of the cassette.
Figure 43:
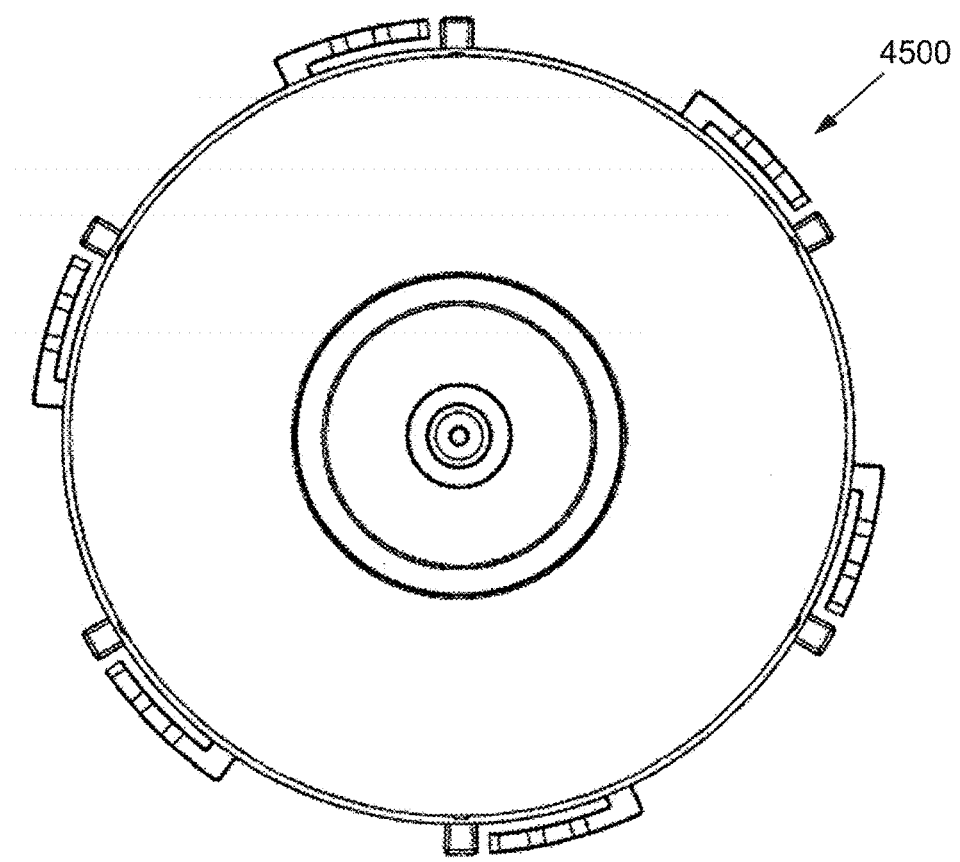
FIG. 43 is bottom plan view of the cassette.
Figure 44:
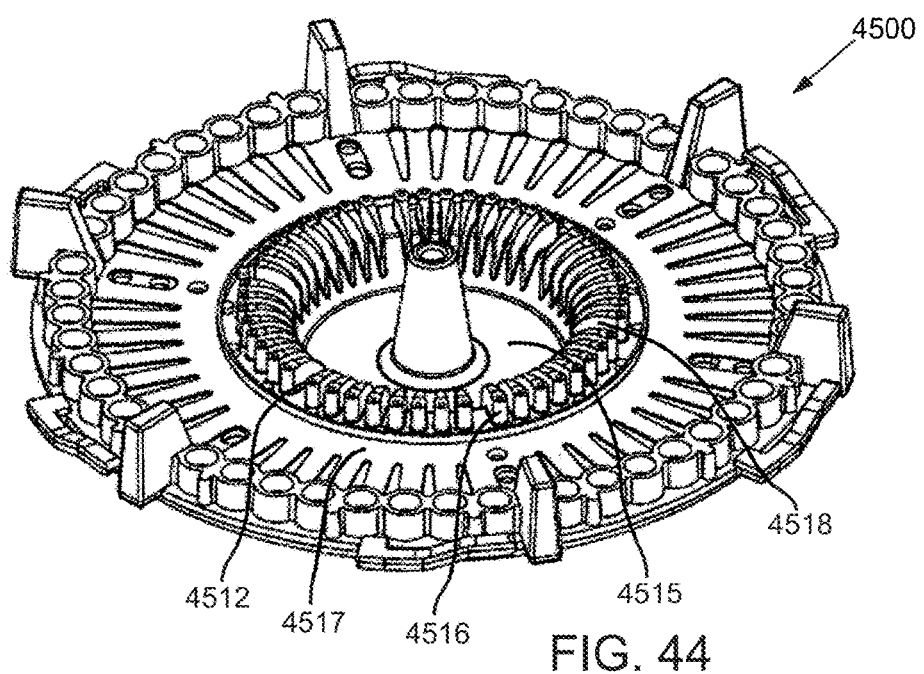
FIG. 44 is a perspective view of the cassette showing the top surface.
Figure 45:
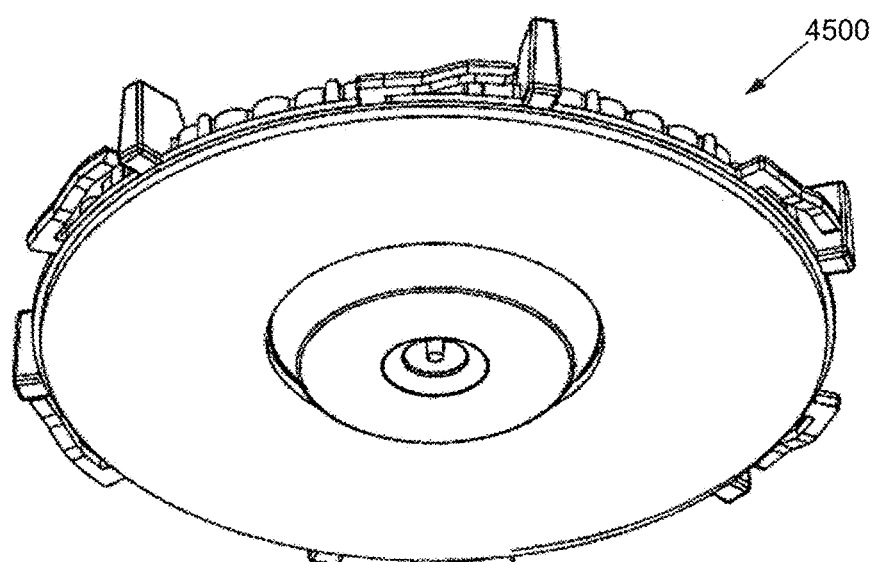
FIG. 45 is another perspective view of the cassette showing the bottom surface.
Figure 46:
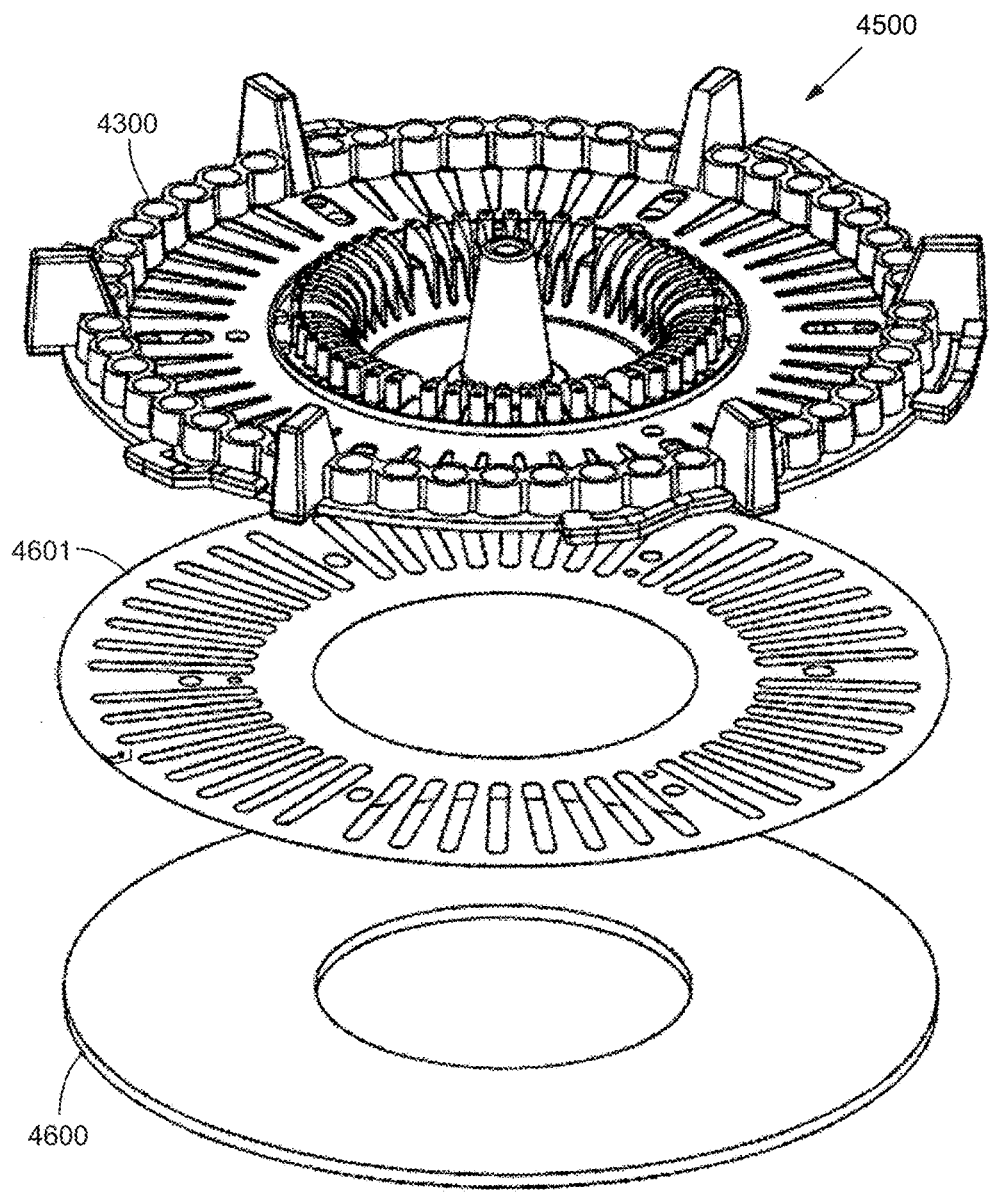
FIG. 46 is an exploded perspective view showing the cassette top, the glass support and a laminate layer.

As also shown in FIG. 41, the cassette 4500 may also include features for user handling, such as a central cone or spindle 4505 and/or tabs 4506 distributed around the perimeter of the cassette. Likewise, the cassette may include features for interfacing with a cassette stage, such as a plurality of locking spring arms 4507 around the perimeter of the cassette that provide a friction fit with a corresponding feature located on the cassette stage such that the cassette is stably and vibrationally coupled to the cassette stage. A common waste well 4515 can be defined in a central area that is bounded by a circular waste retaining wall 4519.

The cassette top 4300 can comprise a polymeric portion/region of the cassette that may be molded from an injection-moldable optically clear polymer such as ZEONOR (e.g., ZEONORE 1060R) and ZEONEX. The bottom surface of cassette top 4300 may be coated with an optically clear conductive layer such as ITO, either entirely or in the area of the sample channel, such as the bottom surface 4308 of the cassette top 4300 forming the top of a sample channel flowcell (i.e., a flowcell-forming relief area 4309 of a cassette top 4300) as well as the side walls of a flowcell-forming relief area in the bottom of the cassette top 4300. ITO may be applied to the cassette top 4300 to provide a sheet resistance of about 5 to about 200 ohms/sq., or about 30 to about 170 ohms/sq., or about 50 to about 120 ohms/sq., or about 70 to about 100 ohms/sq. In various embodiments, the sheet resistance may be less than about 100 ohms/sq., or less than about 80 ohms/sq., or less than about 60 ohms/sq., or less than about 40 ohms/sq., or less than about 20 ohms/sq., or less than about 10 ohms/sq.

FIGS. 37A-37C show details of the cassette top 4300. FIG. 37B shows a mask 4311 around a slot in the cassette top 4300. FIG. 41 shows a section of the cassette top in elevation illustrating one of the inlet ports 4503 in relation to its associated outlet port 4504. Select surfaces of the inlet port 4503 can be coated with ITO.

Figure 38:
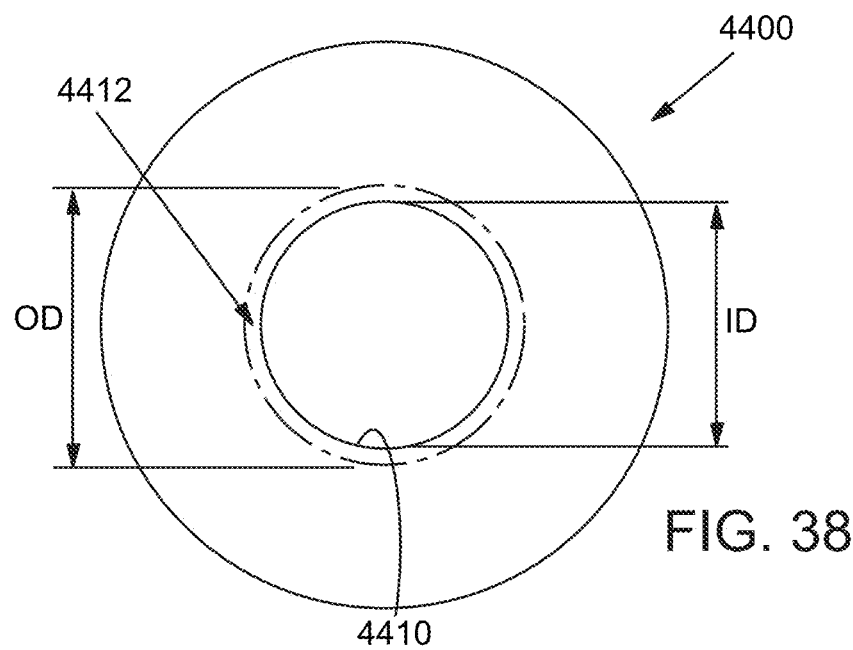
FIGS. 38-40 are top plan, side elevation and perspective views, respectively, of a glass support.
Figure 39:
Figure 40:
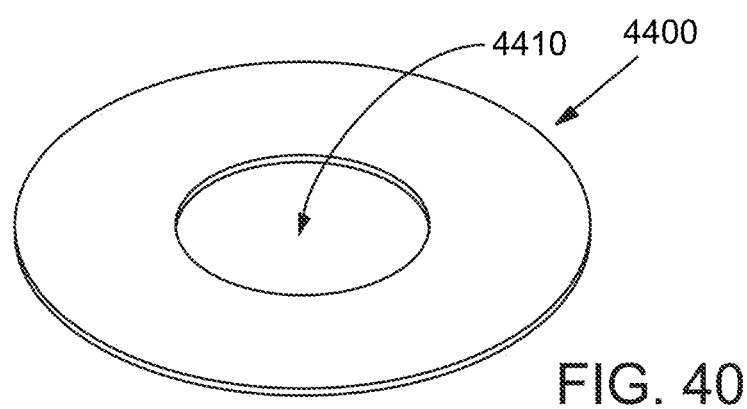
Figure 49:
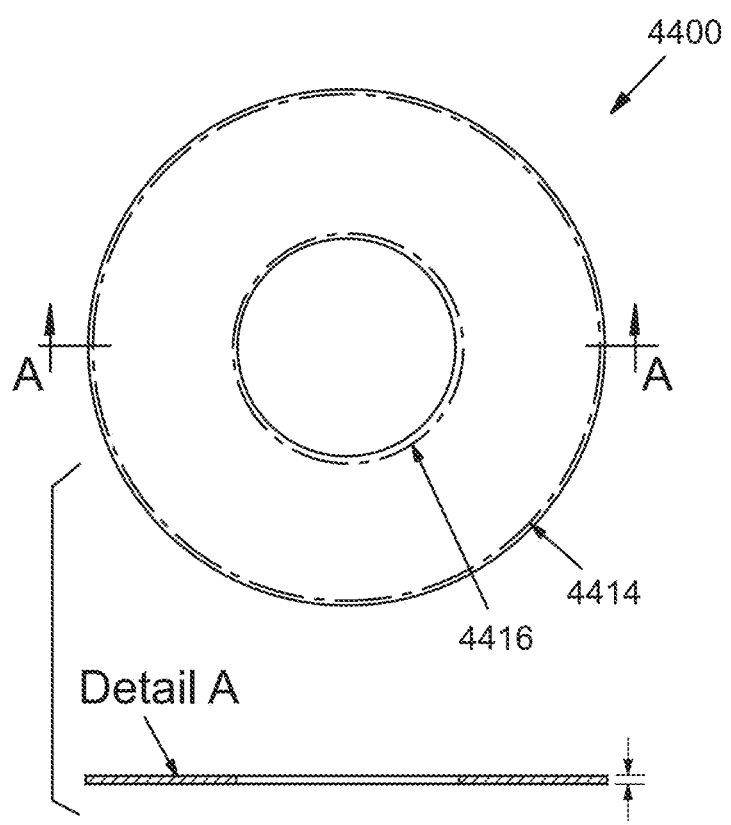
FIG. 49 is a section view in elevation of the glass support.
Figure 50:
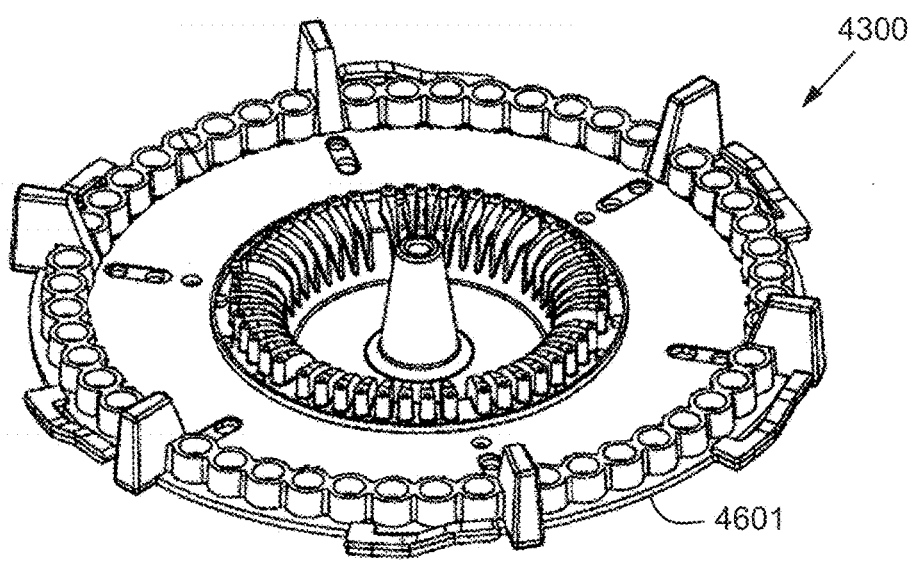
FIGS. 50 and 51 are perspective views of the cassette where the glass support has been removed to show the laminate layer.
Figure 51:
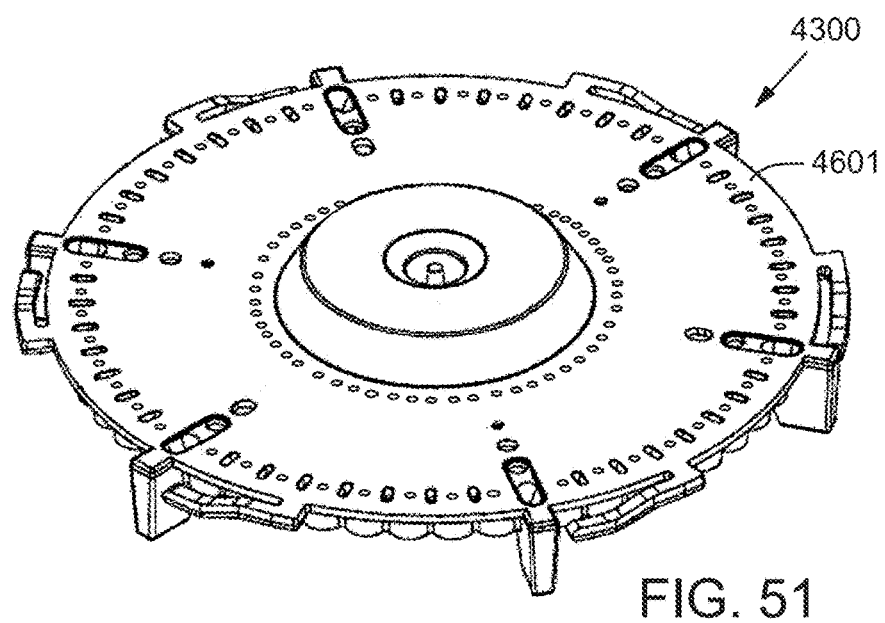
Figure 52A:
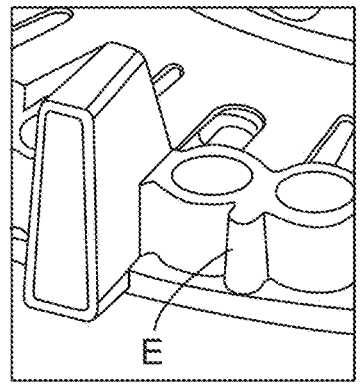
FIGS. 52A and 53A are partial perspective views illustrating a cassette before and after ejector pads have been removed.

The glass support 4400 as shown in FIGS. 38-40 may comprise a flat, annular-shaped glass slide with an outer diameter and an interior opening 4410 defined by an interior diameter. The glass may have properties of high light transmittance and high chemical stability, such as Schott B 270 i Ultra-White Glass or similar glass material. The interior opening 4410 may be configured to receive a central depression of the plastic top portion of the cassette. ITO may be applied to a surface of the glass support to provide a sheet resistance of about 5 to about 200 ohms/sq., or about 30 to about 170 ohms/sq., or about 50 to about 120 ohms/sq., or about 70 to about 100 ohms/sq. In various embodiments, the sheet resistance may be less than about 100 ohms/sq., or less than about 80 ohms/sq., or less than about 60 ohms/sq., or less than about 40 ohms/sq., or less than about 20 ohms/sq., or less than about 10 ohms/sq. The glass support may be masked near the interior opening, such as is represented at region 4412 in FIG. 38, so that the ITO coating does not extend to the edge of the interior opening 4410 of the glass support. The region can have boundaries of an inner diameter (ID) and an outer diameter (OD) as shown. Following ITO treatment, the glass support may be further coated with poly-L-lysine ("PLL"). As shown in FIG. 49, inner and outer edges of the glass support 4400 may be edge chipped or chamfered to the outside of the boundary 4414 and to the inside of the inner boundary 4416.

The cassette 4500 can include EKC slots 4520 and EKC holes 4522, which are shown aligned in FIG. 41. In the illustrated embodiment, there are three evenly spaced sets of the EKC slots 4520 and the EKC holes 4522. In addition, the cassette 4500 can include inner fiducial holes 4530 and outer fiducial holes 4532. In the illustrated implementation, there are three evenly spaced sets of the inner fiducial holes 4530 and the outer fiducial holes 4532 that are interspersed between the three sets of the EKC slots and holes.

Figure 47A:
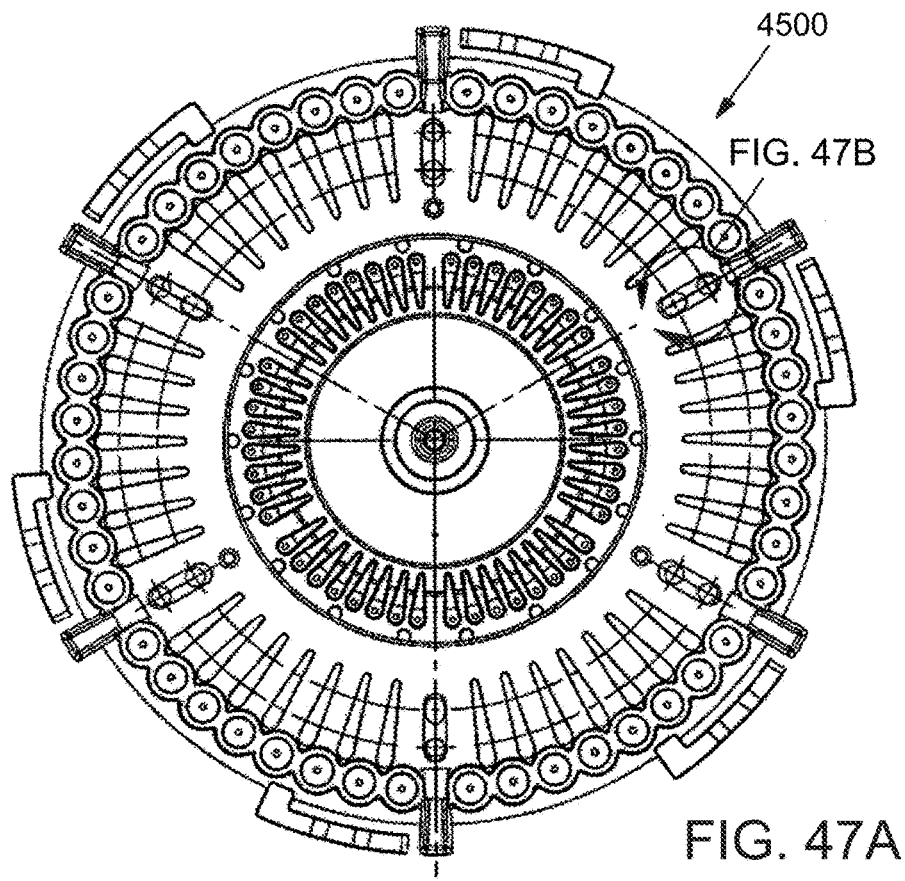
FIG. 47A is a plan view of the cassette showing a detail of the aligned fiducial holes.
Figure 47B:
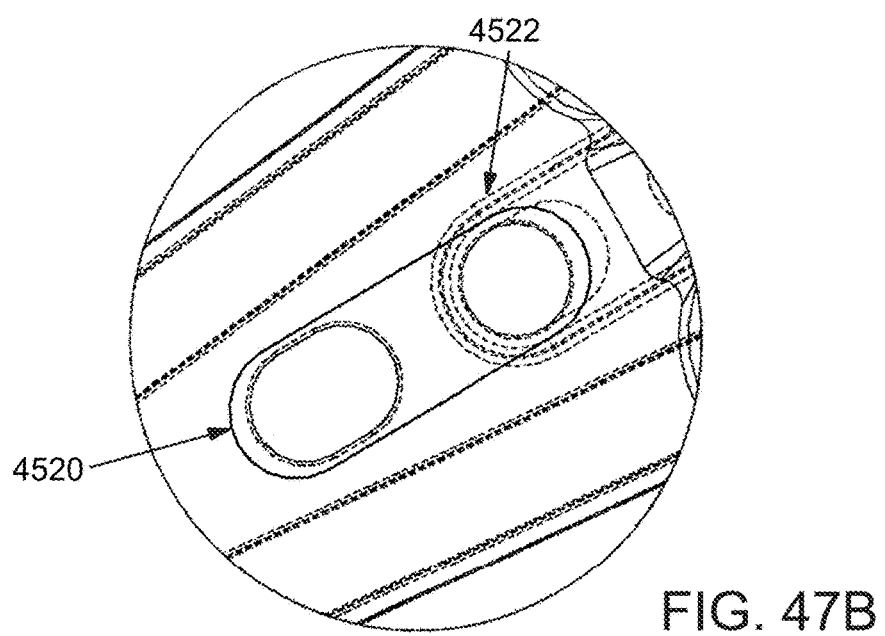
FIG. 47B is a magnified view of the fiducial holes detail in FIG. 47A.

As best shown in FIG. 47A and the detail view of FIG. 47B, the areas of each EKC slot 4520 and each EKC hole 4522 can be selectively coated with silver paint or other suitable substance to ensure conductivity throughout the aligned slots and holes in the various components.

Figure 48A:
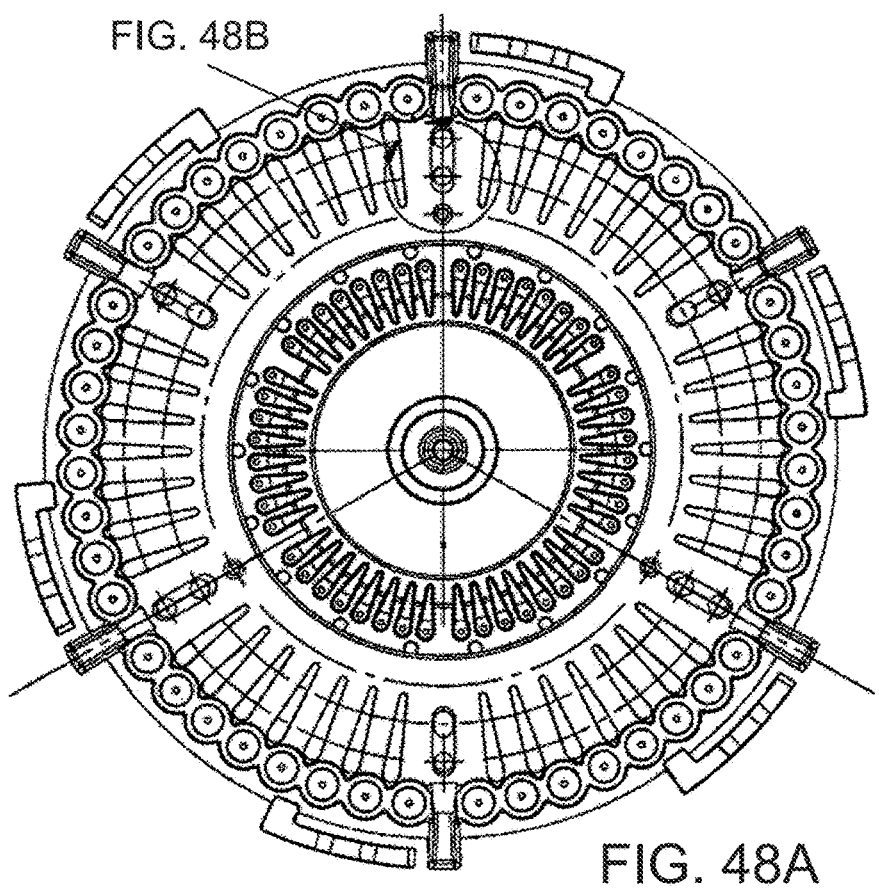
FIG. 48A is a plan view of the cassette showing a detail of the aligned fiducial marks on the glass support and the laminate layer.
Figure 48B:
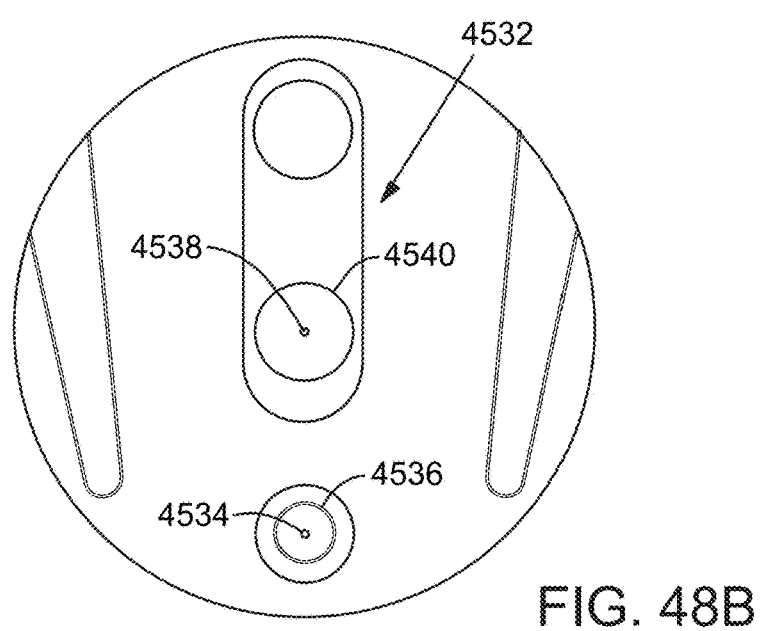
FIG. 48B is a magnified view of the detail in FIG. 48A.

FIG. 48A and the detail view of FIG. 48B show the inner fiducial holes 4530 and the outer fiducial holes 4532. Referring to FIG. 48B, a fiducial mark 4534 on the glass support 4400 is positioned to be centered within a circular hole 4536 in the laminate layer 4601. Similarly, a fiducial mark 4538 on the glass support 4400 is positioned to be centered within a circular hole 4540 in the laminate layer 4601.

Figure 53A:
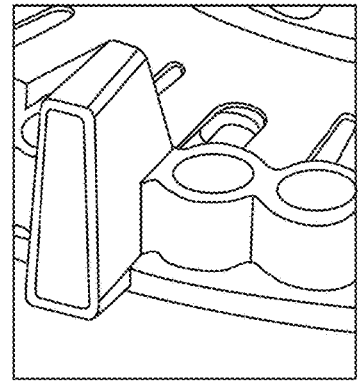
Figure 52B:
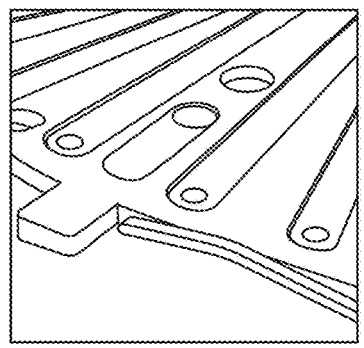
FIGS. 52B and 53B are partial perspective views illustrating a cassette before and after pockets have been added.
Figure 53B:
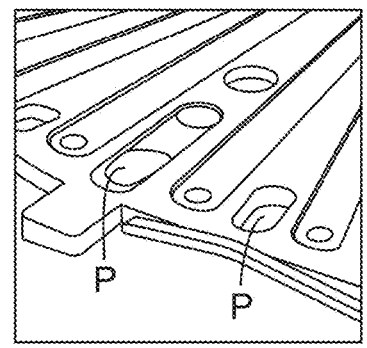
Figure 52C:
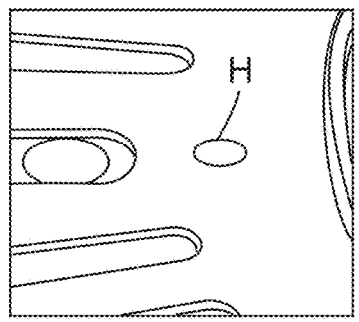
FIGS. 52C and 53C are partial perspective views illustrating a cassette before and after chamfers have been added.
Figure 53C:
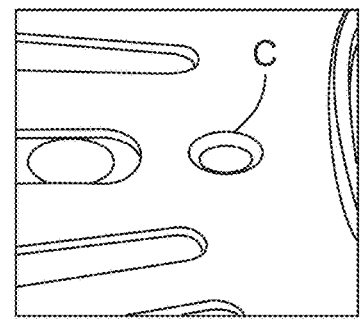

FIG. 53A shows a portion of a cassette without an ejector pad E (FIG. 52A), in an alternate embodiment. FIG. 52B shows a portion of a cassette and FIG. 53B shows the same portion in which pockets P have been formed in an alternate embodiment. FIG. 52C shows a hole in a portion of the cassette and FIG. 53C shows a chamfer C added to the hole H in an alternate embodiment.

Figure 65:
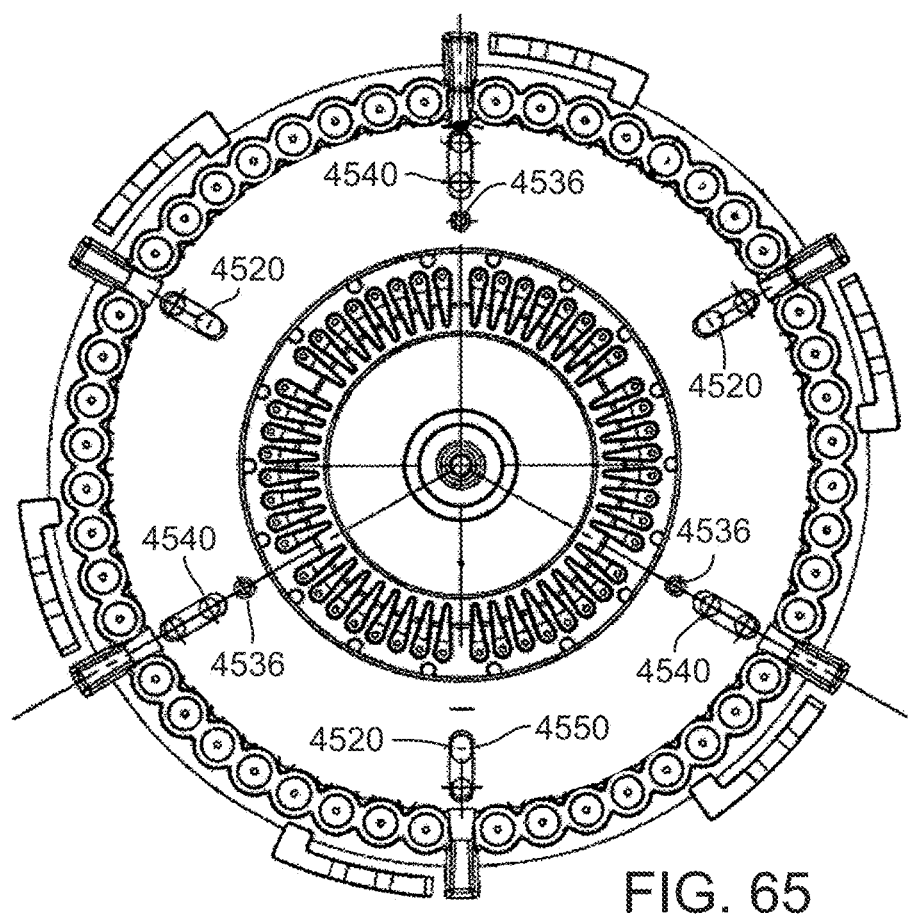
FIG. 65 is a plan view of the cassette following final assembly.

FIG. 65 is a plan view an alternate design of the cassette 4500, in which the inner slot 4520 is painted with silver paint after being masked when the glass support 4400 is coated with ITO, the fiducial marks are aligned within the respective holes 4540 and 4536, and a barcode 4550 is provided.

Figure 54:
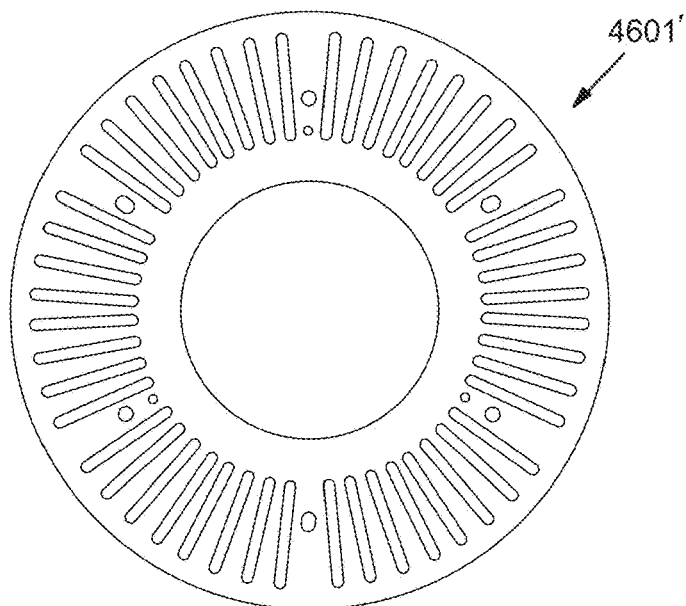
FIG. 54 is a perspective view of a laminate layer having a first thickness.
Figure 55:
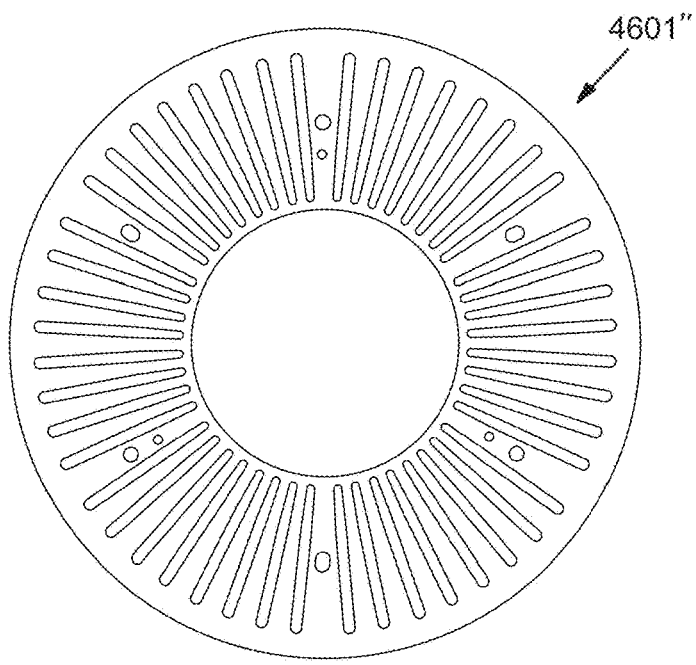
FIG. 55 is a perspective view of a laminate layer having a second thickness.

FIGS. 54 and 55 are perspective views of alternative laminate layers. In some examples, the alternative laminate layer 4601' has a thickness of approximately 0.0035 inch, with a construction comprising 0.001 inch PSA (clear), 0.0015 inch PET (blue) and 0.001 inch PSA (clear). In some examples, the alternative laminate layer 4601" has a thickness of approximately 0.0135 inch, with a construction comprising 0.00175 inch PSA (clear or blue), 0.010 inch PET (clear) and 0.00175 inch PSA (clear or blue).

Figure 59:
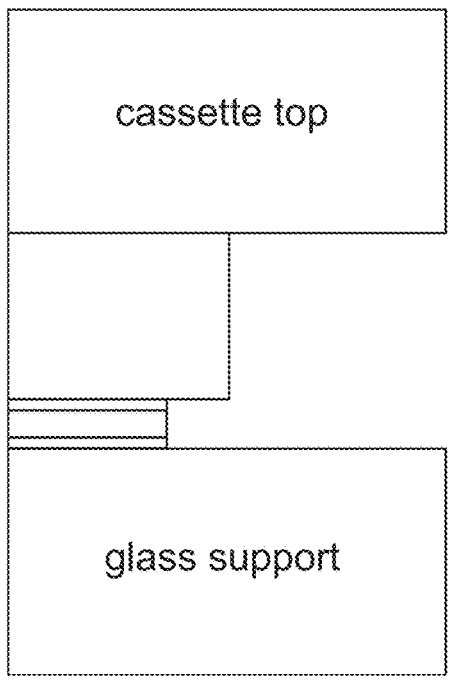
FIGS. 59 and 60 are schematic cross-sectional views in elevation of the cassette channel according to two implementations.

A schematic cross section of a cassette 4700 with a thinner laminate layer is shown in FIG. 59. As shown, the gap between the glass support and the cassette top is smaller, so fluid tends to be trapped in the gap during processing. Because the gap is smaller, the EKC electrical fields are about four times greater than in implementations with larger gaps.

Figure 60:
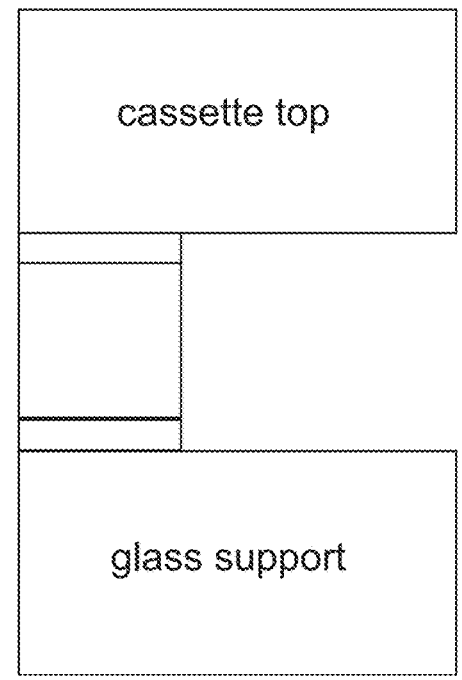

By contrast, FIG. 60 is a schematic cross section of a cassette 4702 with a thicker laminate layer. As shown, the gap between the glass support and the cassette top is larger. The thicker laminate layer can be cut more cleanly. In addition, the thicker PSA layer component may provide better sealing.

Figure 61:
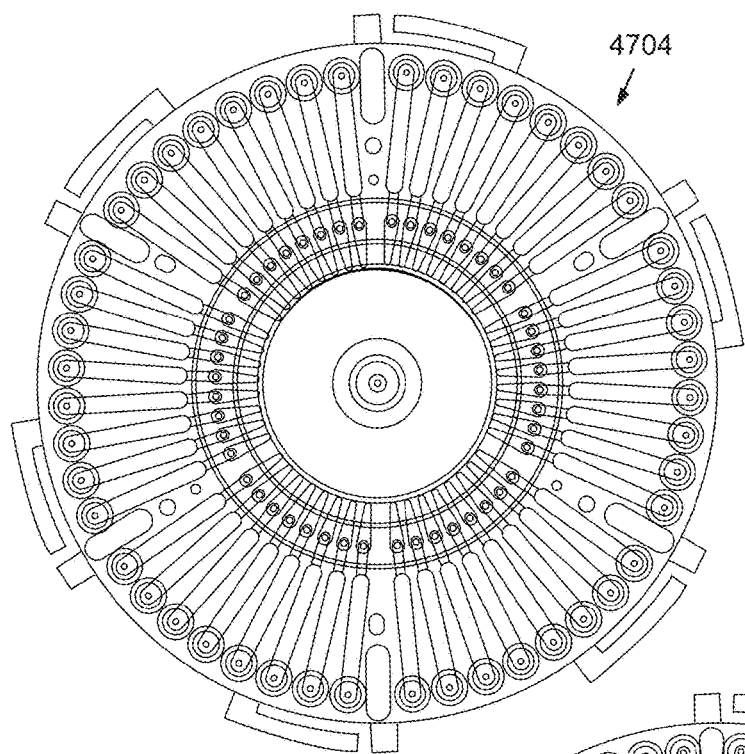
FIG. 61 is a top plan view of a cassette showing channels in the cassette top and in the laminate.
Figure 62:
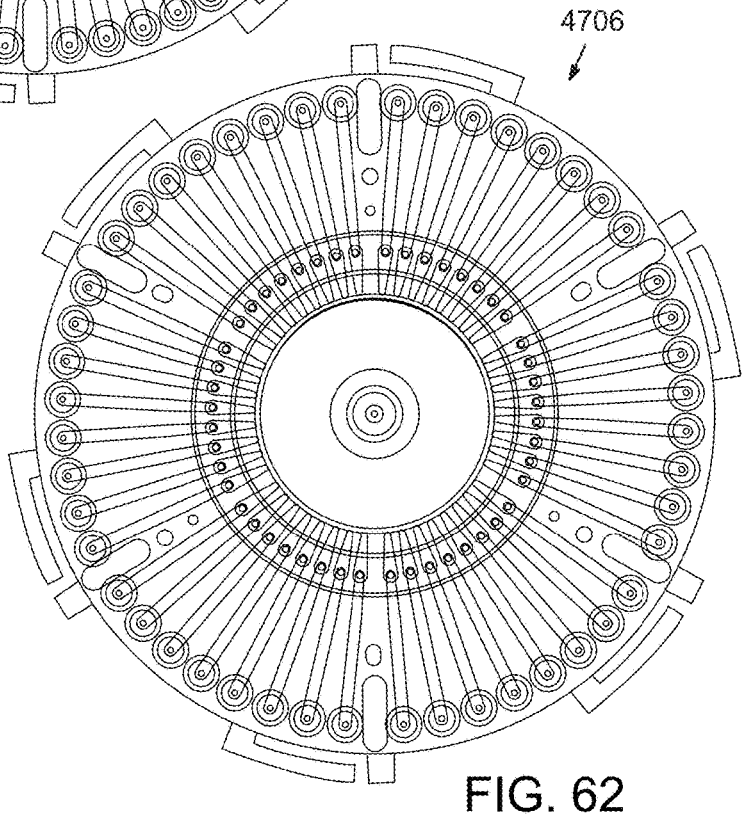
FIG. 62 is a top plan view of a cassette showing channels only in the laminate.
Figure 63:
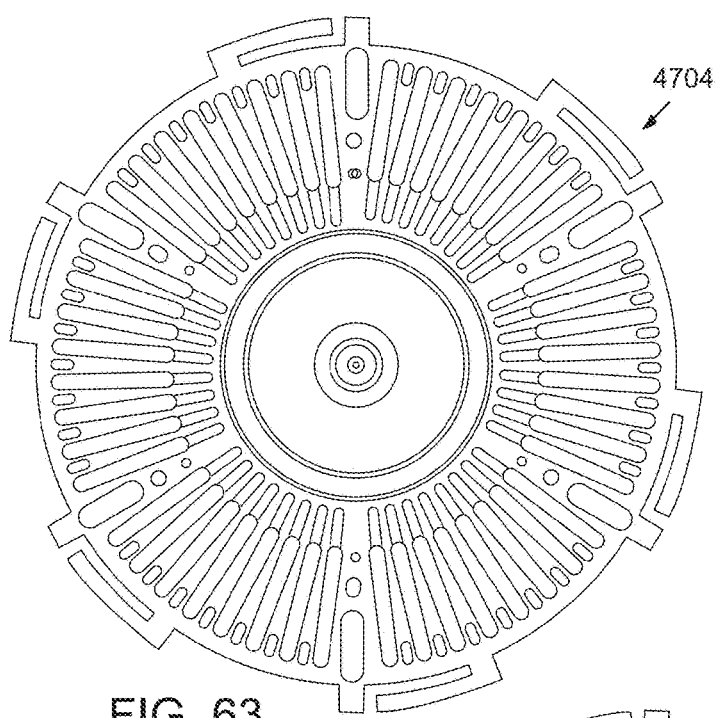
FIG. 63 is a bottom plan view of the cassette of FIG. 61.
Figure 64:
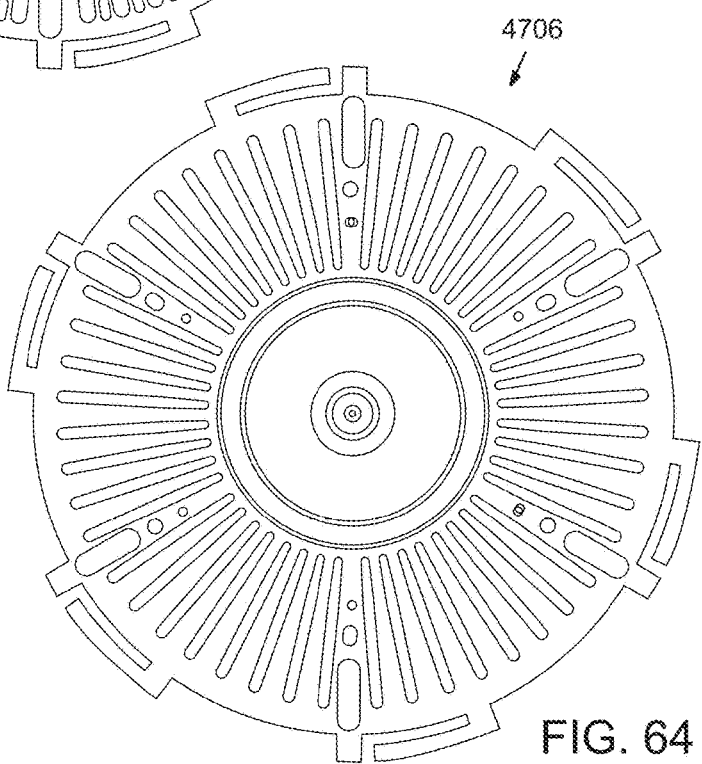
FIG. 64 is a bottom plan view of the cassette of FIG. 62.

FIGS. 61 and 63 show top plan and bottom plan views, respectively, of a cassette 4704 in which the channels are formed in both the cassette top and in the laminate layer. FIGS. 62 and 64 show top plan and bottom plan views, respectively, of a cassette 4706 in which the channels are formed only in the laminate layer.

As best shown in FIG. 57, each individual sample channel 5702 comprises one of the inlet ports 4503 in fluid communication with a flowcell 5711, with the flowcell further in fluid communication with the associated one of the outlet ports 4504. The inlet port 4503 is configured to receive a pipette tip attached to the pipettor assembly and to interface with the pipette tip in a manner that creates a seal suitable to substantially prevent fluid expelled from a pipette tip from filling the inlet port above the tip end (i.e., fluid expelled from the tip is preferentially directed into the inlet port channel and the flowcell due to the seal created by the interface between the pipette tip and the inlet port). The inlet port 4503 may have a conical shape with an inside diameter at the top of the inlet port that is greater than the outside diameter of the pipette tip. The inside diameter of the inlet port may decrease toward the bottom of the inlet port, tapering toward an inlet port channel 5712 that is smaller than the pipette tip to facilitate receiving the pipette tip lowered into the inlet well by the pipettor and guiding the pipette tip to a position substantially coaxial with the vertically oriented inlet port channel. The inlet port structure may be configured so that the top of the inlet port and/or inlet port channel is located at a raised inlet port height in relation to the level of the flowcell in a manner configured to create a positive pressure head (i.e., a hydraulic head) with respect to the flowcell to further produce gravity-driven fluid flow from the inlet port into the flowcell (i.e., the sample channel design and configuration of the inlet port, the sample channel flowcell, and the outlet port are suitable to facilitate pipettor-driven fluid flow through the sample channel in response to positive pressure at the inlet port by the pipettor, as well as gravity and surface tension driven flow through the sample channel from the inlet port to the outlet port when each port is at ambient pressure and the channel is fluid-filled with the fluid level reaching the tops of the inlet port channel and the outlet port channel (i.e., the outlet port nozzle)). In various embodiments, the configuration of the inlet port 4503, the flowcell 5711 and the outlet port 4504 may be suitable to prevent fluid backflow when the sample channel is fluid-filled and the fluid level reaches the top of the inlet port channel and the outlet port nozzle 4512, respectively (i.e., the sample channel is continuously fluid filled from the top of the inlet port channel to the top of the outlet port channel (i.e., the outlet port nozzle)) with the inlet port and the outlet port at ambient pressure.

The flowcell 5711 can comprise a horizontally oriented chamber configured to facilitate distribution of sample objects across a region of the cassette defined by the flowcell boundaries for EKC and imaging. In various embodiments, a flowcell may have a height of about 300 μm to about 350 μm, a width of about 2.2 mm (in an imaging region), and a length of about 22.5 mm. A flowcell may comprise a flowcell imaging region 5713 and a flowcell outlet region 5714. The flowcell imaging region 5713 may be about 16.5 mm in length. The flowcell outlet region 5714 may be about 6 mm in length and decrease or taper in width from the width of about 2.2 mm in the imaging region to a narrower width at the interior end (i.e., located radially inward) of the flowcell located near the outlet port. FIG. 58 is an alternative view/perspective of FIG. 57.

FIG. 56 is a drawing of a portion of a cassette showing a configuration having a misaligned channel, which may be disadvantageous, but still may be functional under many conditions. The flowcell 5711 is an alternative design that avoids this challenge because there is no channel misalignment, there is no fluid flow over the laminate layer and the exit transition is smoother. There is an increased tolerance for slight deviations in the imaging location. Further, the EKC gap is uniform in this embodiment, and no ITO is required in the sides of the channel. The estimated change in the volume of the channel is on the order of +1 microliter from the embodiment configured in FIG. 56.

In accordance with various embodiments, the configuration of the flowcell outlet region may reduce or substantially eliminate diffusion of waste products or contaminants from the outlet channel. While not wishing to be bound by theory, the time t required for a molecule to travel a distance L may be represented by the equation:

$$t=L^2/(10D),$$

where D is a diffusion coefficient that depends on the size and shape of the molecule in question as well as its interaction with the solvent and the viscosity of the solvent. A value of D of $1E-3$ mm$^2$/s may be used to represent a typical small molecule that may be present in a fluid used in a cassette. Using this value of D in the equation above, the time required for a molecule to diffuse 1 mm is 1000 s. Thus, the time required for a molecule with the same diffusion coefficient to travel 6 mm would be 3.6E4 s, or 10 hr. In various embodiments, reagents may be exchanged through the flowcell in a manner calculated to move waste reagents from the flowcell into the outlet channel, and the separation of the imaging region of the flowcell from the outlet port channel by the flowcell outlet region may prevent solutes in the outlet channel from diffusing into the imaging region of the flowcell in a timeframe in which ID, AST, or other assays are performed.

An outlet port of a sample channel may be configured to permit excess fluid to exit the sample channel upon displacement by fluid expelled into the inlet port by the pipettor. A cassette may be configured with a common waste well 4515 that receives excess fluid exiting from the each of the plurality of sample channel outlet ports 4504.

In various embodiments, an outlet port 4504 may be configured to prevent fluid backflow from the outlet port or a waste well back to the sample channel. In addition, a cassette and/or each sample channel outlet port may be configured to encourage fluid flow into the common waste well 4515. Pressure head differentials between an outlet port and an inlet port (i.e., negative pressure head from the inlet port to the outlet port) can produce backflow effects from the outlet port toward the sample channel. Likewise, a variety of phenomena can produce fluid flow against gravity that can result in backflow or contamination from a common waste well, including various surface tension-induced effects such as capillary action, wicking, and Marangoni flows. Although the use of separate waste wells for each sample channel can alleviate concern regarding sample channel cross-contamination due to backflow, separate waste wells for each channel requires increased cassette size or increased fluid handling. Additionally, backflow from an individual sample channel waste well must still be prevented.

Various parameters of an outlet port may be configured to provide desired outlet port performance with respect to waste fluid. These parameters include (but are not limited to): the length, the diameter, the surface treatment of an outlet port channel; the orientation of the outlet port channel end (i.e., the outlet port "nozzle"); the configuration and surface treatment of the surface surrounding the outlet port nozzle; the height of the outlet port nozzle above common waste well; the distance of the outlet port channel structure (i.e., the structure housing the outlet port channel) from adjacent outlet port channel structures; and the like. These features may be configured to produce capillary action within the outlet port channel and other hydraulic effects with respect to droplet formation and droplet behavior at the outlet port nozzle for the various fluids and fluid mixtures used in the sample channel over the course of instrument operation to perform ID and AST. These parameters may be configured to reduce the occurrence of backflow from the outlet port channel toward the sample channel and to prevent fluid flow from the common waste well into the outlet port.

In various embodiments, an outlet port may comprise a cylindrical channel located above the end of the flowcell and oriented vertically upward. The outlet port channel may have a small diameter suitable to provide surface effects that create a level of capillary action to extend the height of the outlet port channel sufficiently above the common waste level to create a separation barrier while maintaining a negative pressure head relative to the inlet port filled to the top of the inlet port channel (at ambient pressure; i.e., without a positive pressure from the pipettor). The outlet port channel may be located in an outlet port structure 4516. The outlet port structure 4516 may be configured to extend vertically upward from the top surface 4517 of the cassette. The outlet port structure may define the outlet port channel as a substantially vertically oriented cylindrical channel within the outlet port structure. The outlet port structure may comprise an arcuate fin or rib 4518 extending radially inward toward the central common waste well 4515. The plane of the outlet port nozzle may be oriented orthogonally to the outlet port channel axis. The area of the tops of the outlet port structures surrounding the outlet port nozzles and the distance between the tops of adjacent outlet port structures may be configured to prevent waste fluid droplets that form at the outlet port nozzles from contacting the tops and/or nozzles of adjacent outlet port structures. In various embodiments, the outlet port structure may be configured with a geometry having a ratio of height to distance between outlet port structures that exceeds a critical value such that fluid surface forces are insufficient to overcome fluid body forces, thereby preventing fluid backflow by wicking and/or capillary action. Stated differently, the height of each outlet port structure and the distance between adjacent outlet port structures may be sufficient to prevent capillary action of fluid in the common waste well from overcoming gravity and reaching the tops of the outlet port structures. In various embodiments, the arcuate conformation of the outlet port structure fin may wick a waste fluid droplet downward toward the common waste well. The configuration of the outlet port structures may provide for capillary action between adjacent outlet port structures in a direction away from the outlet port nozzles, drawing waste fluid downward and/or radially inward toward the center of the cassette and the common waste well.

In various embodiments, the configuration of the cassette and the outlet ports does not require individual outlet ports or waste wells to be emptied by a pipettor. The common waste well can be emptied periodically if necessary when the pipettor is not required for other operations.

In various embodiments, the outlet port does not require a mineral oil overlay or similar treatment to reduce or prevent evaporation in the sample channel. Fluid evaporation from the outlet port may reduce a pressure head in the outlet port, producing fluid flow through the sample channel from the inlet port, reducing a fluid level in the inlet port channel. In various embodiments, both the inlet port channel and the outlet port channel may be configured such that evaporation of fluid from the open surfaces of each over the course of an assay such as ID or AST is less than a critical value such that each of the inlet port channel and the outlet port channel store excess fluid volume and fluid volume depletion by evaporation does not deplete fluid from the flowcell and/or otherwise influence the solution properties of the fluid contained in the flowcell. In various other embodiments, the inlet port and/or the outlet port may be covered with mineral oil or any other reagent suitable to overlay an aqueous fluid and reduce evaporation of the fluid.

In various embodiments, an outlet port may be configured to provide a reduced pressure head relative to a pressure head of the inlet port, thereby reducing or substantially preventing backflow into the sample channel. An outlet port may be configured to provide a reduced pressure head by maintaining a small outlet port channel volume, such as by configuring the outlet port channel with a low outlet port channel height. In various embodiments, an outlet port channel may be configured with a reduced channel diameter, such that a reduced outlet port channel volume is provided per unit of outlet port channel height, and further providing for an increased surface tension force (i.e., capillary action) on fluid in the outlet port channel that counteracts the gravitational force contributing to the pressure head. In this manner, the outlet port channel may be configured to maintain a low pressure head while increasing the head height to prevent backflow from the waste well into the outlet port. In accordance with various embodiments, configuring the outlet port to provide a low outlet port pressure head may permit the sample channel inlet port to be configured with a low head height while providing a positive pressure head relative to the outlet port, thereby reducing the height of the inlet port structure required to provide the positive pressure head at the inlet port relative to the outlet port.

In various embodiments, the use of sample channels comprising an outlet port channel diameter that is smaller than the inlet port and/or inlet port channel permits an increased number of sample channels per unit surface area as compared to a cassette comprising sample channels of the same overall configuration but having an outlet port channel of the same diameter as the inlet port channel.

In various embodiments, a vertical outlet port channel configuration is compatible with manufacturing in a single molding stage without additional side-actions or pick outs.

Method of Operation

Overview

An instrument and system in accordance with various embodiments may be used to perform microorganism identification, quantitation, and antimicrobial susceptibility testing in an automated fashion. System architectures and process flows for a system and method of operation in accordance with various embodiments are illustrated in FIGS. 69-75. An overview of the disclosed ID/AST methods is provided, with additional details for various aspects of the methods provided in the following sections. In some embodiments, a patient sample (or portion thereof) is loaded in a sample vial and loaded into the instrument. Patients can include human and veterinary subjects, such as cats, dogs, cows, pigs, horses, sheep, chickens and other birds, fish, and the like. In some examples, a patient is one who is known to have or is suspected of having an infection (such as a bacterial or fungal infection). In one example, the patient is septic. Patient samples include but are not limited to blood (e.g., whole blood, plasma, or serum), respiratory samples (such as bronchoalveolar lavage, oropharyngeal swab, nasopharyngeal swab, or sputum), saliva, urine, rectal swab, vaginal swab, tissue samples, or other biological specimens. Samples can be concentrated, diluted, and/or separated before analysis with the disclosed method and systems. Portions of the sample are introduced into a plurality of microfluidic channels in the cassette. One or more detectably labeled nucleic acid probes (e.g., include a detectable label, such as a fluorophore) are introduced into each of the microfluidic channels. In particular examples, the detectably labeled probes include species-specific (also referred to as target-specific) probes and/or universal probes. Each species-specific probe specifically hybridizes to nucleic acids from a specific target organism (e.g., *E. coli*) or group of target organisms (e.g., *Klebsiella* spp., such as *K. pneumoniae, K oxytoca*, not differentiated). In some examples, the species-specific probes each specifically hybridize to rRNA of a target organism or group of organisms. Each universal probe hybridizes to nucleic acids from a group of class of organisms, such as all bacteria and/or fungi. In one specific example, one species-specific probe is introduced into each microfluidic channel (e.g., a different species-specific probe in each channel) and the universal probe is introduced into all of the channels. The detectably labeled probes are incubated with the sample under conditions sufficient for the probes to hybridize to microorganisms present in the sample.

Images of one or more (such as 1-100, for example, 2-25, 10-40, 30-80, or 50-100) fields of view of one or more microorganisms are captured. Multiple images of the same field of view may be captured, for example under one or more different imaging modalities. In some examples, each field of view is imaged under conditions to detect each of the labeled probes (such as the species-specific probe and the universal probe) and optionally under dark field conditions. The images are subjected to morphological or other analysis (such as morphokinetic analysis) to identify characteristics of the imaged microorganisms, including one or more of signal intensity of the one or more detectably labeled probes, noise, cross-talk, and microorganism morphology. The information from the morphological analysis is input to a probability expectation model of distribution to identify one or more microorganisms present in the patient sample. In some examples, the microorganism is identified based on a combination of posterior probabilities from one or more of the plurality of microfluidic channels. In some examples, the signal pattern of the detected microorganism(s) in the sample are compared or matched with a posterior probability density function (PDF) of a labeled target probe using an empirical threshold value. In additional examples, the posterior distributions are passed through Kernel Density Estimator and integrated to provide a resulting likelihood or probability of an event (e.g., presence or absence of a specific microorganism) in a microfluidic channel. In some examples, the sample includes one microbe (such as one "target" microbe), while in other examples, the sample includes two or more microbes (for example, 2, 3, 4, or more), which is referred to herein as a "polymicrobial" sample.

In some embodiments, the patient sample is subjected to one or more pre-processing steps prior to contacting the sample with the one or more detectably labeled probes. These pre-processing steps include GEF (for example, to remove or reduce lysed cells and debris in the sample) and/or EKC (for example to localize microorganisms to a surface for analysis).

In additional embodiments, following microorganism identification, the patient sample (or a subsample thereof) is subjected to AST analysis. Based on the identity of the microorganism(s) in the sample, a portion of the sample is grown in the presence or absence of one or more antimicrobials and the growth of the identified microorganisms is monitored over time (for example, at least 30 minutes, at least 1 hour, at least 2 hours, at least 3 hours, at least 4 hours, at least 5 hours, or at least 6 hours, such as about 1-6 hours). In some examples, the growth of the microorganisms is monitored by capturing images of the microorganisms at repeated time intervals (such as every 10 minutes for 4.5 hours) and qualitatively or quantitatively measuring the growth (or amount of growth), lack of growth, or lysis of the microorganisms. Based on the behavior of the microorganisms over time in the presence of the one or more antimicrobials (for example, compared to a control that is not exposed to the antimicrobial(s)), a determination of susceptibility (or indeterminate susceptibility) or resistance of the identified microorganisms to each antimicrobial is made. In some examples, the methods also include determining a MIC of the identified microorganisms to one or more antimicrobials.

In some embodiments, prior to AST analysis, the concentration of the microorganism(s) in the patient sample is determined, in order to calculate an appropriate dilution of the sample to utilize in AST. In some examples, the concentration is determined using the dynamic dilution methods described herein. In additional embodiments, the sample or portion thereof is subjected to one or more pre-processing steps prior to AST, for example GEF and/or EKC.

User Input

An instrument user may perform various input functions to prepare an instrument for operation and to prepare the system components and a sample for processing. For example, a user may obtain a sample, such as a biological or clinical specimen. The user may also obtain a package comprising a reagent cartridge kit. The reagent cartridge kit contained in the package may further comprise a sample vial and a cassette. The user may transfer all or a portion of a biological or clinical specimen to the sample vial and load the reagent cartridge and sample vial in the instrument. The user may also insert the cassette into the instrument. The user may enter order information into the controller via a user interface. In various embodiments, the instrument may comprise one or more devices for scanning a barcode or otherwise recognizing information encoded on a cartridge, cassette, and/or sample vial. The instrument may record various information and/or perform instrument functions based on information encoded on the cartridge, cassette, and/or sample vial and recognized by the instrument itself. After all sample preparation, sample loading, and order entry steps are completed, the user may press a "Run" button located on the instrument to initiation the ID/AST process. In accordance with various embodiments, the user input steps that must be completed by a user prior to initiation of an instrument run may be completed by a user in about 15 minutes or less.

Automated Sample Preparation

In various embodiments, following sample loading, an automated sample preparation step is performed. Sample preparation may be performed using gel electrofiltration ("GEF"), such as in the manner described in U.S. Patent Publication No. 2014/0038171A1, which is hereby incorporated by reference in its entirety. An aliquot of the sample may be removed from the sample vial by the instrument pipettor and transferred to a GEF device. A GEF step is performed to separate sample debris from microorganism cells that may be present in the sample. Following the GEF step, the electric field is briefly reversed to displace microorganism cells from the surface of the gel matrix and the prepared sample comprising microorganism cells present in the sample can be removed from the GEF device. In accordance with various embodiments, the instrument and system may be configured to perform two separate GEF steps, with a first GEF step performed to prepare a portion of the sample for FISH ID, and a second GEF step performed to prepare a portion of the sample for AST. Any number of GEF sample preparation steps may be performed to prepare one or more portions of a sample for various assays that may be performed by an instrument in accordance with various embodiments. The sample may be a polymicrobial patient sample in which multiple strains, species or types of microorganisms are present (such as at least 2, at least 3, at least 4, or at least 5 different strains, species or types of microorganisms). The sample may be a direct-from-patient sample.

Cell Immobilization

Following sample preparation by GEF, recovered sample is aliquoted by the pipettor into one or more sample channels of a cassette. In various embodiments, EKC is performed to capture cells on a capture surface of each sample channel flowcell. In other embodiments, cells are immobilized by entombing them in three-dimensional space in a medium that can be phase changed after contacting the cells (e.g., agar). The entombing can occur with or without first performing the capture step. In some embodiments, the entombing creates a microenvironment around the immobilized microorganism, the characteristics of which are not influenced by neighboring microorganisms during the identification and/or susceptibility testing periods. In some examples, the method includes retaining the microorganism on a detection surface of the sample channel, thereby producing a retained microorganism, and subsequently introducing a gel medium (such as one containing agar) into the sample channel, wherein the gel medium is in contact with the retained microorganism following introduction into the sample channel; immobilizing the retained microorganism in the sample channel at the same location where the microorganism is retained, to produce an immobilized microorganism, wherein offspring of the immobilized microorganism remain over time at a location with the immobilized microorganism; and incubating the immobilized microorganism for a period of time to allow for growth of the microorganism.

FISH Identification

Microorganism identification may be performed by hybridization of one or more (such as 1, 2, 3, 4, 5, 6, 7, 8, 9, 10, 11, 12, 13, 14, 15, 16, 17, 18, 19, 20, or more) species-specific probes and/or one or more universal microbial probes (such as a universal bacterial and/or universal fungal probe) in a FISH assay. For example, in specific embodiments, seventeen different species-specific probes, each designed to hybridize to the ribosomal RNA of a specific microorganism species (e.g., the "target"), and a "universal" FISH probe, are prepared by the instrument using reagents contained in the reagent cartridge and the mixtures introduced into seventeen sample channels. Cell permeabilization and washing steps may be performed by the instrument using reagents contained in the reagent cartridge, followed by a hybridization step in which the species-specific probes attach to a target microbial species if cells of the target microbial species are present in the sample and captured in the sample channel. The universal probe hybridizes to any microorganism nucleic acid molecules present. In various embodiments, probe migration and hybridization to microorganism nucleic acids may be accelerated by application of an electrical field in the flowcell by the instrument. Unattached (e.g., non-hybridized) probes may be rinsed out of the channel by the instrument following hybridization.

Each FISH probe has an attached fluorophore that emits light at a peak emission wavelength when illuminated with an appropriate excitation wavelength. For example, the species specific probes may be labeled with a first fluorophore, such as ATTO-532, that provides for emission detection at a first emission wavelength, such as 553 nm, when illuminated by the illuminator using a first laser, such as a green laser providing a first excitation wavelength, such as 520 nm. In some embodiments, each of the species-specific probes is labeled with the same fluorophore, while in other embodiments, one or more of the species-specific probes is labeled with a different fluorophore than at least one of the species-specific probes.

The "universal" FISH probe is configured to hybridize to a plurality of microorganism species, and in some examples is used in conjunction with a second laser, such as a red laser.

Use of a universal probe may serve to facilitate identification of polymicrobial specimens comprising more than one bacterial or fungal species and observing the presence of bacteria not marked by any of the seventeen species-specific probes. In various embodiments, the fluorophore used for a universal probe can comprise a second fluorophore (e.g., a different fluorophore than that used to label one or more of the species-specific probes), such as ATTO-647, that provides for emission detection at a second emission wavelength, such as 669 nm, when illuminated by the illuminator using a red laser providing a second excitation wavelength, such as 637 nm.

Additional fluorophores for labeling the species-specific and or universal probes can be utilized. Exemplary fluorophores include but are not limited to Alexa Fluor® fluorophores, coumarin, fluorescein (FITC), rhodamine, rhodamine Green, rhodamine Red, tetramethylrhodamine (TRITC), Cy®3, Cy®7, and Cy®5 fluorophores, Pacific Green™, Oregon Green™, Pacific Blue™, Pacific Orange™, and Texas Red® fluorophores, PlatinumBright™ fluorophores (Leica), 6-FAM, TAMRA, JOE (6-carboxy-4', 5'-dichloro-2',7'-dimethoxyfluorescein), VIC, tetrachlorofluorescein (TET), hexachlorofluorescein (HEX), ROX (carboxy-X-rhodamine), IRDyes® fluorophores (Li-Cor), and ATTO™ fluorophores. One of ordinary skill in the art can select suitable fluorophores and combinations of fluorophores for labeling the species-specific and/or universal probes utilized in the systems and methods described herein.

Figure 66:
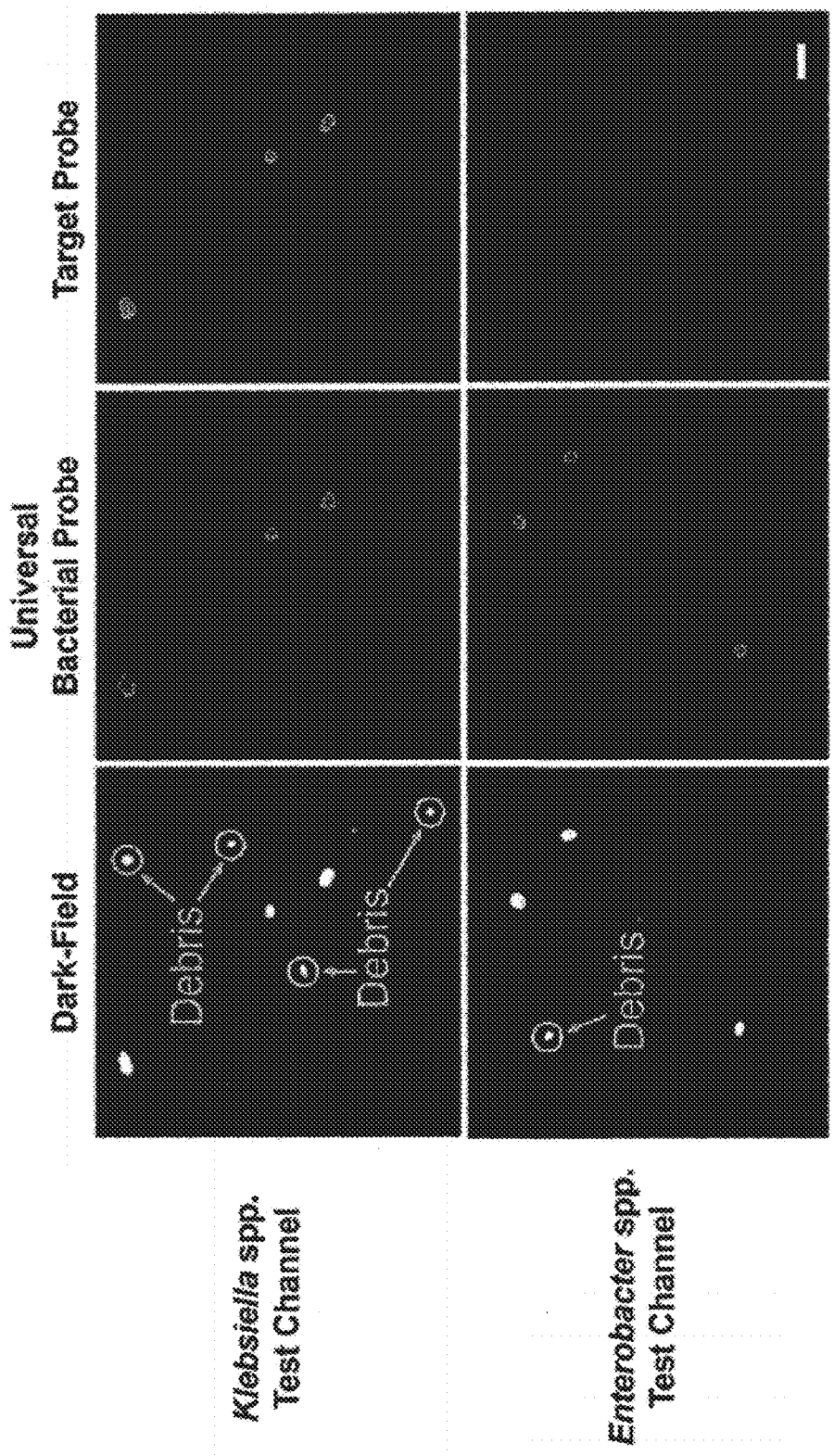
FIG. 66 is a series of images showing representative FISH ID image data acquired with the instrument.

In various embodiments, the system may exclude sample debris from analysis by considering only image objects colocalized using both dark-field imaging and fluorescence imaging during image processing by the controller. An example of FISH ID image data acquired using the AD-1 instrument is illustrated in FIG. 66.

In various embodiments, a universal control stain (such as a DNA intercalating dye) may be combined with a prepared sample and introduced into a sample channel. Exemplary universal control stains include but are not limited to acridine orange, propidium iodide, and 4'6-diamidino-2-phenylindole (DAPI). Image data from all flowcells may be used to determine the total number of organisms present in a sample and permit evaluation of the sample for the presence of non-target organisms and polymicrobial samples.

In accordance with various embodiments, the instrument can report FISH ID results approximately one hour after sample loading. The ID results may be used by the system to determine the selection of appropriate antibiotics or antifungals for performing AST from the antimicrobial reagent panel included in the reagent cartridge.

Direct-from-patient samples (such as blood, urine, respiratory samples) are generally complex milieus, containing live cells, dead cells and debris that interfere with testing procedures. Typical methods for the identification of microorganisms in patient samples often results in ambiguous quantitation results. Potential errors include organism misclassification, wrong identification and improper quantification of viable organisms. The problem has been addressed in the past by non-quantitative operator judgment. The instrument system employs a dynamic dilution procedure with automated interpretation of data from multiplexed channels and probes to improve accuracy and reduce errors in microbial quantification. Once the microorganisms in a sample are identified, aliquots of the sample may be subjected to antimicrobial susceptibility testing to determine the best course of therapy to treat the particular strain of microorganism (or strains of multiple microorganisms) infecting an individual.

Antimicrobial Susceptibility Testing (AST)

Figure 67:
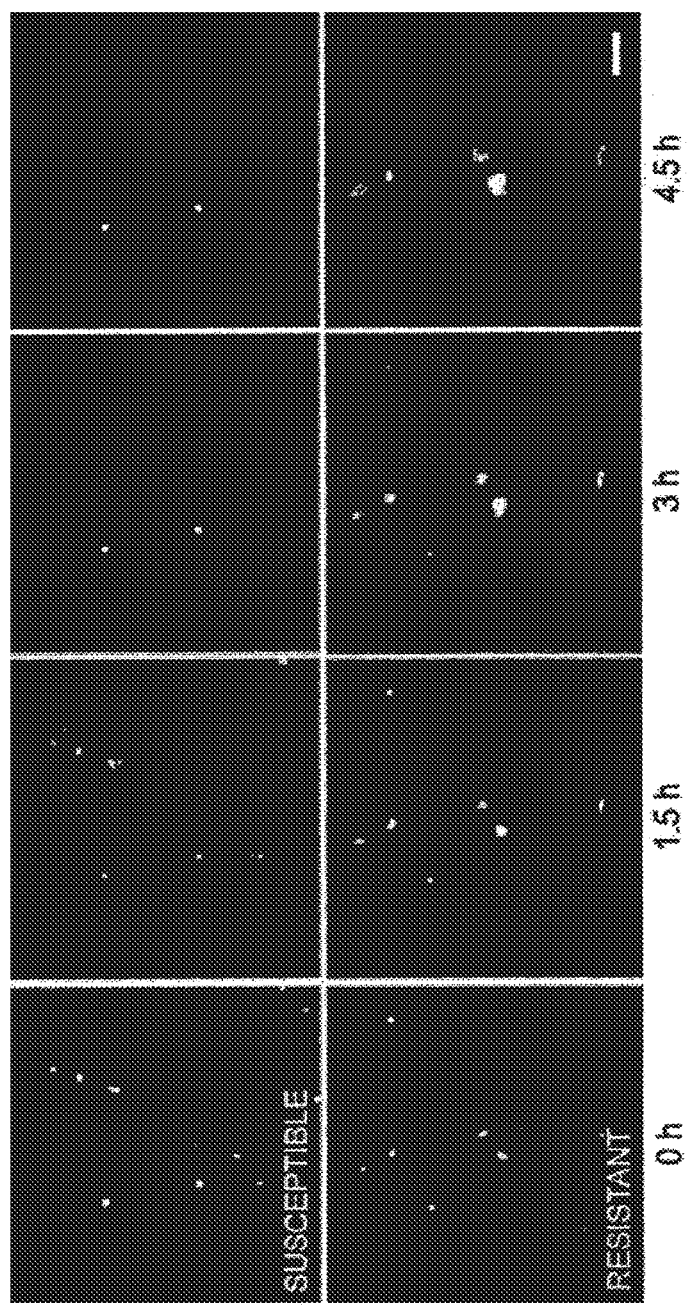
FIG. 67 is a series of images for susceptible and resistant microorganisms at four different times.

In various embodiments, the instrument may combine a sample prepared by GEF (or a subsample thereof) with growth media and subject the sample to a pre-growth step during the approximately 1-hour FISH ID assay. The pre-growth step performed by the instrument may normalize microorganism growth rates prior to AST. The instrument may determine organism concentration in the pre-grown sample by performing (and/or repeating) a cell quantitation process using a universal nucleic acid-binding stain. Based on the organism concentration of a sample following the pre-growth step, the instrument may dilute the sample to provide an appropriate cell concentration for AST. Following automated sample preparation and EKC, the instrument may add growth media (e.g., MHA) containing single concentrations of each test antimicrobial (such as antibiotics prepared by the instrument) to separate sample channels. The instrument may provide temperature control of the enclosure, the cassette, and reagents in the reagent cartridge. In various embodiments, different temperatures may be provided by the instrument over time and/or for specific components of the instrument. For example, the instrument may provide separate temperature control and temperature profiles (e.g., changes in temperature over the time course of an assay and/or instrument operation) for the subassemblies of the cassette that contain the MHA and the antibiotic reagents. Following distribution of growth media to the sample channels, the instrument may periodically acquire photomicrographs of microorganism cells in each sample channel flowcell for an AST assay period, for example, about every 5-30 minutes (such as about every 5 minutes, 10 minutes, 15 minutes, 20 minutes, 25 minutes, or 30 minutes) for about 1 to 8 hours, such as up to about 1.5 hours, 2 hours, 3 hours, 4 hours, 4.5 hours, 5 hours, 6 hours, 7 hours, or 8 hours, creating a time-lapse record of microorganism growth. Examples of photomicrograph images for susceptible and resistant microorganisms at time=0 hr, 1.5 hr, 3 hr, and 4.5 hr are shown in FIG. 67.

Figure 68:
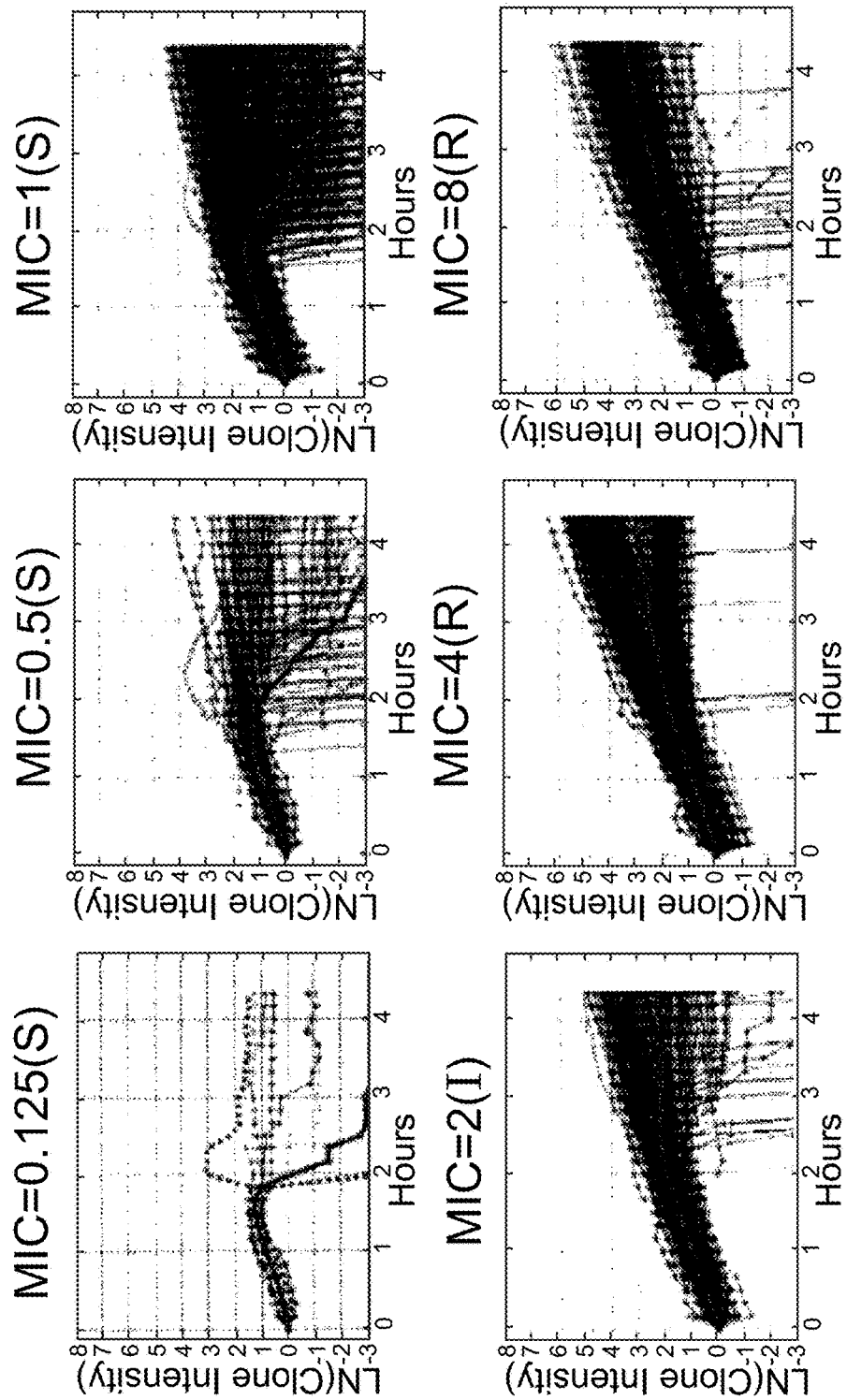
FIG. 68 is a series of graphs showing microorganism growth curves.
Figure 69:
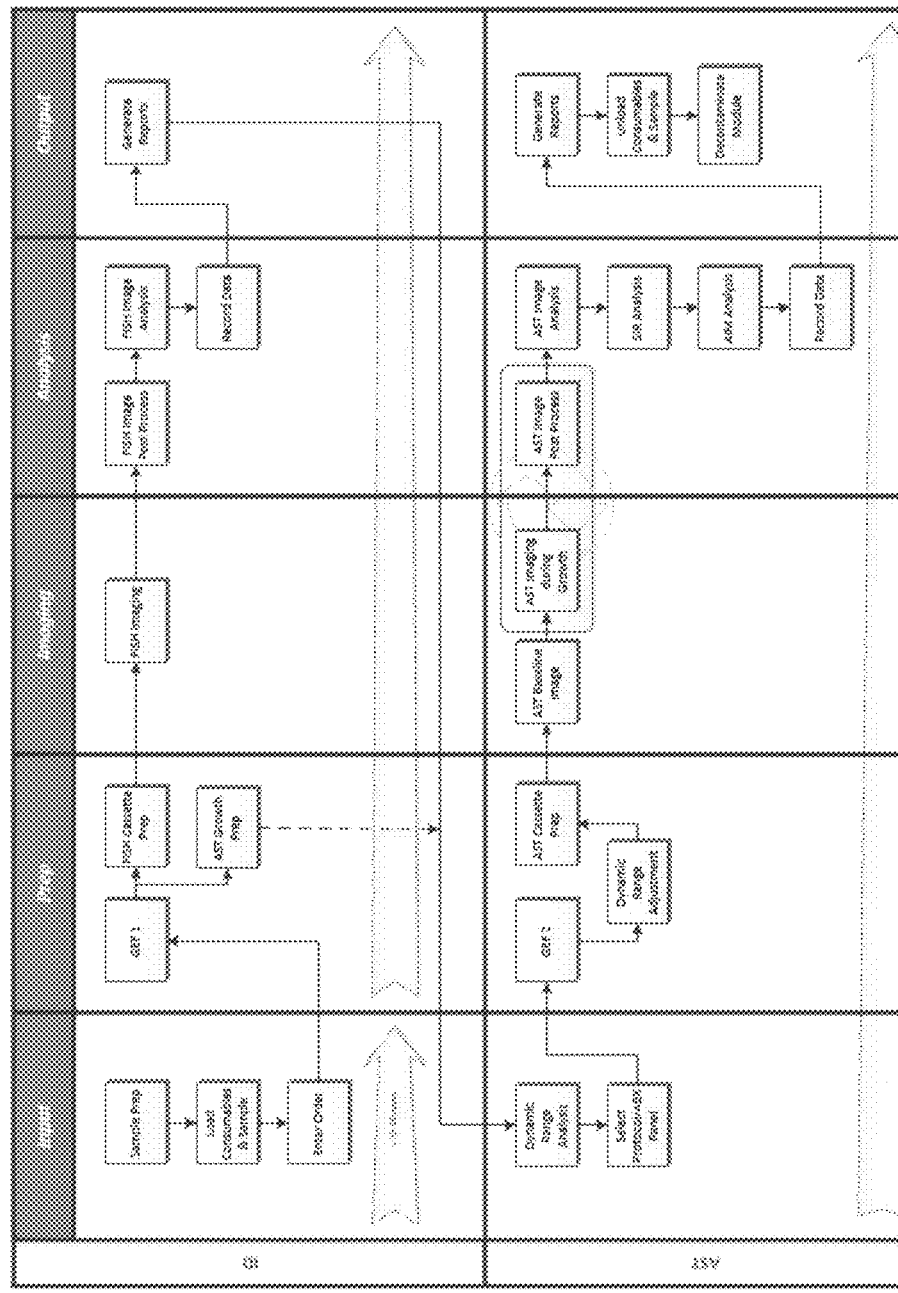
FIGS. 69-75 are diagrams of system architectures and process flows for a system and method of operation in accordance with various embodiments.
Figure 70:
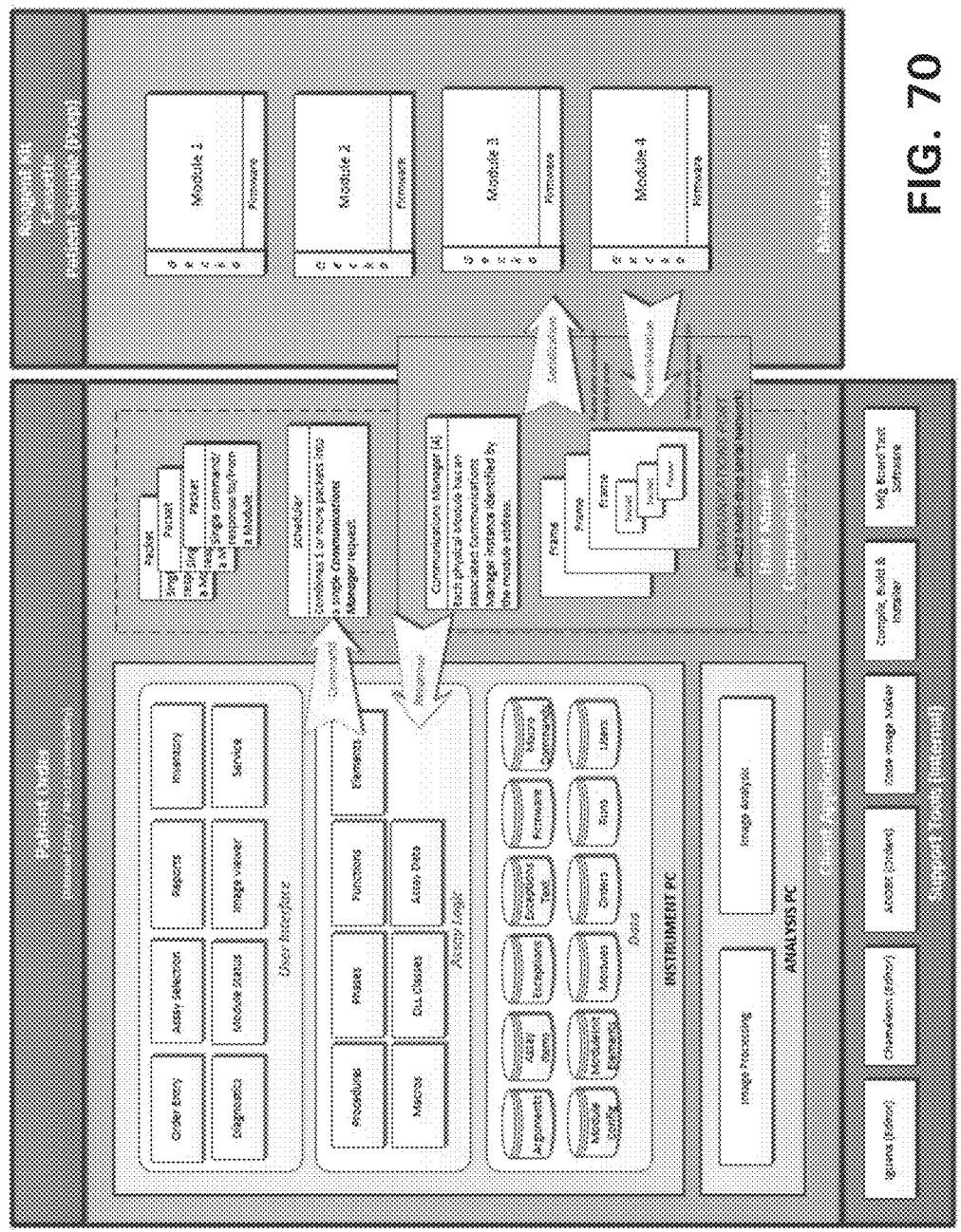
Figure 71:
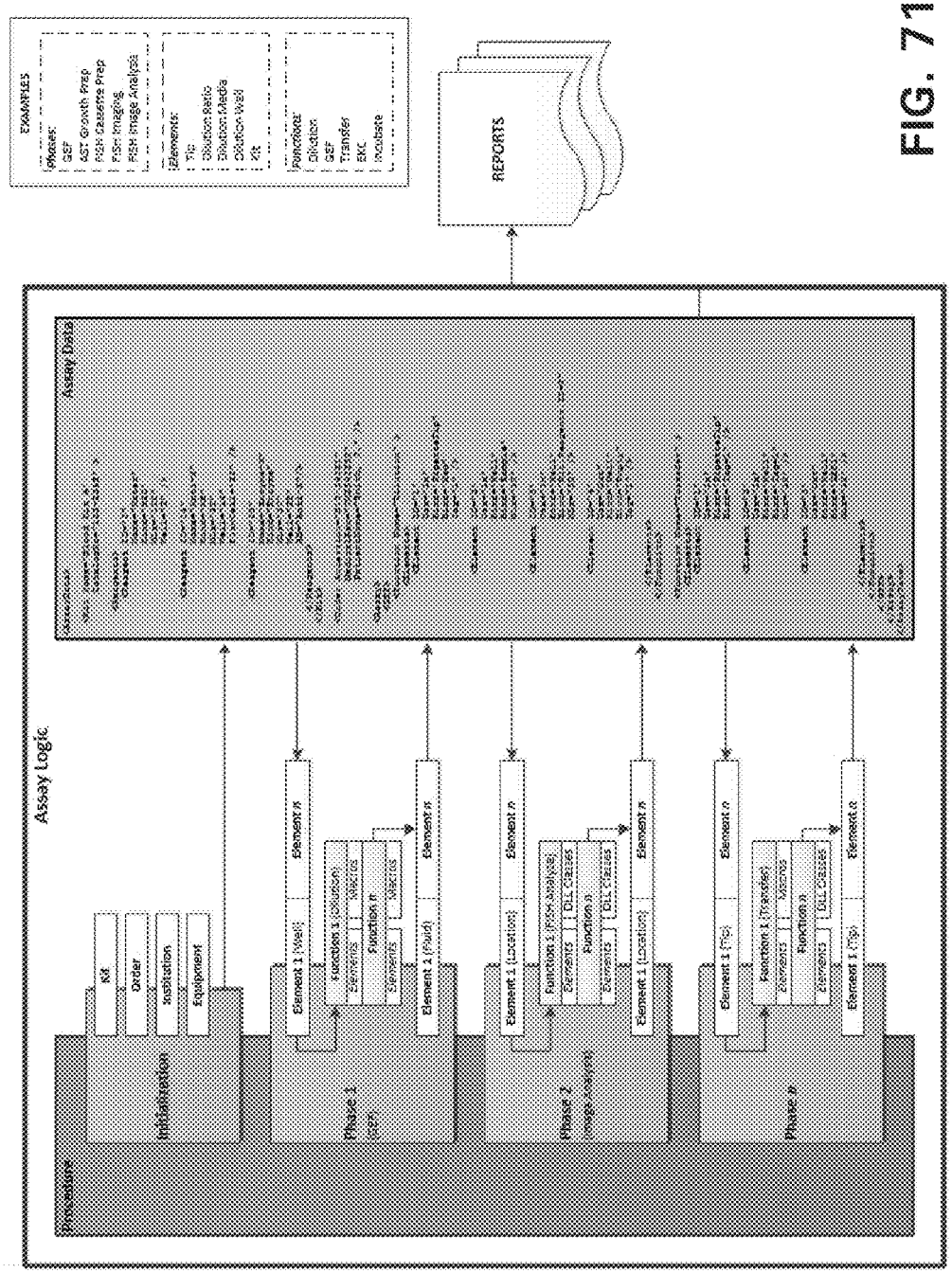
Figure 72:
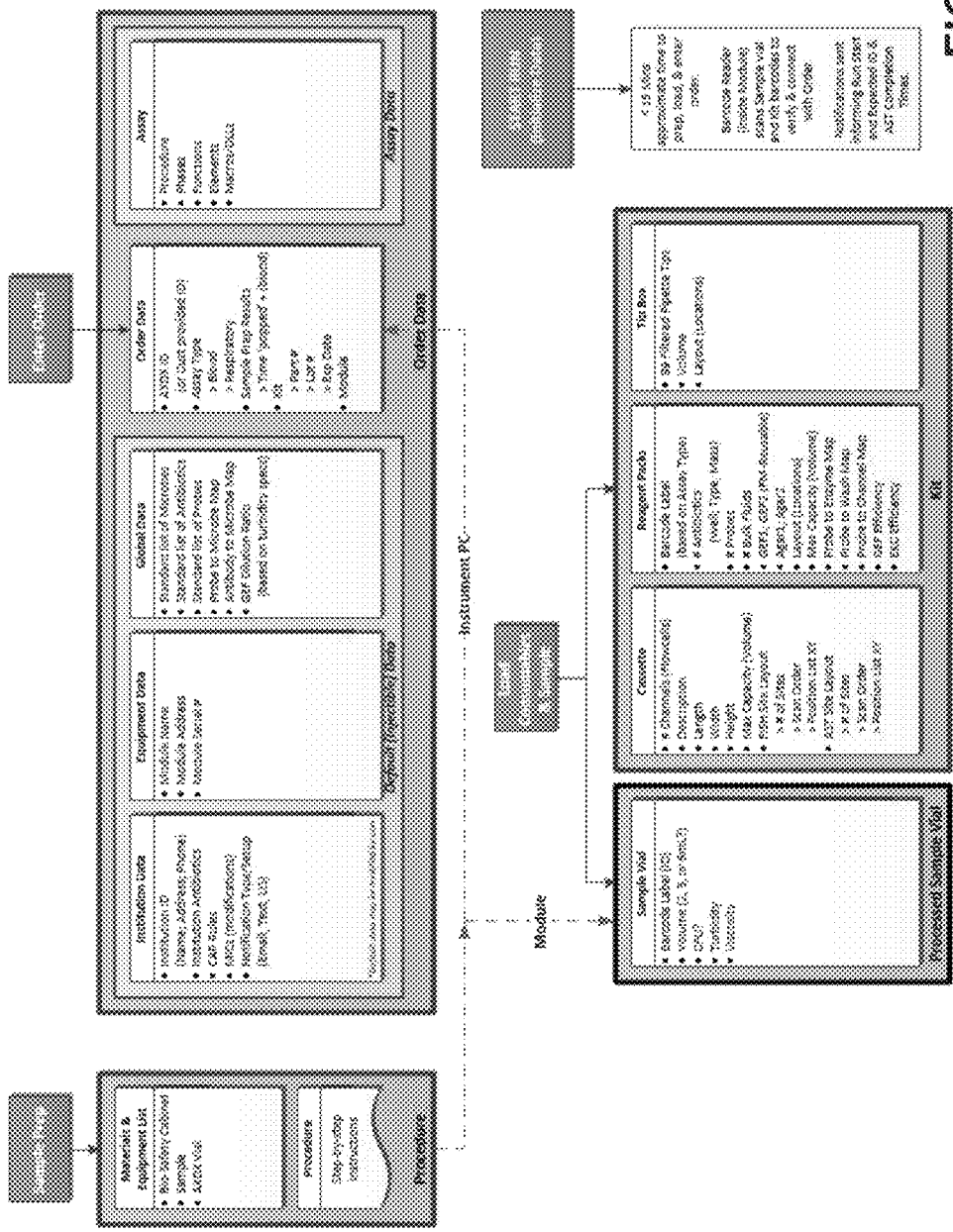
Figure 73:
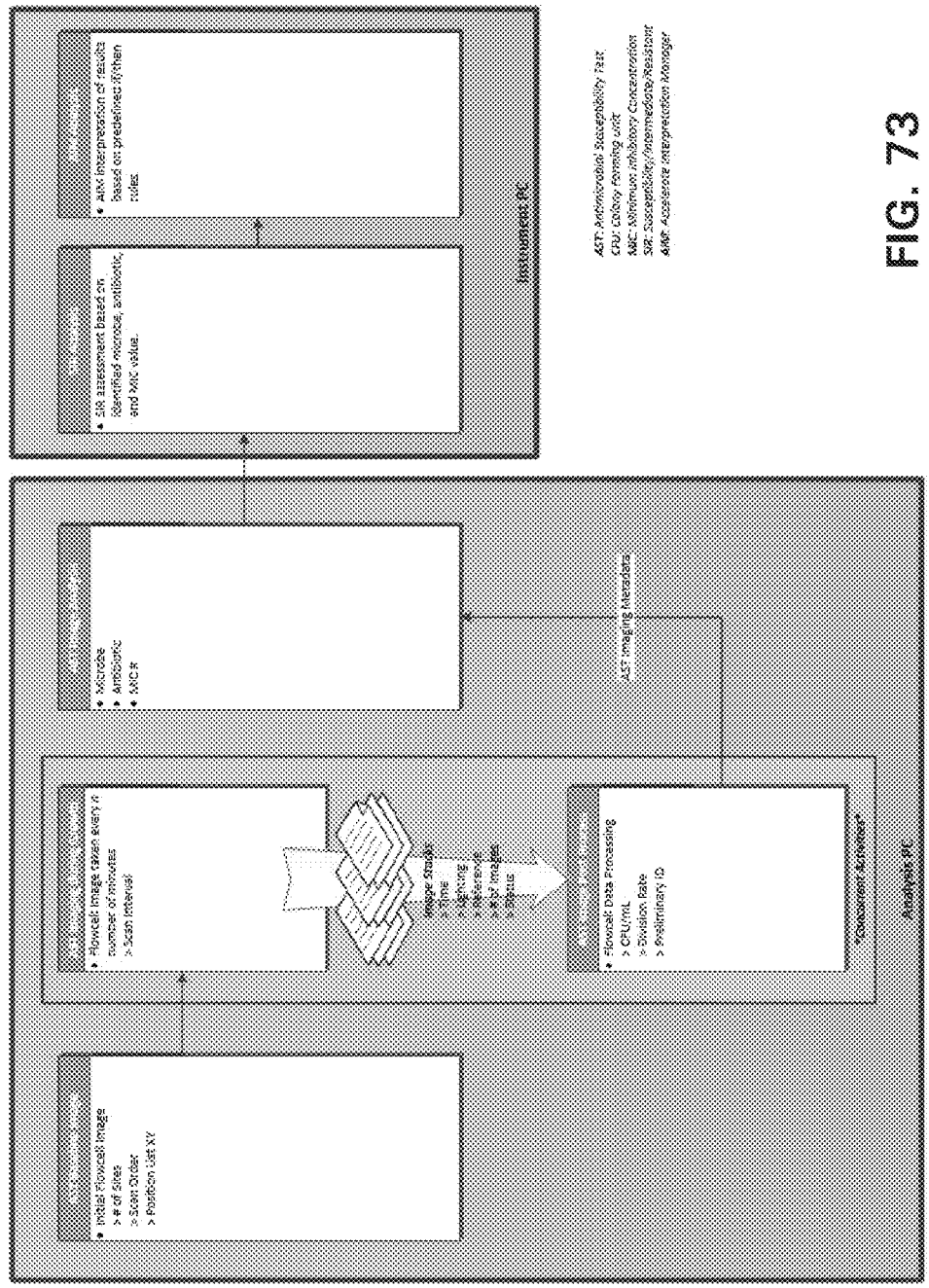
Figure 74:
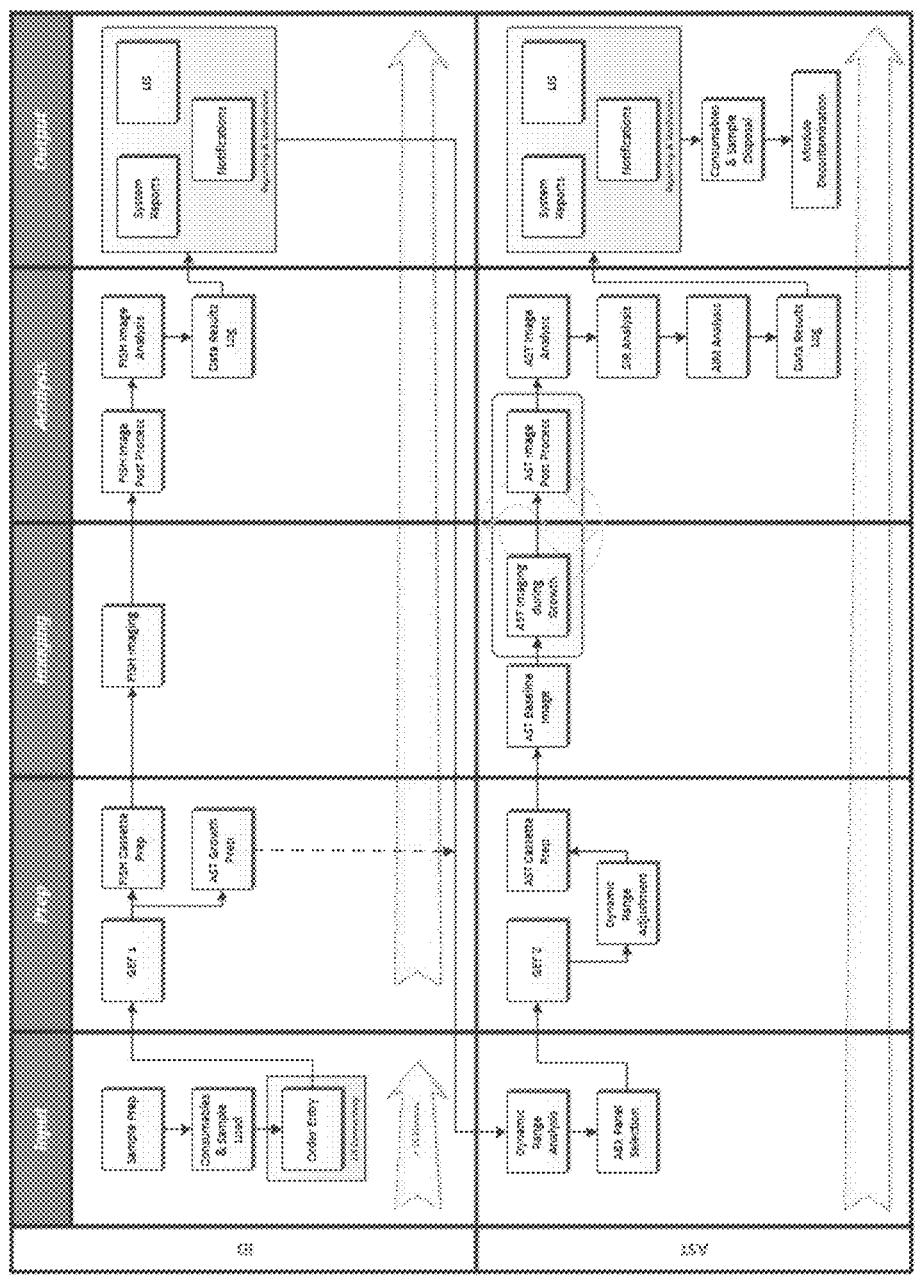
Figure 75:
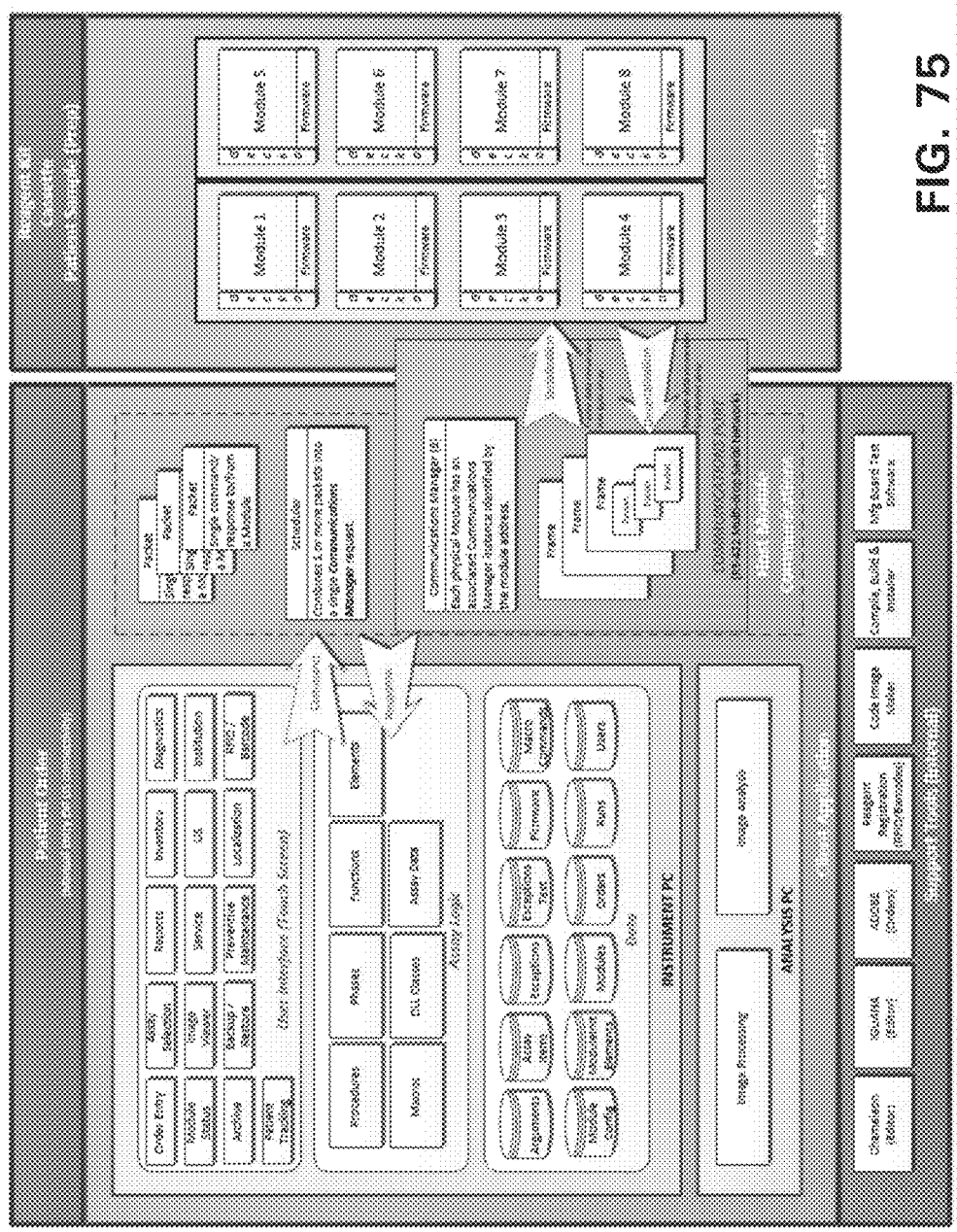
Figure 76:
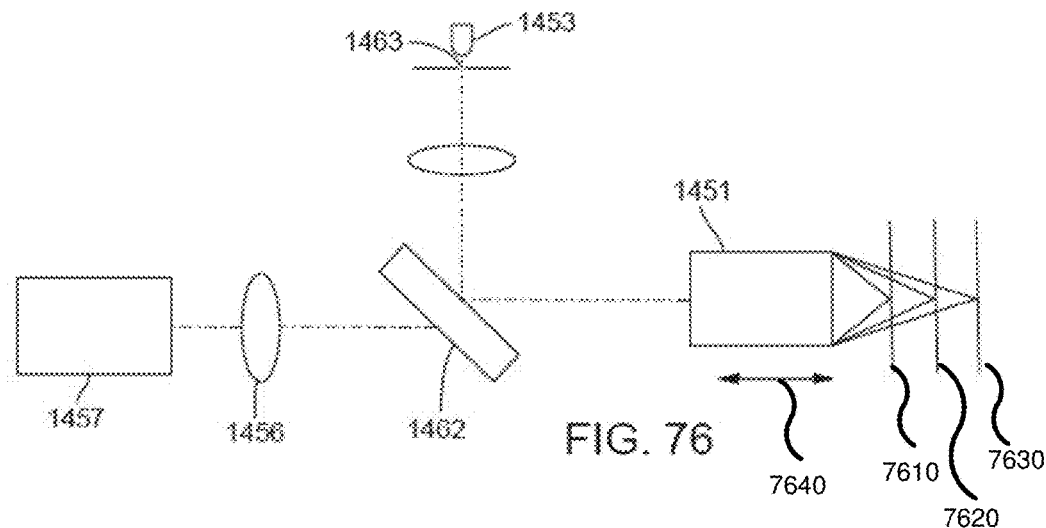
FIG. 76 is a schematic diagram of an alternative optical system.

During the AST process, various microorganism clone features are measured, such as division rates of specific species and the light intensity of a growing clone, and used for analysis. For example, a quantitative measurement of an individual clone growth rate over time can be used to determine antimicrobial efficacy. Onboard software algorithms determine quantitative identification of the target organism(s), derive minimum inhibitory concentration (MIC) values, and apply appropriate expert rules for proper interpretation and reporting of categorical interpretations such as "S," "I," or "R" (susceptible, intermediate, or resistant) or "S" or "NS" (susceptible or not susceptible). In accordance with various embodiments, AST can be performed in approximately 5 hours. Examples of microorganism growth curves demonstrating S, I, and R growth interpretations are illustrated in FIG. 68.

In some embodiments, the system reports susceptibility, intermediate, or resistance to one or more antimicrobials (e.g., susceptible to one or more of the antimicrobials in Table 5 or other antimicrobial provided herein) and/or an MIC for one or more antimicrobials. In other embodiments, the following resistance phenotypes may be reported by the system in response to AST data analysis: Methicillin-resistant *Staphylococcus aureus* (MRSA), methicillin-resistant staphylococci (MRS), vancomycin-resistant *S. aureus* (VRSA), vancomycin-resistant *Enterococcus* species (VRE), high-level aminoglycoside resistance (HLAR) and macrolide-lincosamide-streptogramin B resistance (MLSb).

Dynamic Dilution

In general, susceptibility testing requires that standard concentrations of viable inoculates be combined with set concentrations of antimicrobial agents. Accordingly, in order to perform an antimicrobial susceptibility test on an unknown bacterial sample, the starting concentration of the sample inoculum must be determined. Commonly, the inoculum concentration is determined by plating—which takes one to two days to complete—or through use of a McFarland turbidity assay. Although faster than traditional plating assays, turbidometric measure of bacterial cell concentration in a sample is not highly accurate, as this method only provides an approximation of colony forming units. This approximation is calculated from the amount of scatter achieved when light passes through a suspension of microorganisms, which serves as an indicator of the biomass of cells present in the suspension.

Because turbidity assays rely on light scattering through a bacterial culture, these assays neither directly count the number of bacterial cells present, nor do they directly measure colony forming units as is accomplished with plating. According to the United States Pharmacopeia, the estimated measure of cells obtained via a turbidity assay should be confirmed by a plate count as a control after the test is underway. The confirmation value is then utilized to calibrate the size of the inoculum used in the subsequent susceptibility test. Such techniques prolong the time for identifying the best course of therapy for critically ill patients. And because light scattering is a gross approach to estimating bacterial mass, a typical McFarland-based test is nonlinear. Nonlinearity is due in part to errors that arise because volumetric turbidity tests cannot discern between dead cells and viable ones. Yet, scientists generally treat such test data as linear. In addition, McFarland-based tests do not distinguish multiple species or strains of microorganisms in a single patient sample. Proper identification of the members of polymicrobial populations of microorganisms in patient blood samples can be important in the accurate diagnosis and treatment of bacteremia and sepsis.

These and other drawbacks of known counting procedures are overcome by the disclosed instrument system. This system is designed to accurately and precisely quantitate bacterial concentrations in a patient sample by 1) quantifying the relative abundance of viable microbial cells and 2) using that quantification, dynamically calculating the dilution factor needed to initiate antimicrobial testing. One beneficial aspect of the disclosed system, which reduces the time required to tailor a treatment to the specific microbe (e.g., bacterium), infecting a patient, is its ability to accept a larger sample concentration input range than other antimicrobial susceptibility test systems.

The process starts with the most concentrated amount of a specimen at hand, from which one or more aliquots are diluted as needed. The process follows this conservative approach as it is easier to further dilute a sample into the target range than it is to concentrate samples that have been diluted past the lower end of the target range. The objective is to obtain the most concentrated sample possible that will work within the disclosed instrument/device. Detecting a sample's microbial concentration and diluting it to a target concentration can be accomplished by known methods, albeit rather slowly and somewhat inaccurately. But dynamically diluting a microbial (e.g., bacterial) inoculum to achieve an appropriate range for accurate susceptibility testing of a given organism during each run is a unique aspect of the disclosed system.

Certain prior art instruments have a specified, pre-determined concentration range (set a priori) that is targeted for sample dilution. For example, one known system requires growing colonies on a plate, picking them, and placing the colonies in a tube to establish a culture of the bacterial isolate. Samples are mixed with a diluent to achieve a suspension, and then inserted into a spectrophotometer to obtain a concentration reading. For such systems, the lab technician must acquire a densiometric reading in a narrow range, such as 0.46-0.54 (less than about 300 CFU ($\times 10^6$/mL)), to estimate the number of colony forming units present (e.g., using a McFarland scale). If both dead and live bacterial cells are present, the final dilution of the sample will not accurately reflect the number of viable cells present in the sample for antimicrobial sensitivity testing. Moreover, depending upon the amount of time between removing an initial aliquot of sample and the output of the estimated bacterial cell concentration, the population of bacteria may have doubled one or more times, thereby introducing further error into the concentration calculus.

By contrast, translating a cell growth reading into a susceptibility report and/or MIC figure using the disclosed system is possible without the preliminary plating step. The disclosed system utilizes a target range of 10-130 clones per field of view (such as about 10-100, 20-80, 30-60, 10-50, 40-80, or 50-100 clones per field of view) to achieve optimal bacterial growth. In particular examples, about 20-80 (such as about 20, 25, 30, 35, 40, 45, 50, 55, 60, 65, 70, 75, or 80) growing clones per field of view is the target range. If too few clones are present, then statistically more fields must be viewed to detect bacteria, if they can be detected at all. Too many microbial clones in a field causes crowding and growth inhibition.

For monomicrobial samples, the ideal dilution point of a bacterial sample destined for AST evaluation can be the midpoint of the upper limit and the lower limit of the targeted range (e.g., target number of clones per field of view) of the bacterial inoculum. If an inoculum sample is polymicrobial, for example containing a mixture of bacterial species or strains, then two paths may be followed for obtaining the ideal dilution point. One option is to dilute the samples such that the bacterial counts of both species (e.g., bacterial species A and B) are centered between the upper and lower limits of the inoculum. A second option is to dilute the sample such that the amount of one bacterial species (for example, species A) is diluted to the midpoint of the inoculum upper and lower limits, which dilutes bacterial species B to a point below the lower limit of the inoculum. Under these circumstances, antimicrobial susceptibility testing for bacterial species B is not initiated, and culturing or a second run would be required to quantitate the amount of species B present in the sample.

Thus, the disclosed system uses a process superior to McFarland-based turbidity methods typically used in the clinical laboratory in order to obtain the concentration of bacteria needed for MIC assessment. The detection system and staining process together comprise the dynamic dilution aspect of the disclosed system. One skilled in the art will recognize that the disclosed dynamic dilution method can be used with other systems and methods (such as other systems for detecting or measuring microorganisms), in addition to those disclosed herein.

As discussed below, at least in some cases, an effective dilution curve for a sample can be non-linear. Therefore, the disclosed system uses one or more subsamples of a patient sample (such as 1, 2, 3, 4, 5, or more subsamples) to estimate a non-linear effective dilution curve for a sample. The estimated non-linear effective dilution curve is then used to determine a target dilution factor for diluting the sample to achieve the target number of clones per field of view prior to antimicrobial sensitivity testing.

FIG. 102 is a flowchart of an example method 10200 of determining a target dilution factor using dynamic dilution and diluting a sample using the target dilution. The different process blocks described below for FIG. 102 and FIG. 103 can be accomplished using the hardware components shown in FIG. 101. Additionally, such a method can be used with the disclosed methods and systems, or can be used with other antimicrobial detection and AST systems and methods.

Thus, in some embodiments, at 10202, cell concentrations are determined for multiple subsamples of a sample, wherein each subsample is diluted using a different dilution factor. In some embodiments, the dilution factors include one or more of 0.04, 0.2, and 0.625 (or 25-fold, 5-fold, and 1.6-fold) from a post-GEF sample. However, one will recognize that additional or different dilution factors (including, but not limited to 2-fold, 3-fold, 10-fold, or 20-fold) can also be used in the methods disclosed herein. The multiple subsamples can be extracted from the sample and stored separately from the remaining sample. For example, an instrument pipettor can be used to extract the subsamples from a sample vial and to place in separate flowcells of a cassette. In some embodiments, at least three subsamples (such as at least 3, 4, or 5 subsamples) are used in the dynamic dilution process. When the subsamples are placed in flowcells of a cassette, a trade-off can exist between storage space and estimation accuracy. Using a higher number of subsamples can lead to a more accurate model of the effective non-linear dilution curve for the sample. However, a higher number of subsamples take up more flowcells on the cassette. In certain cases, a range of three to five subsamples can provide a good balance between accuracy and available flowcells on the cassette.

Each subsample is diluted using a distinct sample dilution factor, e.g., no two subsamples are diluted using the same dilution factor. In some embodiments, the sample dilution factors are preselected to produce diluted subsamples that are representative of a range of possible sample concentrations. In some embodiments, sample dilution factors are selected such that a target cell concentration is likely to fall within a range created by the diluted subsamples.

After the subsamples are diluted using the sample dilution factors, a cell concentration of each diluted subsample is determined. Determining a cell concentration can comprise counting a number of cells in a diluted subsample. In particular non-limiting embodiments, cell number is determined by contacting each subsample with a universal nucleic acid stain (such as acridine orange or propidium iodide) and counting the number of cells. In some examples, the cells are imaged and cell counting is determined from the image. In a particular example, determining a cell concentration of a subsample comprises using electrokinetic concentration to produce a migration of cells in the subsample toward a surface (e.g., a glass surface of a cassette) prior to staining, optionally imaging, and counting the cells in the subsample. The cell concentration for a subsample can be a ratio between a number of cells in a diluted subsample and a volume of fluid in the diluted subsample.

After the cell concentrations of the subsamples have been determined, at 10204 a non-linear dilution curve is approximated using the subsample concentrations and the associated dilution factors. Approximating the non-linear dilution curve can comprise creating dilution test points for the subsamples, wherein each dilution test point comprises one of the subsample cell concentrations and the corresponding sample dilution factor that was used to dilute the subsample. The dilution test points can represent points on a non-linear effective dilution curve in a two-dimensional space, wherein dilution factor is one dimension and resulting cell concentration is the other dimension.

In some embodiments, the non-linear dilution curve is estimated by interpolating between the dilution test points. For example, the dilution curve can be estimated by performing multiple linear interpolations and/or multiple spline interpolations between the dilution test points. The non-linear dilution curve can be estimated by creating a model of the curve. In some embodiments, a model of the non-linear dilution curve can be created using multiple interpolations between the dilution test points.

In a particular example, a model of the dilution curve is created using linear interpolations between multiple dilution test points corresponding to multiple subsamples. In one example utilizing three subsamples, the following formula can be used to create the model:

$$D_T = \begin{cases} \frac{C_1 D_1}{C_T}, \text{ for } C_T \leq C_1 \\ \left[C_T - C_1 + \left(\frac{D_2^{-1} - D_1^{-1}}{C_2 - C_1}\right)D_1^{-1}\right]^{-1}\left(\frac{C_2 - C_1}{D_2^{-1} - D_1^{-1}}\right), \text{ for } C_1 < C_T < C_2 \\ \left[C_T - C_2 + \left(\frac{D_3^{-1} - D_2^{-1}}{C_2 - C_2}\right)D_2^{-1}\right]^{-1}\left(\frac{C_3 - C_2}{D_3^{-1} - D_2^{-1}}\right), \text{ for } C_T \geq C_2 \end{cases}$$

wherein $D_T$ is a target dilution factor for the sample, $C_T$ is a target cell concentration for the sample, $C_1$ is a determined cell concentration for a first subsample, $D_1$ is a first sample dilution factor associated with $C_1$ in a first dilution test point, $C_2$ is a second determined cell concentration for a second subsample, $D_2$ is a second sample dilution factor associated with $C_2$ in a second dilution test point, $C_3$ is a third determined cell concentration for a third subsample, and $D_3$ is the third sample dilution factor associated with $C_3$ in a third dilution test point. In this example, $C_1<C_2<C_3$. Using linear interpolations between three dilution test points is sometimes referred to herein as a "3-point dilution." Although this particular example uses three subsamples, and therefore three dilution test points, other numbers of subsamples and test points are also possible.

In at least one embodiment, creating the model of the non-linear dilution curve comprises determining an average cell concentration using a proportionality constant. The average cell concentration can be determined by multiplying each subsample cell concentration by its corresponding sample dilution factor raised to a power of a proportionality constant, summing the products, and dividing the sum by a count of the subsamples. In a particular example, the following formula can be used to determine an average cell concentration:

$$C_{avg} = \frac{1}{N}\sum_{i=1}^{N} C_i D_i^X$$

wherein $C_{avg}$ is the average cell concentration, N is a number of the subsamples, $C_i$ is a determined cell concentration for a subsample i, $D_i$ is a corresponding sample dilution factor for subsample i, and X is a proportionality constant with a value less than 1 and greater than 0. The value chosen for the proportionality constant can be an important factor in accurately estimating the non-linear dilution curve. In some embodiments, the proportionality constant is a value less than 1 and greater than or equal to 0.5. In some cases where cells are captured on a two dimensional surface, a proportionality constant of 0.75 can be effective. A value for the proportionality constant can be determined empirically by experimenting with multiple possible values and comparing expected cell concentrations with observed cell concentrations.

At 10206, the approximation of the non-linear dilution curve is used, along with a target cell concentration for the sample, to determine a target dilution factor. The target cell concentration can be a cellular concentration for the sample that is conducive to performing antimicrobial susceptibility testing. In some cases, a range of possible cellular concentrations are acceptable. In such cases, the target cell concentration can be a selected value within the range of acceptable values, such as a midpoint.

In embodiments where the approximation of the non-linear dilution curve comprises a model of the curve created using multiple interpolations, one of the interpolations can be used to determine the target dilution factor. For example, determining the target dilution factor can comprise identifying a first of the multiple dilution test points with a subsample cell concentration that is less than the target cell concentration, identifying a second of the multiple dilution test points with a subsample cell concentration that is greater than or equal to the target cell concentration, and using an interpolation between the first and second identified dilution test points to determine the target dilution factor. In cases where the multiple interpolations are linear interpolations, using the interpolation between the first and second identified subsample comprises using a linear interpolation between the test points. In a particular example, the following formula can be used to determine the target dilution factor:

$$D_T = \left[C_T - C_1 + \left(\frac{D_2^{-1} - D_1^{-1}}{C_2 - C_1}\right)D_1^{-1}\right]^{-1}\left(\frac{C_2 - C_1}{D_2^{-1} - D_1^{-1}}\right)$$

In this example formula, $D_T$ is the target dilution factor, $C_T$ is the target cell concentration for the sample, $C_1$ is the cell concentration of the first identified dilution test point, $D_1$ is the corresponding dilution factor for $C_1$, $C_2$ is the cell concentration of the second identified dilution test point, and $D_2$ is the corresponding dilution factor for $C_2$.

In cases where the target cell concentration is less than a lowest of the subsample cell concentrations, determining the target dilution factor can comprise using a ratio between a product of the lowest subsample cell concentration and its corresponding dilution factor and the target cell concentration. The following example formula is illustrative of such a ratio:

$$D_T = \frac{C_1 D_1}{C_T}$$

In this example formula, $D_T$ is the target dilution factor, $C_T$ is the target cell concentration for the sample, $C_1$ is the lowest subsample cell concentration, and $D_1$ is the corresponding dilution factor for $C_1$.

In embodiments where the approximation of the non-linear dilution curve comprises a model of the dilution curve comprising an average cell concentration and a proportionality constant, determining the target dilution factor can comprise determining a ratio between the average cell concentration and the target cell concentration, and then raising the ratio to a power of a reciprocal of the proportionality constant. In a particular example, determining the target dilution factor comprises using the following formula:

$$D_T = \left(\frac{C_{avg}}{C_T}\right)^{X-1}$$

wherein $D_T$ is the target dilution factor, $C_T$ is the target cell concentration for the sample, $C_{avg}$ is the average concentration, and X is the proportionality constant.

At 10208, a portion of the sample is diluted to the target concentration using the target dilution factor. In some cases, the portion of the sample is the remainder of the sample that is left after the subsamples are extracted. In some cases, only part of the remaining sample is diluted for antimicrobial susceptibility testing and the rest of the sample is left undiluted for other purposes.

In some examples, cell population in a sample can continue to increase while the target dilution factor is being determined. If this continued cell growth is not accounted for, then diluting the sample using the target dilution factor can result in a diluted sample with a cell concentration different from the target cell concentration. In some embodiments, the target dilution factor can be adjusted to account for cell growth in the sample while the target dilution factor is being determined Additionally, a portion of the cells counted in the subsample cell concentrations may be non-viable cells. Such non-viable cells may be included in the approximation of the estimate of the non-linear dilution curve. However, these non-viable cells will not contribute to growing cell concentrations.

A growth factor can be used to adjust a determined target dilution factor to account for cell growth in the sample. The growth factor can also adjust the target dilution factor to account for a rate of non-viable cells, for example a rate of non-viable cells associated with the identified species. Microbial cell viability is generally accounted for by developing an assay that maximizes the health of the sample regardless of what type of microorganism is in it. Nonetheless, some targets will produce more viable growing clones as a proportion of the total number of microorganisms than others. For example, a particular targeted bacteria might have a growth rate that would cause a doubling in number during the period in which the dynamic dilution occurs. However, if only 90% of those bacteria are viable, then less than 100% of the bacterial population are actually functional and divide for growth purposes. The objective is to only count these viable cells as growing clones in the flowcell channel. Growth factors can be determined using data across multiple runs and many isolates per target group (for example 10, 50, 100, or more samples per growth factor). Because the growth factor is determined empirically, it is ultimately a factor of the timing of the assay itself, the health of the bacteria during the process of sample preparation and dilution, the growth rate for the individual target, and the growth "efficiency" of the individual target (non-growing clones/growing clones).

FIG. 103 is a flowchart of an example method 10300 of determining a target dilution factor for a sample using a growth factor. At 10302, a growth factor associated with a microorganism in the sample is identified. The growth factor can be a single factor that accounts for both a growth rate of the microorganism and a rate of nonviable cells.

Different species of microorganisms can be associated with different growth factors. Table 1 lists example growth factors associated with various species of microorganisms. Identifying a growth factor associated with a microorganism in the sample can comprise identifying a species of the microorganism in the sample and selecting a predetermined growth factor associated with the identified species. The growth factor is used to adjust the determined target dilution factor, for example, to take into account cell growth in the sample while the target dilution factor is being determined. The growth factor is determined empirically for each microbe (or combination of microbes) being tested. In some examples, the growth factor is determined for a particular microbe or combination of microbes by selecting a median of the ratio of the actual number of growing clones and the intended number of clones, determined from multiple experiments where a sample is diluted to a dilution expected to produce the target number of clones.

TABLE 1

Example growth factors for microorganisms.

| Microorganism(s) (FISH ID) | Growth Factor |
|---|---|
| *Proteus vulgaris, Proteus mirabilis* (PRO) | 0.75 |
| *Acinetobacter baumannii* (ABA) | 1 |
| *Enterobacter aerogenes, Enterobacter cloacae* (ENT) | 0.78 |
| *Enterococcus faecalis* (EFS) | 0.86 |
| *Enterococcus faecium* (EFM) | 0.75 |
| *Klebsiella oxytoca, Klebsiella pneumoniae* (KLE) | 0.93 |
| *Pseudomonas aeruginosa* (PAE) | 0.57 |
| *Staphylococcus lugdunensis* (SLU) | 1.21 |
| *Staphylococcus aureus* (SAU) | 1.15 |
| Coagulase negative *staphylococcus* (CNS) | 0.86 |
| *Citrobacter freundii, Citrobacter koseri* (CIT) | 1.11 |
| *Serratia marcescens* (SMA) | 1.3 |
| *Escherichia coli* (ECO) | 0.99 |

At 10304, at least three subsamples of the sample are diluted using different sample dilution factors. The dilution factors can be similar to the dilution factors described above with respect to example method 10200. At 10306, cell concentrations are determined for each of the three or more diluted subsamples. Any of the example methods for determining cell concentrations described herein can be used to determine the concentrations of the diluted subsamples.

At 10308, a model of a non-linear dilution curve is created using the at least three determined cell concentrations and the at least three sample dilution factors. Techniques used to create the model of the non-linear dilution curve can be similar to at least some of the techniques described above with respect to example method 10200, such as interpolation between multiple dilution test points, determining an average cell concentration using a proportionality constant, etc. In some embodiments, the model of the non-linear dilution curve can be adjusted to account for the growth factor. The growth factor is selected based on the identity of the microbe, which in some examples can be determined by the FISH assays described herein. In a particular example, where the model of the non-linear dilution curve comprises linear interpolations between three dilution test points, the following adjusted formula can be used to account for the growth factor:

$$D_T = \begin{cases} \dfrac{C_1 D_1 G}{C_T}, \text{ for } C_T \leq GC_1 \\ \left[\dfrac{C_T}{G} - C_1 + \left(\dfrac{D_2^{-1} - D_1^{-1}}{C_2 - C_1}\right) D_1^{-1}\right]^{-1} \left(\dfrac{C_2 - C_1}{D_2^{-1} - D_1^{-1}}\right), \\ \qquad \text{for } GC_1 < C_T < GC_2 \\ \left[\dfrac{C_T}{G} - C_2 + \left(\dfrac{D_3^{-1} - D_2^{-1}}{C_2 - C_2}\right) D_2^{-1}\right]^{-1} \left(\dfrac{C_3 - C_2}{D_3^{-1} - D_2^{-1}}\right), \text{ for } C_T \geq GC_2 \end{cases}$$

wherein, G is the growth factor, $D_T$ is the target dilution factor, $C_T$ is the target cell concentration, $C_1$ is a first determined cell concentration for a first subsample, $D_1$ is a first sample dilution factor associated with $C_1$, $C_2$ is a second determined cell concentration for a second subsample, $D_2$ is a second sample dilution factor associated with $C_2$, $C_3$ is a third determined cell concentration for a third subsample, $D_3$ is a third sample dilution factor associated with $C_3$.

At 10310, a target dilution factor is determined for the sample using the model of the non-linear dilution curve, the growth factor, and a target cell concentration for the sample.

In embodiments where the approximation of the model of the curve is created using interpolations between dilution test points, determining the target dilution factor can comprise identifying a first of the dilution test points with a subsample cell concentration that, when adjusted by the growth factor, is less than the target cell concentration; identifying a second of the dilution test points with a subsample cell concentration that, when adjusted by the growth factor, is greater than or equal to the target cell concentration, and using an interpolation between the first and second identified dilution test points to determine the target dilution factor and adjust the target dilution factor using the growth factor. In a particular example, the following formula can be used to determine the target dilution factor and adjust it using the growth factor:

$$D_T = \left[\dfrac{C_T}{G} - C_1 + \left(\dfrac{D_2^{-1} - D_1^{-1}}{C_2 - C_1}\right) D_1^{-1}\right]^{-1} \left(\dfrac{C_2 - C_1}{D_2^{-1} - D_1^{-1}}\right)$$

wherein G is the growth factor, $D_T$ is the target dilution factor, $C_T$ is the target cell concentration for the sample, $C_1$ is the cell concentration of the first identified dilution test point, $D_1$ is the corresponding dilution factor for $C_1$, $C_2$ is the cell concentration of the second identified dilution test point, and $D_2$ is the corresponding dilution factor for $C_2$.

In cases where the target cell concentration is less than a lowest of the subsample cell concentrations adjusted by the growth factor, determining the target dilution can comprise determining a product of the lowest subsample cell concentration, the dilution factor corresponding to the lowest concentration, and the growth factor. A ratio between the determined product and the target cell concentration can then be used as the target dilution factor. The following example formula is illustrative of such a ratio:

$$D_T = \dfrac{C_1 D_1 G}{C_T}$$

In this example formula, G is the growth factor, $D_T$ is the target dilution factor, $C_T$ is the target cell concentration for the sample, $C_1$ is the lowest subsample cell concentration, and $D_1$ is the corresponding dilution factor for $C_1$.

In embodiments where the model of the dilution curve comprises an average cell concentration determined using a proportionality constant, determining a target dilution factor, and adjusting it using the growth factor, can comprise adjusting the average concentration using the growth factor, determining a ratio between the adjusted average cell concentration and the target cell concentration, and raising the ratio to a power of a reciprocal of the proportionality constant. In a particular example, determining the target dilution factor comprises using the following formula:

$$D_T = \left(\dfrac{GC_{avg}}{C_T}\right)^{X^{-1}}$$

wherein G is the growth factor, $D_T$ is the target dilution factor, $C_T$ is the target cell concentration for the sample, $C_{avg}$ is the average concentration, and X is the proportionality constant.

In any of the example dilution methods described herein, the dilution of the sample can be validated during a subsequent antimicrobial sensitivity testing. For example, a growing cell density of the diluted sample can be quantified in a growth control channel during antimicrobial sensitivity testing. If a final growing clone density of the diluted sample is outside an acceptable range, then the antimicrobial sensitivity testing can be aborted.

Any of the example dilution methods described herein can be performed by a system comprising a system controller. The system controller comprises a processor and a computer-readable storage medium. The computer-readable storage medium can store instructions that, when executed by the processor, cause the system controller to perform any of the dilution method described herein. In a particular example, the system comprises disclosed instrument (e.g., instrument 100 in FIG. 1) with an attached system controller operable to control the instrument.

Another aspect of the disclosed system is its ability to account for morphology changes of microorganisms during antibiotic susceptibility testing. Some bacteria change morphology during the first few hours of antibiotic exposure during growth in nutrient medium. For example, some *Pseudomonas* and Enteric bacteria species elongate and become filamentous during the first few hours of growth in the presence of beta-lactam antibiotics. This morphology shift toward larger bacterial cells may be perceived by automated microscopy systems as growth in the presence of such antibiotics. Under these circumstances, the bacteria would be erroneously characterized as antibiotic resistant by the automated system, even though the bacteria eventually may lyse and die in response to the antibiotic. This produces a challenge for an automated, rapid AST system designed to determine in less than a few hours whether a bacterial isolate is truly resistant to a given antimicrobial drug. The standard process for addressing this issue is to simply allow the bacteria to grow in culture for an extended period of time, thereby sacrificing the efficiency of antibiotic susceptibility assessment in the determination of minimal inhibitory concentrations of the antibiotics tested.

The bacterial system addresses this problem by employing an innovative medium formulation containing a reduced level of nutrient components compared to standard growth media. This is counter to standard thinking, as nutrient depletion typically would retard growth of bacterial cells and therefore hasten their death. For example, significantly reducing the solute concentration of Mueller-Hinton agar creates an efficient testing system for differentiating true antibiotic-resistant bacterial cells from susceptible bacterial cells that pass through a temporary filamentous phase before dying. Truly resistant bacterial cells continue to grow for up to about 4-5 hours under such nutrient-depleted conditions, whereas susceptible bacterial cells undergo a short period of elongation and then lyse within the first 1-2 hours of antibiotic exposure.

In a similar vein, certain bacterial species, such as *Serratia*, exhibit delayed or slower growth patterns under standard AST conditions. Likewise, fastidious bacterial species such as *Streptococcus* typically require special nutrient media containing blood components to grow in an AST system, and grow slowly without blood enrichment. Without proper growth conditions, these bacteria are difficult to test for antibiotic susceptibility, particularly in automated systems designed to produce results in less than 5 hours. Therefore, a novel media was developed for enhanced antibiotic susceptibility testing with bacterial species that demonstrate fastidious or delayed growth patterns under standard culture conditions. The novel medium formulation combined peptone ingredients in specific proportions without added blood to support the growth of *Serratia* in the presence of antibiotics and fastidious *Streptococcus* during AST evaluations for establishing minimal inhibitory concentrations for bacterial isolates from patient samples. This new culture medium demonstrated excellent results, enabling rapid susceptibility testing of problematic organisms/antimicrobial combinations to yield minimal inhibitory concentration and categorization (SIR) results.

Quality Control Testing

In some embodiments, an automated quality control (QC) assay is performed, for example using the disclosed system. The term "quality control" generally refers to the control of errors in the performance of laboratory tests and the verification of test results. In the context of a manufactured product, quality control testing ensures that the product performs to a defined set of criteria. All materials, equipment and procedures utilized in an assay protocol are adequately controlled to ensure accurate test results. Historically, QC testing was performed manually, even for automated instruments. The traditional approach is complex, labor-intensive, and wasteful. Typically, Master clones of reference microorganisms used in a testing panel are streaked onto agar nutrient plates, cultured, and then aliquoted for storage. Thereafter, aliquots of the test organisms are removed from the Master stock, streaked on agar nutrient plates, and cultured for each QC test run. This latter streaking process generally requires 18-24 hours to accomplish. Colonies of the microorganisms are then harvested and suspended in solution, the concentration of which is estimated using a McFarland turbidity assay incorporating a 0.5 standard ($1.5 \times 10^8$ cfu/mL, which are created for each assay). Only after each of these steps is performed can a laboratory professional manually load the microorganisms onto an automated platform to initiate a Quality Control analysis. To make matters more complicated, this process is often run in parallel for multiple microorganisms included in an automated assay panel, meaning multiple manual QC tests must be run to validate a typical set of patient results. This laborious manual QC process is prone to human error, which reduces the effective QC pass rate.

User and product requirements were developed for an automated Quality Control assay for routine usage on the System, thereby avoiding the lengthy timeline associated with manual QC testing. To further this objective, an automated test was developed to serve as an external quality control to assess the accuracy of microorganism identification ("ID") calls made by the AD-1 Instrument System. If desired, the ID QC test may be designed to comply with Clinical Laboratory Standards Institute ("CLSI") guidelines. For organism identification, preferably all ID probe cocktails are tested simultaneously in a single QC run. For example, "synthetic" (e.g., simulated biologic) ID QC assays may be designed to test blood culture kit probe cocktails and permeabilization solutions, while enzymes, the universal bacterial probe, and universal eukaryotic probe are tested with two frozen isolates (e.g., *C. albicans* and *S. aureus*). The synthetic ID test assesses the function of probe cocktails in the blood culture kit by testing them against a complementary target sequence unique to each probe cocktail. This complementary sequence is coupled to polymer microspheres that are close to bacterial cells in size. The probes hybridize to these target beads in the same manner as the probes would hybridize to cellular rRNA sequences in the blood culture ID assay performed on patient samples. A positive ID is indicated by a fluorescent signal from a detectable label associated with the probe (such as a fluorescent green signal). The absence of signal from the target microspheres is indicative of a false negative result for a given ID QC test. An increase in fluorescent signal of a different wavelength (such as a red fluorescent signal) from the universal probe above expected background levels indicates a failure of the negative control. In one non-limiting example, a cocktail of ATTO-532 (green) fluorescently labeled DNA probe(s) designed to bind to the rRNA of each identification target is added to different flowcells. Each cocktail also includes an ATTO-647 (red) labeled universal microbial probe capable of binding bacterial or yeast cells. In the negative control flowcell, no signal should be present; however, presence of signal from the universal probe indicates failure of the negative control, as it indicates that the universal probe is binding to something where nothing should be present.

A schematic of this process is depicted in FIG. 107, which shows an exemplary target sequence (SEQ ID NO: 1) coupled to a microsphere, which is complementary to a fluorescently labeled probe sequence (SEQ ID NO: 2). Binding of the detectably labeled probe to the target sequence results in fluorescence from the label. FIG. 107 illustrates this with a random target sequence and complementary probe; however, any target sequence that allows microbial identification and its complementary probe can be used in the ID QC test component and methods using the ID QC test component.

In one embodiment, each probe cocktail in a sample test kit is QC tested with a unique target bead. In another embodiment, a small number of pathogens may be used to test multiple probe cocktails. For example, *C. albicans* and *S. aureus* may be used to test their respective cocktails as well as the other components used for the ID portion of a blood culture test kit. To synthesize the target beads, a cross-linker can be used to couple an amine-modified ssDNA sequence that is a complement of the probes used in a given sample test kit. This reaction results in an amide linkage between the amine on the ssDNA and the carboxyl-modified polymer microsphere. Various known linkers may be used with blood culture or other types of sample kits, e.g., respiratory, skin, cerebrospinal fluid, or urine test kits. In one embodiment, a zero-length cross-linker is preferred. In other embodiments the ssDNA is coupled to a microsphere through a linker moiety such as a chain of 1-15 carbon atoms (such as 1, 2, 3, 4, 5, 6, 7, 8, 9, 10, 11, 12, 13, 14, or 15 carbon atoms) or other known linking groups (such as amide, hydrazide, thiol, or polyalkeneglycol). Suitable linking groups can be identified by one of ordinary skill in the art.

In particular embodiments, ID QC tests are designed to be run in conjunction with a second automated Quality Control assay, preferably one developed as an external QC process for assessing the accuracy of antimicrobial susceptibility testing ("AST") calls made by the AD-1 Instrument System. An automated AST QC test may be designed to comply with published verification guidelines. For example, antimicrobial agents employed in assessing antibiotic susceptibility of pathogens from blood culture samples may be included in an automated QC assay. Such QC assays may be designed to use each antimicrobial agent with one of the isolates connected with accepted published standards. For example, ATCC QC isolates recognized by the Clinical Laboratory Standards Institution (CLSI M100-526, Performance Standards for Antimicrobial Susceptibility Testing) may be used.

The reportable range for the AST QC assay in some examples are adjusted such that the selected QC isolates have an MIC that is within the reportable range of the QC Assay. These extended ranges are only applied to QC testing and are not applied to AST assessment of patient samples. The process for assigning an MIC value to the QC organisms is the same or similar to that used for patient samples. However, the concentration of antimicrobial agent is modified (typically lowered) to accommodate the QC range for the isolate and the interpretation algorithms may be slightly adjusted for this range. This approach allows testing of, for example, CLSI recommended QC isolates without affecting the algorithms that are optimized around antimicrobial breakpoints. The algorithms used in ID QC or AST QC testing include those described above, for example, when the QC test samples are microbial isolates. For ID QC testing utilizing target microbial nucleic acids coupled to a bead, positive detection is achieved by comparing the cumulative count in the target (e.g., Green fluorescence channel) only against a threshold of objects that have brightness exceeding bead autofluorescence. Negative control detection is achieved by doing the same for eubacteria (e.g., Red fluorescence) channel only. For example, the number of bright red objects should not exceed a threshold in order to pass negative control.

In addition, the CLSI required QC isolates for the relevant antimicrobial resistance phenotype assays (MRSA/MSA, and MLSb) may also be tested. When following CLSI recommendations, routine testing of a designated susceptible isolate as well as testing of designated resistant isolates for each new lot and/or new shipment of reagent kits should be performed. These isolates, therefore, may be included in the QC Assay. For example, Cefoxitin may be tested with *Staphylococcus aureus* ATCC 29213 as the susceptible isolate and *Staphylococcus aureus* ATCC 43300 may be tested as the resistant isolate.

If desired, each of the automated ID QC and AST QC tests may be run independently of one another. However, the ID and AST QC test criteria should match the ID and AST criteria relevant to the regulatory clearances and registration requirements of a given jurisdiction.

These ID and AST Quality Control assays are simple to run, permitting minimally trained personnel to conduct the assays and obtain Quality Control results within about 8 hours of initiating these assays. Specifically, the inventive automated QC assays eliminate the need to maintain frozen stocks of microorganisms, avoid multiple culturing steps, obviate the need to create McFarland standards, and eschew the manual loading of pathogenic inocula onto an ID/AST platform. This is not an insignificant achievement compared to the standard manual Quality Control assays currently used in clinical microbiology. This new automated QC test methodology has demonstrated about a 20%-30% improvement in the effective pass rate over manual QC test procedures. Thus, for example, the percentage of units that fail to meet specific standards decreases when the quality control process itself is improved and is therefore more reliable. Automating the QC procedure permits the validation of test results in a much shorter period of time than the traditional manual protocol, and reduces the amount of biohazardous waste produced in the process. This outcome is better for both patients and the environment.

The AST QC testing, with or without ID QC testing, is performed using the systems and methods disclosed herein. Thus, in some examples, an AST QC test component is inserted in the patient sample location of a reagent cartridge described herein. If present, the protective cover over the AST QC component is removed. If an ID QC test is to be performed simultaneously, an ID QC test component is also inserted in the sample vial location of the reagent cartridge; the AST QC test component and the ID QC test component should fit together snugly and be flush with one another. The protective cover on the ID QC test component is left in place. A cassette is inserted in the system and the reagent cartridge is then inserted in the system. A QC run is performed and results are provided in a report indicating pass/fail of the test for each microbe and/or antibiotic tested. The report may include additional information, including but not limited to, expected results and the results of each test.

In some examples, the ID QC and AST QC test components are supplied as a kit. In one embodiment, the kit includes at least one ID QC test component and at least one AST QC test component. In other examples the kit includes one or more AST QC test components. The AST and ID QC assay test kits may be kept in cold storage to improve shelf life. In some examples, AST QC assay kits may be stored at temperatures between −60° C. and −85° C. In other examples, microbial ID QC assay test kits are stored, for example, at between 2° C. and 8° C. until used. Preferably, such QC test kits should be stable for at least 15 minutes at room temperature after removal from cold storage; longer periods of stability at room temperature are even more preferred. Regardless of the specific storage temperature selected, identification and antimicrobial susceptibility test QC kits should be formulated to be robust and stable upon deployment for routine laboratory use. Optimally, such QC assays perform reliably in order to pass at a high enough rate to meet laboratory regulatory requirements. A run-to-run QC pass rate of greater than 95% assessed across multiple days, lots, and operators is preferred.

Quality Control reports may be generated to display the results of each assay. Each microorganism and antimicrobial agent tested may have a set of results reported for each assay. For example, MIC acceptance range, measured MIC, and pass/fail readings may be compiled. A graphical user interface on a display screen and printed reports preferably delineate Quality Control data from patient sample runs to avoid confusion. Pass or fail information may be viewed for individual organisms and antimicrobial agents tested. Exemplary QC reports are presented with the QC Example below (Example 6). Each QC assay should profile every AST and ID test run on a patient sample. The results of QC assay runs may be portable to Laboratory Information Systems for storage and retrieval purposes. If desired, laboratory personnel may retrieve multiple QC reports over a period of time to satisfy regulatory inspection or auditing needs. After a QC assay is complete, all testing components may be disposed of as biohazardous waste.

Verification of the platform confirms that the AD-1 System performs to intended specifications. Verification procedures also are geared to ensuring that laboratory staff can accurately produce test results using the System. Both of these activities are typically governed by the regulatory requirements of a given locality. For example, an Individualized Quality Control Plan ("IQCP") may be required to establish a daily or alternate QC procedure that embraces risk assessment, a quality control plan, and a quality assessment review. A preferred verification study designed for the AD-1 Instrument System calls for inclusion of a minimum of 30 microorganisms for ID and AST QC testing. Ideally, every antimicrobial agent should be tested 30 times during the verification process. QC test results are employed to assess reproducibility of this analysis. In addition to the minimum 30 microorganisms, a supplemental set of microorganisms demonstrating high and low Minimum Inhibitory Concentration ("MIC") values that are not found in routine testing should be included. For example this "challenge set" of microorganisms may test known resistance phenotypes, such as Methicillin-resistant *Staphylococcus aureus* ("MRSA"), Extended spectrum beta-lactamase ("ESBL")-producing organisms, and *Klebsiella pneumoniae* carbapenemase-("KPC") producing bacteria. A verification schedule may include the use of 25× fresh/prospective clinical blood culture samples and 37× seeded/challenge isolates seeded into blood culture bottles. These isolates may be selected from a published guideline, such as from CSLI M52. ID and AST QC assays may be run in parallel for about 20-30 days to establish the maximum QC test interval for ID and AST QC post-verification. After a daily ICPQ is established, ID and AST QC analysis may be run weekly. After verification has been established, post-verification AST analysis may be run weekly and ID analysis may be run monthly. Verification acceptance criteria may include, for example:

Accuracy ≥90% ID Agreement and ≥90% essential and categorical agreement;

Precision (Reproducibility) ≥95% within QC specifications; and/or

Establishment of an IQCP ≥90% within QC specifications for 30-day plan.

EXAMPLES

Example 1

The disclosed system performs a rapid microbial counting assay immediately before commencing antimicrobial susceptibility testing (AST). This requires calibration across multiple dilutions. An equivalent McFarland-based test using FISH takes too much time to complete (at least one hour or more). The disclosed bacterial counting procedure begins by subjecting a sample containing (or suspected of containing) microorganisms to gel electrofiltration (GEF) to substantially remove debris. Then, in some instances, the sample is mixed with L-DOPA and introduced into microfluidic flowcells. In the presence of an electrical potential and a poly-1-lysine coated flowcell channel surface, sample bacteria adhere to the poly-1-lysine coated surface in the chamber. Thus, the captured bacteria are concentrated onto the flowcell surface via electrokinetic concentration (EKC). Unbound bacteria are washed from the flowcell, and then a dynamic dilution (discussed above) is performed. Next, the bacterial sample is subjected to treatment with one or more permeabilizing agents, such as alcohol, an enzyme, a detergent, and the like. For example, 80% ethanol is pipetted into the channel to permeabilize the bacteria present when small molecular sized stains (e.g., propidium iodide) are used. When larger sized permeant molecules are utilized (for example, with certain Gram-positive organisms), bacteria may be treated with a combination of permeabilizing agents, such as ethanol and one or more enzymes. The permeabilization process enables stain molecules to enter the bacterial cells for visualization as discussed above. A nucleic acid stain (such as 1 µg/mL propidium iodide, PI) is used, which intercalates into bacterial DNA upon washing over the bacteria captured on the poly-1-lysine surface. The sample is then illuminated at an appropriate excitation wavelength (e.g., 535 nm for PI) and bound stain fluoresces (e.g., for PI, green at an emission maximum of 617 nm). The automated detection component of the disclosed system quantifies the signal emitted from stained bacterial cells. This is achieved by overlaying dark field images of the field of view, which permits visualization of cells and debris not present in green fluorescent laser images of stained cells. The signal cutoff is 5-fold signal over background, thereby eliminating from the count any auto-fluorescence emanating from debris.

The concentration of bacteria in the channel is back-calculated to establish a total amount of bacteria in the sample. If the calculated amount is, for example, 60 clones, then the sample is within the middle of the target range necessary to get an accurate viewing of bacteria upon dilution. If the calculated amount is too high (for example, 3,000 clones), then the sample must be diluted to a range of 40-80 clones. The objective is to hit the middle of this target range in each channel for every run.

Figure 83:
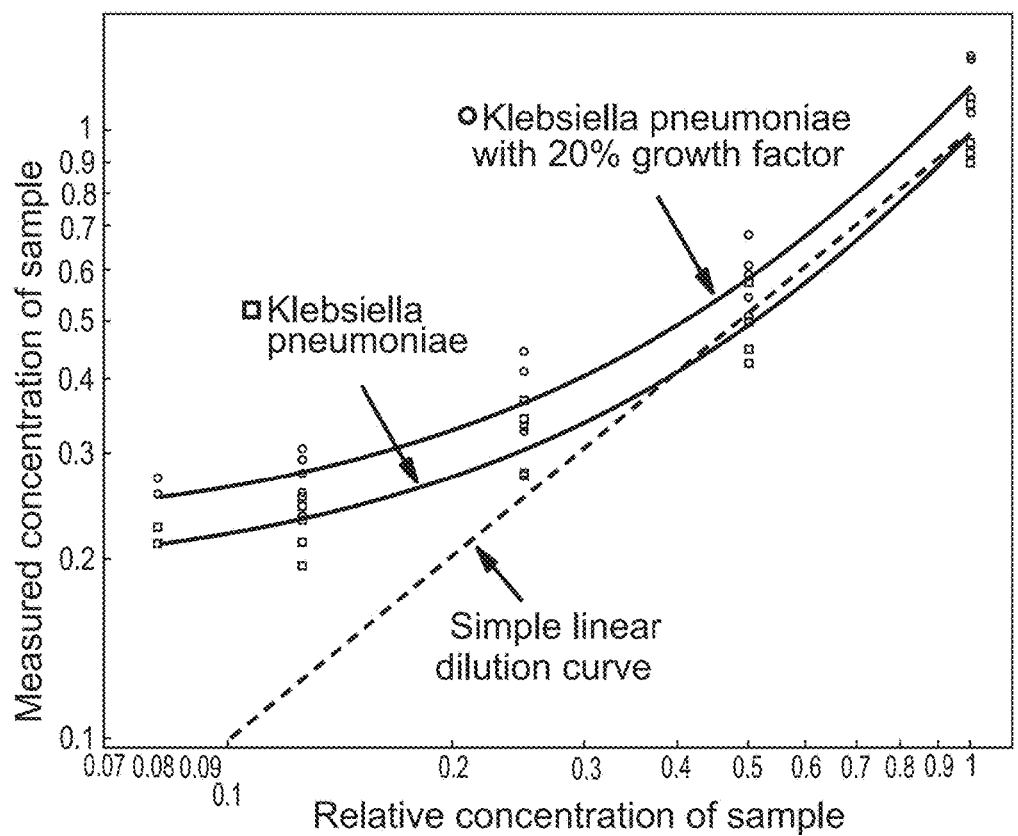
FIG. 83 is a series of calibration curves for the output range of *Klebsiella pneumoniae*, showing a simple linear dilution curve, a curve calculated by dynamic dilution, and a curve calculated by dynamic dilution including a 20% growth factor.

As graphically shown in FIG. 83, a comparison of calibration curves for the output range for *Klebsiella pneumoniae* highlights the effect of using a multipoint, non-linear curve for quantitating bacteria for dynamic dilution versus a simple, single point linear curve approximation. In a perfect serial dilution, a sample having a relative concentration of 1 (set forth on the x-axis) should theoretically have a relative concentration of 0.1 following a 1:10 dilution, which would plot as a straight line. However, when multiple dilution points are actually measured and the resulting concentrations plotted, it becomes clear that *Klebsiella pneumoniae* (like most other microorganisms) does not follow a linear progression at lower concentration ranges. Rather the curve is biased toward the left, and there are far more bacteria actually present than would be predicted from a single point linear dilution curve. Nonetheless, this non-linear curve (labeled as "*Klebsiella pneumoniae*") is also not completely accurate, as it does not take into account the fact that bacteria in the patient sample will be replicating during the period in which the dilutions and concentration calculations transpire. Thus, the disclosed system empirically applies the identification information obtained prior to the sample dilution step to factor a growth constant into the concentration calculus. The difference for *Klebsiella pneumoniae* is that the "*Klebsiella pneumoniae*" concentration curve plotted without the growth constant, is lower than the true concentration curve (labeled as "*Klebsiella pneumoniae* with 20% growth factor").

Figure 84A:
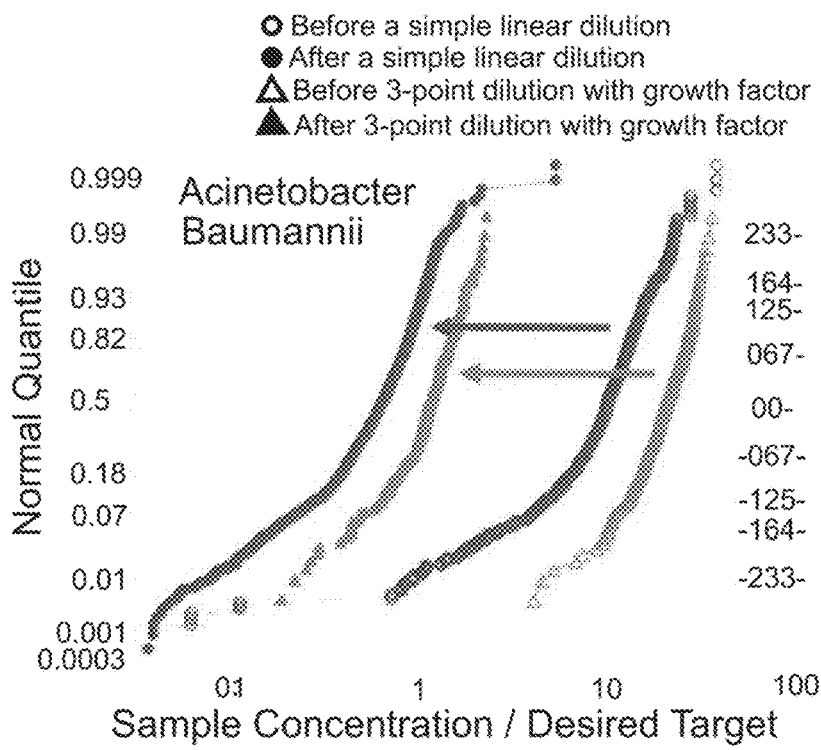
FIGS. 84A-84D are a series of normal probability plots comparing the effect of sample dilution of simple linear dilution curves (● and ○) and three-point dilution curves utilizing a growth factor (Δ and ▲) for *Acinetobacter baumannii* (FIG. 84A), *Pseudomonas aeruginosa* (FIG. 84B), *Klebsiella pneumoniae* (FIG. 84C), and *Serratia marcescens* (FIG. 84D).
Figure 84B:
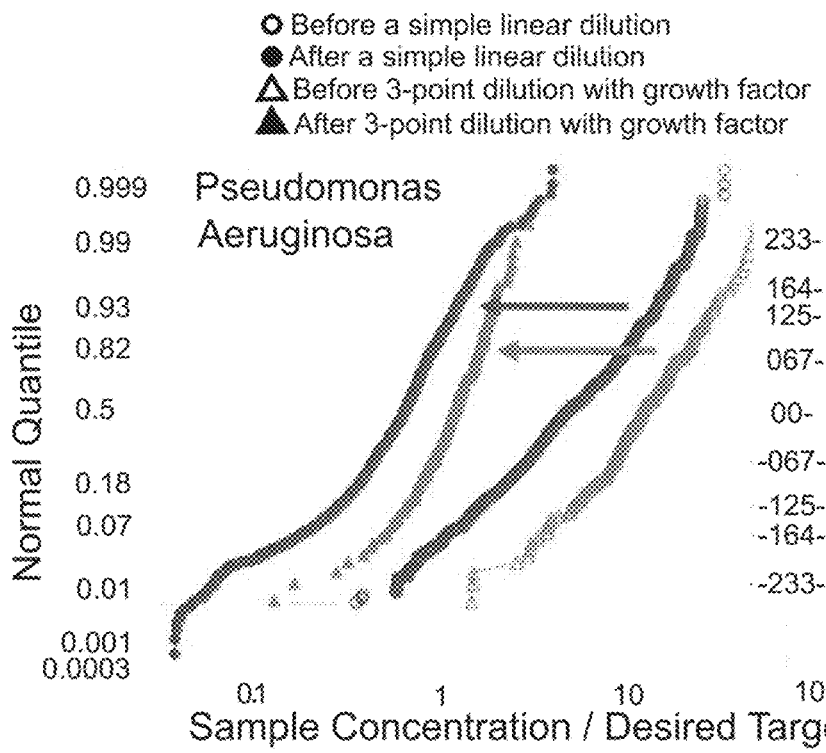
Figure 84C:
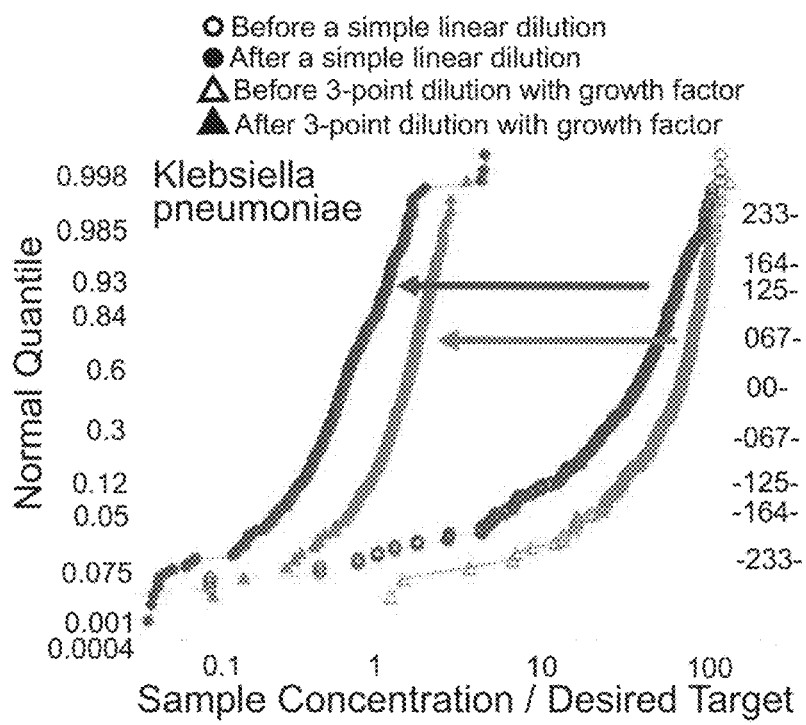
Figure 84D:
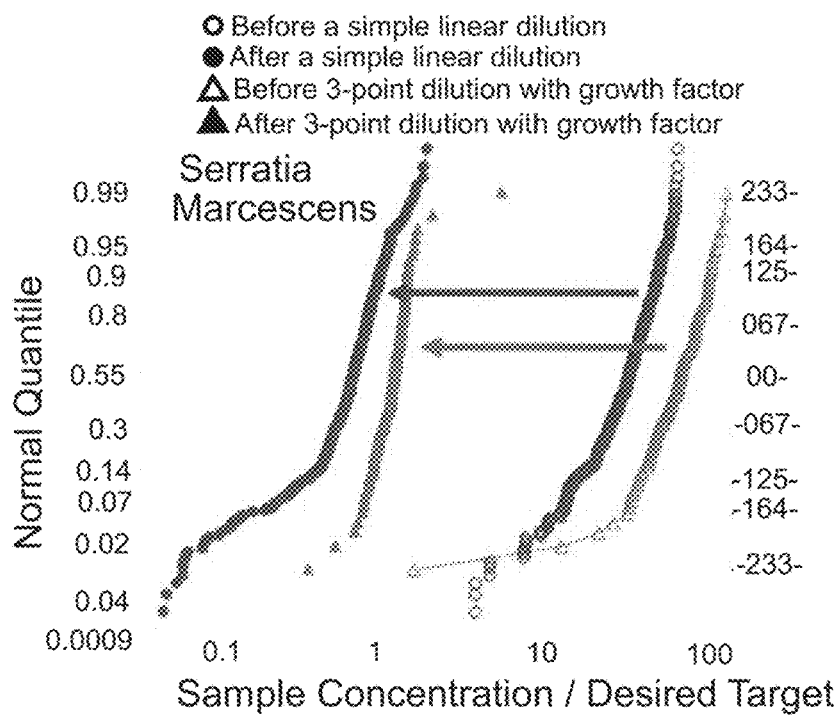

FIGS. 84A-D further demonstrate this principle in the form of a normal probability plot comparing the effect of sample dilution of simple linear dilution curves compared to three-point dilution curves utilizing a growth factor specific for each of the four types of bacteria tested (*Acinetobacter baumannii*—FIG. 84A, *Pseudomonas aeruginosa*—FIG. 84B, *Klebsiella pneumoniae*—FIG. 84C, and *Serratia marc-* escens—FIG. 84D). Each plot summarizes approximately 1500 experiments. The three-point curves demonstrate that dilution merely shifted the curve to the left along the x-axis, but did not discernably alter the lower end of the curve. By contrast, the simple linear curves demonstrate that dilution not only shifts the curve to the left, but also drives the lower range downward forming a tail, leading to inaccurate concentration estimations.

In sum, linear dilution curves or curves that fail to account for microbial (e.g., bacterial) growth rates will under-report the actual concentration of the patient sample. This error directs the user to under dilute the aliquot of patient sample destined for antimicrobial sensitivity testing, which results in samples that are too concentrated being used in that phase of evaluation. Because the sample will not be diluted enough, too many colonies will be present in a test chamber (flowcell) and will impair the growth of those colonies in the presence of antimicrobial agents. This obscures the true effect of a given antimicrobial agent on the growth of the bacteria at issue. Ultimately, the appropriate therapeutic may not be selected for patient treatment as a consequence of faulty AST data. In contrast, utilizing the dynamic dilution described herein, results in more accurate estimation of cell number in a sample and therefore, more accurate dilution of the sample to obtain a target number of colonies in a flowcell (such as about 20-80 colonies per field of view). Thus, the disclosed system improves the precision and accuracy of the AST process over traditional methods known in the art.

Example 2

Figure 85A:
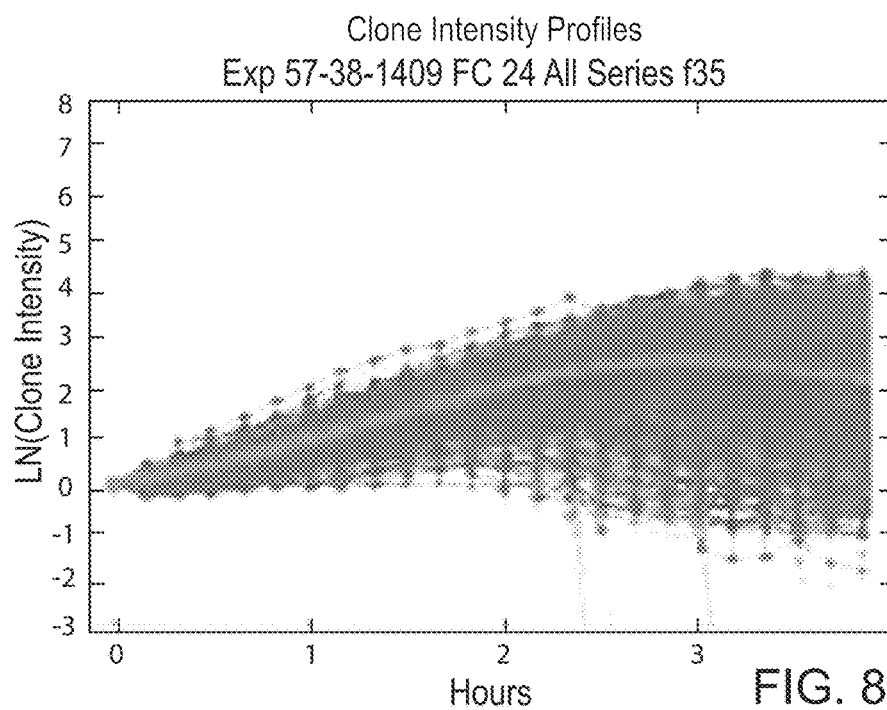
FIGS. 85A-85F are a series of graphs of results showing growth of *Pseudomonas* strains in nutrient-depleted media in the presence of piperacillin/tazobactam antibiotic.
Figure 85B:
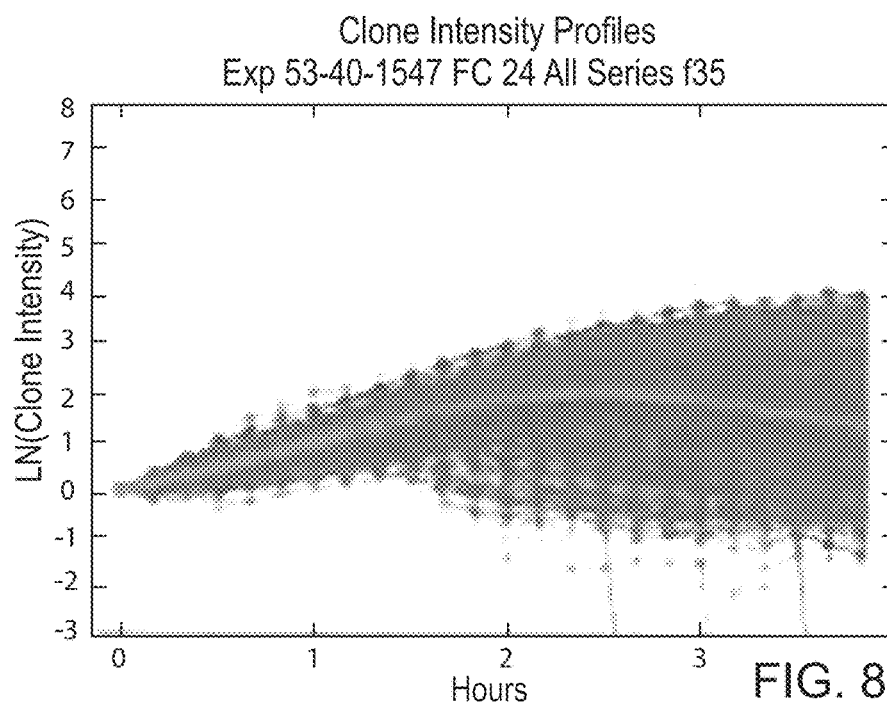
Figure 85C:
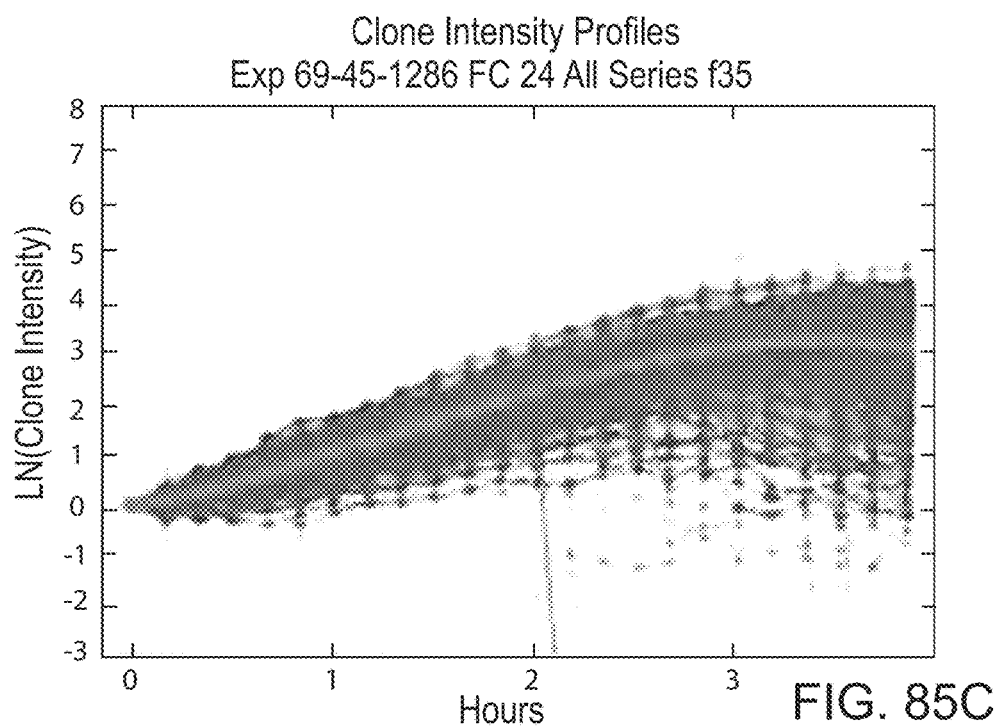
Figure 85D:
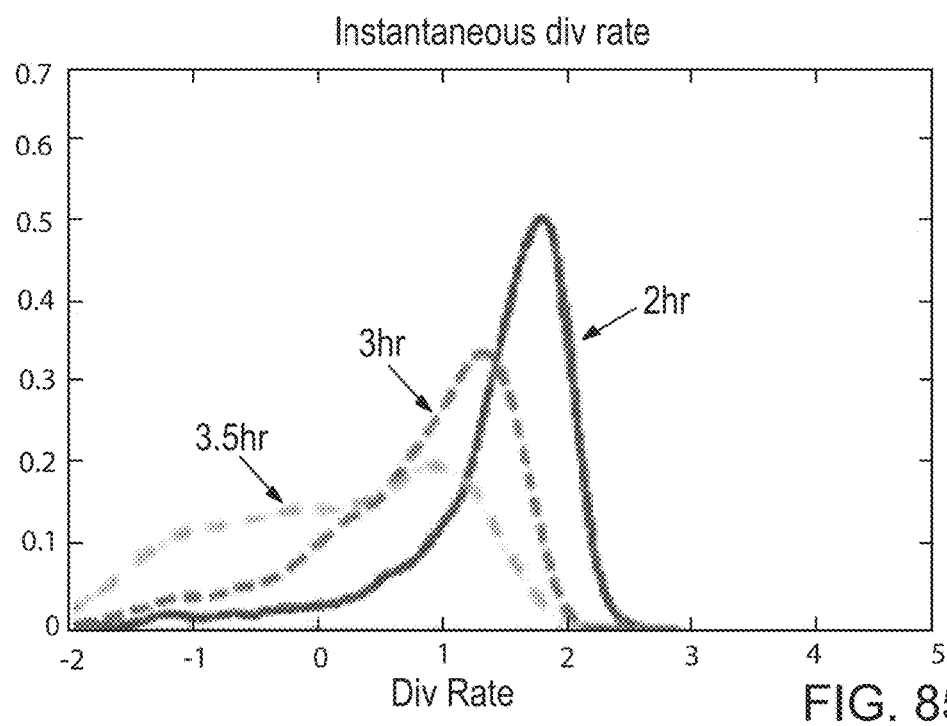
Figure 85E:
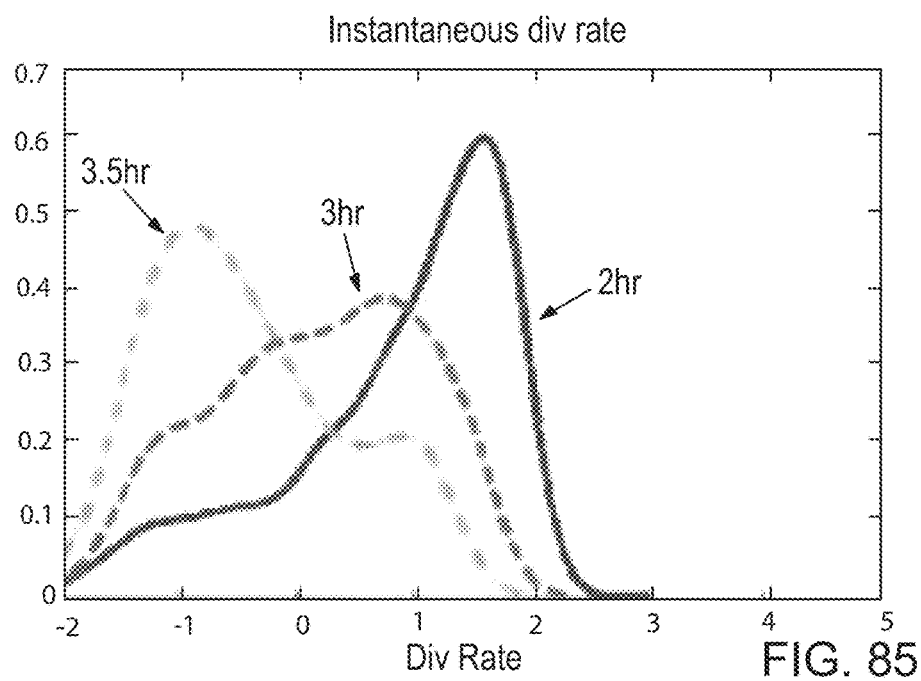
Figure 85F:
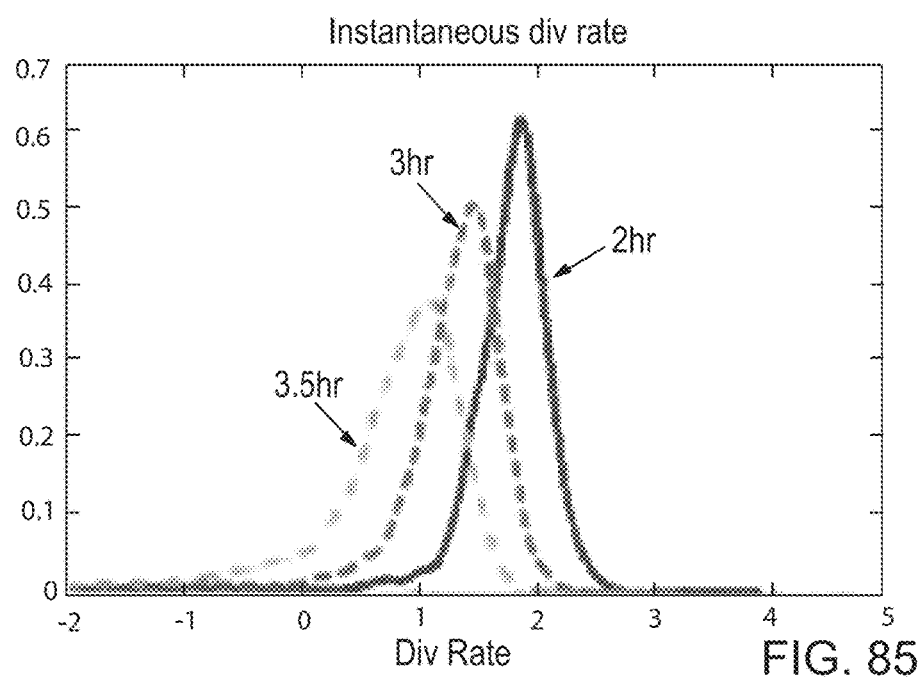

A series of growth media was formulated with 0.5%, 0.25%, and 0.125% strength of standard Mueller-Hinton nutrients (3 g beef infusion 17.5 g casein hydrolysate, 1.5 g starch, the final product being pH adjusted to neutral at 25° C.) while maintaining the agar concentration at 0.94% in the culture media. The effect of this depleted-nutrient media formulation on bacterial cell growth was evaluated with more than 50 strains of *Pseudomonas* in the presence of a panel of beta-lactam antibiotics. Cells were imaged using automated microscopy as described above. Exemplary results are shown in FIGS. 85A-F, in which *Pseudomonas* strains were grown in nutrient-depleted media in the presence of a piperacillin/tazobactam antibiotic combination FIGS. 85A-B demonstrates the effect the antibiotic combination on bacterial growth in a medium having an approximately 87% reduction in Mueller-Hinton nutrients, compared to growth in standard Mueller-Hinton media as shown in FIG. 85C. FIGS. 85A-C plots the log of bacterial dark phase intensity versus time, which is proportional to measuring cell mass in culture. FIGS. 85D-F are a quantitative representation of the data presented in panels FIGS. 85A-C expressed as rate of bacterial cell division.

The light colored line in FIG. 85C is generally straight over most of the time course, indicating normal bacterial replication with a small bit of variation in the tail end. The light colored lines in FIGS. 85A-B are curved with a high degree of variability, indicative of impaired replication. In FIGS. 85D-F, bacterial growth at 2 hours, 3 hours and 3.5 hours is depicted graphically. Bacterial cells grown in depleted nutrient media (FIGS. 85D-E) demonstrated great variability in the presence of antibiotics between 2 hours and 3.5 hours of exposure, whereas little variability was exhibited by cells replicating in nutrient-rich media (FIG. 85F). Therefore, no discernable antibiotic effect was evident in filamentous cells grown in standard media during the relevant time period, even though the bacteria are indeed susceptible to piperacillin/tazobactam. By comparison, bacterial cells of the same isolate grown in nutrient-depleted media show a dramatically different replication pattern, exhibiting substantially impaired growth in the presence of piperacillin/tazobactam within 3.5 hours. The results demonstrate that this nutrient-depleted media is very effective at differentiating true, antibiotic-resistant bacterial cells from filamentous, antibiotic-susceptible bacterial cells within about 12 hours of growth or less (such as 1-4 hours), depending upon the strain of bacterial cell tested. Use of this nutrient-depleted media permits rapid, accurate determination of antimicrobial susceptibility of filamentous bacteria and assessment of MIC values via the disclosed system.

Example 3

To address problems with testing for the slow growing and/or fastidious bacteria, a novel medium was formulated with cocktails of peptone products in Mueller-Hinton agar. The new medium increased certain nutrient concentrations without the need for blood components as shown in Table 2 below.

TABLE 2

Accelerate Peptone Medium Formulation

| 1% Phytone Tryptose CAMHB | |
|---|---|
| Combine: | 110 g Cation Adjusted Mueller-Hinton Broth dehydrated culture media |
| | 50 g Tryptose |
| | 50 g Phytone |
| | 5 L 18 M´Ω water |
| Heat: | Heat, then boil 1 min, remove from heat |
| Autoclave: | 121° C. for 45 minutes |
| 1% Phytone Tryptose MHA | |
| Combine: | 375 mL 1% Phytone Tryptose Cation Adjusted Mueller-Hinton Broth (CAMHB) |
| | 3.5401 g Ultrapure agar |
| Weigh: | Record weight |
| Autoclave: | 121° C. for 45 minutes |
| Re-weigh: | Add back volume of water needed to replace weight differential if vapor loss occurs during sterilization |

The new medium formulation was evaluated with at least 50 strains each of *Serratia* or *Streptococcus* in the presence of various antibiotics. *Serratia* isolates were tested with piperacillin/tazobactam, Aztreonam, Cefepime, and Ceftazidime. For *Streptococcus pneumoniae* the growth response of the isolates along with the following antibiotics were tested, Cefrtiaxone, Erythromycin, Levofloxacin, Penicillin. In the presence of this new medium, the disclosed system rapidly and accurately informed users of the susceptibility growth patterns of *Serratia* without experiencing delayed or slow growth typical of this bacteria. Fastidious *Streptococcus* strains showed healthy growth in the new medium without added blood components and were rapidly evaluated with the disclosed system. Thus, the combination of customized phytone tryptose Mueller-Hinton Agar with the disclosed system technologies provides a means for quickly obtaining the minimal inhibitory concentrations of various antibiotics that are effective against *Serratia* and *Streptococcus* species. This customized media approach should aid in the accurate susceptibility testing of other fastidious microorganisms (including but not limited to *Neisseria gonorrhoeae, Bordatella pertussis, Haemohilus influenzae, Campylobacter* spp., or *Helicobacter* spp.).

Example 4

Model Development

The disclosure provides an improvement in fluorescence identification of unknown microorganisms, particularly a mixture of microorganisms, in patient samples using a rapid, massively multiplexed automated single cell microscopy system. Traditional microscopy relies upon subjective human evaluation of microbial specimens when looking though a microscope. The microscopist identifies microorganisms by assessing objects in a field of view that are recognizable by shape, size, etc. A novice microscopist tends to be far less accurate than a highly experienced scientist, who—after reviewing many, many specimens—will have developed a trained eye for recognizing the characteristics of particular microorganisms. Likewise, the accuracy of an automated single cell microscopy system, such as the disclosed instrument system, turns on the ability of that system to recognize features characteristic of a given microbe. Accurate identification in such a system requires proper training of the system to reflect the same type of experience acquired by a seasoned human microscopist. One advantage to using a properly trained automated microscopy system is the efficiency with which it can accurately identify microorganisms in multiple samples in a short period of time.

For automated identification of unknown microbes via FISH, one drawback is the potential for an unfavorable signal to noise ratio. A substantial amount of non-cellular noise may be present in samples, which can confound accurate detection of microbes during an automated read of the samples. In various embodiments disclosed herein, this problem is addressed by using a universal probe as a control and one or more target probes in the same analysis. The control and target probes can be tagged with different detectable labels that can be co-locally detected on a single microorganism following excitation at different wavelengths. Thus, for example, in a two-color instrument, the universal control probe will indicate that an object is a microbe (e.g., bacterium or fungi) and the second color probe will identify the species of the microbe. A third color probe (three layer system) enables system identification of an object, for example identifying the object as a bacterium, its category, and species. Labeled FISH probes may be designed to recognize microorganisms in many ways, including—but not limited to—native and synthetically derived probes that recognize and bind to rRNA sequences in the target organism. Some microbial identification tests are commercially available, but do not employ an internal control for each test, which leads to increased levels of inaccuracy. By contrast, embodiments of the innovative identification process and system disclosed herein provide internal controls for each individual identification test.

Variation exists to some degree within most—if not all—aspects of biologically-based microbial identification assays. For example, variation may arise between species of bacteria, between bacterial isolates, and within components of a given detection system. Within a detection system, each probe channel may demonstrate signal variation. There may be variable noise, variation from reagents, variation due to temperature shifts, etc., all of which contribute to system variation. Thus, for example, a single bacterial population will exhibit variation and noise within each probe channel of a detection instrument. It is important to ensure robust signal detection from such probes, to quantify how many objects are present in a visual field, and then to determine the confidence with which the probes in question actually bind to target rRNA sequences. In various embodiments, the identification process disclosed herein takes into account this complex mix of sources that can contribute to microbial misidentification. Thus, the disclosed system employs probabilistic expectation models of multiple sources of signal and noise during the microbe identification process. This approach 1) ensures that what is being detected is not merely an artifact emitting a signal due to non-specific probe interaction, and 2) discriminates between known and unknown microorganisms.

To do so, the disclosed process and system determines how to account for the milieu of sources of variability that may emanate from a given probe channel. Recognizing and accounting for these variables permits the innovative identification process disclosed herein to be continuously refined during training to incorporate this variation into multiple probabilistic expectation models. The disclosed system combines, e.g., signal, noise (for example, background), and crosstalk (such as binding of a species-specific probe to non-target species) data points to inform the system of microbial identification parameters with a certain level of confidence. Expectations are constructed in the model such that observations will generate optimal fit. Fitting expectations over a number of queries is the automated system's equivalent of human learning. Thus, the probabilistic expectation model provides a unified framework for assigning probability scores for a plurality of events that arise during identification assays.

As it queries relevant events, the disclosed system uses Bayesian techniques to assign weighted probabilities to each answer received based on prior knowledge acquired during training, and (when applicable) previous sample runs. In essence, the system learns what noise and crosstalk look like for each target probe and heavily leverages this knowledge in order to identify a signature signal pattern for each target probe. This combination of bits of pertinent information for decision making by the system permits the distinction between signal, crosstalk and noise. Even the lack of an apparent target signal can produce data indicative of the presence of a microorganism, e.g., one that is not represented by a target probe in the assay panel. A human technician, by contrast, would likely not recognize this, as they are biased toward identifying positive target probe signals, but not able to assimilate the information present in what might otherwise be considered negative results. The outcome is a high degree of both sensitivity and specificity not possible with conventional identification processes.

The methods and systems herein place more confidence in producing signal than parsing out irrelevant data sources (noise, etc.). Accordingly, the identification process prospectively models noise-connected signals as well as structure noise (e.g., crosstalk, etc.) because noise can be reproducibly measured and yields superior performance results. The inventive identification process employs an agglomerative approach to decision making. This decision making methodology subscribes to the notion that with an increasing number of observations of a given population, one approaches a finite point for quantifying important features of objects (e.g., mean, dispersion, etc.). If a snapshot is captured of a system, probes, reagents, and the like, all of these components interact to form the totality of the variability that must be recognized and captured by a robust probabilistic expectation model based on signal production.

This is accomplished in part by fine tuning the illumination and detection procedure in the system and matching the expectation of signal, thereby closing the loop on the system performance of agglomeration expectation. Therefore, with repeated observations over time, the system enables the prediction of probe performance. In other words, the variability of an entire system becomes finite after a large number of observations. Once these parameters are known and accounted for in a probability model, the identification process increases in accuracy and approaches 100%.

During training, the instrument system crafts a normal distribution of microbes in a reference panel, such as a standard panel of bacterial and fungal probes. An informed distribution pattern acts like a fingerprint specific for each target organism represented in the panel. If an object fluoresces during a patient sample run that does not fit model expectations, then the system determines that the object is an outlier. In doing so, the system and its operator can tell which experiments worked and which ones did not. As an example, if the goal is 95% accuracy for an identification system, a microscopist should be able to determine whether the identification system is working by observing probe patterns. If the probes are dim, or are not specific, the microscopist will know based on the expectation model whether the 95% accuracy threshold will be met. And as mentioned above, the trained system can recognize signal patterns that do not fit a microorganism represented in the reference panel, but are not simply noise. By using a combination of signals generated by a universal probe, dark field images, and fluorescent expressions in the acridine orange control channel, the system can detect the presence of an off-panel microbe in a sample. That information can then direct a clinician to test the patient sample against additional probes to identify the off-panel organism.

To develop the inventive probabilistic expectation model, Bayesian analysis was used to set system accuracy and performance levels. Thus, the total system performance was in view of normal variance and system components adjusted to reach a 95% accuracy level. More particularly, a Bayesian solution is a statement of probability concerning a parameter value given fixed bounds (data). Bayesian reasoning assesses the likelihood of a thing being true in view of the evidence at hand, which is captured in a theorem:

$$p(A|B)=p(B|A)p(A)/p(B)$$

This equation provides for the probability of A given B ("p(A|B)"), wherein the equation calculates the probability of observing event A given that evidence B is present. The application of Bayes theorem in, for example, the microbial identification context, directs that the true likelihood of a microorganism being properly identified in laboratory testing turns on inputting the right data into the identification calculus, as opposed to relying upon intuitive perception. Pursuant to Bayesian theory, the methodology begins with existing prior beliefs in a given subject. These existing beliefs are updated with new information to formulate "posterior" beliefs, which are subsequently used as a foundation for inferential decisions.

Using this approach, training on a reference dataset enables artifact detection (bubbles, polymicrobial samples, etc.) to be accomplished by a signal-based probability expectation model. Likewise, the model enables the accurate detection of multiple microorganisms in a single sample. Built into the model is the expectation of each organism in a reference panel and the ability to discriminate expression of an unknown microbe in a sample. Thus, the probabilistic expectation model is built on an expectation for expression of unknown organisms in a patient sample, and can discriminate their signals from noise. This process incorporates probabilistic modeling as feedback for experimental design such that overall system performance (via probe selection, etc.) is optimized. A key aspect of the model is the creation of a relationship by good estimation of cell counts based on signals, not noise. This is especially important when trying to unmix multiple bacteria in a sample, especially if the proportion of the bacteria in the sample is unknown. Accordingly, accurate identification of bacteria according to aspects of the invention hinge on model driven development, artifact discrimination, and model driven performance.

Model Evaluation

In certain embodiments, the disclosed FISH identification algorithm begins with the development of a large reference dataset from which a given unknown microbial type can be identified based on predictable, known features or parameters characteristic of that microbe. In FIG. 93A, an initial dataset was established in an experimental assay consisting of 17 bacterial probe flow cells plus an acridine orange (AO) control flow cell applied to a blood sample spiked with known bacteria. These reference samples were processed in standard fashion and subjected to automated FISH analysis using dark field, green fluorescent (target microbe) and red fluorescent (universal for bacteria and fungi) illumination conditions. Three images were captured per site, with 10 to 24 sites per flow cell. The images were processed to identify true expression, defined to be signal-over-background in target/universal probe space per object per flow cell. Large debris, such as bubbles, were identified and discarded from the calculus using dark field image features. Objects of interest were detected in all three imaging modes, but only those objects that co-localized (e.g., were spatially co-occurring) were retained as true objects of interest (i.e., tagged microorganisms). FIG. 94 graphically depicts the distribution of signal emissions plotting target probe detection on the x-axis and universal microbial probe on the y-axis.

Flow cells containing samples are invariably populated with a milieu of materials in addition to the targeted microbial cells. For example, samples may contain contaminants that include—but are not limited to—biological debris (such as ruptured cells, partial cell membranes, etc.) and artifacts (such as bubbles, instrument cassette impurities). The sample debris and/or artifacts may generate background noise that will skew quantification unless taken into account during the analysis process. This sample debris and/or artifacts compete with signals emitted from targeted microbial cells bound to fluorescently tagged probes, thereby making it difficult to distinguish images of "true" targets from debris and artifacts. In other cases (depending upon the structure of the instrument involved), tagged target cells are "light-starved" increasing signal-to-noise variability over the field of view. Furthermore, flow cell cross-talk may arise, such as through cross-hybridization between target probes. To confound these identification challenges, unknown organisms may be fluorescently tagged by FISH probes due to an overlap of sequences shared with target organisms, and these organisms may not be represented in a reference panel utilized in the experiment. Finally, if a microorganism(s) is present in a sample only in very low concentrations (e.g., <10 clones per field of view), then it may be difficult to achieve confident detection of the organism of interest.

Internally spiked blood bottles were used to create reference samples that were employed in building signal-mediated probabilistic expectation models of labeled bacteria and fungi. Initial model training is typically based on these reference samples. Once the trained models are established, expression data obtained from patient samples may be added to prior observations ("priors") from the training runs. Doing so models the variability of different bacterial isolates obtained from multiple blood incubation or storage systems. For example, medical treatment facilities around the world use an array of different blood bottles for patient blood incubation, each of which may have slightly different properties that may (or may not) ultimately affect bacterial characteristics used in the inventive identification algorithmic process. This "bottle type variability" has the potential to affect expression data distribution, and thus it's fit to a given model. Adding this source of variability to a model after initial model development permits the adaptation of the model to any shift in expression that becomes evident in view of patient sampling conditions. In other words, signal-mediated probabilistic expression models may be updated post-hoc to include Bayesian information that can modify priors to ensure accurate probability. In essence, the algorithm permits instruments to mimic the human learning process to generate a teaching system that conveys what is viewed through the microscope as if viewed by a person. The result is that the error rate decreases with time and then stabilizes at some point due to data from the large reference population being enhanced by patient sampling data, which is a feature of agglomerative decision theory, as noted previously.

Accordingly, the process typically begins with quantifying a "normal" or baseline expression of target microorganisms and/or probes in a reference sample subjected to analysis. This aspect of the analysis process generates models for use in evaluation of subsequent sample observations. After "normal" or baseline models are generated, the cross-talk expression of probes is quantified to account for noise that would impair the accuracy of the microbial discrimination/identification analysis. Such cross-talk related noise may arise from numerous sources, including—but not limited to—off-target "noise" and background/process "noise." Quantification of the "normal" expression of target organisms together with the quantification of cross-talk expression of probes permits generalization for polymicrobial expression interpretation of samples. In a rapid, automated single cell identification system, such as the disclosed system, the identification of microorganisms from patient samples can be accomplished in about an hour once an aliquot of is loaded into the disclosed instrument for analysis. The exemplary *Enterobacter* distribution panel of FIG. 93A demonstrates that with proper system training and the use of appropriately specific probes, the disclosed system was able to craft a probability density function ("PDF") that behaves as an expression "fingerprint" for identifying *Enterobacter* bacteria in a patient sample. Thus, whenever the disclosed system encounters such distribution, it will identify the presence of *Enterobacter* in a patient sample. This is especially important when identifying microorganisms in a mixed population (polymicrobial) sample.

General Method Steps:
1. Obtain test sample;
2. Introduce aliquot of sample to vial;
3. Incubate for time sufficient to establish that one or more microbes exist in sample;
4. Transfer aliquot to flow cell;
5. Introduce labeled universal control probe and one or more labeled target probes, as well as an acridine orange control stain;
6. Capture images of multiple fields of view of one or more microbes;
7. Perform morphokinetic analysis to identify characteristics of imaged microbes;
8. Apply analysis data to probability model to identify microbe using FISH identification algorithmic process.

In particular, the process further comprises:
Features per imaged object identified via morphological and other analysis are processed through Bayesian framework (i.e., signal, noise, and crosstalk models) to attain posterior distributions for each microfluidic flow channel;
Posterior distributions are passed through Kernel Density Estimator (KDE) and integrated to attain a resulting "likelihood" of an event per microfluidic flow channel; and
Off-panel detection logic is invoked to determine the presence or absence of one or more off-panel microorganisms.

FIG. 93B is a flowchart of an exemplary method for the identification algorithm. As shown at 9310, three different images of a same point in a flow cell are captured using different light sources. Image 9312 is a dark field image, while images 9314, 9316 are two different fluorescent images using light sources of different wavelengths. Thus, image acquisition occurs with at least three modes of illumination. In one embodiment, different laser diodes can be used to generate the fluorescent signals, while the dark field image can be generated using a broadband LED. The images are input into an image processing stack 9320, which extracts features for a plurality of objects in the images. Example features include shape features, intensity, orientation, fluorescent channel matching, etc. The image processing stack 9320 generates an object/features matrix table 9330, which describes each of the features found for all objects in the flow cells. Based on the features found, some of the objects can be filtered as known noise, debris, etc. in module 9340.

The remaining objects/features are compared in parallel to multiple models, shown generally at 9350. The multiple models 9350 take into account signal, noise and cross-talk information for each of the dark field and fluorescent imaging wavelengths. The models 9350 are generated as described below and can be based on past observations of known microorganisms. The models are associated with expectations of features attributable to known microorganisms and represent statistical models that take into account variability that arises through observations of large populations of cells. Such observations are used to train the models so that probabilities can be determined from the models during cell identification. The signal information relates to the intensity of light from probes attached to the imaged objects. The noise information can be defined as background signal, for example, due to binding of a detectably labeled probe or nucleic acid dye to non-nucleic acid components in a sample, such as debris. Noise also includes background signal in a field of view (for example, fluorescence in a field of view containing a detectably labeled probe but no biological sample). The cross-talk signal relates to how the presence of other organisms in other channels impacts the organism being identified. The cross-talk can be associated with non-specific probe binding and is a repeatable signal that is modeled. More specifically, cross-talk includes hybridization of a detectably labeled species-specific probe to a non-target microorganism (also referred to as non-specific binding or non-specific hybridization). Cross-talk can occur when a species-specific probe hybridizes non-specifically or at a lower stringency (for example, lower Tm) to a non-target microorganism, such as a microorganisms that is relatively closely related to the target microorganism. As a specific, non-limiting example, an *E. coli* species-specific probe may also hybridize to a lesser extent to related microorganisms, such as *Citrobacter* spp.

The models 9350 are coupled in parallel to a target presence module 9360 that computes a probability distribution for signal ($S_i$), noise ($N_i$) and cross-talk ($C_i$) for each object identified. Additionally, module 9360 determines a quantity of objects that meet thresholds for satisfying each of the signal, noise and cross-talk models. If module 9360 determines that there is a low-probability of a signal and cross-talk, then identification for the object of interest has not succeeded and control is passed to module 9370, which determines an off-panel presence. The off-panel presence module receives a nucleic acid stain signal (such as an acridine orange control 9372) and can definitively determine whether or not an organism is present that is not on the panel. If a target is identified in module 9360, off-panel presence can still be determined at module 9380, which also receives the acridine orange control 9372. The output of module 9380 is the identified target plus any off-panel presence information, or just the target if no further off-panel information is provided.

Thus, image acquisition occurs for at least three modes of illumination, including multiple fluorescent modes and a dark field mode for a single cell. Additional controls, such as a non-specific nucleic acid stain (for example, acridine orange) image can be used. Imaging a target probe with imaging any other optical control, such as dark field imaging and/or imaging of a universal probe, can be used on a per-cell level in the identification process described herein. Cell-specific control with multiple modes of illumination at the same field of view and same resolution and modeling for signal, noise and cross-talk provides optimal identification of the cells, as well as definitively concluding that a cell is present, as well as that a cell is not present. For example, one channel can be determined positive for a specific microorganism (such as *E. coli*), but with high certainty other microorganisms can be conclusively determined not present. In this way, target information and non-target information, such as noise and cross-talk, all combine to provide positive information to assist in identification of a microorganism. The individual probabilities of the signal, cross-talk and noise combine to maximize the probability of proper identification. An aspect of various embodiments employing the probabilistic model using Bayesian analysis is the determination of the likelihood per expression for each probe. The process directs the evaluation of some posterior quality per probe according to the formula:

$$L_i \propto P(_{Mi}|\{F_G, F_R\})$$

The FISH identification algorithmic process uses fairly robust methods for building expectations. Identification of organisms can be made utilizing various characteristics, such as bacteria-specific morphology features. The characteristic variables measured are not necessarily orthogonal, thus requiring full Bayesian formulation. The assessment may be increased by one or two more dimensions, if the additional data points will improve microbe discrimination. Population-based metrics have a requirement of a higher minimum clone count per flow cell. In one embodiment, the overall minimum limit of detection is 12 cells per flow cell. In other embodiments, methods were employed for thresholding at 50<count<150 experiments.

Intra-channel "polymicrobial populations" (e.g., samples containing two or more different microorganisms) can be a confounding factor in identifying microbial entities in a patient sample. Process and/or fluidics artifacts can lead to sub-populations within a flow cell, meaning that off-panel organisms can produce additional expressing populations. Posterior PDF estimates allow for detection of multiple sub-populations (Gaussian Mixture Models or the like are employed). By definition, a Gaussian mixture model is a probabilistic statistical model that assumes all data points pertinent to an analysis are generated from a mixture of a finite number of Gaussian distributions with unknown parameters. In other words, the Gaussian mixture model is a semiparametric approach to density estimation based on the use of a model that best fits the input data. Various estimations of Gaussian mixture models may be crafted to correspond to different estimation strategies. A Gaussian Mixture Model object may implement an Expectation-Maximization (EM) or Maximum Likelihood Estimation algorithm for fitting a mixture of Gaussian models and determining model parameters. It can also draw confidence ellipsoids for multivariate models, and compute the Bayesian Information Criterion to assess the number of clusters in the data. A Gaussian Mixture Model learns from a training data set to find the probability density function of a data set based on the criteria found in images acquired from the training set. Various techniques may be utilized for editing the reference data set. For example, the mean and standard deviation of each descriptor may be obtained from a large sampling population and then the assumption of that the descriptor will be approximated by Gaussian distribution. In this case, objects in a sample field of view whose descriptors are lower than 3 standard deviations of the mean will be rejected. Thus, the method can assign to each sample the class of the Gaussian it mostly probably belongs to using a Gaussian Mixture Model "predict" method. Gaussian Mixture Models come with different options to constrain the covariance of the different classes estimated. This class approach allows for easier evaluation of, sampling from, and maximum-likelihood estimation of the parameters of a Gaussian Mixture Model distribution.

FIG. 93C is a flowchart of a method for identifying a target microorganism. In process block 9385, multiple images are captured using a camera of an object using different modalities of light. The different modalities can include different wavelengths of light. In process block 9387, features of the objects identified can be determined. Typically, the hardware components in FIG. 101 are used to perform such a determination, which can be embedded on the control board 321. Features can include shape, orientation, intensity, etc. In process block, 9389, a plurality of models are provided based on signals, noise and/or cross-talk. The models can include only signals and noise or signals and cross-talk. The models can be stored in memory, such as memory 10120 or 10125. The models can further be stored in storage 10140. In process block 9391, a probability distribution is calculated for a signal and at least one of the noise or cross-talk. The probability distribution can be computed using the central processing unit 10110 or the graphics processing unit 10115. In process block 9393, a determination is made whether or not the microorganism is present in at least one of the captured multiple images using the calculated probability distribution. Such a determination can be made using the computing environment 10100.

FIG. 94 takes the expression data presented in FIG. 93A and presents it as bivariate PDF patterns for each of the microorganisms tested. Thus, the expression of each microorganism is characterized by the unique patterns developed after repeated training and sampling experiments. The PDF patterns were "learned" by the disclosed system independent of bias and provide a reliable expectation of how these microbes would respond to probes tested against an unknown patient sample. The disclosed system applies an empirical threshold value for matching the signal pattern of an unknown microorganism with the PDF of a panel probe. As is evident in FIG. 94, some of the PDF patterns are highly skewed along the y-axis, whereas others are highly aligned along the x-axis. Dead center of each ellipse is colored deep red, which indicates the location of the majority of signal distribution for each microorganism tested. The *Enterobacter* sample (framed in a black rectangle in FIG. 94) shows a balanced Log-Normal distribution.

As previously noted, variability in microbial identification can arise from multiple sources, including (but not limited to), probes, instruments, reagents, and the like, which can shift a sample reading to outlier status. These sources of variability were taken into account when performing test runs while developing the training data set. Test runs were performed on multiple instruments in order to observe normal between-instrument variability. Readings outside of normal values were rejected. Initial instrument training began with between approximately 50 and 466 isolates per species of microorganism. The second set of training runs utilized about 25 isolates per species of microorganism. Training of the automated instrument was undertaken to generate a Maximum Likelihood Estimation ("MLE") which incorporates values that maximize the likelihood function given a set of observed data. This approach applies the principle that the best parameters are those that maximize the probability of observing current values in statistical modeling. Thus, the MLE was intended to estimate expression patterns of fluorescently tagged bacteria and fungi using observational data from the reference panel of microorganisms. The primary goal of modeling is to deduce the form of the underlying process by testing the viability of a model. The model is tested by evaluating the goodness of fit of observed data, i.e., assessing how well the model fits the observed data. Goodness of fit is measured by parameter estimation, which entails finding the parameter values of a model that best fit the observed data.

As shown in FIG. 95, multiple test runs of *Enterobacter* samples were performed to generate distribution patterns during instrument training. As with FIG. 93A, the graphs plot target signal distribution on the x-axis against universal probe signal distribution along the y-axis. The pink spots represent noise which is used in the calculus for modeling signal. The MLE calculation involved combining the estimated likelihood of an occurrence being present for the distribution patterns for *Enterobacter*. A subset of the estimated 466 total experiments used for training the instrument were combined to craft the MLE for each probe. Thus, for *Enterobacter*, for example, the ENT "model" (delineated as MENT) was created. This can be characterized mathematically as multivariate log-normal function:

$$f(x)=\exp(N(\mu,\Sigma))$$

The combined parameters from the subset of experiments were plotted in FIG. 95 as a black and white image contour of data distribution for MENT. Model evaluation using Bayesian formulation was undertaken. Sampling distribution $p(X|\theta)$ is an observation (experimental data) where X is $\{Fg, Fr\}$ and $\theta$ is the parametric model M (obtained from Training) Prior distribution $p(\theta)$ is unknown (assume it equals p1). Thus, posterior distribution of the *Enterobacter* training (or any given experiment) is:

$$p(M|\{Fg, Fr\}) = \frac{p(\{Fg, Fr\}|M)p(M)}{p(\{Fg, Fr\})} \propto p(\{Fg, Fr\}|M)$$

where $p(\{Fg,Fr\})$ is a normalizing constant representing all possible expressions over the parameter space involved. Evaluation options include employing a Maximum-a-Posteriori ("MAP") probability estimate and/or employing a bounded posterior integration: $Li=\int_a^{1.0} PM$, where PM is the estimated probability density function of $p(M|\{Fg, Fr\})$. By using a Bayesian pathway, the inventive process assigns a probability as to whether probe binding by microorganisms in a patient sample will match that of known microorganisms in a reference panel. Identification of pathogens using this process is based on a combination of posterior probabilities from multiple flow channels.

Although a probability model can be "finalized" based on a given training regimen, the process can continue to monitor microorganism identification data to augment posterior beliefs of the probes used, permitting continual evaluation of expectations—and thus the identification models based on those expectations. This provides user confidence for augmenting the system with new probes to address newly developed variability should it arise. For example, an identification expectation model was developed using a reference panel of bacteria and fungi that included 90% of blood pathogens, creating a great knowledge base. Microscopists using this model know what the majority of pathogenic blood microbes look like in the inventive system, and provides confidence that testing for these pathogens using this system is both sensitive and specific. But there is room for improving the expectation models should new bacterial strains arise.

*Enterobacter* modeling is presented as an exemplary case, but the principles apply equally to any probe for microbes in the reference panel. A good match case is illustrated in FIG. 96, in which model fit was 0.94 (94%). The left upper panel of FIG. 96 is a graphic that shows fluorescing microbial cells detected by the system. As before, the x-axis plots target probe signal distribution, while the y-axis plots universal probe signal distribution. The right panel of FIG. 96 adds a colored probability scale to the graphic, in which 0 indicates no probability of *Enterobacter* being present (noise, as depicted by white dots in the elliptical pattern) and 1.0 representing a 100% probability of the presence of *Enterobacter* (as depicted by black dots in the elliptical pattern). A small tail is evident toward the graph origin, which is noise (not present in dark field) and therefore is not counted toward signal. Experimental evaluation assessed cell signal against kernel density, which approached nearly 100% probability. A kernel density estimation is a fundamental data smoothing tool useful where inferences are made about a population in light of a finite data sample. Kernel modeling takes the posterior distribution and provides a PDF, from which a Maximum-a-Posteriori estimate may be derived. Kernel modeling will scan across an entire histogram and the observation is assigned a value of 1; the PDF must then integrate to 1 to fill in gaps, as shown in the bottom right histogram of FIG. 96. Because the innovative process uses a kernel density estimation on a posterior distribution—as opposed to, for example, raw input data—the system can compare probability for experiments having varying sample population densities.

By contrast, FIG. 97 depicts the probability model for a less robust *Enterobacter* test, which generated a model fit at 0.74 (74%). Here the data points are fairly confined to a specific region of the expected distribution pattern, but are sparse, and therefore gaps exist in the ellipse. Under these circumstances, integrating probability with fewer cells is a challenge; performing a kernel density estimate aided in overcoming the shortfall. Kernel modeling, as noted above, provided a posterior PDF distribution and a PDF, which is particularly useful when data points are sparse in a given model. It normalizes for cells by evaluating and filling in gaps assuming local Gaussian distribution. This gap filling essentially permits the genesis of continuous space for data that needs to be fit to a model. In the context of FISH identification, the root cause of the scarce data may be due to problems such as dimmer isolates or a shift in the entire operating point (high background is one dimension, etc.).

A compact model of *Enterobacter* signal distribution, as shown in FIG. 98, has a lower score of 0.64 (64%) than the more robust model depicted in FIG. 95. Nonetheless, the compact model exhibited more bacterial data points than were present in, for example, the "scarce" model of FIG. 97. The distinction lies with the fact that the probability model of FIG. 97 has more data points than the "scarce" model, but they are not as broadly distributed within the confidence space as they are in the "good" model.

Finally, FIG. 99 shows an example of a "not-so-good" case of this type of modeling, with an MAP estimate of 0.13 (13%). The data points are skewed toward the 0,0 origin and there were not enough points to fill most of the elliptical patterning space. This may be due to few or even no target cells being present, meaning that most of the "signal" is actually noise or artifacts.

Example 5

Basic Principles of Multiplexed Automated Digital Microscopy

Figure 86:
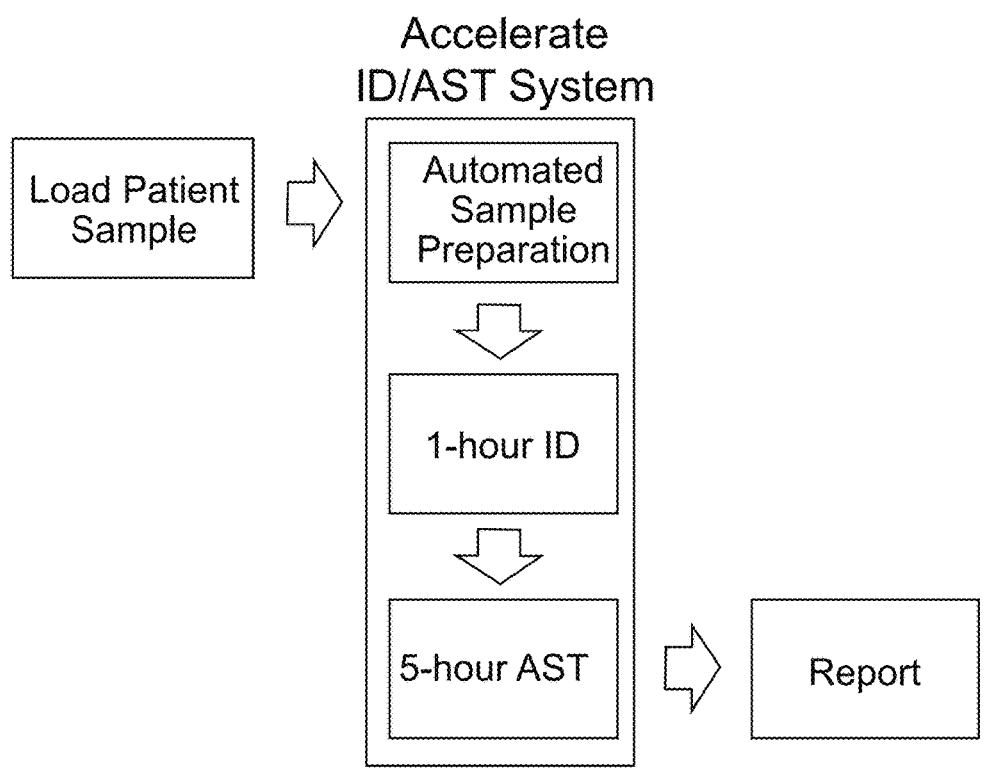
FIG. 86 is a diagram illustrating a fully-automated multiplex automated digital microscopy system workflow, including automated sample preparation, ID (identification), AST (antimicrobial susceptibility testing) and reporting.

Multiplexed automated digital microscopy uses a multi-channel test cassette and cell immobilization to enable microscopy-based, single-cell analysis for organism identification in about one (1) hour and antimicrobial susceptibility testing in about five (5) hours directly from clinical specimens. Bacterial and fungal (yeast) cell-by-cell identification was performed using fluorescence in situ hybridization. Susceptibility reports were generated by digital microscopic observation of individual, live, growing immobilized microbial cells in near real-time (approximately every 10 minutes) in the presence of antimicrobial agents. Antimicrobials for susceptibility testing were selected based on the organism identification result. Organisms that were not identified by a specific FISH assay (non-target organisms) were reported as detected but not identified, and susceptibility testing was not performed on these microbes. The technology enables the analysis of polymicrobial specimens, and an integrated, automated sample preparation process was developed for certain specimen types. The general process flow for a fully automated system is illustrated in FIG. 86.

Automated Sample Preparation—Gel Electro-Filtration (GEF)

Figure 87A:
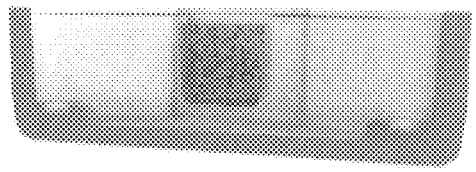
FIGS. 87A-87C illustrate separation of sample impurities, such as lysed blood cells and debris, from bacterial/yeast cells using automated gel electrofiltration.
Figure 87B:
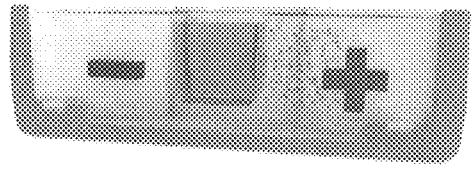
Figure 87C:
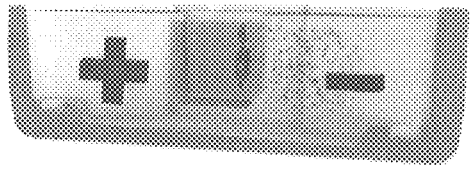

Automated sample preparation was performed using a gel electro-filtration process, which is based on gel electrophoresis principles (FIG. 87). Clinical samples were automatically transferred to an agarose gel containing pores smaller than bacterial and yeast cells. The gel was immersed in an electrokinetic buffer that causes bacterial and yeast cells to carry a negative charge. When a voltage was applied, sample impurities such as lysed blood cells and debris passed into the gel, while the larger bacterial and yeast cells remained trapped in the well. At the end of the process, the voltage was briefly reversed to liberate the bacterial and yeast cells from the wall of the well. The purified inoculum was then pipetted into individual flowcells of a multichannel test cassette for cell immobilization and identification or antimicrobial susceptibility testing.

Cell Capture Via Electrokinetic Concentration (EKC)

Figure 88A:
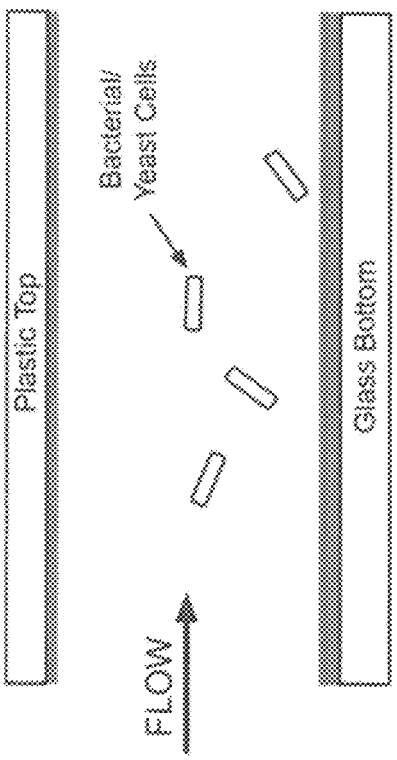
FIGS. 88A-88B illustrates capture of bacterial/yeast cells on the lower surface of flowcells (side view) by electrokinetic concentration.
Figure 88B:
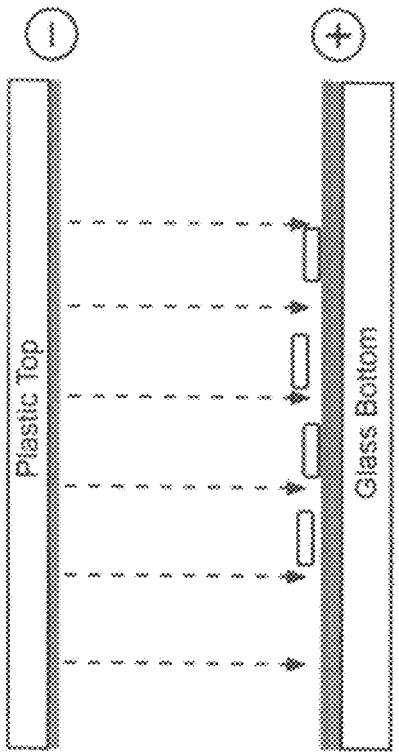

A multichannel test cassette composed of a transparent glass bottom and plastic top that is molded to form parallel flowcell channels was used. The top and bottom surfaces of each flowcell channel were coated with a layer of conductive indium tin oxide (ITO) that serves as electrodes. The bottom surface has an additional cationic poly-L-lysine layer that acts as a capture surface. Inoculum was added to the flowcell and a low voltage briefly applied that caused negatively-charged bacterial and yeast cells to migrate to the lower surface where they were captured, and ready to undergo identification or antimicrobial susceptibility testing (FIG. 88).

Identification by Fluorescence In Situ Hybridization (FISH)

Once cells were immobilized, a FISH assay was performed for identification. Following permeabilization and washing steps, cocktails of ATTO-532 (green) fluorescently labeled DNA probe(s) designed to bind to the rRNA of each identification target were added to different flowcells. Each cocktail also contained an ATTO-647 (red) labeled universal microbial probe capable of binding bacterial or yeast cells. The universal microbial probe binds to rRNA of all bacterial and yeast cells, thereby identifying the presence of such cells even if they are not recognized by target probes. This aids in the detection of off-panel microorganisms in biological samples. Each microfluidic flowcell was imaged using an epifluorescence microscope with a camera at 532 nm, 647 nm and in dark-field.

Figure 89:
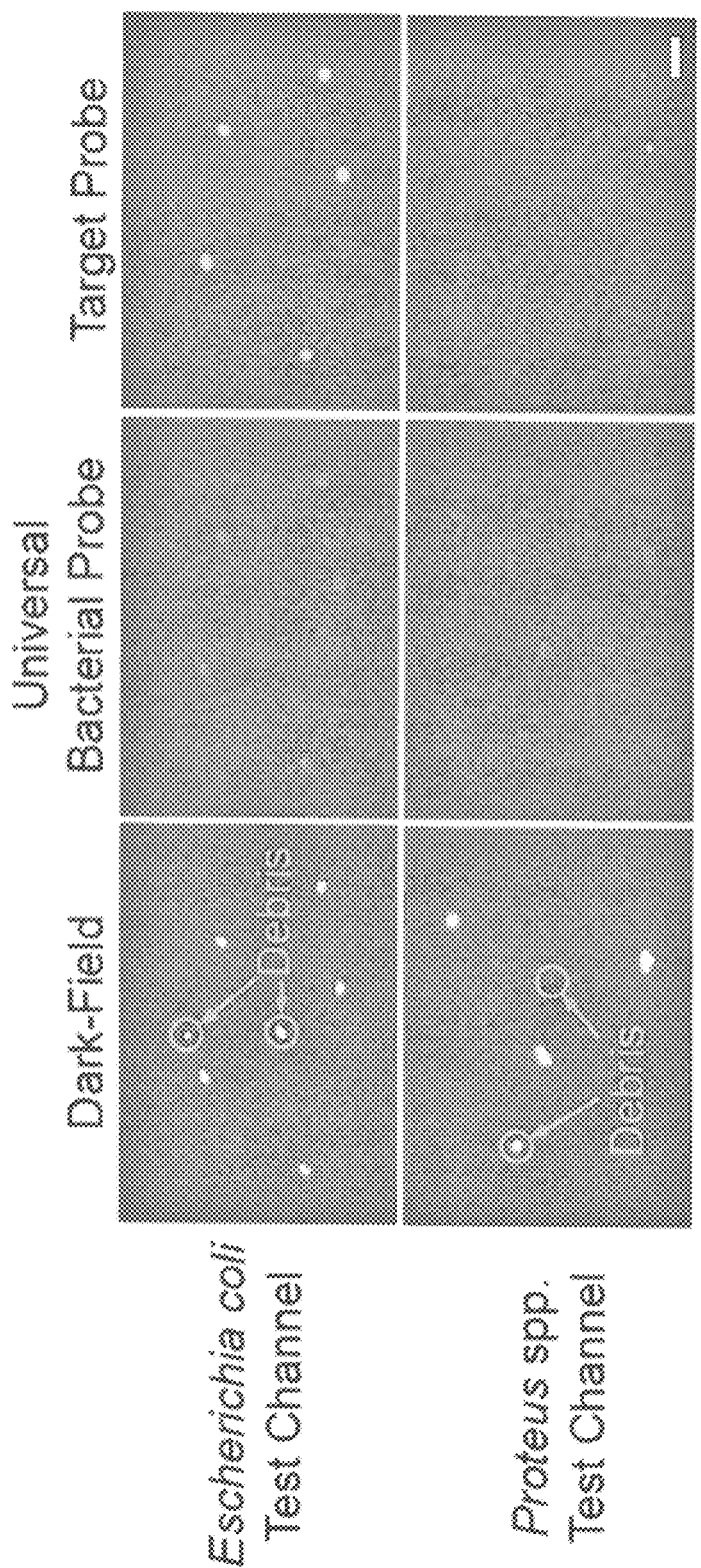
FIG. 89 illustrates representative images of an *Escherichia coli* sample in two different test channels with probes targeting *E. coli* and *Proteus* spp. Images were taken in dark-field, 647 nm (universal bacterial probe), and 532 nm (target probes). The universal bacterial probe binds to all bacterial cells to differentiate bacteria from debris. Co-localization of universal and target probe signals identifies target bacteria. Images magnified to view individual cells. Scale bar in lower right image is 10 μm.

After image collection, custom image analysis software measured the signal-to-background ratio for each fluorescent and dark-field object in each microfluidic flowcell. To exclude debris, only dark-field objects co-localized with universal probe signal were included in the analysis. Co-localization of target probe signal and universal probe signal identified a target organism (FIG. 89). The software can also be used to quantitate the number of objects in a flowcell. A universal nucleic acid stain (e.g., acridine orange, propidium iodide, or DAPI) is added to an additional flowcell as a control in order to quantitate the total number of organisms present per flowcell in the sample. Comparing the relative numbers of each target organism to objects lit up with universal bacterial, yeast, or nucleic acid probes allowed for the detection of non-target organisms and identification of polymicrobial samples.

Antimicrobial Susceptibility Testing (AST)

Figure 90:
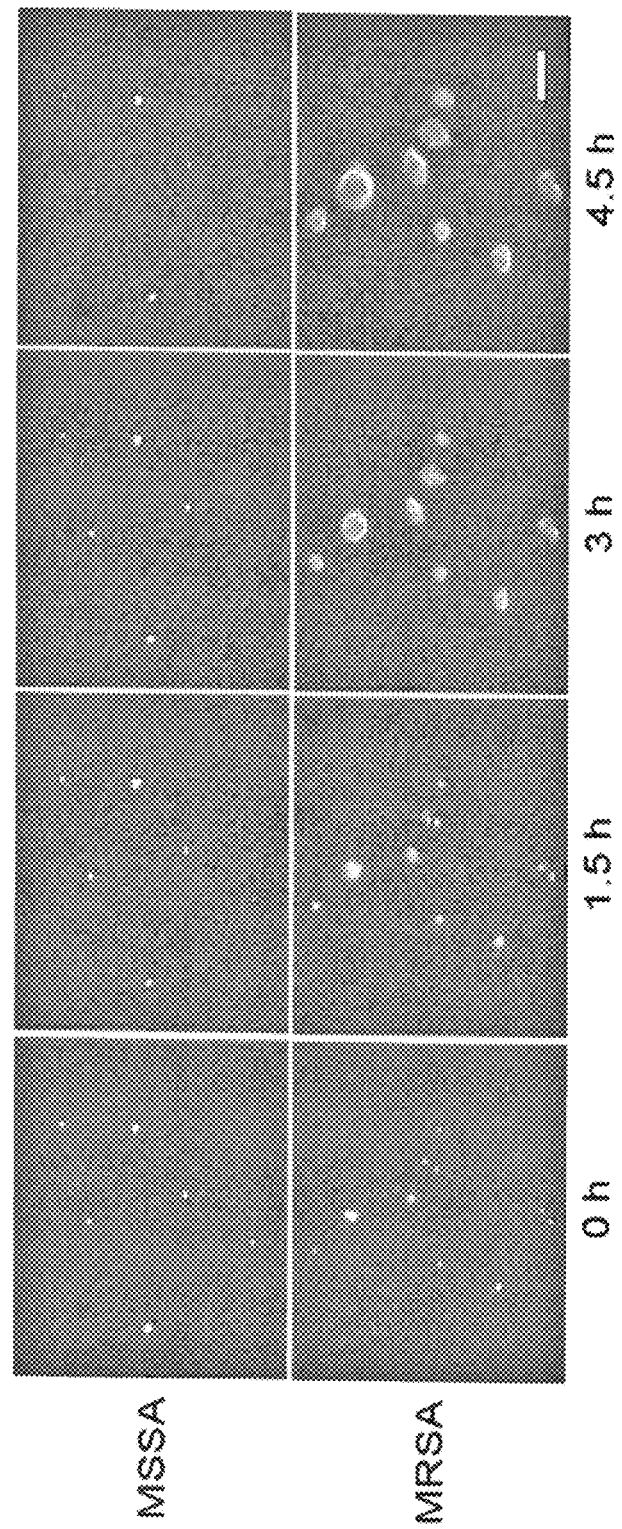
FIG. 90 illustrates time-lapse images of methicillin-susceptible *S. aureus* (MSSA) and methicillin-resistant *S. aureus* (MRSA) isolates growing in cefoxitin at 0, 1.5, 3, and 4.5 hours. By 4.5 hours, susceptible clones have arrested or lysed while resistant clones continue to grow. Images are magnified to show individual bacterial clones. Scale bar in lower right image is 20 μm.

The results of the identification assay drive antibiotic selection for antimicrobial susceptibility testing. The remaining samples undergo a pre-growth step to normalize growth rates during the approximately 1-hour FISH ID assay. The concentration of organisms in the purified inoculum was determined by repeating the quantitation process with a universal nucleic acid stain as previously described herein. Based on these results, additional flowcells were filled with the purified inoculum subjected to dynamic dilution to the appropriate target range for antimicrobial susceptibility testing. Following cell immobilization, antimicrobial solutions in Mueller-Hinton agar were dispensed into the flowcells. Different antimicrobials were tested in separate flowcells, and only a single concentration of each antimicrobial was used. A growth control consisting of Mueller-Hinton agar without any antimicrobial was included for each run. A dark-field microscope and camera produced time-lapse images approximately every 10 minutes of progenitor cells growing into clones of daughter cells in each flowcell. The agar ensured daughter cells were immobilized and remained localized to each growing clone. Resistant clones grew while susceptible clones arrest or lyse over time (FIG. 90).

Figure 91:
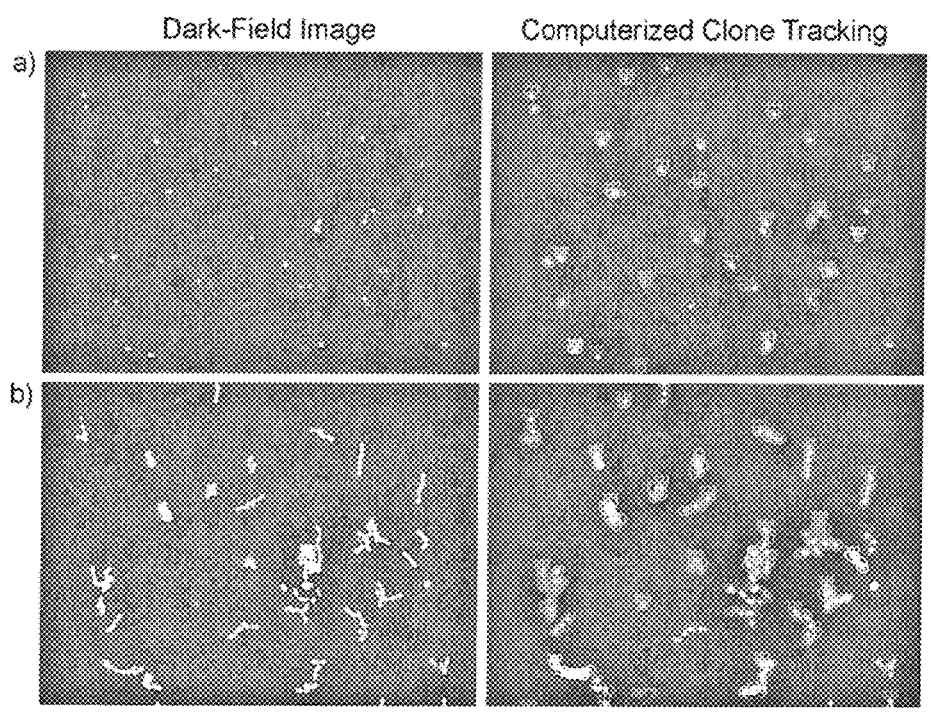
FIG. 91 illustrates computerized clone tracking of individual progenitor bacterial cells (top panels) as they grow into clones of daughter cells, and following multiple division cycles (bottom panels).
Figure 92:
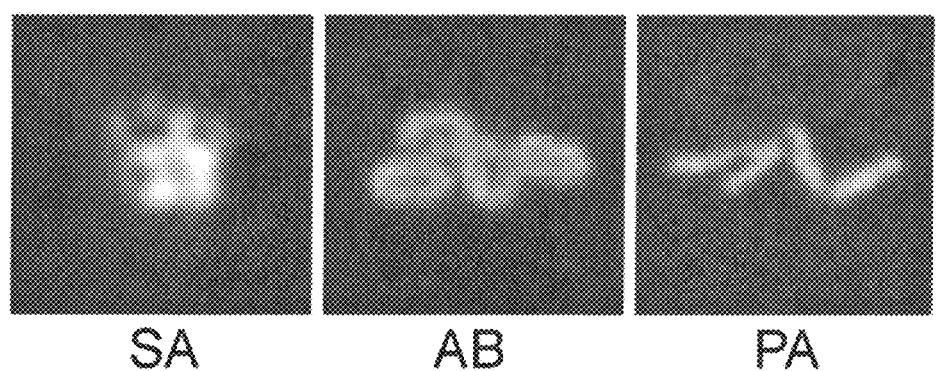
FIG. 92 illustrates microscopic images of *Staphylococcus aureus* (SA), *Acinetobacter baumannii* (AB) and *Pseudomonas aeruginosa* (PA). Cell morphology differences are clearly visible between species and can be detected by the software. The software uses this and other morphokinetic features to differentiate multiple species in polymicrobial samples.

Custom image analysis software assigned unique spatial XY coordinates to individual progenitor cells (FIG. 91), allowing each growing clone across a series of time-lapse images to be identified. The intensity of each clone can be used as a metric of clone mass in each image. By measuring over time, this metric was used to generate growth curves for each individual clone (FIG. 92). The pattern of cell responses was used to determine the susceptibility of the overall population. Computer algorithms developed for each organism-antimicrobial combination convert microbial growth response into an MIC value using a mathematical regression model based on the response of isolates with known MICs for a single-concentration of a given antimicrobial. Once obtained, MIC values were interpreted using FDA, CLSI or EUCAST breakpoints along with expert rules to determine the categorical result (susceptible (S), intermediate (I) or resistant (R)). In addition to MICs, this technique was applied to phenotypic resistance mechanism detection.

In certain embodiments, the determination of antimicrobial susceptibility may further comprise subjecting identified microorganisms to antimicrobial susceptibility analysis, wherein the microorganisms are grown in Mueller Hinton nutrient-depleted media to differentiate antimicrobial-resistant cells from filamentous, antimicrobial-susceptible cells within about 12 hours of growth. In some embodiments, fastidious microorganisms are grown in 1% phytone tryptose Mueller Hinton Agar for determination of antimicrobial susceptibility and/or minimum inhibitory concentration of antimicrobials.

Polymicrobial Sample Analysis

FISH ID was performed in several different flowcells. Target channels enabled the identification of multiple target species as well as the detection of non-target species in polymicrobial samples. Antimicrobial susceptibility testing was performed on up to two target organisms in the same sample.

Cell morphokinetic image analysis was used for species recognition in polymicrobial infections, and enabled the analysis software to assign an MIC to each species during AST testing. Morphokinetic features including cell morphology (FIG. 93A), division rates, growth patterns and signal intensity were used to distinguish organism species.

Quantitative FISH assay results provided an estimation of the relative abundance of multiple species in polymicrobial samples so both species can be diluted to the appropriate concentration for AST testing in the same test run. However, if dilution of one species causes the other species to be out of range, only the AST results for the in-range species was reported. In addition, if morphokinetic features were insufficient to distinguish multiple species from one another, MIC values were not reported, and additional susceptibility testing was required.

Performance of Multiplexed Automated Digital Microscopy

The performance of multiplexed automated digital microscopy for positive blood culture samples was evaluated. Clinical isolates were seeded into simulated positive blood cultures, grown overnight, and run directly on a custom engineering iteration of the instrument. FISH ID performance showed 98% sensitivity (192/195 target organisms) and 99% specificity (211/214 non-target organisms) (Table 3). Antimicrobial susceptibility testing results showed 96% agreement with 'gold standard' broth microdilution MIC results for 520/542 representative organism-antimicrobial combinations (Table 4). Additional results showed accurate phenotypic detection of 49/50 *Staphylococcus aureus* isolates with resistance mechanisms (98% sensitivity) and 87/90 *Staphylococcus aureus* isolates without (97% specificity) (Table 5). A comprehensive listing of Gram positive and Gram negative bacteria from an ID/AST reference panel are presented in Tables 6 and 7. Fungi (*Candida albicans* and *Candida glabrata*) are identified only in the ID/AST reference panel.

TABLE 3

Performance of multiplexed automated digital microscopy for the identification of clinical isolates seeded into simulated positive blood cultures compared to known identification references.

| Target Group | Sensitivity | Specificity |
|---|---|---|
| *Staphylococcus aureus* | 16/16 (100%) | 16/16 (100%) |
| *Staphylococcus lugdunensis* | 8/8 (100%) | 12/12 (100%) |
| coagulase-negative staphylococci | 14/16 (88%) | 16/16 (100%) |
| *Enterococcus faecalis* | 8/8 (100%) | 8/8 (100%) |
| *Enterococcus faecium*[a] | 8/8 (100%) | 8/8 (100%) |
| *Streptococcus* genus | 18/18 (100%) | 12/12 (100%) |
| *Streptococcus pneumoniae* | 6/6 (100%) | 7/7 (100%) |
| *Streptococcus agalactiae* | 8/8 (100%) | 5/6 (83%) |
| *Streptococcus pyogenes* | 8/8 (100%) | 7/7 (100%) |
| *Escherichia coli* | 12/12 (100%) | 22/22 (100%) |
| *Klebsiella oxytoca* + *K. pneumoniae* | 15/16 (94%) | 18/19 (95%) |
| *Enterobacter aerogenes* + *E. cloacae* | 14/14 (100%) | 16/16 (100%) |
| *Citrobacter freundii* + *C. koseri* | 12/12 (100%) | 20/20 (100%) |
| *Proteus mirabilis* + *P. vulgaris* | 15/15 (100%) | 4/4 (100%) |
| *Serratia marcescens* | 7/7 (100%) | 17/18 (94%) |
| *Acinetobacter baumannii* | 15/15 (100%) | 8/8 (100%) |
| *Pseudomonas aeruginosa* | 8/8 (100%) | 15/15 (100%) |
| Total | 192/195 (98%) | 211/214 (99%) |

[a]*Enterococcus faecium* and other *Enterococcus* spp., not differentiated, excluding *Enterococcus faecalis*

TABLE 4

Comparison of multiplexed automated digital microscopy with CLSI standard frozen broth microdilution for antimicrobial susceptibility testing of clinical isolates seeded into simulated positive blood cultures.

| Organism | Antibiotic | Essential Agreement |
|---|---|---|
| *Staphylococcus aureus* | Doxycycline | 45/47 (96%) |
| *Staphylococcus aureus* | Ceftaroline | 43/44 (98%) |
| *Streptococcus pneumoniae* | Penicillin | 27/28 (96%) |
| *Streptococcus pneumoniae* | Ceftriaxone | 18/19 (95%) |
| *Enterococcus* spp. | Ampicillin | 43/45 (96%) |
| *Enterococcus* spp. | Vancomycin | 44/48 (92%) |
| *Enterococcus* spp. | Linezolid | 44/47 (94%) |
| *Pseudomonas aeruginosa* | Ciprofloxacin | 47/47 (100%) |
| *Pseudomonas aeruginosa* | Amikacin | 48/48 (100%) |
| *Acinetobacter baumannii* | Ciprofloxacin | 39/41 (95%) |
| *Acinetobacter baumannii* | Amikacin | 37/40 (93%) |
| *Acinetobacter baumannii* | Imipenem | 44/45 (98%) |
| *Acinetobacter baumannii* | Minocycline | 41/43 (95%) |
| Total | | 520/542 (96%) |

TABLE 5

Performance of multiplexed automated digital microscopy for the detection of phenotypic resistance mechanisms in *S. aureus* clinical isolates seeded into simulated positive blood cultures.

| Resistance Mechanism | Sensitivity | Specificity |
|---|---|---|
| MRSA | 24/24 (100%) | 22/22 (100%) |
| VRSA | 12/12 (100%) | 41/43 (95%) |
| MLSb | 13/14 (93%) | 24/25 (96%) |
| Total | 49/50 (98%) | 87/90 (97%) |

MRSA = methicillin-resistant *S. aureus*; VRSA = vancomycin-resistant *S. aureus*; MLSb = macrolide-lincosamide-streptogramin b resistance.

TABLE 6

Accelerate ID/AST System test panel for Gram-positive blood culture samples.

| Organism | Ampicillin | Penicillin | Ceftaroline | Ceftriaxone | Doxycycline | Levofloxacin | Erythromycin | Trimethoprim-Sulfamethoxazole |
|---|---|---|---|---|---|---|---|---|
| *S. aureus* | | | X | | X | | X | X |
| *S. lugdunensis* | | | | | X | | X | X |
| CONS spp.[b] | | | | | X | | X | X |
| *E. faecalis* | X | | | | X | | | |
| *E. faecium*[c] | X | | | | X | | | |
| *S. pneumoniae* | | X | | X | | X | X | |
| *S. pyogenes*[a] | | | | | | | | |
| *S. agalactiae*[a] | | | | | | | | |
| *Streptococcus* spp.[ad] | | | | | | | | |

| Organism | Daptomycin | Linezolid | Vancomycin | MRSA (Cefoxitin) | MLSb (Erythromycin-Clindamycin) | HLAR (High-Level Gentamicin) | HLAR (High-Level Streptomycin) |
|---|---|---|---|---|---|---|---|
| *S. aureus* | X | X | X | X | X | | |
| *S. lugdunensis* | X | X | X | X | X | | |
| CONS spp.[b] | X | X | X | X | X | | |
| *E. faecalis* | X | X | X | | | X | X |
| *E. faecium*[c] | X | X | X | | | X | X |
| *S. pneumoniae* | | | | | X | | |
| *S. pyogenes*[a] | | | | | | | |
| *S. agalactiae*[a] | | | | | | | |
| *Streptococcus* spp.[ad] | | | | | | | |

MRSA = methicillin-resistant *S. aureus*;
MLSb = macrolide-lincosamide-streptogramin b resistance;
HLAR = high-level aminoglycoside resistance
[a] ID only
[b] Coagulase-negative *Staphylococcus* species (*Staphylococcus epidermidis*, *Staphylococcus haemolyticus*, *Staphylococcus hominis*, *Staphylococcus capitis*, not differentiated)
[c] *Enterococcus faecium* and other *Enterococcus* spp., not differentiated, excluding *Enterococcus faecalis*
[d] *Streptococcus mitis*, *Streptococcus pyogenes*, *Streptococcus gallolyticus*, *Streptococcus agalactiae*, *Streptococcus pneumoniae*, not differentiated

TABLE 7

Accelerate ID/AST System test panel for Gram-negative blood culture samples.

| Organism | Ampicillin-Sulbactam | Piperacillin-Tazobactam | Cefazolin | Cefepime | Ceftazidime | Ceftriaxone | Ertapenem | Imipenem |
|---|---|---|---|---|---|---|---|---|
| *E. coli* | X | X | X | X | X | X | X | |
| *Klebsiella* spp.[a] | X | X | X | X | X | X | X | |
| *Enterobacter* spp.[b] | | X | | X | X | X | X | |
| *Proteus* spp.[c] | X | X | | X | X | X | X | |
| *Citrobacter* spp.[d] | | X | | X | X | X | X | |
| *S. marcescens* | | X | | X | X | X | X | |

TABLE 7-continued

Accelerate ID/AST System test panel for Gram-negative blood culture samples.

|  | 1 | 2 | 3 | 4 | 5 | 6 | 7 |
|---|---|---|---|---|---|---|---|
| P. aeruginosa |  | X |  | X | X |  | X |
| A. baumannii | X | X |  | X |  |  | X |

| Organism | Meropenem | Amikacin | Gentamicin | Tobramycin | Ciprofloxacin | Minocycline | Aztreonam | Colistin |
|---|---|---|---|---|---|---|---|---|
| E. coli | X | X | X | X | X |  | X | X |
| Klebsiella spp.[a] | X | X | X | X | X |  | X | X |
| Enterobacter spp.[b] | X | X | X | X | X |  | X | X |
| Proteus spp.[c] | X | X | X | X | X |  | X |  |
| Citrobacter spp.[d] | X | X | X | X | X |  | X | X |
| S. marcescens | X |  | X |  | X |  | X |  |
| P. aeruginosa | X | X | X | X | X |  | X | X |
| A. baumannii | X | X |  |  | X | X |  | X |

[a] Klebsiella oxytoca + K. pneumoniae
[b] Enterobacter aerogenes + E. cloacae
[c] Proteus mirabilis + P. vulgaris
[d] Citrobacter freundii + C. koseri FIG. 101 depicts a generalized example of a suitable computing environment 10100 in which the described innovations may be implemented. The computing environment 10100 is not intended to suggest any limitation as to scope of use or functionality, as the innovations may be implemented in diverse general-purpose or special-purpose computing systems. For example, the computing environment 10100 can be any of a variety of computing devices (e.g., desktop computer, laptop computer, server computer, tablet computer, etc.) Alternatively, the computing environment 10100 can be part of the control board 321 of FIG. 3.

With reference to FIG. 101, the computing environment 10100 includes one or more processing units 10110, 10115 and memory 10120, 10125. In FIG. 101, this basic configuration 10130 is included within a dashed line. The processing units 10110, 10115 execute computer-executable instructions. A processing unit can be a general-purpose central processing unit (CPU), processor in an application-specific integrated circuit (ASIC) or any other type of processor. In a multi-processing system, multiple processing units execute computer-executable instructions to increase processing power. For example, FIG. 101 shows a central processing unit 10110 as well as a graphics processing unit or co-processing unit 10115. The tangible memory 10120, 10125 may be volatile memory (e.g., registers, cache, RAM), non-volatile memory (e.g., ROM, EEPROM, flash memory, etc.), or some combination of the two, accessible by the processing unit(s). The memory 10120, 10125 stores software 10180 implementing one or more innovations described herein, in the form of computer-executable instructions suitable for execution by the processing unit(s).

In any of the examples described herein, computing environment 10100 can be a system controller attached to an instrument and operable to control the instrument.

A computing system may have additional features. For example, the computing environment 10100 includes storage 10140, one or more input devices 10150, one or more output devices 10160, and one or more communication connections 10170. An interconnection mechanism (not shown) such as a bus, controller, or network interconnects the components of the computing environment 10100. Typically, operating system software (not shown) provides an operating environment for other software executing in the computing environment 10100, and coordinates activities of the components of the computing environment 10100.

The tangible storage 10140 may be removable or non-removable, and includes magnetic disks, magnetic tapes or cassettes, CD-ROMs, DVDs, or any other medium which can be used to store information in a non-transitory way and which can be accessed within the computing environment 10100. The storage 10140 stores instructions for the software 10180 implementing one or more innovations described herein.

The input device(s) 10150 may be a touch input device such as a keyboard, mouse, pen, or trackball, a voice input device, a scanning device, or another device that provides input to the computing environment 10100. The output device(s) 10160 may be a display, printer, speaker, CD-writer, or another device that provides output from the computing environment 10100.

The communication connection(s) 10170 enable communication over a communication medium to another computing entity. The communication medium conveys information such as computer-executable instructions, audio or video input or output, or other data in a modulated data signal. A modulated data signal is a signal that has one or more of its characteristics set or changed in such a manner as to encode information in the signal. By way of example, and not limitation, communication media can use an electrical, optical, RF, or other carrier.

Example 6

Quality Control Testing

A reagent cartridge designed for patient sample testing was removed from refrigerated storage. The empty patient sample vial was removed from the cartridge and discarded, as Quality Control components were used in lieu of patient sample material during the QC test run. An antimicrobial susceptibility test QC assay consumable insert (AST QC assay insert) in a "pi" configuration was removed from −70° C. storage. Using the top edge of the AST QC assay insert, a post and top edge clips were guided into holes located on the reagent cartridge just above the semi-circle location typically occupied by a sample vial. Thereafter, the bottom edge of the AST QC insert was pressed until clips on the bottom of the insert snapped into place within the sample vial location on the reagent cartridge. The AST QC test insert was seated level with the cartridge at this point. A clear adhesive film was carefully removed from the AST QC test insert exposing reagent wells without touching the open wells in the process.

Next, an ID QC assay insert was removed from refrigerated storage and was positioned adjacent to the AST QC assay insert that was previously attached to the reagent cartridge. The "E" configuration of the ID QC assay insert complemented the "pi" configuration of the AST QC assay insert, allowing the center post and edges of the ID QC assay consumable to be pressed into place. Security clips on the ID QC assay insert were engaged on the AST QC assay insert. A foil seal covering the reagent wells on the ID QC assay insert remained intact during the attachment process; the foil seal was pierced by the instrument when interacting with the reagents contained therein. Barcode tabs from each QC insert aligned vertically such that the barcodes on these tabs were on top of one another.

Next, a cassette was removed from its packaging and was nested in the center of the AD-1 Instrument. The protective cover was removed from the pipette tips section of the reagent cartridge containing the AST and ID QC assay inserts; thereafter, the reagent cartridge was inserted into the AD-1 Instrument. The instrument start button was pressed, at which point the instrument read the barcodes identifying the AST and ID inserts, and then automatically initiated the QC run.

ID QC Panel

In this test, the ID portion of the automated QC assay consisted of testing both frozen isolates and target beads with sequences that are specific to each probe cocktail tested. The frozen isolates (*Candida albicans* and *Staphylococcus aureus*) were located in the AST component of the consumable QC insert (wells 18 and 25 in the dark gray shaded "pi" shaped aspect of FIG. 108). These frozen isolates tested the functionality of tris (2-carboxyethyl) phosphoine ("TCEP") and gel electrofiltration components of the AD-1 Instrument System using *C. albicans*, and the enzymes were tested using *S. aureus*. Each isolate was also tested with its respective probe cocktail.

The target beads were located in the ID component (E-shaped) portion of the consumable QC insert, as depicted in light gray shading in FIG. 108. Eleven wells in the E-shaped aspect of the QC insert contained a total of 14 different target beads. Three wells (wells 1, 3, and 4) contained two sets of target beads in each well. All other wells contained a single target bead. This configuration reflects the limited space afforded in this particular QC insert, but may not be necessary for other QC insert designs. All beads, except for the KLE/CNS beads (well 1), were tested independently in different flowcells (FC). For example, well 3 in FIG. 108 contained both EFM and CGL target beads. The contents from this well were loaded into flowcells 23 and 29. Flowcell 23 was treated with the EFM probe cocktail, while flowcell 29 was treated with the CGL cocktail. Table 8 depicts the cassette layout and probes tested. For the wells containing multiple target beads, the QC insert layout was designed to match the ID assay conditions for both target beads present in each of those wells.

TABLE 8

Layout of Cassette Flowcells in ID QC Assay

| FC | Test | Isolate or beads | Probes |
|---|---|---|---|
| 1 | TCEP & GEF | CALB 96268 | CAL |
| 3 | Enzymes | SAUR 43300 | SAU |
| 5 | FISH probes | KLE/CNS | KLE/CNS |
| 7 | FISH probes | ABA | ABA/SAU |

TABLE 8-continued

Layout of Cassette Flowcells in ID QC Assay

| FC | Test | Isolate or beads | Probes |
|---|---|---|---|
| 9 | FISH probes | EFS | EFS |
| 11 | FISH probes | PRO | PRO |
| 13 | FISH probes | STR/ENT | STR |
| 15 | FISH probes | ECO | ECO |
| 17 | FISH probes | SLU | SLU |
| 19 | FISH probes | CIT | CIT |
| 21 | FISH probes | SMA | SMA |
| 23 | FISH probes | EFM/CGL | EFM |
| 25 | FISH probes | PAE | PAE |
| 27 | FISH probes | STR/ENT | ENT |
| 29 | FISH probes | EFM/CGL | CGL |

Only one set of beads was tested in a single flowcell in this example, namely the KLE and CNS beads located in well 1 of the QC insert (FIG. 108). The KLE and CNS beads were tested within a single flowcell due to space restrictions on the ID QC insert in view of its configuration for use with the configuration of the reagent cassette utilized in this example. The contents of well 1 were loaded into flowcell 5 and are treated with both the KLE probe cocktail and the CNS probe cocktail.

AST QC Panel

In this example, the AST QC consumable insert consisted of 8 wells configured in a "pi" shape, as shown in the dark gray shading in FIG. 109. The AST QC panel was composed of seven CLSI recommended isolates that provide "on-scale" MIC results for all of the antimicrobial agents included in a sample blood culture test. A *C. albicans* isolate was used for Quality Control assessment of the gel electrophoresis component of the AD-1 Instrument System.

Table 9 below lists each organism and the corresponding antimicrobial agent that was tested in the AST QC assay. All isolates were simultaneously tested in a single run by loading the AST QC insert containing pre-prepared 1 McFarland frozen isolates. The instrument ran the QC-specific program that directed the addition of various organism suspensions to specific flow cells containing corresponding antimicrobial agents. At the conclusion of the run, a report was generated listing the MIC values (or interpretation for phenotypic positive/negative tests), the expected result, and a pass/fail outcome for each antimicrobial agent. These results are presented below in Tables 10 and 11.

TABLE 9

AST QC panel.

| QC isolate | Reported with | Patient Sample Reportable Range | Organism QC Range |
|---|---|---|---|
| *Escherichia coli* ATCC 25922 | | | |
| Cefazolin | *Escherichia coli* | ≤0.5 to ≥16 | 1-4 |
| **Ceftriaxone | Enterobacteriaceae | ≤0.25 to ≥8 | 0.03-0.12 |
| **Minocycline | *Acinetobacter baumannii* | ≤1 to ≥32 | 0.25-1 |
| Ceftazidime | Enterobacteriaceae | ≤1 to ≥32 | 1-4 |
| | *Pseudomonas aeruginosa* | ≤2 to ≥64 | |
| *Pseudomonas aeruginosa* ATCC 27853 | | | |
| **Amikacin | *Acinetobacter baumannii*, Enterobacteriaceae, *Pseudomonas aeruginosa* | ≤4 to ≥128 | 1-4 |

TABLE 9-continued

AST QC panel.

| QC isolate | Reported with | Patient Sample Reportable Range | Organism QC Range |
|---|---|---|---|
| Aztreonam | Enterobacteriaceae, Pseudomonas aeruginosa | ≤1 to ≥32 ≤2 to ≥64 | 2-8 |
| **Cefepime | Enterobacteriaceae Acinetobacter baumannii, Pseudomonas aeruginosa | ≤1 to ≥32 ≤2 to ≥64 | 0.5-4 |
| Ciprofloxacin | Acinetobacter baumannii, Enterobacteriaceae, Pseudomonas aeruginosa | ≤0.25 to ≥8 | 0.25-1 |
| Colistin | Acinetobacter baumannii, Enterobacteriaceae, Pseudomonas aeruginosa | ≤0.5 to ≥8 ≤0.5 to ≥16 | 0.5-4 — |
| **Ertapenem | Enterobacteriaceae | ≤0.125 to ≥4 | 2-8 |
| **Gentamicin | Enterobacteriaceae, Pseudomonas aeruginosa | ≤1 to ≥32 | 0.5-2 |
| Imipenem | Acinetobacter baumannii, Pseudomonas aeruginosa | ≤0.5 to ≥16 | 1-4 |
| Meropenem | Enterobacteriaceae Acinetobacter baumannii Pseudomonas aeruginosa | ≤0.25 to ≥8 ≤0.5 to ≥16 | 0.25-1 |
| **Tobramycin | Enterobacteriaceae, Pseudomonas aeruginosa | ≤1 to ≥32 | 0.25-1 |
| | Escherichia coli ATCC 35218 | | |
| Ampicillin-Sulbactam | Enterobacteriaceae, Acinetobacter baumannii | ≤2 to ≥64 | 8/4-32/16 |
| Piperacillin-Tazobactam | Enterobacteriaceae, Pseudomonas aeruginosa, Acinetobacter baumannii | ≤4 to ≥256 | 0.5/4-2/4 |
| | Enterococcus faecalis ATCC 29212 | | |
| **Ampicillin | Enterococcus faecalis, Enterococcus faecium | ≤2 to ≥32 | 0.5-2 |
| Ceftaroline | Staphylococcus aureus | ≤0.25 to ≥8 | 0.25-2 |
| Daptomycin | Staphylococcus aureus Staphylococcus lugdunensis, Coagulase negative Staphylococcus | ≤1 to ≥16 | 1-4 |
| | Enterococcus faecalis, Enterococcus faecium | ≤0.25 to ≥4 | |
| Doxycycline | Staphylococcus aureus Staphylococcus lugdunensis, Coagulase negative Staphylococcus, Enterococcus faecalis, Enterococcus faecium | ≤1 to ≥32 | 2-8 |
| Linezolid | Staphylococcus aureus, Staphylococcus lugdunensis, Coagulase negative Staphylococcus | ≤0.5 to ≥16 | 1-4 |
| | Enterococcus faecalis, Enterococcus faecium | ≤1 to ≥16 | |
| Vancomycin | Staphylococcus aureus | ≤0.5 to ≥32 | 0.5-2 |
| | Staphylococcus lugdunensis, Coagulase negative Staphylococcus, Enterococcus faecalis, Enterococcus faecium | ≤1 to ≥64 | |
| | Staphylococcus aureus ATCC 29213 | | |
| Cefoxitin | Staphylococcus aureus, Staphylococcus lugdunensis, Coagulase negative Staphylococcus | Positive/Negative | Negative |
| Erythromycin | Staphylococcus aureus, Staphylococcus lugdunensis, Coagulase negative Staphylococcus | ≥0.125 to ≥16 | 0.25-1 |
| MLSb | Staphylococcus aureus, Staphylococcus lugdunensis, Coagulase negative Staphylococcus | Positive/Negative | Negative |
| Trimethoprim-sulfamethoxazole | Staphylococcus aureus, Staphylococcus lugdunensis, Coagulase negative Staphylococcus | ≤0.5 to ≥8 | ≤0.5/9.5 |
| | Staphylococcus aureus ATCC 43300 | | |
| Cefoxitin | Staphylococcus aureus, Staphylococcus lugdunensis, Coagulase negative Staphylococcus | ≥8 | Positive |
| | Staphylococcus aureus ATCC BAA-977 | | |
| MLSb | Staphylococcus aureus, Staphylococcus lugdunensis, Coagulase negative Staphylococcus | Positive/Negative | Positive |

Cells with asterisks (**) used a concentration of antimicrobial agent that is different from that which is used for patient testing. This approach is consistent with industry practice of using extended dilutions of antimicrobial agents to cover QC organisms.

TABLE 10

AST only report.

QUALITY CONTROL REPORT: DMIS000048A
Blood Culture QC Pi Ctl 27 of 27 Passed

ORDER DETAILS
ORDER INFORMATION
Operator: System Administrator (Administrator)
Description: AST Panel
Run Status: Completed

| Antimicrobial | Expected | Result | Pass/Fail |
|---|---|---|---|
| *Escherichia coli*: Escherichia_coli_ATCC_25922F | | | |
| Cefazolin | 1-4 | 2 | Passed |
| Ceftriaxone | 0.03-0.125 | 0.0525 | Passed |
| Minocycline | 0.25-1 | 0.5 | Passed |
| Ceftazidime | 0.06-0.5 | 0.25 | Passed |
| *Escherichia coli*: Escherichia_coli_ATCC_35218F | | | |
| Ampicillin-Sulbactam | 8/4-32/16 | 16 | Passed |
| Piperacillin-Tazobactam | 0.5/4-2/4 | 1 | Passed |
| *Staphylococcus aureus*: Staphylococcus_aureus_ATCC_29213F | | | |
| Erythromycin | 0.25-1 | 0.6 | Passed |
| Cefoxitin | NEG | NEG | Passed |
| MLSb | NEG | NEG | Passed |
| Trimethoprim-Sulfamethoxazole | 0/0-0.5/9.5 | 0.25 | Passed |
| *Enterococcus faecalis*: Enterococcus_faecalis_ATCC_29212F | | | |
| Ampicillin | 0.5-2 | 1 | Passed |
| Ceftaroline | 0.25-2 | 1 | Passed |
| Daptomycin | 1-4 | 2 | Passed |
| Doxycycline | 2-8 | 4 | Passed |
| Linezolid | 1-4 | 2 | Passed |
| Vancomycin | 1-4 | 2 | Passed |
| *Pseudomonas aeruginosa*: Pseudomonas_aeruginosa_ATCC_27853F | | | |
| Amikacin | 1-4 | 2 | Passed |
| Aztreonam | 2-8 | 4 | Passed |
| Ciprofloxacin | 0.25-1 | 0.5 | Passed |
| Colistin | 0.5-4 | 2 | Passed |
| Ertapenem | 2-8 | 4 | Passed |
| Cefepime | 0.5-4 | 2 | Passed |
| Gentamicin | 0.5-2 | 1 | Passed |
| Meropenem | 0.25-1 | 0.5 | Passed |
| Tobramycin | 0.25-1 | 0.5 | Passed |
| *Staphylococcus aureus*: Staphylococcus_aureus_ATCC_43300F | | | |
| Cefoxitin | POS | POS | Passed |
| *Staphylococcus aureus*: Staphylococcus_aureus_ATCC_977F | | | |
| MLSb | POS | POS | Passed |

TABLE 11

ID and AST Report

ORDER DETAILS        39 of 39 Passed

ORDER INFORMATION
Operator: System Operator (User)
Description: ID/AST Panel
Run Status: Completed

TABLE 11-continued

ID and AST Report

IDENTIFICATION RESULTS

| Species | Expected | Result | Pass/Fail |
|---|---|---|---|
| *Acinetobacter baumannii* | POS | POS | Passed |
| *Citrobacter* spp. | POS | POS | Passed |
| *Enterobacter* spp. | POS | POS | Passed |
| *Escherichia coli* | POS | POS | Passed |
| *Klebsiella* spp. | POS | POS | Passed |
| *Proteus* spp. | POS | POS | Passed |
| *Pseudomonas aeruginosa* | POS | POS | Passed |
| *Serratia marcescens* | POS | POS | Passed |
| Coagulase-negative *Staphylococcus* spp. | POS | POS | Passed |
| *Enterococcus faecalis* | POS | POS | Passed |
| *Enterococcus faecium* | POS | POS | Passed |
| *Staphylococcus aureus* | POS | POS | Passed |
| *Staphylococcus lugdunensis* | POS | POS | Passed |
| *Streptococcus* spp. | POS | POS | Passed |
| *Candida albicans* | POS | POS | Passed |
| *Candida glabrata* | POS | POS | Passed |

SUSCEPTIBILITY RESULTS

| Antimicrobial | Expected | Result | Pass/Fail |
|---|---|---|---|
| *Escherichia coli*: Escherichia_coli_ATCC_25922F | | | |
| Ceftriaxone | 0.03-0.125 | 0.0525 | Passed |
| Minocycline | 0.25-1 | 0.5 | Passed |
| Ceftazidime | 0.06-0.5 | 0.25 | Passed |
| *Escherichia coli*: Escherichia_coli_ATCC_35218F | | | |
| Piperacillin-Tazobactam | 0.5/4-2/4 | 1 | Passed |
| *Staphylococcus aureus*: Staphylococcus_aureus_ATCC_29213F | | | |
| Cefoxitin | NEG | NEG | Passed |
| MLSb | NEG | NEG | Passed |
| Trimethoprim-Sulfamethoxazole | 0/0-0.5/9.5 | 0.25 | Passed |
| *Enterococcus faecalis*: Enterococcus_faecalis_ATCC_29212F | | | |
| Ceftaroline | 0.25-2 | 1 | Passed |
| Daptomycin | 1-4 | 2 | Passed |
| Doxycycline | 2-8 | 4 | Passed |
| Linezolid | 1-4 | 2 | Passed |
| Vancomycin | 1-4 | 2 | Passed |
| *Pseudomonas aeruginosa*: Pseudomonas_aeruginosa_ATCC_27853F | | | |
| Amikacin | 1-4 | 2 | Passed |
| Aztreonam | 2-8 | 4 | Passed |
| Ciprofloxacin | 0.25-1 | 0.5 | Passed |
| Colistin | 0.5-4 | 2 | Passed |
| Ertapenem | 2-8 | 4 | Passed |
| Cefepime | 0.5-4 | 2 | Passed |
| Gentamicin | 0.5-2 | 1 | Passed |
| Meropenem | 0.25-1 | 0.5 | Passed |
| Tobramycin | 0.25-1 | 0.5 | Passed |
| *Staphylococcus aureus*: Staphylococcus_aureus_ATCC_43300F | | | |
| Cefoxitin | POS | POS | Passed |
| *Staphylococcus aureus*: Staphylococcus_aureus_ATCCBAA_977F | | | |
| MLSb | POS | POS | Passed |

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods.

Any of the disclosed methods can be implemented as computer-executable instructions stored on one or more computer-readable storage media (e.g., one or more optical media discs, volatile memory components (such as DRAM or SRAM), or non-volatile memory components (such as flash memory or hard drives)) and executed on a computer (e.g., any commercially available computer, including smart phones or other mobile devices that include computing hardware). The term computer-readable storage media does not include communication connections, such as signals and carrier waves. Any of the computer-executable instructions for implementing the disclosed techniques as well as any data created and used during implementation of the disclosed embodiments can be stored on one or more computer-readable storage media. The computer-executable instructions can be part of, for example, a dedicated software application or a software application that is accessed or downloaded via a web browser or other software application (such as a remote computing application). Such software can be executed, for example, on a single local computer (e.g., any suitable commercially available computer) or in a network environment (e.g., via the Internet, a wide-area network, a local-area network, a client-server network (such as a cloud computing network), or other such network) using one or more network computers.

For clarity, only certain selected aspects of the software-based implementations are described. Other details that are well known in the art are omitted. For example, it should be understood that the disclosed technology is not limited to any specific computer language or program. For instance, the disclosed technology can be implemented by software written in C++, Java, Perl, JavaScript, assembly language, or any other suitable programming language. Likewise, the disclosed technology is not limited to any particular computer or type of hardware. Certain details of suitable computers and hardware are well known and need not be set forth in detail in this disclosure.

It should also be well understood that any functionality described herein can be performed, at least in part, by one or more hardware logic components, instead of software. For example, and without limitation, illustrative types of hardware logic components that can be used include Field-programmable Gate Arrays (FPGAs), Application-specific Integrated Circuits (ASICs), Program-specific Standard Products (ASSPs), System-on-a-chip systems (SOCs), Complex Programmable Logic Devices (CPLDs), etc.

Furthermore, any of the software-based embodiments (comprising, for example, computer-executable instructions for causing a computer to perform any of the disclosed methods) can be uploaded, downloaded, or remotely accessed through a suitable communication means. Such suitable communication means include, for example, the Internet, the World Wide Web, an intranet, software applications, cable (including fiber optic cable), magnetic communications, electromagnetic communications (including RF, microwave, and infrared communications), electronic communications, or other such communication means.

The disclosed methods, apparatus, and systems should not be construed as limiting in any way. Instead, the present disclosure is directed toward all novel and nonobvious features and aspects of the various disclosed embodiments, alone and in various combinations and subcombinations with one another. The disclosed methods, apparatus, and systems are not limited to any specific aspect or feature or combination thereof, nor do the disclosed embodiments require that any one or more specific advantages be present or problems be solved.

In view of the many possible embodiments to which the principles of the disclosed invention may be applied, it should be recognized that the illustrated embodiments are only examples of the disclosure and should not be taken as limiting the scope of the invention. Rather, the scope of the invention is defined by the following claims. We therefore claim as our invention all that comes within the scope of these claims.

The disclosure presented herein is believed to encompass at least one distinct invention with independent utility. While the at least one invention has been disclosed in exemplary forms, the specific embodiments thereof as described and illustrated herein are not to be considered in a limiting sense, as numerous variation are possible. Equivalent changes, modifications and variations of the variety of embodiments, materials, compositions, and methods may be made within the scope of the present disclosure, achieving substantially similar results. The subject matter of the at least one invention includes all novel and non-obvious combinations and sub-combinations of the various elements, features, functions and/or properties disclosed herein and their equivalents.

The methods described herein may be implemented to facilitate rapid culturing and detection of microbial cells from samples. Benefits, other advantages, and solutions to problems have been described herein with regard to specific embodiments. However, the benefits, advantages, solutions to problems, and any element or combination of elements that may cause any benefits, advantage, or solution to occur or becomes more pronounced are not to be considered as critical, required, or essential features or elements of any or all the claims of the at least one invention. Many changes and modifications within the scope of the instant disclosure may be made without departing from the spirit thereof, and the one or more inventions described herein include all such modifications. Corresponding structures, materials, acts, and equivalents of all elements in the claims are intended to include any structure, material, or acts for performing the functions in combination with other claim elements as specifically recited. The scope of the one or more inventions should be determined by the appended claims and their legal equivalents, rather than by the examples set forth herein.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the inventions. The scope of the inventions is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Systems, methods and apparatus are provided herein. In the detailed description herein, references to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f), unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

We claim:

1. An automated antibiotic susceptibility testing (AST) quality control (QC) component, comprising:
    a frame including a plurality of wells;
    at least one clip attached to the frame, wherein the at least one clip includes at least one clip that interacts with a reagent cartridge;
    at least one microbial isolate in at least one of the plurality of wells; and
    a means of identifying the component as an AST QC test by an automated system.

2. The AST QC component of claim 1, wherein the at least one clip includes at least one clip that-interacts with a microbial identification QC component.

3. The AST QC component of claim 1, wherein the plurality of wells comprises 8-12 wells.

4. The AST QC component of claim 1, wherein the microbial isolate comprises *Escherichia coli, Pseudomonas aeruginosa, Enterococcus faecalis, Staphylococcus aureus*, or *Candida albicans*.

5. The AST QC component of claim 4, wherein the *E. coli* is *E. coli* ATCC 25922 and/or *E. coli* ATCC 35218, the *Pseudomonas aeruginosa* is *P. aeruginosa* ATCC 27853, the *Enterococcus faecalis* is *E. faecalis* ATCC 29212, the *Staphylococcus aureus* is *S. aureus* ATCC 29213, *S. aureus* ATCC 43300, and/or *S. aureus* ATCC BAA-977, and/or the *Candida albicans* is *C. albicans* ATCC 96268.

6. The AST QC component of claim 1, wherein the means of identifying the component as an AST QC test comprises a bar code or an RFID tag.

7. An automated microbial identification (ID) quality control (QC) component, comprising
    a frame including a plurality of wells;
    at least one clip attached to the frame;
    at least one target microbial nucleic acid molecule in at least one of the plurality of wells, wherein the microbial ID QC component is configured to interlock with an antibiotic susceptibility QC component; and
    a means of identifying the component as a microbial ID QC test by an automated system.

SEQUENCE LISTING

<160> NUMBER OF SEQ ID NOS: 2

<210> SEQ ID NO 1
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 1
agctaggtac atta                                                14

<210> SEQ ID NO 2
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 2
tcgatccatg taat                                                14

8. The microbial ID QC component of claim 7, wherein the at least one clip interacts with an antibiotic susceptibility testing QC component.

9. The microbial ID QC component of claim 7, wherein the plurality of wells comprises 11-13 wells.

10. The microbial ID QC component of claim 7, wherein the at least one target nucleic acid molecule is from *Acinetobacter baumannii, Citrobacter* spp., *Enterobacter* spp., *Escherichia coli, Klebsiella* spp., *Proteus* spp., *Pseudomonas aeruginosa, Serratia marcescens*, Coagulase-negative *Staphylococcus* spp., *Enterococcus faecalis, Enterococcus faecium, Staphylococcus aureus, Staphylococcus lugdunensis, Streptococcus* spp., *Candida albicans*, or *Candida glabrata*.

11. The microbial ID QC component of claim 7, wherein the means of identifying the component as a microbial ID QC test comprises a bar code or an RFID tag.

12. A kit comprising one or more automated AST QC components of claim 1.

13. The kit of claim 12, further comprising one or more automated microbial identification (ID) quality control (QC) components comprising:
a frame including a plurality of wells;
at least one clip attached to the frame;
at least one target microbial nucleic acid molecule in at least one of the plurality of wells, wherein the one or more microbial ID QC components are configured to interlock with the one or more AST QC components; and
a means of identifying the one or more microbial ID QC components as a microbial ID QC test by an automated system.

14. A method of performing automated quality control (QC) testing, comprising:
(a) attaching the AST QC component of claim 1 to a reagent cartridge, wherein the reagent cartridge comprises:
a plurality of wells comprising reagents; and
an opening,
wherein the plurality of wells comprising reagents comprise at least one well comprising a probe and at least one well comprising an antimicrobial agent;
(b) inserting the reagent cartridge with the attached AST QC component into a system, wherein the system comprises:
a reagent stage comprising an annular shape defining an interior opening, wherein the reagent stage is configured to rotate in a first plane and wherein the reagent stage is configured to receive the reagent cartridge;
a cassette comprising a plurality of microfluidic sample channels structured to receive samples, each of the plurality of microfluidic sample channels comprising an inlet port configured to receive a pipette tip;
a cassette stage located within the interior opening of the reagent stage, wherein the cassette stage is configured to rotate and move laterally in the first plane, and wherein the cassette stage is configured to receive the cassette;
a pipettor assembly configured to move a plurality of reagents between the plurality of wells of the reagent cartridge and the inlet ports of each of the plurality of microfluidic sample channels;
an optical scanning device configured to identify a QC component;
an optical detection system configured to obtain darkfield and fluorescence photomicrographs of one or more microorganisms contained in the plurality of microfluidic sample channels; and
a controller configured to direct operation of the system and process microorganism information derived from photomicrographs obtained by the optical detection system;
(c) introducing one or more microbial isolates from the AST QC component to the plurality of microfluidic channels of the cassette of the system;
(d) growing the one or more microbial isolates in the presence or absence of one or more antimicrobial agents;
(e) monitoring the growth of the microbial isolates over time;
(f) determining susceptibility or resistance of the one or more microbial isolates to the one or more antimicrobial agents; and
(g) reporting accuracy of the microbial isolate antimicrobial susceptibility or resistance provided by the system.

15. The method of claim 14, wherein determining susceptibility or resistance of the one or more microbial isolates to the one or more antimicrobial agents further comprises qualitatively or quantitatively measuring growth or lysis of the one or more microbial isolates in the presence of the one or more antimicrobial agents compared to a control that is not exposed to the antimicrobial agents.

16. The method of claim 14, wherein the one or more microbial isolates are grown in Mueller-Hinton nutrient-depleted media or are grown in 1% phytone tryptose Mueller-Hinton agar.

17. The method of claim 14, wherein the one or more antimicrobial agents comprise one or more of amikacin, ampicillin, ampicillin-sulbactam, aztreonam, cefazolin, cefepime, ceftaroline, ceftazidime, ceftriaxone, ciprofloxacin, colistin, daptomycin, doxycycline, erythromycin, ertapenem, gentamicin, imipenem, linezolid, meropenem, minocycline, piperacillin-tazobactam, tobramycin, trimethoprim-sulfamethoxazole and vancomycin.

18. The method of claim 14, further comprising:
(a) attaching a microbial identification (ID) quality control (QC) component to the reagent cartridge prior to inserting the reagent cartridge in the system, wherein the microbial ID QC component comprises:
a frame including a plurality of wells;
at least one clip attached to the frame;
at least one target microbial nucleic acid molecule in at least one of the plurality of wells, wherein the microbial ID QC component is configured to interlock with the AST QC component; and
a means of identifying the component as a microbial ID QC test by an automated system;
(b) introducing the at least one target microbial nucleic acid molecules into the plurality of microfluidic channels of the cassette;
(c) introducing one or more labeled target probes that recognize and bind sequences of the at least one target microbial nucleic acid molecule into the at least one of the plurality of microfluidic channels;
(d) incubating the labeled probes with the at least one target microbial nucleic acid molecule for a time sufficient to enable binding of the probes to target microbial nucleic acid molecules; and
(e) detecting a signal from the one or more labeled target probes, wherein presence of a signal indicates a positive ID result and absence of a signal indicates a negative ID result; and (f) reporting accuracy of microbial identification provided by the system.

19. The method of claim 18, wherein the at least one target microbial nucleic acid molecule is coupled to a microsphere.

20. The method of claim 18, wherein the at least one target microbial nucleic acid molecule is complementary to a nucleic acid from one or more of *Staphylococcus aureus, Staphylococcus lugdunensis*, coagulase-negative *Staphylococcus* species, *Enterococcus faecalis, Enterococcus faecium, Streptococcus pneumoniae, Streptococcus agalactiae, Streptococcus* spp., *Pseudomonas aeruginosa, Acinetobacter baumannii, Klebsiella* spp., *Escherichia coli, Enterobacter* spp., *Proteus* spp., *Citrobacter* spp., *Serratia marcescens, Candida albicans* and *Candida glabrata*.

21. The method of claim 14, wherein the automated quality control method achieves about a 20% to about a 30% improvement in the effective pass rate over a manual quality control test procedure.

22. The method of claim 18, wherein the automated quality control method achieves about a 20% to about a 30% improvement in the effective pass rate over a manual quality control test procedure.

\* \* \* \* \*